(12) United States Patent
Donaldson et al.

(10) Patent No.: US 9,297,029 B2
(45) Date of Patent: *Mar. 29, 2016

(54) FERMENTIVE PRODUCTION OF FOUR CARBON ALCOHOLS

(71) Applicant: BUTAMAX ADVANCED BIOFUELS LLC, Wilmington, DE (US)

(72) Inventors: Gail K. Donaldson, Newark, DE (US); Andrew C. Eliot, Wilmington, DE (US); Dennis Flint, Newark, DE (US); Lori Ann Maggio-Hall, Wilmington, DE (US); Vasantha Nagarajan, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/585,261

(22) Filed: Dec. 30, 2014

(65) Prior Publication Data

US 2015/0119608 A1    Apr. 30, 2015

Related U.S. Application Data

(63) Continuation of application No. 12/939,315, filed on Nov. 4, 2010, now Pat. No. 8,951,774, which is a continuation of application No. 11/586,315, filed on Oct. 25, 2006, now Pat. No. 7,851,188.

(60) Provisional application No. 60/730,290, filed on Oct. 26, 2005.

(51) Int. Cl.
| | |
|---|---|
| *C12P 7/16* | (2006.01) |
| *C12N 15/70* | (2006.01) |
| *C12N 15/81* | (2006.01) |
| *C12N 15/74* | (2006.01) |
| *C12N 9/04* | (2006.01) |
| *C12N 9/02* | (2006.01) |
| *C12N 9/06* | (2006.01) |
| *C12N 9/10* | (2006.01) |
| *C12N 9/88* | (2006.01) |
| *C12N 15/52* | (2006.01) |
| *C12N 15/75* | (2006.01) |

(52) U.S. Cl.
CPC ............. *C12P 7/16* (2013.01); *C12N 9/0006* (2013.01); *C12N 9/0008* (2013.01); *C12N 9/0016* (2013.01); *C12N 9/1022* (2013.01); *C12N 9/1096* (2013.01); *C12N 9/88* (2013.01); *C12N 15/52* (2013.01); *C12N 15/70* (2013.01); *C12N 15/74* (2013.01); *C12N 15/746* (2013.01); *C12N 15/75* (2013.01); *C12N 15/81* (2013.01); *C12Y 102/04004* (2013.01); *C12Y 202/01006* (2013.01); *C12Y 101/01001* (2013.01); *C12Y 101/01002* (2013.01); *C12Y 101/01086* (2013.01); *C12Y 401/01072* (2013.01); *C12Y 402/01009* (2013.01); *Y02E 50/10* (2013.01); *Y02E 50/343* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,424,275 A | 1/1984 | Levy | |
| 4,568,643 A | 2/1986 | Levy | |
| 5,210,032 A | 5/1993 | Kashket | |
| 5,210,296 A | 5/1993 | Cockrem et al. | |
| 5,530,189 A | 6/1996 | Ausich et al. | |
| 5,686,276 A | 11/1997 | Laffend et al. | |
| 6,013,494 A | 1/2000 | Nakamura et al. | |
| 6,177,264 B1 | 1/2001 | Eggeling et al. | |
| 6,358,717 B1 | 3/2002 | Blaschek et al. | |
| 6,579,330 B2 | 6/2003 | Nakahama et al. | |
| 6,660,507 B2 | 12/2003 | Cheng et al. | |
| 6,787,334 B1 | 9/2004 | Elischweski et al. | |
| 7,632,663 B1 | 12/2009 | Eggeling et al. | |
| 7,851,188 B2 | 12/2010 | Donaldson et al. | |
| 7,993,889 B1 | 8/2011 | Donaldson et al. | |
| 8,017,375 B2 | 9/2011 | Feldman et al. | |
| 8,178,328 B2 | 5/2012 | Donaldson et al. | |
| 8,273,558 B2 | 9/2012 | Donaldson et al. | |
| 8,283,144 B2 | 10/2012 | Donaldson et al. | |
| 8,735,114 B2 | 5/2014 | Donaldson et al. | |
| 8,889,385 B2 | 11/2014 | Donaldson et al. | |
| 8,951,774 B2 * | 2/2015 | Donaldson ........... | C21N 9/0006 435/157 |
| 9,068,190 B2 | 6/2015 | Donaldson et al. | |
| 2002/0028492 A1 | 3/2002 | Lenke et al. | |
| 2004/0146996 A1 | 7/2004 | Yocum et al. | |
| 2004/0157301 A1 | 8/2004 | Chotani et al. | |
| 2009/0081746 A1 | 3/2009 | Liao et al. | |

(Continued)

FOREIGN PATENT DOCUMENTS

| | | |
|---|---|---|
| AU | 620802 B2 | 2/1992 |
| CA | 2039245 A1 | 10/1991 |

(Continued)

OTHER PUBLICATIONS

50 Disruptive Companies: Company Profile: Joule Unlimited, MIT Technology Review (2013), 2 Pages, accessed at http://www2.technologyreview.com/tr50/jouleunlimited/ on May 14, 2014.

Action Closing Prosecution in Inter Partes Reexamination of U.S. Pat. No. 7,851,188, mailed Sep. 20, 2013, U.S. Control No. 95/001,857, filed Dec. 19, 2011.

Action Closing Prosecution in Inter Partes Reexamination of U.S. Patent No. 8,178,328, mailed Mar. 19, 2014, U.S. Control No. 95/001,998, filed Jun. 21, 2012.

(Continued)

*Primary Examiner* — Christian Fronda

(57) ABSTRACT

Methods for the fermentative production of four carbon alcohols is provided. Specifically, butanol, preferably isobutanol is produced by the fermentative growth of a recombinant bacterium expressing an isobutanol biosynthetic pathway.

18 Claims, 1 Drawing Sheet

(56) References Cited

U.S. PATENT DOCUMENTS

| | | |
|---|---|---|
| 2009/0226991 A1 | 9/2009 | Feldman et al. |
| 2009/0305363 A1 | 12/2009 | Anthony et al. |
| 2010/0081182 A1 | 4/2010 | Paul et al. |
| 2010/0120105 A1 | 5/2010 | Anthony et al. |
| 2010/0129886 A1 | 5/2010 | Anthony et al. |
| 2010/0151545 A1 | 6/2010 | Roessler et al. |
| 2011/0053235 A1 | 3/2011 | Festel et al. |
| 2011/0111472 A1 | 5/2011 | Donaldson et al. |
| 2011/0112334 A1 | 5/2011 | Donaldson et al. |
| 2011/0160442 A1 | 6/2011 | Pietarinen et al. |
| 2011/0313206 A1 | 12/2011 | Donaldson et al. |
| 2013/0171706 A1 | 7/2013 | Donaldson et al. |
| 2013/0183731 A1 | 7/2013 | Donaldson et al. |
| 2014/0030794 A1 | 1/2014 | Donaldson et al. |
| 2014/0051151 A1 | 2/2014 | Donaldson et al. |
| 2014/0335582 A1 | 11/2014 | Donaldson et al. |

FOREIGN PATENT DOCUMENTS

| | | |
|---|---|---|
| EP | 0112459 A1 | 7/1984 |
| EP | 0282474 A1 | 9/1988 |
| EP | 0315949 A2 | 5/1989 |
| EP | 1149918 A1 | 10/2001 |
| JP | S61209594 A | 9/1986 |
| JP | S6317695 A | 1/1988 |
| JP | S63102687 A | 5/1988 |
| JP | S63254986 A | 10/1988 |
| JP | 2000041655 A | 2/2000 |
| WO | WO-9002193 A1 | 3/1990 |
| WO | WO-9851813 A1 | 11/1998 |
| WO | WO-0050624 A1 | 8/2000 |
| WO | WO-0121772 A2 | 3/2001 |
| WO | WO-2008072920 A1 | 6/2008 |
| WO | WO-2008072921 A1 | 6/2008 |

(56) References Cited

OTHER PUBLICATIONS

Agricultural Futures, in The Wall Street Journal, U.S Edition, Thursday, Jun. 28, 2012, 8 pages, accessed at http://online.wsj.com/mdc/public/page/2_3023-fut_agricultural-futures.html?mod=mdc_c, Dow Jones & Company, Inc., United States.

Alasfour, F.N., "NOx Emission from a Spark Ignition Engine using 30% Iso-Butanol-Gasoline Blend: Part 1—Preheating Inlet Air," Appl. Thermal Eng'g 18(5):245-56, Elsevier Science Ltd., England (1998).

Alasfour, F.N., "NOx Emission from a Spark Ignition Engine using 30% Iso-Butanol-Gasoline Blend; Part 2—Ignition Timing," Appl. Thermal Eng'g 18(8):609-18, Elsevier Science Ltd., England (1998).

Alberts, et al., "Chapter 3, Macromolecules: Structure, Shape and Information," in Molecular Biology of the Cell, 3rd Ed., pp. 134-135, Garland Publishing, United States (1994).

Albertsen, L., et al., "Diversion of Flux toward Sequiterpene Production in *Saccharomyces cerevisiae* by Fusion of Host and Heterologous Enzymes," Applied and Enviro. Microbiol. 77(3):1033-1040, American Society for Microbiology, United States (2011).

Amended Complaint filed on Aug. 11, 2011 by Plaintiff Butamax™ against Defendant Gevo, Inc. in the United States District Court for the District of Delaware, Case 1:11-cv-00054-SRL-MPT.

Amended Final Judgment of District Judge Robinson, in *ButamaxTM Advanced Biofuels LLC* vs. *Gevo, Inc.*, Case 1:11-cv-00054-SLR, United States District Court for the District of Delaware, filed Apr. 10, 2013; 2 pages.

Amendment No. 4 to Form S-1 Registration Statement, United States Securities and Exchange Commission, Registration No. 333-168792, filed Jan. 19, 2011, 303 Pages.

Answer to Amended Complaint filed on Sep. 13, 2011 by Defendant Gevo, Inc. in the United States District Court for the District of Delaware, Case 1:11-cv-00054-SRL-MPT.

Answer to Complaint, *Butamax™ Advanced Biofuels LLC* v. *Gevo, Inc.*, 1:11-cv-00054-SLR, U.S. District Court, District of Delaware, filed Mar. 25, 2011.

Answer to Complaint, Butamax™ Advanced Biofuels LLC v. Gevo, Inc., 1:12-cv-00602-SLR, U.S. District Court, District of Delaware, filed Jun. 8, 2012.

Atsumi, S. and Liao, J.C., "Metabolic engineering for advanced biofuels production form *Escherichia coli*," Curr. Op. Biotechnol. 19:414-419, Elsevier Ltd., England (2008).

Atsumi, S., et al., "Acetolactate synthase from Bacillus subtilis serves as a 2-ketoisovalerate decarboxylase for isobutanol biosynthesis in *Escherichia coli*," Appl. Environ. Microbiol. 75(19):6306-11, American Society for Microbiology, United States (Oct. 2009; Epub.: Aug. 2009).

Atsumi, S., et al., "Direct photosynthetic recycling of carbon dioxide to isobutyraldehyde," Nat. Biotechnol. 27(12):1177-80, Nature Publishing Group, England (2009).

Atsumi, S., et al., "Non-fermentative pathways for synthesis of branched-chain higher alcohols as biofuels," Nature 451(7174):86-89, Nature Publishing Group, England (2008).

Avalos, J.L., et al., "Compartmentalization of metabolic pathways in yeast mitochondria improves the production of branched-chain alcohols," Nature Biotechnology, Advance Online Publication:1-9, Nature America, Inc., United States (2013).

Ayrapaa, T., "Formation of Higher Alcohols by Various Yeasts," J. Inst. Brewing 74:169-178, W. Heffer & Sons, Ltd, England (1968).

Ayrapaa, T., "Formation of Higher Alcohols From 14C-Labelled Valine and Leucine," J. Inst. Brewing, 73:17-30, W. Heffer & Sons, Ltd, England (1967).

Ayrapaa, T., "The Formation of Phenethyl Alcohol from 14C-Labelled Phenylalanine," J. Inst. Brewing 71:341-347, W. Heffer & Sons, Ltd, England (1965).

Bailey, J.E., "Toward a Science of Metabolic Engineering," Science 252:1668-1675, American Association for the Advancements of Science, United States (1991).

Balk, J & Lill R., "The Cell's Cookbook for Iron-Sulfur Clusters: Recipes for Fool's Gold?" ChemBioChem 5: 1044-1049 (2004).

Bayrock, D., "Fusel Oil Recycle—A Silent, Odorous Killer," Ethanol Producer Magazine, BBI International, United States, accessed at http://ethanolproducer.com/articles/8774/fusel-oil-recycleundefineda-silent-odorous-killer, May 10, 2012.

Becker, J.V.W., et al., "Metabolic Engineering of *Saccharomyces cerevisiae* for the synthesis of the wine-related antioxidant resveratrol," FEMS Yeast Res. 4:79-85, Elsevier B.V., Netherlands (2003).

Bekkaoui, F., et al., "Isolation and structure of an acetolactate synthase gene from Schizosaccharomyces pombe and completion of the ilv2 mutation in *Saccharomyces cerevisiae*," Current Genetics 24:544-547, Springer-Verlag, Germany 1993.

Bevill, K., et al., "Proposed Ethanol Plant List: 2008 United States & Canada Part 1," Ethanol Producer Magazine, EthanolProducer.com Apr. 1, 2008, 9 pages, accessed at http://www.ethanolproducer.com/articles/3851/proposed-ethanol-plant-list-2008-united-states-and-canada-part-1.

Blombach, B., et al., "Corynebacterium glutamicum Tailored for Efficient Isobutanol Production," Appl. Environ. Microbiol. 77(10):3300-3310, The American Society for Microbiology, United States (2011).

Boer, V.M., et al., "The Genome-wide Transcriptional Responses of *Saccharomyces cerevisiae* Grown on Glucose in Aerobic Chemostat Cultures Limited for Carbon, Nitrogen, Phosphorus, or Sulfur," J. Biol. Chem. 278:3265-3274, The American Society for Biochemistry and Molecular Biology, Inc., United States (2003).

Bolotin, A., "The Complete Genome Sequence of the Lactic Acid Bacterium *Lactocuccus lactis* ssp. *lactis IL1403*," Genome Res. 11(5):731-753, Cold Spring Harbor Press, United States (2001).

Boonstra, B., et al., "Cofactor Regeneration by a Soluble Pyridine Nucleotide Transhydrogenase for Biological Production of Hydromorphone," Applied and Environmental Microbiology 66(12):5161-5166, American Society for Microbiology, United States (2000).

(56) References Cited

OTHER PUBLICATIONS

Boosting Biomass-to . . . Butanol?, Green Car Congress, Jul. 20, 2005, available at http://www.greencarcongress.com/2005/07/boosting_biomass.html.

Boulton, C., et al., Brewing Yeast & Fermentation, Chapter 3, first ed., Blackwell Science Ltd, E. Oxford, United Kingdom, pp. 69-259, 2001.

Brat, D., et al., "Cytosolic re-localization and optimization of valine synthesis and catabolism enables increased isobutanol production with the yeast *Saccharomyces cerevisiae*," Biotechnology for Biofuels 5(65):1-16, BioMed Central Ltd., England (2012).

BRENDA Comprehensive Enzyme Information System entry for EC 1.1.1.2 alcohol dehydrogenase (NADP+) in *E. coli*, accessed www.brenda-enzymes.org, accessed on Jun. 1, 2012, 8 pages.

Bricker, D.K., et al., "A Mitochondrial Pyruvate Carrier Required for Pyrovate Uptake in Yeast, *Drosophila*, and Humans," Science 337:96-100, American Association for the Advancement of Science, United States (2012).

Bryan, T., "Adsorbing it All," Biodiesel Magazine, Mar. 1, 2005, 3 Pages, accessed at http://www.biodieselmagazine.com/articles/239/adsorbing-it-all on May 17, 2014.

Burtis, P.R., et al., "California's Cleantech Industry: Annual Venture Capital Investment Update 2006," Environmental Entrepreneurs and Cleantech Venture Network LLC, 15 Pages.

Bussey, H. and Umbarger, H.E., "Biosynthesis of Branched-Chain Amino Acids in Yeast: Regulation of Synthesis of the Enzymes of Isoleucine and Valine Biosynthesis," Journal of Bacteriology 98(2):623-628, American Society for Microbiology, United States (1969).

Butalco to Begin Cellulosic Ethanol Production in Summer 2010 in Germany, published Feb. 24, 2010, available at http://www.greencarcongress.com/2010/02/butalco-20100224.html.

*Butamax™ Advanced Biofuels LLC* v. *Gevo, Inc.*, No. 13-1342, Joint Appendix vol. II of III, A10447-A10495, ECF No. 49.

*Butamax™ Advanced Biofuels LLC* vs. *Gevo, Inc.* (Fed. Cir. 2014), dated Feb. 18, 2014 [Appeal from the United States District Court for the District of Delaware in No. 11-cv-00054, Judge Sue L. Robinson].

Butamax and Highwater Ethanol Break Ground on Biobutanol Retrofit Project Including Installation of Novel Corn Oil Separation Technology, published Oct. 2, 2013, Butamax™ Advanced Biofuels LLC.

Butamax Early Adopters Group surpasses capacity targets with addition of Big River; Membership represents 11 production facilities and nearly 900 million gallons of ethanol capacity, published Jun. 26, 2012, available at http://www.prnewswire.com/news-releases/butamax-early-adopters-group-surpasses-capacity-targets-with-addiction-of-big-river-membership-represents-11-production-facilities-and-nearly-900-million-gallons-of-ethanol-capacity-160348995.html#.

Butamax expands Biobutanol Early Adopters Group with Four New Members; Brings Capacity to Half a Billion Gallons, published Jun. 18, 2012, Butamax™ Advanced Biofuels LLC.

Butamax Expands Early Adopters Group as Two New Ethanol Producers Join for Early Access to Biobutanol Production, available at http://www.butamax.com/_assets/pdf/butamax%20-announces%202%20new%20eag%20may%201%202012.pdf, May 1, 2012.

Butamax™ Technology & Intellectual Property FAQ, accessed at http://butamaxpatents.com/FAQ.aspx on Nov. 18, 2013, Butamax™ Advanced Biofuels LLC.

Byrne, K.L. and Meacock, P.A., "Thiamin auxotrophy in yeast through dependence of the enzyme acetohydroxyacid synthase," Microbiology 147:2389-2398, SGM, Great Britain (2001).

Card, J.C., et al., "Separation of Alcohol-Water Mixtures Using Salts," in Technical Reports of Oak Ridge National Laboratory, Chemical Technology Division, Contract No. W-7405-eng-26, United States (1982).

Carlini et al., "Guerbet Condensation of Methanol with N-Propanol to Isobutanol Alcohol Over Heterogeneous Copper Chromite/Mg-Al Mixed Oxides Catalysts," J. Mol. Catal. A: Chem. 220:215-220, Elsevier B.V., Netherlands (2004).

Catalog Receipt from U.S.D.A. National Agricultural Library of Smit, Ph.D. Thesis, Wageningen Universiteit (Wageningen, The Netherlands), Formation of Amino Acid Derived Cheese Flavour Compounds, MARC Record View, 2 pages, indicating date cataloged as 20041003 (i.e., Oct. 3, 2004) via MARC Code "005".

Causey, T.B., et al., "Engineering the metabolism of *Escherichia coli* W3110 for the conversion of sugar to redox-neutral and oxidized products: Homoacetate production," PNAS 100(3):825-832, National Academy of Sciences, United States (2003).

Causton, H.C., et al., "Remodeling of Yeast Genome Expression in Response to Environmental Changes," Mol. Biol. Cell 12:323-337, The American Society for Cell Biology, United States (2001).

Chen, E. C.-H., "The Relative contribution of Ehrlich and Biosynthetic Pathways to the Formation of Fusel Alchols," J. Amer. Soc. Brewing Chem. 36(1):39-43, American Society of Brewing Chemists, Inc., United States (1978).

Chen, E.C.-H., "Keto Acid Decarboxylase and Alcohol Dehydrogenase Activities of Yeast in Relation to the Formation of Fusel Alcohols," Can. Inst. Food Sci. Technol. J. 10:27-30, Canadian Institute of Food Science and Technology, Canada (1977).

Chen, et al., "Increased isobutanol production in *Saccharomyces cerevisiae* by overexpression of genes in valine metabolism," Biotechol. Biofuels 4(21):1-12 BioMed Central Ltd., England (2011).

Chen, Ph.D. Thesis, McGill University (Montreal, Canada), "Formation and Analysis of Fusel Alcohols in Beer," submitted to the Faculty of Graduate Studies and Research, Department of Agricultural Chemistry 1978.

Chica, R.A., et al., "Semi-rational Approaches to Engineering Enzyme Activity: Combining the Benefits to Directed Evolution and Rational Design," Current Opinion in Biotechnology 16:378-384, Elsevier Ltd., England (2005).

Chin, M., "UCLA researchers develop method for production of more efficient biofuels," UCLA Newsroom, Jan. 2, 2008, available at http://newsroom.ucla.edu/portal/ucla/ucla-engineering-researchers-develop-42502.aspx, UC Regents, United States.

Christen, P., et al., "Ethanol Extraction by Supported Liquid Membrane During Fermentation," Biotechnology and Bioengineering 36:116-123, John Wiley & Sons, Inc., United States (1990).

Complaint, *Butamax™ Advanced Biofuels LLC* v. *Gevo, Inc.*, 1:11-cv-00054-SLR, U.S. District Court, District of Delaware, filed Jan. 14, 2011.

Complaint, Butamax™ Advanced Biofuels LLC v. Gevo, Inc., 1:12-cv-00602-SLR, U.S. District Court, District of Delaware, filed May 15, 2012.

Cordier, H., et al., "A metabolic and genomic study of engineered *Saccharomyces cerevisiae* strains for high glycerol production," Metabolic Engineering 9:364-378, Academic Press, United States (2007).

Day, R., "Methanotech and Turtle Island Recycling," Cleantech Investing: Greentech Media, Aug. 30, 2005, accessed at http://www.greentechmedia.com/cleantech-investing/post/methanotech-and-turtle-island-recycling-151 on May 7, 2014.

De Kok, S., et al., "Energy coupling in *Saccharomyces cerevisiae*: selected opportunities for metabolic engineering," Federation of European Microbiological Societies FEMS Yeast Re 12:387-397, Blackwell Publishing Ltd., England (2012).

De La Plaza, M., et al., "Biochemical and molecular characterization of alpha-ketoisovalerate decarboxylase, an enzyme involved in the formation of aldehydes from amino acids by Lactococcus lactis," FEMS Microbiol. Lett. 238(2):367-74. Elsevier/North Holland on behalf of the Federation of European Microbiological Societies, England, (Sep. 2004).

de la Plaza Sequence Genbank entry and Clustal W alignment with SEQ ID No. 8, provided with Third Party Requester Comments After Patent Owner Response to Action Closing Prosecution, filed Feb. 28, 2014, Inter Partes Reexamination of U.S. Pat. No. 7,851,188, U.S. Control No. 95/001,857, filed Dec. 19, 2011.

Debourg, A., "Yeast in Action: From Wort to Beer," Cerevisia 27(3):144-154, St. Martens-Latem Associations D Anciens Etudiants Des Ecole De Brasserie Belges, Belgium (2002).

(56) References Cited

OTHER PUBLICATIONS

Declaration of Dr. Alexander M. Klibanov Accompanying Response to Inter Partes Reexamination Office Action, in Inter Partes Reexamination of U.S. Pat. No. 8,178,328, filed Jun. 21, 2012, U.S. Control No. 95/001,998.
Declaration of Dr. Janice Pero Accompanying Response to Inter Partes Reexamination Office Action, in Inter Partes Reexamination of U.S. Pat. No. 8,178,328, filed Jun. 21, 2012, U.S. Control No. 95/001,998.
Declaration of Dr. Larry C. Anthony Accompanying Response to Inter Partes Reexamination Office Action, in Inter Partes Reexamination of U.S. Pat. No. 8,178,328, filed Jun. 21, 2012, U.S. Control No. 95/001,998.
Declaration of Dr. Stephanolpoulos, filed Sep. 12, 2012, U.S. Control No. 90/012,503, filed Sep. 12, 2012.
Declaration of Gregory N. Stephanopoulos, Ph.D., Accompanying Third Party Requester Comments to Patent Owner's Response to Inter Partes Reexamination Office Action, in Inter Partes Reexamination of U.S. Pat. No. 8,178,328, filed Jun. 21, 2012, U.S. Control No. 95/001,998.
Deloache, W.C. and Dueber, J.E., "Compartmentalizing metabolic pathways in organelles," Nature Biotech. 31:320-321, Nature America, Inc., United States (2013).
Derrick, S. and Large, P.J., "Activities of the enzymes of the Ehrlich Pathway and formation of branched-chain alcohols in *Saccharomyces cervisiae* and Candida utilis grown in continous culuture on valine or ammonium as sole nitrogen source," J. Gen. Microbiol. 139:2783-2792, Society for General Microbiology, England (1993).
Dickinson, J.R., et al., "An Investigation of the Metabolism of Valine to Isobutyl Alcohol in *Saccharomyces cerevisiae*," J. Biol. Chem. 273(40): 25751-25756, The American Society for Biochemistry and Molecular Biology, Inc., United States, (1998).
Dickinson, J.R., et al., "The Catabolism of Amino Acids to Long Chain and Complex Alcohols in *Saccharomyces cerevisiae*," J. Biol. Chem. 278(10): 8028-8034, The American Society for Biochemistry and Molecular Biology, Inc., United States, 2003.
Diet beer offers a slim hope, http://www.independent.co.uk/news/diet-beer-offers-a-slim-hope-1305762.html, The Independent Newspaper, Apr. 20, 1996.
Dijkhuizen, L., et al., "Methanol, a potential feedstock for biotechnological processes," Trends in Biotechnology 3(10):262-267, Elsevier Science Publishers, B.V., Netherlands (1985).
Divakaruni, A.S. and Murphy, A.N., "A Mitochondrial Mystery, Solved," Science 337:41-43, American Association for the Advancement of Science, United States (2012).
Djaman, O., et al., "Repair of Oxidized Iron-Sulfur Clusters in *Escherichia coli*," The Journal of Biological Chemistry 279(43):44590-44599, American Society for Biochemistry and Molecular Biology, United States (2004).
Dumas, R., et al., "Isolation and kinetic properties of acetohydroxy acid isomeroreductase from spinach (*Spinacia oleracea*) chlorplasts overexpressed in *Escherichia coli*," Biochem. J. 288:865-874, Published by Portland Press, England (1992).
DuPont Receives U.S. EPA's Presidential Green Chemistry Award for New Innovation, Jun. 24, 2003, 2 Pages, accessed at http://www2/dupont.com/Media_Center/en_US/news_releases/2003/nr06_24_03a.html on May 13, 2014.
Durre, "New Insights and Novel Developments in Clostridial Acetone/Butanol/Isopropanol Fermentation," Applied Microbiology and Biotechnology, 49:639-648, Springer-Verlag, Germany (1998).
Eberhardt, I., et al., "Autoregulation of yeast pyruvate decarboxylase gene expression requires the enzyme but not its catalystic activity," Eur. J. Biochem. 262(1):191-201, Federation of European Biochemical Societies, England (1999).
Eden, A., et al., "Involvement of branched-chain amino acid aminotransferases in the production of fusel alcohols during fermentation in yeast," Appl. Microbiol. Biotechnol. 55:296-300, Springer-Verlag, Germany (2001).

Enari, T.-M., "Genetic Modification of Food and Beverage Yeast," Annals New York Acad. Sci, 646:181-192, New York Academy of Sciences, United States (1991).
Engineered Yeast Produces Ethanol and Butanol from C5 and C6 Sugars from Biomass Feedbacks, published Mar. 29, 2010, available at http://www.greencarcongress.com/2010/03/weber-20100329.html.
English language abstract for JP 61-209594, File 347, Accession No. 1995494, Derwent WPI English language abstract for JP 61-209594, published Sep. 17, 1986.
English language abstract for JP 63-017695, File 347, Accession No. 2400795, Derwent WPI English language abstract for JP 63-017695, published Jan. 25, 1988.
English language abstract for JP 63-102687, File 347, Accession No. 2485787, Derwent WPI English language abstract for JP 63-102678, published May 7, 1988.
English language abstract for JP 63-254986, File 347, Accession No. 2638086, Derwent WPI English language abstract for JP 63-254986, published Oct. 21, 1988.
File History for U.S. Appl. No. 60/868,326, filed Dec. 1, 2006, named inventors Meinhold, et al.
File History for U.S. Appl. No. 61/016,483, filed Dec. 23, 2007, named inventors Feldman, et al.
File History for U.S. Appl. No. 61/017,141, filed Dec. 27, 2007, named inventors Evanko, et al.
Final Judgment of District Judge Robinson, in *Butamax™ Advanced Biofuels LLC* vs. *Gevo, Inc.*, Case 1:11-cv-00054-SLR, United States District Court for the District of Delaware, filed Apr. 5, 2013; 2 pages.
First Request for Reexamination of U.S. Pat. No. 7,851,188, U.S. Control No. 95/001,718, filed on Aug. 18, 2011.
First Yeast to Produce Biobutanol, published Sep. 7, 2009, available at http://www.pressebox.de/pressemitleilung/butalco-gmbh/First-Yeasts-to-Produce-Biobutanol/boxid/286731.
Flint, D., "*Escherichia coli* Contains a Protein That Is Homologous in Function and N-terminal Sequence to the Protein Encoded by the nifS Gene of Azotobacter vinelandii and That Can participate in the Synthesis of the Fe-S Cluster of Dihydroxy-acid Dehydratase," J. Biol. Chem. 271(27): 16068-16074 (1995).
Flint, D.H., et al., "The Role and Properties of the Iron-Sulfur Cluster in *Escherichia coli* Dihydroxy-acid Dehydratase," J. Biol. Chem. 268 (20):14732-14742, American Society for Biochemistry and Molecular Biology, Inc., United States (1993).
Flint, D.H., et al., "The Inactivation of Dihydroxy-acid Dehydratase in *Escherichia coli* Treated with Hyperbaric Oxygen Occurs Because of the Destruction of Its Fe—S Cluster, but the Enzyme Remains in the Cell in a Form That Can Be Reactivated," J. Biol. Chem. 268(34):25547-25552, The American Society for Biochemistry and Molecular Biology, Inc., United States (1993).
Frodyma, M.E. and Downs, D., "ApbA, the Ketopantoate Reductive Enzyme *Salmonella typhimurium* is Required for the Synthesis of Thiamine via the Alternative Pyrimidine Biosynthetic Pathway," J. Biol. Chem. 273:5572-76, The American Society for Biochemistry and Molecular Biology, Inc., United States (1998).
Fujiki M. & Verner, K., "Coupling of Cytosolic Protein Synthesis and Mitochondrial protein Import in Yeast," J. Biol. Chem. 268(3): 1914-1920 (1993).
Garcia et al., "Fusel Alcohols Production in Beer Fermentation Processes," Process Biochemistry 29:303-309, Elsevier Applied Science, England (1994).
Geertmam, J-M.A., et al., "Physiological and genetic engineering of cytosolic redox metabolism in *Saccharomyces cerevisiae* for improved glycerol production," Metabolic Engineering 8:532-542, Elsevier Inc., United States (2006).
Genbank Entry showing Yocum's B. Subtilis PY79 Strain AlsS protein, entry history, and Sequence Comparison with SEQ ID No. 178, provided with Third Party Requester Comments After Patent Owner Response to Action Closing Prosecution, filed Feb. 28, 2014, Inter Partes Reexamination of U.S. Pat. No. 7,851,188, U.S. Control No. 95/001,857, filed Dec. 19, 2011.
Gerber, J., et al., "The Yeast Scaffold Proteins Isu1p and Isu2p Are Required Inside Mitochondria for Maturation of Cytosolic Fe/S Pro-

(56) References Cited

OTHER PUBLICATIONS teins," Molecular and Cellular Biology 24 (11): 4848-4857, American Society for Microbiology, United States (2004).

Getting Published in Nature: The Editorial Process, accessed at http://www.nature.com/nature/authors/get_published, accessed on Dec. 19, 2012.

Gevo Announces Successful Startup of World's First Commercial Biobased Isobutanol Plant, Gevo Investor Relations News Release, May 24, 2012, 2 pages, accessed at http://ir.gevo.com/phoenix.zhtml?c=238618&p=irol-newsArticle&ID=1699401&highlight=.

Gevo Investor Relations FAQs, Gevo, accessed at http://ir.gevo.com/phoenix.zhtml?c=238618&p=irol-faq on May 7, 2014.

Gevo Licenses UCLA Technology, Socialtech.com, Jan. 3, 2008, accessed at http://www.socialtech.com/gevo_licenses_ucla_technology/s-0012927.html.

Gevo Ramps Up Post-IPO: Executive Team Leads Next Round of Renewables, Chemical Week Oct. 3/10, 2011, IHS, Inc., accessed at http://www.gevo.com/wp-content/uploads/2011/10/044_cwk_101011_comp.pdf, accessed on Dec. 20, 2012.

Giudici, P., et al., "A biometric study of higher alcohol production in Saccharomyces cerevisiae," Can. J. Microbiol. 36:61-64, The National Research Council of Canada, Canada (1990).

Glassner, D.A., "Hydrocarbon Fuels from Plant Biomass" available at http://www1.eere.energy.gov/biomass/pdfs/Biomass_2009_Adv_Biofuels_II_Glassner.pdf (2009).

Glick, B.R., "Metabolic Load and Heterologous Gene Expression," Biotechnol. Adv. 13:247-261, Elsevier Science, Ltd., England (1995).

Goossens, et al., "Decreased diacetyl production in lager brewing yeast by integration of the ILV5 gene," Proceedings European Brewery Convention Congress, 1993, 251-258.

Gray, M.W., et al., "Mitoehondrial Evolution," Science 283:1476-1481, American Association for the Advancement of Science, United States (1999).

Gray, M.W., et al., "The origin and early evolution of mitochondria," Genome Biology 2(6): 1018.1-1018.5, BioMed Central Ltd., United Kingdom (2001).

Hackel, B.J., et al., "Production of Soluble and Active Transferring Receptor-Targeting Single-Chain Antibody Using Saccharomyces cerevisiae," Pharm. Res. 23:790-797, Springer Science+Business Media, Inc., United States (2006).

Hammond, J.R.M., "Brewer's Yeasts," in The Yeasts, vol. 5, 2nd Edition, Rose, A.H. and Harrison, J.S., eds., pp. 7-67, Academic Press, United States (1993).

Hammond, J.R.M., "Genetically-modified brewing yeasts for the 21st century. Progress to date," Yeast 11(16):1613-27, John Wiley & Sons Ltd, United States (1995).

Hansen, J. and Kielland-Brandt, "5 Brewer's yeast: genetic structure and targets for improvement," in Topics in Current Genetics, Chapter, 5, vol. 2, J.H. de Winde (Ed.): Functional Genetics of Industrial Yeasts, Springer-Verlag Berlin Heidelberg, Germany, pp. 143-170, (2003).

Hansen, J. and Kielland-Brandt, M.C., "Modification of biochemical pathways in industrial yeasts," J. Biotechnol. 49:1-12, Elsevier Science B.V., Netherlands (1996).

Harris et al., "Characterization of Recombinant Strains of the Clostridium acetobutylicum Butrate Kinase Inactivation Mutant: Need for New Phenomenological Models for Solventogenesis and Butanol Inhibition," Biotechnology and Bioengineering 67:1-11, John Wiley & Sons, Inc., 2000.

Herman, R.G., "Advances in catalytic synthesis and utilization of higher alcohols," Catalysis Today 55(3):233-245, Elsevier B.V., Netherlands (2000).

Herzig, S., et al., "Identification and Functional Expression of the Mitochondrial Pyruvate Carrier," Science 337:93-96, American Association for the Advancement of Science, United States (2012).

Highwater 10-K for fiscal year ended Oct. 31, 2013, dated Jan. 15, 2014.

Hohmann, S. and Cederberg, H., "Autoregulation may control the expression of yeast pyruvate decarboxylase structural genes PDC1 and PDC5," Eur. J. Biochem. 188(3):615-621, Federation of European Biochemical Societies, England (1990).

Holmberg, S. and Litske Petersen, J.G., "Regulation of isoleucine-valine biosynthesis in Saccharomyces cerevisiae," Curr. Genet. 13:207-217, Springer-Verlag, Germany (1988).

Homegrown for the Homeland: Ethanol Industry Outlook 2005, 20 Pages, Renewable Fuels Association, Washington, DC, United States (2005).

Hutson, S.M. and Rannels, S.L., "Characterization of a Mitochondrial Transport System for Branced Chain α-Keto Acids," J. Biol. Chem. 260(26):14189-14193, American Society of Biological Chemists, Inc., United States (1985).

Information on EC 1.1.1.86—ketol-acid reductoisomerase, accessed at http://www.brenda-enzymes.org/php/result_flat.php4?ecno=1.1.1.86, accessed on Dec. 16, 2013, 42 pages.

Information on EC 2.2.1.6—acetolactate synthase, accessed at http://www.brenda-enzymes.org/php/result_flat.php4?ecno=2.2.1.6, accessed on Dec. 16, 2013, 126 pages.

Information on EC 4.2.1.9—dihydroxy-acid dehydratase, accessed at http://www.brenda-enzymes.org/php/result_flat.php4?ecno=4.2.1.9, accessed on Dec. 16, 2013, 24 pages.

Ingraham, J.L., and Guymon, J.F., "The Formation of Higher Aliphatic Alcohols by Mutant Strains of Saccharomyces cerevisiae," Arch. Biochem. Biophys. 88:157-166, Academic Press, Inc., United States (1960).

Inoue, T., "Mechanism of Higher Alcohol Formation During Wort Fermentation by Brewer's Yeast," Rept. Res. Lab. Kirin Brewery Co. 18:13-16, The Research Laboratories of Kirin Brewery Co., Ltd., Japan (1975).

International Preliminary Report on Patentability of corresponding PCT/US2006/041602, mailed May 8, 2008.

International Search Report and Written Opinion of corresponding PCT/US2006/041602, mailed Apr. 11, 2007.

Ishige, T., et al., "Whole organism biocatalysis." Current Opinion in Chemical Biology 9:174-180, (2005) Elesevier, The Netherlands.

Japanese Patent Application No. JP 2000-041655 A, with unverified English language Translation.

Jayaraj, R. and Smooker, P.M., "So you Need a Protein A Guide to the Production of Recombinant Proteins," The Open Veterinary Science Journal 3:28-34 (2009).

Jessen, H., "Highwater Moves Forward with Corn Oil Technology Installation," Ethanol Producer Magazine Oct. 8, 2013, accessed at <a href="http://ethanolproducer.com/articles/10330/highwater-moves-forward-with-corn-oil-technology-installation" >http://ethanolproducer.com/articles/10330/highwater-moves-forward-with-corn-oil-technology-installation</a>.

Jones, D.T. and Woods, D.R., "Acetone-Butanol Fermentation Revisited," Microbiol. Rev. 50(4):484-524, American Society for Microbiology, United States (1986).

Kassow, A., Metabolic effects of deleting the region encoding the transit peptide in Saccharomyces cerevisiae ILV5, Thesis for the Cand. Scient. Degree at Institute of Genetics, Univeristy of Copenhagen, Department of Yeast Genetics, 48 pages, Denmark (1992).

Keasling, J.D. and Chou, H., "Metabolic engineering delivers next-generation biofuels," Nature Biotechnology 26(3):298-299, Nature Publishing Group, England (2008).

Kim, E-J, et al., "Expression of hepatitis B surface antigen S domain in recombinant Saccharomyces cerevisiae using GAL1 promoter," J. Biotechnol. 141:155-159, Elsevier B.V., Netherlands (2009).

Kispal, G., et al., "Mitochondrial and Cytosolic Branched-chain Amino Acid Transaminases from Yeast, Homologs of the myc Oncogene-regulated Eca39 Protein," J. Biol. Chem. 271(40):24458-24464, The American Society for Biochemistry and Molecular Biology, Inc., United States (1996).

Kohlhaw, G.B., "Leucine Biosynthesis in Fungi: Entering Metabolism through the Back Door," Microbiol. Mol. Biol. Rev. 67:1-15, American Society for Microbiology, United States (2003).

Kolkman, A., et al., "Comparative Proteome Analysis of Saccharomyces cerevisiae Grown in Chemostat Cultures Limited for Glucose or Ethanol," Mol. Cell. Proteom 4:1-11, The American Society for Biochemstry and Molecular Biology, Inc., United States (2005).

(56) References Cited

OTHER PUBLICATIONS

Kotula, L and Curtis, P.J., "Evaluation of Foreign Gene Codon Optimization in Yeast: Expression of a Mouse IG Kappa Chain," Nature Biotechnology 9:1386-1389, Nature Publishing Group, England (1991).

Kwiatkowski, J.R., et al., "Modeling the process and costs of fuel ethanol production by the corn dry-grind process," Industrial Crops and Products 23:288-296, Elsevier B.V., Netherlands (2006).

Lagier, M.J., et al., "Mitochondrial-type iron—sulfur cluster biosynthesis genes (IscS and IscU) in the apicomplexan Cryptosporidium parvum," Microbiology 149:3519-3530, SGM, England (2003).

Larroy, C., et al., "Characterization of the *Saccharomyces cerevisiae* YMR318C (ADH6) gene product as a broad specificity NADPH-dependent alcohol dehydrogenase: relevance in aldehyde reduction," Biochem J. 361:163-172, Biochemical Society, Great Britain, 2002.

Larroy, C., et al., "Properties and Functional Significance of *Saccharomyces cerevisiae* ADHVL," Chemico-Biological Interactions 143-144:229-238, Elesevier, The Netherlands, 2003.

Lee et al., Metabolic Engineering, first ed., Marcel Dekker, New York, NY, p. 292, United States (1999).

Lee, W., et al., "Application of sequential integration for metabolic engineering of 1,2-propanediol production in yeast," Metabolic Engineering 8:58-65, Elsevier, Inc., United States (2006).

Lehninger Principles of Biochemistry, 3rd ed., David L. Nelson and Michael M. Cox, Eds., Worth Publishers, New York, NY, pp. 293-294, 2000.

Lill, R. and Muhlenhoff, U., "Iron—sulfur-protein biogenesis in eukaryotes," TRENDS in Biochemical Sciences 30(3):133-141, Elsevier Ltd., England (2005).

Llopis, J., et al., "Measurement of cytosolic, mitochondrial, and Golgi pH in single lving cells with green flourescent proteins," Proc. Natl. Acad Sci. USA 95:6803-6808, The National Academy of Sciences, United States (1998).

Magee, P.T. and De Robichon-Szulmajster, H., "The Regulation of Isoleucine-Valine Biosynthesis in *Saccharomyces cerevisiae*," European J. Biochem. FEBS 3:507-511, Federation of European Biochemical Societies, Germany (1968).

Magliano, P., et al., "Contributes of the peroxisome and β-oxidation cycle to biotin synthesis in fungi," J. Biol. Chem. 286:42133-42140, American Society for Biochemistry and Molecular Biology, United States (2011).

Marobbio, C.M.T., et al., "α-Isopropylmalate, a Leucine biosynthesis Intermediate in Yeast , is Transported by the Mitochondrial Oxalacetate Carrier," J. Biol. Chem. 283(42):28445-28453, The American Society for Biochemistry and Molecular Biology, Inc., United States (2008).

Marquet, A., et al., "Biosynthesis of biotin and lipoic acid," Vitam. Horm. 61:51-101, Academic Press, United States (2001).

Martin, V.J.J., et al., "Engineering a mevalonate pathway in *Escherichia coli* for production of terpenoids," Nature Biotechnology 21(7):796-802, Nature Publishing Group, England (2003).

Matak-Vinkovic, D., et al., "Crystal Structure of *Escherichia coli* Ketopantoate Reductase at 1.7 Å resolution and Insight into the Enzyme Mechanism," Biochemistry 40:14493-14500, American Chemical Society, United States, 2001.

Matsuda, F., et al., "Construction of an Artificial Pathway for Isobutanol Biosynthesis in the Cytosol of *Saccharomyces cerevisiae*," Biosci. Biotechnol. Biochem. 76(11):2139-2141, Japan Society for Bioscience, Biotechnology, and Agrochemistry, Japan (2012).

McCourt, J.A., et al., "Facile crystallization of *Eshcerichia coli* ketol-acid reductoisomerase," Acta Crystallographica D60:1432-1434, International Union of Crystallography by Munksgaard, United States (2004).

Meinhold, P., et al., "Direct Conversion of Ethane to Ethanol by Engineered Cytochrome P450 BM3," ChemBioChem 6:1765-1768, Wiley-VCH Verlag GmbH & Co. KGaA, Germany (2005).

Memorandum Opinion of District Judge Robinson, in *ButamaxTM Advanced Biofuels LLC* vs. *Gevo, Inc.*, Case 1:11-cv-00054-SLR, United States Court for the District of Delaware, dated Jun. 19, 2012; 26 pages.

Memorandum Opinion of District Judge Robinson, in *ButamaxTM Advanced Biofuels LLC* vs. *Gevo, Inc.*, Case 1:11-cv-00054-SLR, United States District Court for the District of Delaware, filed Mar. 19, 2013; 57 pages.

Memorandum Opinion of District Judge Robinson, in *Gevo, Inc.* vs. *ButamaxTM Advanced Biofuels LLC and E.I. Dupont De Nemours and Company*, Case 1:13-cv-00576-SLR, United States District Court for the District of Delaware, filed Jul. 26, 2013; 46 pages.

Minahan, D.M., et al., "Synthesis of Fuel Alcohols and MTBE form Syngas Using Spinel Oxide Based Catalysts," Preprints Div. Fuel Chem. ACS 42(2):715-719, American Chemical Society, United States (1997).

Moller, K., et al., "Pyruvate decarboxylases from the petite-negative yeast *Saccharomyces kluyveri*," Mol. Genet. Genomics 270(6):588-568, Springer-Verlag, Germany (2004).

Natural Gas Weekly Update for Week Ending Jun. 27, 2012, Release Date Jun. 28, 2012, U.S. Energy Information Administration, 10 pages, accessed at http://205.254.135.7/naturalgas/weekly.

Norbeck et al., "Metabolic and regulatory changes associated with growth of *Saccharomyces cerevisiae* in 1.4 M NaCl Evidence for osmotic induction of gylcerol dissimilation via the dihydroxyacetone pathway," J Biol Chem. 272(9):5544-54, American Society for Biochemistry and Molecular Biology, United States (1997).

Occurance of higher alcohols, in Aroma of Beer, Wine and Distilled Alcoholic Beverages, Nykanen, L. Ed., pp. 22-25, Akademie-Verlag, Berlin, Germany.

Office Action in Inter Partes Reexamination of U.S. Pat. No. 7,851,188 mailed Mar. 5, 2012, U.S. Control No. 95/001,857, filed Dec. 19, 2011.

Office Action in Inter Partes Reexamination of U.S. Pat. No. 7,993,889, mailed Jan. 22, 2013, U.S. Control No. 90/012,503, filed Sep. 12, 2012.

Office Action in Inter Partes Reexamination of U.S. Pat. No. 7,993,889, mailed Jun. 12, 2015, U.S. Control No. 95/001,735, filed Sep. 1, 2011.

Office Action in Inter Partes Reexamination of U.S. Pat. No. 7,993,889 mailed Nov. 25, 2011, U.S. Control No. 95/001,735, filed Sep. 1, 2011.

Office Action in Inter Partes Reexamination of U.S. Pat. No. 7,993,889 mailed Sep. 4, 2014, U.S. Control No. 95/001,735, filed Sep. 1, 2011.

Office Action mailed on Aug. 15, 2014 in U.S. Appl. No. 13/539,125, inventors Donaldson et al., filed Jun. 29, 2012.

Office Action mailed Sep. 21, 2012 in Inter Partes Reexamination of U.S. Pat. No. 8,178,328, filed Jun. 21, 2012, U.S. Control No. 95/001,998.

Olson, E.S., et al., "Higher-alcohols biorefinery: Improvement of catalyst for ethanol conversion," Appl. Biochem. Biotechnol. 113-116:913-932, Humana Press, United States (2004).

Omura, F., "Targeting of mitochondrial *Saccharomyces cerevisiae* ILv5p to the cytosol and its effect on vicinal diketone formation in brewing," Appl. Microbiol. Biotecnol. 78:503-513, Springer-Verlag, Germany (2008).

Opposition to Petition of Patent Owner Under 37 CFR §§1.181 and/or 1.183 to Vacate the Order Granting Second Reexamination Request, mailed Apr. 2, 2012, U.S. Control No. 95/001,857, filed Dec. 19, 2011.

Order Denying Request, mailed Oct. 27, 2011, U.S. Control No. 95/001,718, filed Aug. 18, 2011.

Order Granting Request for Inter Partes Reexamination of U.S. Pat. No. 7,851,188, mailed Mar. 5, 2012, U.S. Control No. 95/001,857, filed Dec. 19, 2011.

Order Granting Request for Inter Partes Reexamination of U.S. Pat. No. 7,993,889, mailed Nov. 25, 2011, U.S. Control No. 95/001,735, filed Sep. 1, 2011.

Order Granting Request for Inter Partes Reexamination of U.S. Pat. No. 8,178,328, filed Jun. 21, 2012, U.S. Control No. 95/001,998.

(56) References Cited

OTHER PUBLICATIONS

Order of District Judge Robinson, in *Butamax™ Advanced Biofuels LLC* vs. *Gevo, Inc.*, Case 1:11-cv-00054-SLR, United States District Court for the District of Delaware, filed Mar. 19, 2013; 2 pages.
Oshita et al., "Clarification of the relationship between fusel alcohol formation and amino acid assimilation by brewing yeast using 13C-labeled amino acid," Proceedings of the European Brewery Convention Congress, pp. 387-394 (1995).
Ottenhoff, H.H., et al., "Organisation of the pantothenate (vitamin B5) biosynthesis pathway in higher plants," Plant J. 37:61-72, Blackwell Scientific Publishers, England (2004).
Outten, C.E. and Culotta, V.C., "Alternative Start Sites in the *Saccharomyces cerevisiae* GLR1 Gene Are Responsible for Mitchondrial and Cytosolic Isoforms of Glutahione Reductase," J. Biol. Chem. 279(9):7785-7791, The American Society for Biochemistry and Molecular Biology, Inc., United States (2004).
Palomares, L.A., et al., "Production of Recombinant Proteins: Challenges and Solutions," Methods in Molecular Biology 267:15-52, Humana Press Inc., United Staes (2004).
Pang, S.S., et al., "The Crystal Structures of Klebsiella pneumoniae Acetolactate Synthase with Enzyme-bound Cofactor and with an Unusual Intermediate," J. Biol. Chem. 279(3):2242-2253, American Society for Biochemistry and Molecular Biology, Inc., United States (2004).
Patent Owner Declaration of Larry C. Anthony, filed Jun. 5, 2012 in Reexamination of U.S. Pat. No. 7,851,188, U.S. Control No. 95/001,857, filed Dec. 19, 2011.
Patent Owner Declaration of Professor Klibanov, filed Feb. 24, 2012, U.S. Control No. 95/001,735, filed Sep. 1, 2011.
Patent Owner Declaration of Professor Klibanov, filed Jun. 5, 2012 in Re-examination of U.S. Pat. No. 7,851,188, U.S. Control No. 95/001,857, filed Dec. 19, 2011.
Patent Owner Response filed Jun. 6, 2012 in Inter Partes Reexamination of U.S. Pat. No. 7,851,188, U.S. Control. No. 95/001,857, filed Dec. 19, 2011.
Patent Owner Response to Action Closing Prosecution filed May 19, 2014 in Inter Partes Reexamination of U.S. Pat. No. 8,178,328, U.S. Control No. 95/001,998, filed Jun. 21, 2012.
Patent Owner Response to Action Closing Prosecution filed Nov. 20, 2013 in Inter Partes Reexamination of U.S. Pat. No. 7,851,188, U.S. Control. No. 95/001,857, filed Dec. 19, 2011.
Patent Owner Response to Office Action filed Nov. 4, 2014 in Inter Partes Reexamination of U.S. Pat. No. 7,993,889, U.S. Control No. 95/001,735, filed Sep. 1, 2011.
Peng, H.L., et al., "Cloning, sequencing and heterolgous expression of a Klebisella penumoniae gene encoding an FAD-independent acetolactate synthase," Gene 117(1):125-130, Elesevier Science Publishers B.V., Netherlands, 1992.
Petersen, J.G.L., et al., "The JLV5 gene of *Saccharomyces cerevisiae* is highly expressed," Nucl. Acids Res. 14:9631-9651, IRL Press Limited, England, 1986.
Petition Denial Under 37 CFR 1.181 mailed Mar. 5, 2012, U.S. Control No. 95/001,718, filed Aug. 18, 2011.
Petition of Patent Owner to Seek Supervisory Review of Dismissal of Petition to Vacate the Order Granting Third Party Requester's Second Reexamination Request, filed Jun. 11, 2012, in Reexamination of U.S. Pat. No. 7,851,188, U.S. Control No. 95/001,857, filed Dec. 19, 2011.
Petition of Patent Owner Under 37 CFR §§1.181 and/or 1.183 to Vacate the Order Granting Second Reexamination Request, mailed Mar. 19, 2012, U.S. Control No. 95/001,857, filed Dec. 19, 2011.
Petition under 37 C.F.R. 1.927, filed Nov. 28, 2011, U.S. Control No. 95/001,718, filed Aug. 18, 2011.
Pirkov, I., et al., "Ethylene production by metabolic engineering of the yeast *Saccharomyces cerevisiae*," Metabolic Engineering 10:276-280, Elsevier, Inc., United States (2008).
Plaintiff's Opening Brief in Support of its Motion for a Preliminary Injunction (Reduced Version) filed on Sep. 30, 2011 in the United States District Court for the District of Delaware, Case 1:11-cv-00054-SRL-MPT.

Polaina, J., "Cloning of the IIV2, ILV3, and ILV5 Genes of *Saccharomyces cerevisiae*," Carlsberg Res. Commun. 49:577-584. Springer-Verlag, Germany (1984).
Popuri, S.S.S. and Bata, R.M., "A Performance Study of Iso-Butanol-, Methanol-, and Ethanol-Gasoline Blends Using a Single Cylinder Engine," Truck Alternative Fuels and Exhaust Gas Emission, SP-1001, 932953, pp. 41-60, The Society of Automotive Engineers, Inc., United States (1993).
Presecan, E., "The Bacillus subtilis genome from gerBC (311°) to licR (334°)," Microbiology 143:3313-3328, SGM, England (1997).
Pretorius, I.S., et al., "Designer Yeasts for the Fermentation Industry of the 21st Century," Food Technol. Biotechnol 41(1):3-10, Journal of the Faculty of Food Technology and Biotechnology, Croatia (2003).
Pronk, J.T., et al., "Pyruvate Metabolism in *Saccharomyces cerevisia*," Yeast 12:1607-1633, John Wiley Sons, Ltd., United States (1996).
Raab, A.M., et al., "Metabolic engineering of *Saccharomyces cerevisiae* for the biotechonological production of succinic acid," Metabolic Engineering 12:518-525, Elsevier Inc., United States (2010).
Radmacher, E., et al., "Linking Central Metabolism with Increased Pathway Flux: L-Valine Accumulation by Corynebacterium glutamicum," App Environ. Micro. 68:2246-2250, American Society for Microbiology, United States, 2002.
Rai, M. and Padh, H., "Expression systems for production of heterologous proteins," Current Science 80(9):1121-1128, Academy of Sciences, United States (2001).
Rainbow, C., in The Yeasts, vol. 5, Rose, A.H. and Harrison, J.S., eds., pp. 190-199, Academic Press, United States (1970).
Reazin, G., et al., "Mechanism of Major Congener in Alcoholic Grain Fermentations," J. Agr. Food Chem. 18(4):585-589, American Chemical Society, United States (1970).
Reexamination Terminated, mailed May 23, 2012, U.S. Control No. 95/001,718, filed Aug. 18, 2011.
Renna, M.C., et al., "Regulation of the Bacillus subtilis alsS, alsD, and alsRGenes Involved in Post-Exponential-Phase Production of Acetoin," J. Bacteriology 175:3863-3875, American Society for Microbiology, United States, 1993.
Request for Ex Parte Reexamination of U.S. Pat. No. 7,993,889 with Exhibits, U.S. Control No. 90/012,503, filed Sep. 12, 2012.
Request for Inter Partes Reexamination of U.S. Pat. No. 7,993,889 filed Sep. 1, 2011, U.S. Control No. 95/001,735, filed on Sep. 1, 2011.
Request for Re-examination of U.S. Pat. No. 8,178,328, U.S. Control No. 95/001,998, filed May 25, 2012.
Requester's Opposition Petition to Return or Expunge Patent Owner's Petition, filed Jun. 20, 2012, in Reexamination of U.S. Pat. No. 7,851,188, U.S. Control No. 95/001,857, filed Dec. 19, 2011.
Researchers Boost Isobutanol Production in Yeast, published Jul. 28, 2011, available at http://www.greencarcongress.com/2011/07/tud-20110728.html.
Researchers Significantly Boost Yield of Isobutanol from Engineered Yeast Using New Synthesis Pathway Located in the Cytosol, published Nov. 6, 2012, available at http://www.greencarcongress.com/2012/11/boles-20121106.html.
Response filed Feb. 24, 2012 in Inter Partes Reexamination of U.S. Pat. No. 7,993,889, U.S. Control No. 95/001,735, filed Sep. 1, 2011.
Response filed Feb. 27, 2012 in Inter Partes Reexamination of U.S. Patent No. 7,993,889, U.S. Control No. 95/001,735, filed Sep. 1, 2011.
Response to Inter Partes Reexamination Office Action filed Dec. 21, 2012, in Inter Partes Reexamination of U.S. Pat. No. 8,178,328, filed Jun. 21, 2012, U.S. Control No. 95/001,998.
Right of Appeal Notice, mailed Feb. 26, 2015, in Inter Partes Reexamination of U.S. Pat. No. 8,178,328, U.S. Control No. 95/001,998, filed Jun. 21, 2012.
Right of Appeal Notice, mailed May 11, 2015 in Inter Partes Reexamination of U.S. Pat. No. 7,851,188, U.S. Control No. 95/001,857, filed Dec. 19, 2011.
Ro, D-K., et al., "Production of the antimalarial drug precursor artemisinic acid in engineered yeast," Nature 440:940-943, Nature Publishing Group, England (2006).

(56) References Cited

OTHER PUBLICATIONS

Rosenfield, E. and Beauvoit, B., "Role of the non-respiratory pathways in the utilization of molecular oxygen by *Saccharomyces cerevisiae*," Yeast 20:1115-1144, John Wiley & Sons, Inc., United States, 2003.
Ryan, E.D. and Kohlhaw, G.B., "Subcellular Localization of Isoleucine-Valine Biosynthetic Enzymes in Yeast," J. Bacteriol. 120(2):631-637, American Society for Microbiology, United States (1974).
Sanchez, A.M., et al., "Efficient Succinic Acid Production form Glucose through Overexpression of Pyruvate Carboxylase in an *Escherichia coli* Alcohol Dehydrogenase and Lactate Dehydrogenase Mutant," Biotechnol. Prog. 21:358-365, American Chemical Society and American Institute of Chemical Engineers, United States (2005).
Sarthy, A.V., et al., "Expression of the *Eshecrichia coli* Xylose Isomerase Gene in *Saccharomyces cerevisiae*," Appl. Environ. Microbiol. 53(9):1996-2000, American Society for Microbiology, United States (1987).
Sauer, M., et al., "Production of L-Ascorbic Acid by Metabolically Engineered *Saccharomyces cerevisiae* and Zygosaccharomyces bailil," Applied and Environ. Microbiol. 70(10):6086-6091, American Society for Microbiology, United States (2004).
Savrasova, E.A., et al., "Use of the valine biosynthetic pathway to convert glucose into isobutanol," J. Ind. Microbiol. Biotechnol. 38:1287-1294, Springer, Germany (2011).
Schreier, H.J., et al., "Heterologous expression in the Archaea: transcription from Pyrococcus furiosus gdh and mlrA promoters in Haloferax volcanii," Extremophiles 3:11-19, Springer-Verlag, Germany (1999).
Schulthess, D. and Ettlinger, L., "Influence of the Concentration of Branched Chain Amino Acids on the Formation of Fusel Alcohols," J. Inst. Brew. 84:240-243, W. Reffer & Sons, Ltd, England (1978).
Schwartz, D., "AIM Interview: Sapphire Energy's Tim Zenk," Algae Industry Magazine (2010), 11 Pages, accessed at http://www.algaeindustrymagazine.com/tim-zenk/ on May 15, 2014.
Screen capture of http://enzyme.expasy.org/EC/2.2.1.6, the ExPASy Bioformatics Resource Portal Enzyme Nomenclature Database for EC No. 2.2.1.6, ExPASy Proteomics Server [retrieved on Aug. 16, 2011].
Screen capture of http://www.chem.qmul.ac.uk/iubmb/enzyme/EC2/2/1/6.html, the IUBMB Enzyme Nomenclature Database for EC No. 2.2.1.6, [retrieved on Aug. 29, 2011].
Second Request for Reexamination of U.S. Pat. No. 7,851,188, U.S. Control No. 95/001,857, filed Dec. 19, 2011.
Seffernick, J.L., et al., "Melamine Deaminase and Atrazine Chlorohydrolase: 98 Percent Identical But Functionally Different," Journal of Bacteriology 183(8):2405-2410, American Society for Microbiology, United States (2001).
Sen, S., et al., "Developments in Directed Evolution for Improving Enzyme Functions," Appl Biochemistry Biotechnology 143(3):212-223, Humana Press, United States (2007).
Sequence Alignment SEQ ID No. 2 vs Peng's Accession No. P27696, provided with Third Party Requester Comments After Patent Owner Response to Non-Final Office Action, filed Jul. 5, 2012, Inter Partes Reexamination of U.S. Pat. No. 7,851,188, U.S. Control No. 95/001,857, filed Dec. 19, 2011.
Sheldon-Coulson, G.A., "Production of Levulinic Acid in Urban Biorefineries," M.S. Thesis., Sep. 12, 2011, 84 pp., Massachusetts Institute of Technology, United States.
Singer, E., "A Better Biofuel: A California biotech company is engineering microbes to produce cheap biofuels that could outcompete ethanol," MIT Technology Review, Apr. 3, 2007, 2 Pages, accessed at http://www.technologyreview.com/news/407629/a-better-biofuel/ on May 19, 2014.
Smit, Ph.D. Thesis, Wageningen Universiteit (Wageningen, The Netherlands), Formation of Amino Acid Derived Cheese Flavour Compounds, orally defended on Apr. 23, 2004, cataloged into the U.S.D.A. National Agricultural Library system on Oct. 3, 2004.

Stephanopolous Deposition Testimony Transcript, pp. 258-265, *Butamax™ Advanced Biofuels LLC* v. *Gevo, Inc.*, Case 11-054-SLR-MPT, U.S. District Court for the District of Delaware, Nov. 19, 2012.
Stephanopolous, G.A. et al., in Metabolic Engineering Principles and Methodologies, pp. 1-15 and 26-37, Academic Press, United States (1998).
Stephanopoulos Preliminary Injunction Hearing Transcript, pp. 114-117, *Butamax™ Advanced Biofuels LLC* v. *Gevo, Inc.*, Case 11-054-SLR-MPT, U.S. District Court for the District of Delaware, Mar. 1, 2012.
Strain, J., et al., "Suppressors of Superoxide Dismutase (SOD1) Deficiency in *Saccharomyces cerevisiae*," The Journal of Biological Chemistry 273(47):31138-31144, The American Society for Biochemistry, and Molecular Biology, Inc., United States (1998).
Streit, W.R. and Entcheva, P., "Biotin in microbes, the genes involved in its biosynthesis, its biochemical role and perspectives for biotechnological production," Appl. Microbiol. Biotechnol. 61:21-31, Springer Verlag, Germany (2003).
Strive to Become a Company 'Growing for Good', accessed at http://www.suntory.com/president/index.html on Nov. 15, 2003, Suntory Holdings Limited.
Swiegers, J.H., et al., "The development of yeast strains as tools for adjusting the flavor of fermented beverages to market specifications," Chapter 1, D. Havkin-Frenkel & F.C. Belanger (Eds.): Biotechnology in Flavor Production, 1-55, Blackwell Publishing Ltd, Oxford, United Kingdom (2008).
Ter Schure, E.G., et al., "Pyruvate Decarboxylase Catalyzes Decarboxylation of Branched-Chain 2-Oxo Acids But Is Not Essential for Fusel Alcohol Production by *Saccharomyces cerevisiae*," Appl. Environ. Microbiol. 64(4):1303-1307, American Society for Microbiology, United States (1998).
The Presidential Green Chemistry Challenge Awards Program: Summary of 2010 Award Entries and Recipients, United States Environmental Protection Agency, 58 pages.
Third Party Declaration of Dr. Glassner, filed Jul. 5, 2012, U.S. Control. No. 95/001,857, filed Dec. 19, 2011.
Third Party Requester Comments After Non-Final Office Action, filed Mar. 26, 2012 in Inter Partes Reexamination of U.S. Pat. No. 7,993,889, U.S. Control No. 95/001,735, filed Sep. 1, 2011.
Third Party Requester Comments After Non-Final Office Action, filed Sep. 4, 2013 in Inter Partes Reexamination of U.S. Pat. No. 8,178,328, filed Jun. 21, 2012, U.S. Control No. 95/001,998.
Third Party Requester Comments After Patent Owner Response to Non-Final Office Action, filed Jul. 5, 2012, Inter Partes Reexamination of U.S. Pat. No. 7,851,188, U.S. Control No. 95/001,857, filed Dec. 19, 2011.
Third Party Requester Comments, filed Mar. 6, 2015 in Inter Partes Reexamination of U.S. Pat. No. 7,993,889, U.S. Control No. 95/001,735, filed Sep. 1, 2011.
Third Party Requester Comments to Patent Owner's Response to Action Closing Prosecution, filed Feb. 28, 2014 in Inter Partes Reexamination of U.S. Pat. No. 7,851,188, U.S. Control No. 95/001,857, filed Dec. 19, 2011.
Third Party Requester Comments to Patent Owner's Response to Action Closing Prosecution, filed Sep. 17, 2014 in Inter Partes Reexamination of U.S. Pat. No. 8,178,328, U.S. Control No. 95/001,998, filed Jun. 21, 2012.
Third Party Requester Declaration of Dr. Porter After Non-Final Office Action, filed Mar. 26, 2012, U.S. Control No. 95/001,735, filed Sep. 1, 2011.
Third Party Requester Declaration of Dr. Stephanopoulos After Non-Final Office Action, filed Mar. 26, 2012, U.S. Control No. 95/001,735, filed Sep. 1, 2011.
Third Party Requester Declaration of Dr. Stephanopoulos, filed Jul. 5, 2012, U.S. Control No. 95/001,857, filed Dec. 19, 2011.
Third Party Requester Declaration of Dr. Stephanopoulos, filed May 25, 2012, U.S. Control No. 95/001,998, filed May 25, 2012.
Third Party Requester Declaration of Dr. Stephanopoulos, filed Nov. 28, 2011, U.S. Control No. 95/001,718, filed Aug. 18, 2011.
Toivari, M.H., et al., "Enhancing the flux of D-Glucose to the pentose phosphate pathway in *Saccharomyces cerevisiae* for the production of D-Ribose and ribitol," Appl Microbiol Biotechnol 85:731-739, Springer-Verlag, Germany (2010).

(56) References Cited

OTHER PUBLICATIONS

Top Value Added Chemicals from Biomass: vol. 1—Results of Screening for Potential Candidates from Sugars and Synthesis Gas, U.S. Department of Energy—Energy Efficiency and Renewable Energy, Eds., Werpy, T. and Petersen, G., 76 Pages, National Renewable Energy Laboratory, United States (2004).
Trinh, C.T., et al., "Redesigning *Escherichia coli* Metabolism for Anaerobic Production of Isobutanol," Appl. Env. Microbiol. 77:4894-904, American Society for Microbiology, United States (2011).
UCLA Professor Joins Gevo Scientific Advisory Board, Dec. 31, 2007, accessed at http://ir.gevo.com/phoenix.zhtml?c=238618&p=irol-newsArticle&ID=1491592&highlight=.
Ullmann's Encyclopedia of Industrial Chemistry, 6th Edition, 5:716-719, 2003.
Underwood, R.P., et al., "Development of Alternative Fuels from Coal-Derived Syngas," pp. 65-85, Air Products & Chemicals, Inc., United States (1991).
United States Court of Appeals for the Federal Circuit Decision, Case No. 11-CV-0054-SLR; Appeal from United States District Court for the District of Delaware, Nov. 16, 2012.
U.S. Appl. No. 60/900,477, Liao et al., filed Feb. 9, 2007.
U.S. Appl. No. 60/900,546, Liao et al., filed Feb. 9, 2007.
U.S. Appl. No. 61/016,483, Feldman et al., filed Dec. 23, 2007.
Vai, M., et al., "Improved Secretion of Native Human Insulin-Like Growth Factor 1 from gas1 Mutant *Saccharomyces cerevisiae* Cells," Applied and Enviro Microbiol 66(12):5477-5479, American Society for Microbiology, United States (2000).
Van Bergen, B., "Diacetyl: identification and characterisation of molecular mechanisms for reduction in yeeast and their application in a novel enzyme based assay for quantification in fermentation systems," Ph.D. Thesis, McGill University, Montreal, Canada (2006).
Van Maris, A.J.A., et al., "Directed Evolution of Pyruvate Decarboxylase-Negative *Saccharomyces cerevisiae*, Yielding a C2-Independent, Glucose-Tolerant, and Pyruvate-Hyperproducing Yeast," Appl. Environ. Microbiol. 70(1):159-166, American Society, for Microbiology, United States (2004).
Velasco, J.A., et al., "Cloning of the dihydroxyacid dehydratase-encoding gene (ILV3) from *Saccharomyces cerevisiae*," Gene 137:179-185, Elsevier Sciense B.V., Netherlands (1993).
Vellanki, R.N., et al., "Expression of hepatitis B surface antigen in *Saccharomyces cerevisiae* utilizing glyceraldeyhyde-3-phosphate dehydrogenase promoter of *Pichia pastoris*," Biotechnol. Lett. 29:313-318, Springer Science+Business Media B.V., United States (2007).
Villa, K.D. and Lee, S., "Control of Vicinal Diketone Production by Brewer's Yeast. I. Effects of ILV5 and ILV3 Gene Amplification on Vicinal Diketone Production and ILV Enzyme Activity," ASBCA Journal 53(2):49-53, American Society of Brewing Chemists, Inc., United States (1995).
Villanueba, K.D., et al., "Subthreshold Vicinal Diketome Levels in Lager Brewing Yeast Fermentations by Means of ILV5 Gene Amplifications," ASBCA Journal 48:(3):111-114, American Society of Brewing Chemists, Inc., United States (1990).
Vuralhan, Z. et al., "Physiological Characterization of the ARO10-Dependent, Broad-Substrate-Specificity 2-Oxo Acid Decarboxylase Activity of *Saccharomyces cerevisiae*," Appl. Envrion. Microbiol. 71(6):3276-3284, American Society for Microbiology, United States (2005).
Walker, G.M., "Yeast Technology," in Yeast Physiology and Biotechnology, John Wiley & Sons, Ltd, Chichester, England, pp. 265-320 (1998).
Watanabe et al., "Mutants of bakers' yeasts producing a large amount of isobutyl alcohol or isoamyl alcohol, flavour components of bread," Applied Microbiology and Biotechnology 34:154-159, Springer-Verlag, Germany (1990).
Webb, A.D. and Ingraham, J.L., "Fusel Oil" in Advances in Appl. Microbiol., vol. 5, pp. 317-353, Academic Press Inc., England (1963).
Who Shall Dare: Biobutanol and the intrepid ethanol producer, Biofuelsdiges.com, Jun. 22, 2012, Biofuels Digest, United States, accessed at http://biofuelsdigest.com/bdigest/2012/06/22/who-shall-dare-biobutanol-and-the-intrepid-ethanol-producer/.
Wynn, R.M., et al., "Chaperonins groEL and groES promote assembly of heterotetramers (alpha 2 beta 2) of mammalian mitochondrial branched-chain alpha-keto acid decarboxylase in *Escherichia coli*," J. Biol. Chem. 267(18):12400-3, American Society for Biochemistry and Molecular Biology , United States (Jun. 1992).
Xu, G., et al., "Reconstruction of cytosolic fumaric acid biosynthesis pathways in *Saccharomyces cerevisiae*," Microbiol Cell Factories 11:24, pp. 1-10, BioMed Central Ltd, England (2012).
Yoshimoto et al., "Genetic and physiological analysis of branched-chain alcohols and isoamyl acetate production in *Saccharomyces cervisiae*," Applied Microbiology and Biotechnology 59: 501-508 (2002).
Yoshimoto, H., et al., "Pyruvate Decarboxylase Encoded by the PDC1 Gene Contributes, at Least partially, to the Decarboxylation of α-Ketoisocaporate for Isoamyl Alcohol Formation in *Saccharomyces cerevisiae*," J. Biosci. Bioengineering 92:(1):83-85, Elsevier, Japan (2001).
Yoshizawa et al., "The Formation of Higher Alcohols in the Fermentation of Amino Acids by Yeast. The Formation of Isobutanol and Isoamyl Alcohol from Pyruvic Acid by Washed Yeats Cells," Agricultural and Biological Chemistry 29:672-677, Agricultural Chemical Society of Japan, Japan (1965).
Zaworksi, F., ed., "US Oxo-alcohols sinking lower," ICISpricing Oxo-Alcohols, Jun. 22, 2012, 2 pages, Reed Business Information Limited, England.
Zelle, R.M., et al., "Malic Acid Production by *Saccharomyces cerevisiae*: Engineering of Pyruvate Carboxylation, Oxaloacetate Reduction, and Malate Export," Applied Environ. Microbiol. 74(9):2766-2777, American Society for Microbiology, United States (2009).
Zhang, B., et al., "Engineering the Monomer Composition of Polyhyroxyalkanoates Synthesized in *Saccharomyces cerevisiae*," Applied Environ. Microbiol. 72(1):536-543, American Society for Microbiology, United States (2006).

\* cited by examiner

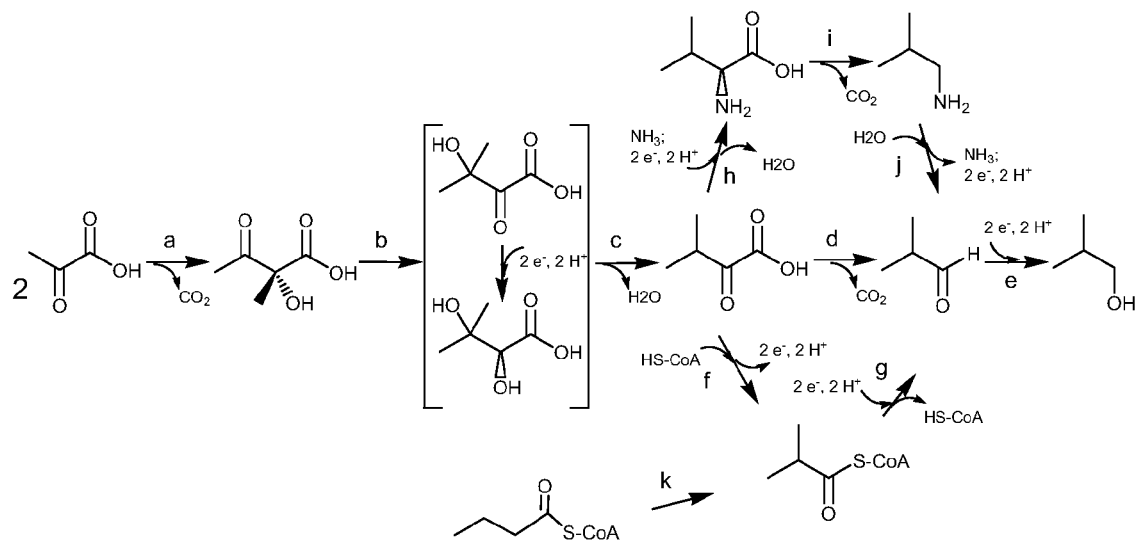

SEQUENCE LISTING

<160> NUMBER OF SEQ ID NOS: 267

<210> SEQ ID NO 1
<211> LENGTH: 1680
<212> TYPE: DNA
<213> ORGANISM: K. pneumoniae

<400> SEQUENCE: 1

```
atggacaaac agtatccggt acgccagtgg gcgcacggcg ccgatctcgt cgtcagtcag      60
ctggaagctc agggagtacg ccaggtgttc ggcatcccg gcgccaaaat cgacaaggtc     120
tttgattcac tgctggattc ctccattcgc attattccgg tacgccacga agccaacgcc     180
gcatttatgg ccgccgccgt cggacgcatt accggcaaag cgggcgtggc gctggtcacc     240
tccggtccgg gctgttccaa cctgatcacc ggcatggcca ccgcgaacag cgaaggcgac     300
ccggtggtgg ccctgggcgg cgcggtaaaa cgcgccgata aagcgaagca ggtccaccag     360
agtatggata cggtggcgat gttcagcccg gtcaccaaat acgccatcga ggtgacggcg     420
ccggatgcgc tggcggaagt ggtctccaac gccttccgcg ccgccgagca gggccggccg     480
ggcagcgcgt tcgttagcct gccgcaggat gtggtcgatg gccggtcag cggcaaagtg     540 ctgccggcca gcgggggccc gcagatgggc gccgcgccgg atgatgccat cgaccaggtg     600
```

-continued

```
gcgaagctta tcgcccaggc gaagaacccg atcttcctgc tcggcctgat ggccagccag    660
ccggaaaaca gcaaggcgct gcgccgtttg ctggagacca gccatattcc agtcaccagc    720
acctatcagg ccgccggagc ggtgaatcag gataacttct ctcgcttcgc cggccgggtt    780
gggctgttta caaccaggc cggggaccgt ctgctgcagc tcgccgacct ggtgatctgc    840
atcggctaca gcccggtgga atacgaaccg gcgatgtgga acagcggcaa cgcgacgctg    900
gtgcacatcg acgtgctgcc cgcctatgaa gagcgcaact acaccccgga tgtcgagctg    960
gtgggcgata tcgccggcac tctcaacaag ctggcgcaaa atatcgatca tcggctggtg   1020
ctctccccgc aggcggcgga gatcctccgc gaccgccagc accagcgcga gctgctggac   1080
cgccgcggcg cgcagctcaa ccagtttgcc ctgcatcccc tgcgcatcgt tcgcgccatg   1140
caggatatcg tcaacagcga cgtcacgttg accgtggaca tgggcagctt ccatatctgg   1200
attgcccgct acctgtacac gttccgcgcc cgtcaggtga tgatctccaa cggccagcag   1260
accatgggcg tcgccctgcc ctgggctatc ggcgcctggc tggtcaatcc tgagcgcaaa   1320
gtggtctccg tctccggcga cggcggcttc ctgcagtcga gcatggagct ggagaccgcc   1380
gtccgcctga agccaacgt gctgcatctt atctgggtcg ataacggcta caacatggtc   1440
gctatccagg aagagaaaaa atatcagcgc ctgtccggcg tcgagtttgg gccgatggat   1500
tttaaagcct atgccgaatc cttcggcgcg aaagggtttg ccgtggaaag cgccgaggcg   1560
ctggagccga ccctgcgcgc ggcgatggac gtcgacggcc cggcggtagt ggccatcccg   1620
gtggattatc gcgataaccc gctgctgatg ggccagctgc atctgagtca gattctgtaa   1680
```

<210> SEQ ID NO 2
<211> LENGTH: 559
<212> TYPE: PRT
<213> ORGANISM: K. pneumoniae

<400> SEQUENCE: 2

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Ile Glu Val Thr Ala Pro Asp Ala Leu
    130                 135                 140

Ala Glu Val Val Ser Asn Ala Phe Arg Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
```

```
            180                 185                 190
Pro Asp Asp Ala Ile Asp Gln Val Ala Lys Leu Ile Ala Gln Ala Lys
            195                 200                 205
Asn Pro Ile Phe Leu Leu Gly Leu Met Ala Ser Gln Pro Glu Asn Ser
        210                 215                 220
Lys Ala Leu Arg Arg Leu Glu Thr Ser His Ile Pro Val Thr Ser
225                 230                 235                 240
Thr Tyr Gln Ala Ala Gly Ala Val Asn Gln Asp Asn Phe Ser Arg Phe
                245                 250                 255
Ala Gly Arg Val Gly Leu Phe Asn Asn Gln Ala Gly Asp Arg Leu Leu
            260                 265                 270
Gln Leu Ala Asp Leu Val Ile Cys Ile Gly Tyr Ser Pro Val Glu Tyr
            275                 280                 285
Glu Pro Ala Met Trp Asn Ser Gly Asn Ala Thr Leu Val His Ile Asp
        290                 295                 300
Val Leu Pro Ala Tyr Glu Glu Arg Asn Tyr Thr Pro Asp Val Glu Leu
305                 310                 315                 320
Val Gly Asp Ile Ala Gly Thr Leu Asn Lys Leu Ala Gln Asn Ile Asp
                325                 330                 335
His Arg Leu Val Leu Ser Pro Gln Ala Ala Glu Ile Leu Arg Asp Arg
            340                 345                 350
Gln His Gln Arg Glu Leu Leu Asp Arg Arg Gly Ala Gln Leu Asn Gln
        355                 360                 365
Phe Ala Leu His Pro Leu Arg Ile Val Arg Ala Met Gln Asp Ile Val
        370                 375                 380
Asn Ser Asp Val Thr Leu Thr Val Asp Met Gly Ser Phe His Ile Trp
385                 390                 395                 400
Ile Ala Arg Tyr Leu Tyr Thr Phe Arg Ala Arg Gln Val Met Ile Ser
                405                 410                 415
Asn Gly Gln Gln Thr Met Gly Val Ala Leu Pro Trp Ala Ile Gly Ala
            420                 425                 430
Trp Leu Val Asn Pro Glu Arg Lys Val Val Ser Val Ser Gly Asp Gly
            435                 440                 445
Gly Phe Leu Gln Ser Ser Met Glu Leu Glu Thr Ala Val Arg Leu Lys
        450                 455                 460
Ala Asn Val Leu His Leu Ile Trp Val Asp Asn Gly Tyr Asn Met Val
465                 470                 475                 480
Ala Ile Gln Glu Glu Lys Lys Tyr Gln Arg Leu Ser Gly Val Glu Phe
                485                 490                 495
Gly Pro Met Asp Phe Lys Ala Tyr Ala Glu Ser Phe Gly Ala Lys Gly
            500                 505                 510
Phe Ala Val Glu Ser Ala Glu Leu Glu Pro Thr Leu Arg Ala Ala
            515                 520                 525
Met Asp Val Asp Gly Pro Ala Val Val Ala Ile Pro Val Asp Tyr Arg
        530                 535                 540
Asp Asn Pro Leu Leu Met Gly Gln Leu His Leu Ser Gln Ile Leu
545                 550                 555

<210> SEQ ID NO 3
<211> LENGTH: 1476
<212> TYPE: DNA
<213> ORGANISM: E. coli

<400> SEQUENCE: 3
```

```
atggctaact acttcaatac actgaatctg cgccagcagc tggcacagct gggcaaatgt      60
cgctttatgg gccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
ctgatgaaag acggcgcggc gctgggctac tcgcacggtt caacatcgt cgaagtgggc      420 gagcagatcc gtaaagatat caccgtagtg atggttgcgc cgaaatgccc aggcaccgaa     480
gtgcgtgaag agtacaaacg tgggttcggc gtaccgacgc tgattgccgt tcacccggaa     540
aacgatccga aggcgaagg catggcgatt gccaaagcct gggcggctgc aaccggtggt     600
caccgtgcgg gtgtgctgga atcgtccttc gttgcggaag tgaaatctga cctgatgggc     660
gagcaaacca tcctgtgcgg tatgttgcag gctggctctc tgctgtgctt cgacaagctg     720
gtggaagaag taccgatcc agcatacgca gaaaaactga ttcagttcgg ttgggaaacc      780
atcaccgaag cactgaaaca gggcggcatc accctgatga tggaccgtct ctctaacccg     840
gcgaaactgc gtgcttatgc gctttctgaa cagctgaaag agatcatggc accccctgttc    900 cagaaacata tggacgacat catctccggc gaattctctt ccggtatgat ggcggactgg     960
gccaacgatg ataagaaact gctgacctgg cgtgaagaga ccggcaaaac gcgtttgaa    1020 accgcgccgc agtatgaagg caaaatcggc gagcaggagt acttcgataa aggcgtactg    1080
atgattgcga tggtgaaagc gggcgttgaa ctggcgttcg aaaccatggt cgattccggc    1140
atcattgaag agtctgcata ttatgaatca ctgcacgagc tgccgctgat tgccaacacc    1200
atcgcccgta agcgtctgta cgaaatgaac gtggttatct ctgataccgc tgagtacggt    1260
aactatctgt tctcttacgc ttgtgtgccg ttgctgaaac cgtttatggc agagctgcaa    1320
ccgggcgacc tggtaaaagc tattccggaa ggcgcggtag ataacgggca actgcgtgat    1380
gtgaacgaag cgattcgcag ccatgcgatt gagcaggtag gtaagaaact gcgcggctat    1440
atgacagata tgaaacgtat tgctgttgcg ggttaa                               1476
```

<210> SEQ ID NO 4
<211> LENGTH: 491
<212> TYPE: PRT
<213> ORGANISM: E. coli

<400> SEQUENCE: 4

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110
```

```
Asp Val Val Arg Thr Val Gln Pro Leu Met Lys Asp Gly Ala Ala Leu
            115                 120                 125

Gly Tyr Ser His Gly Phe Asn Ile Val Glu Val Gly Glu Gln Ile Arg
        130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
        210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
        290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 5
<211> LENGTH: 1851
<212> TYPE: DNA
<213> ORGANISM: E. coli

<400> SEQUENCE: 5
```

```
atgcctaagt accgttccgc caccaccact catggtcgta atatggcggg tgctcgtgcg      60
ctgtggcgcg ccaccggaat gaccgacgcc gatttcggta agccgattat cgcggttgtg     120
aactcgttca cccaatttgt accgggtcac gtccatctgc gcgatctcgg taaactggtc     180
gccgaacaaa ttgaagcggc tggcggcgtt gccaaagagt tcaacaccat tgcggtggat     240
gatgggattg ccatgggcca cgggggatg ctttattcac tgccatctcg cgaactgatc      300
gctgattccg ttgagtatat ggtcaacgcc cactgcgccg acgccatggt ctgcatctct     360
aactgcgaca aaatcacccc ggggatgctg atggcttccc tgcgcctgaa tattccggtg     420
atctttgttt ccggcggccc gatggaggcc gggaaaacca aactttccga tcagatcatc     480
aagctcgatc tggttgatgc gatgatccag ggcgcagacc cgaaagtatc tgactcccag     540
agcgatcagg ttgaacgttc cgcgtgtccg acctgcggtt cctgctccgg atgtttacc      600
gctaactcaa tgaactgcct gaccgaagcg ctgggcctgt cgcagccggg caacggctcg     660
ctgctggcaa cccacgccga ccgtaagcag ctgttcctta tgctggtaa acgcattgtt      720
gaattgacca aacgttatta cgagcaaaac gacgaaagtg cactgccgcg taatatcgcc     780
agtaaggcg cgtttgaaaa cgccatgacg ctggatatcg cgatgggtgg atcgactaac      840
accgtacttc acctgctggc ggcggcgcag gaagcggaaa tcgacttcac catgagtgat     900
atcgataagc tttcccgcaa ggttccacag ctgtgtaaag ttgcgccgag cacccagaaa     960
taccatatgg aagatgttca ccgtgctggt ggtgttatcg gtattctcgg cgaactggat    1020
cgcgcggggt tactgaaccg tgatgtgaaa aacgtacttg gcctgacgtt gccgcaaacg    1080
ctggaacaat acgacgttat gctgacccag gatgacgcgg taaaaaatat gttccgcgca    1140
ggtcctgcag gcattcgtac cacacaggca ttctcgcaag attgccgttg ggatacgctg    1200
gacgacgatc gcgccaatgg ctgtatccgc tcgctggaac acgcctacag caaagacggc    1260
ggcctggcgg tgctctacgg taactttgcg gaaaacggct gcatcgtgaa aacggcaggc    1320
gtcgatgaca gcatcctcaa attcaccggc ccggcgaaag tgtacgaaag ccaggacgat    1380
gcggtagaag cgattctcgg cggtaaagtt gtcgccggag atgtggtagt aattcgctat    1440
gaaggcccga aaggcggtcc ggggatgcag gaaatgctct acccaaccag cttcctgaaa    1500
tcaatgggtc tcggcaaagc ctgtgcgctg atcaccgacg tcgtttctc tggtggcacc     1560
tctggtctt ccatcggcca cgtctcaccg gaagcggcaa gcggcggcag cattggcctg    1620
attgaagatg gtgacctgat cgctatcgac atcccgaacc gtggcattca gttacaggta    1680
agcgatgccg aactggcggc gcgtcgtgaa gcgcaggacg ctcgaggtga caaagcctgg    1740
acgccgaaaa atcgtgaacg tcaggtctcc tttgccctgc gtgcttatgc cagcctggca    1800
accagcgccg acaaaggcgc ggtgcgcgat aaatcgaaac tggggggtta a             1851
```

<210> SEQ ID NO 6
<211> LENGTH: 616
<212> TYPE: PRT
<213> ORGANISM: E. coli

<400> SEQUENCE: 6

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45
```

```
Gly His Val His Leu Arg Asp Leu Gly Lys Leu Val Ala Glu Gln Ile
 50                  55                  60

Glu Ala Ala Gly Gly Val Ala Lys Glu Phe Asn Thr Ile Ala Val Asp
 65                      70                  75                  80

Asp Gly Ile Ala Met Gly His Gly Gly Met Leu Tyr Ser Leu Pro Ser
                     85                  90                  95

Arg Glu Leu Ile Ala Asp Ser Val Glu Tyr Met Val Asn Ala His Cys
                100                 105                 110

Ala Asp Ala Met Val Cys Ile Ser Asn Cys Asp Lys Ile Thr Pro Gly
            115                 120                 125

Met Leu Met Ala Ser Leu Arg Leu Asn Ile Pro Val Ile Phe Val Ser
130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
                180                 185                 190

Gly Ser Cys Ser Gly Met Phe Thr Ala Asn Ser Met Asn Cys Leu Thr
            195                 200                 205

Glu Ala Leu Gly Leu Ser Gln Pro Gly Asn Gly Ser Leu Leu Ala Thr
210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
                260                 265                 270

Ile Ala Met Gly Gly Ser Thr Asn Thr Val Leu His Leu Leu Ala Ala
            275                 280                 285

Ala Gln Glu Ala Glu Ile Asp Phe Thr Met Ser Asp Ile Asp Lys Leu
290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
                340                 345                 350

Leu Gly Leu Thr Leu Pro Gln Thr Leu Glu Gln Tyr Asp Val Met Leu
            355                 360                 365

Thr Gln Asp Asp Ala Val Lys Asn Met Phe Arg Ala Gly Pro Ala Gly
370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
                420                 425                 430

Gly Cys Ile Val Lys Thr Ala Gly Val Asp Asp Ser Ile Leu Lys Phe
            435                 440                 445

Thr Gly Pro Ala Lys Val Tyr Glu Ser Gln Asp Asp Ala Val Glu Ala
450                 455                 460
```

```
Ile Leu Gly Gly Lys Val Ala Gly Asp Val Val Ile Arg Tyr
465                 470                 475                 480

Glu Gly Pro Lys Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
                500                 505                 510

Asp Gly Arg Phe Ser Gly Gly Thr Ser Gly Leu Ser Ile Gly His Val
                515                 520                 525

Ser Pro Glu Ala Ala Ser Gly Ser Ile Gly Leu Ile Glu Asp Gly
            530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
                580                 585                 590

Leu Arg Ala Tyr Ala Ser Leu Ala Thr Ser Ala Asp Lys Gly Ala Val
                595                 600                 605

Arg Asp Lys Ser Lys Leu Gly Gly
    610                 615

<210> SEQ ID NO 7
<211> LENGTH: 1662
<212> TYPE: DNA
<213> ORGANISM: Lactococcus lactis

<400> SEQUENCE: 7
tctagacata tgtatactgt gggggattac ctgctggatc gcctgcacga actgggatt       60 gaagaaattt tcggtgtgcc aggcgattat aacctgcagt cctgaccca gattatctcg      120 cacaaagata tgaagtgggt cggtaacgcc aacgaactga cgcgagcta tggcagat        180 ggttatgccc gtaccaaaaa agctgctgcg tttctgacga cctttggcgt tggcgaactg     240
agcgccgtca acggactggc aggaagctac gccgagaacc tgccagttgt cgaaattgtt    300
gggtcgccta cttctaaggt tcagaatgaa ggcaaatttg tgcaccatac tctggctgat    360
ggggatttta acatttttat gaaaatgcat gaaccggtta ctgcggcccg cacgctgctg    420
acagcagaga tgctacggt tgagatcgac gcgtcctgt ctgcgctgct gaaagagcgc      480
aagccggtat atatcaatct gcctgtcgat gttgccgcag cgaaagccga aagccgtcg     540 ctgccactga aaaagaaaa cagcacctcc aatacatcgg accaggaaat tctgaataaa     600
atccaggaat cactgaagaa tgcgaagaaa ccgatcgtca tcaccggaca tgagatcatc    660
tcttttggcc tggaaaaaac ggtcacgcag ttcatttcta agaccaaact gcctatcacc    720
accctgaact tcggcaaatc tagcgtcgat gaagcgctgc cgagttttct gggtatctat   780
aatggtaccc tgtccgaacc gaacctgaaa gaattcgtcg aaagcgcgga ctttatcctg   840
atgctgggcg tgaaactgac ggatagctcc acaggcgcat ttacccacca tctgaacgag  900
aataaaatga tttccctgaa atcgacgaa ggcaaaatct ttaacgagcg catccagaac   960
ttcgattttg aatctctgat tagttcgctg ctggatctgt ccgaaattga gtataaaggt  1020
aaatatattg ataaaaaaca ggaggatttt gtgccgtcta atgcgctgct gagtcaggat  1080
cgtctgtggc aagccgtaga aaacctgaca cagtctaatg aaacgattgt tgcggaacag  1140
ggaacttcat ttttcggcgc ctcatccatt tttctgaaat ccaaaagcca tttcattggc  1200
caaccgctgt gggggagtat tggttatacc tttccggcgg cgctggggttc acagattgca  1260
```

```
gataaggaat cacgccatct gctgtttatt ggtgacggca gcctgcagct gactgtccag    1320
gaactggggc tggcgatccg tgaaaaaatc aatccgattt gctttatcat caataacgac    1380
ggctacaccg tcgaacgcga aattcatgga ccgaatcaaa gttacaatga catcccgatg    1440
tggaactata gcaaactgcc ggaatccttt ggcgcgacag aggatcgcgt ggtgagtaaa    1500
attgtgcgta cggaaaacga atttgtgtcg gttatgaaag aagcgcaggc tgacccgaat    1560
cgcatgtatt ggattgaact gatcctggca aaagaaggcg caccgaaagt tctgaaaaag    1620
atggggaaac tgtttgcgga gcaaaataaa agctaaggat cc                      1662
```

<210> SEQ ID NO 8
<211> LENGTH: 548
<212> TYPE: PRT
<213> ORGANISM: Lactococcus lactis

<400> SEQUENCE: 8

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300
```

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
530                 535                 540

Gln Asn Lys Ser
545

<210> SEQ ID NO 9
<211> LENGTH: 1164
<212> TYPE: DNA
<213> ORGANISM: E. coli

<400> SEQUENCE: 9
atgaacaact taatctgca caccccaacc cgcattctgt tggtaaagg cgcaatcgct      60 ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
gttcgcgaac agaaagtgac tttcctgctg gcggttggcg gcggttctgt actggacggc    300
accaaattta tcgccgcagc ggctaactat ccggaaaata tcgatccgtg cacattctg    360 caaacgggcg gtaaagagat taaaagcgcc atcccgatgg ctgtgtgct gacgctgcca    420 gcaaccggtt cagaatccaa cgcaggcgcg gtgatctccc gtaaaccac aggcgacaag    480 caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660

```
ttgctgacgc taatcgaaga tggtccgaaa gccctgaaag agccagaaaa ctacgatgtg      720
cgcgccaacg tcatgtgggc ggcgactcag gcgctgaacg gtttgattgg cgctggcgta      780
ccgcaggact gggcaacgca tatgctgggc cacgaactga ctgcgatgca cggtctggat      840
cacgcgcaaa cactggctat cgtcctgcct gcactgtgga atgaaaaacg cgataccaag      900
cgcgctaagc tgctgcaata tgctgaacgc gtctggaaca tcactgaagg ttccgatgat      960
gagcgtattg acgccgcgat tgccgcaacc cgcaatttct ttgagcaatt aggcgtgccg     1020
acccacctct ccgactacgg tctggacggc agctccatcc cggctttgct gaaaaaactg     1080
gaagagcacg gcatgaccca actgggcgaa aatcatgaca ttacgttgga tgtcagccgc     1140
cgtatatacg aagccgcccg ctaa                                            1164
```

<210> SEQ ID NO 10
<211> LENGTH: 387
<212> TYPE: PRT
<213> ORGANISM: E. coli

<400> SEQUENCE: 10

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285
```

-continued

```
Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
caccatggac aaacagtatc cggtacgcc                                    29

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
cgaagggcga tagctttacc aatcc                                        25

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
caccatggct aactacttca atacactga                                    29

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
ccaggagaag gccttgagtg ttttctcc                                     28

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
```
caccatgcct aagtaccgtt ccgccacca                                              29

<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
cgcagcactg ctcttaaata ttcggc                                                 26

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
caccatgaac aactttaatc tgcacaccc                                              29

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18
caccatgaac aactttaatc tgcacaccc                                              29

<210> SEQ ID NO 19
<211> LENGTH: 45
<212> TYPE: DNA
<213> ORGANISM: Artificial Sequence
<220> FEATURE:
<223> OTHER INFORMATION: Primer

<400> SEQUENCE: 19
gcatgcctta agaaaggagg ggggtcacat ggacaaacag tatcc                            45

<210> SEQ ID NO 20
<211> LENGTH: 39
<212> TYPE: DNA
<213> ORGANISM: Artificial Sequence
<220> FEATURE:
<223> OTHER INFORMATION: Primer

<400> SEQUENCE: 20
atgcatttaa ttaattacag aatctgactc agatgcagc                                   39

<210> SEQ ID NO 21
<211> LENGTH: 45
<212> TYPE: DNA
<213> ORGANISM: Artificial Sequence
<220> FEATURE:
<223> OTHER INFORMATION: Primer

<400> SEQUENCE: 21
gtcgacgcta gcaaaggagg gaatcaccat ggctaactac ttcaa                            45

<210> SEQ ID NO 22
<211> LENGTH: 31
<212> TYPE: DNA

```
<213> ORGANISM: Artificial Sequence
<220> FEATURE:
<223> OTHER INFORMATION: Primer

<400> SEQUENCE: 22
tctagattaa cccgcaacag caatacgttt c                                31

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
tctagaaaag gaggaataaa gtatgcctaa gtaccgttc                         39

<210> SEQ ID NO 24
<211> LENGTH: 31
<212> TYPE: DNA
<213> ORGANISM: Artificial Sequence
<220> FEATURE:
<223> OTHER INFORMATION: Primer

<400> SEQUENCE: 24
ggatccttat taaccccca gtttcgattt a                                  31

<210> SEQ ID NO 25
<211> LENGTH: 39
<212> TYPE: DNA
<213> ORGANISM: Artificial Sequence
<220> FEATURE:
<223> OTHER INFORMATION: Primer

<400> SEQUENCE: 25
ggatccaaag gaggctagac atatgtatac tgtggggga                         39

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
gagctcttag cttttatttt gctccgcaaa c                                 31

<210> SEQ ID NO 27
<211> LENGTH: 39
<212> TYPE: DNA
<213> ORGANISM: Artificial Sequence
<220> FEATURE:
<223> OTHER INFORMATION: Primer

<400> SEQUENCE: 27
gagctcaaag gaggagcaag taatgaacaa ctttaatct                         39

<210> SEQ ID NO 28
<211> LENGTH: 43
<212> TYPE: DNA
<213> ORGANISM: Artificial Sequence
<220> FEATURE:
<223> OTHER INFORMATION: Primer

<400> SEQUENCE: 28
gaattcacta gtcctaggtt agcgggcggc ttcgtatata cgg                    43
```

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
caacattagc gattttcttt tctct                                    25

<210> SEQ ID NO 30
<211> LENGTH: 45
<212> TYPE: DNA
<213> ORGANISM: Artificial Sequence
<220> FEATURE:
<223> OTHER INFORMATION: Primer

<400> SEQUENCE: 30
catgaagctt actagtgggc ttaagttttg aaaataatga aaact              45

<210> SEQ ID NO 31
<211> LENGTH: 61
<212> TYPE: DNA
<213> ORGANISM: Artificial Sequence
<220> FEATURE:
<223> OTHER INFORMATION: Primer N110.2

<400> SEQUENCE: 31
gagctcacta gtcaattgta agtaagtaaa aggaggtggg tcacatggac aaacagtatc    60
c                                                                    61

<210> SEQ ID NO 32
<211> LENGTH: 50
<212> TYPE: DNA
<213> ORGANISM: Artificial Sequence
<220> FEATURE:
<223> OTHER INFORMATION: Primer N111.2

<400> SEQUENCE: 32
ggatccgatc gacttaagcc tcagcttaca gaatctgact cagatgcagc          50

<210> SEQ ID NO 33
<211> LENGTH: 44
<212> TYPE: DNA
<213> ORGANISM: Artificial Sequence
<220> FEATURE:
<223> OTHER INFORMATION: Primer N112.2

<400> SEQUENCE: 33
gagctcctta agaaggaggt aatcaccatg gctaactact tcaa                44

<210> SEQ ID NO 34
<211> LENGTH: 51
<212> TYPE: DNA
<213> ORGANISM: Artificial Sequence
<220> FEATURE:
<223> OTHER INFORMATION: Primer N113.2

<400> SEQUENCE: 34
ggatccgatc gagctagcgc ggccgcttaa cccgcaacag caatacgttt c         51

<210> SEQ ID NO 35
<211> LENGTH: 44
<212> TYPE: DNA

<213> ORGANISM: Artificial Sequence
<220> FEATURE:
<223> OTHER INFORMATION: Primer N114.2

<400> SEQUENCE: 35

```
gagctcgcta gcaaggaggt ataaagtatg cctaagtacc gttc        44
```

<210> SEQ ID NO 36
<211> LENGTH: 52
<212> TYPE: DNA
<213> ORGANISM: Artificial Sequence
<220> FEATURE:
<223> OTHER INFORMATION: Primer N115.2

<400> SEQUENCE: 36

```
ggatccgatc gattaattaa cctaaggtta ttaaccccccc agtttcgatt ta    52
```

<210> SEQ ID NO 37
<211> LENGTH: 46
<212> TYPE: DNA
<213> ORGANISM: Artificial Sequence
<220> FEATURE:
<223> OTHER INFORMATION: Primer N116.2

<400> SEQUENCE: 37

```
gagctcttaa ttaaaaggag gttagacata tgtatactgt ggggga       46
```

<210> SEQ ID NO 38
<211> LENGTH: 49
<212> TYPE: DNA
<213> ORGANISM: Artificial Sequence
<220> FEATURE:
<223> OTHER INFORMATION: Primer 117.2

<400> SEQUENCE: 38

```
ggatccagat ctcctaggac atgtttagct tttattttgc tccgcaaac    49
```

<210> SEQ ID NO 39
<211> LENGTH: 3883
<212> TYPE: DNA
<213> ORGANISM: Escherichia coli

<400> SEQUENCE: 39

```
ctatattgct gaaggtacag gcgtttccat aactatttgc tcgcgttttt tactcaagaa    60
gaaaatgcca aatagcaaca tcaggcagac aatacccgaa attgcgaaga aaactgtctg   120
gtagcctgcg tggtcaaaga gtatcccagt cggcgttgaa agcagcacaa tcccaagcga   180
actggcaatt tgaaaaccaa tcagaaagat cgtcgacgac aggcgcttat caaagtttgc   240
cacgctgtat ttgaagacgg atatgacaca aagtggaacc tcaatggcat gtaacaactt   300
cactaatgaa ataatccagg ggttaacgaa cagcgcgcag gaaaggatac gcaacgccat   360
aatcacaact ccgataagta atgcatttt tggccctacc cgattcacaa agaaaggaat   420
aatcgccatg cacagcgctt cgagtaccac ctggaatgag ttgagataac catacaggcg   480
cgttcctaca tcgtgtgatt cgaataaacc tgaataaaag acaggaaaaa gttgttgatc   540
aaaaatgtta tagaaagacc acgtccccac aataaatatg acgaaaaccc agaagtttcg   600
atccttgaaa actgcgataa aatcctcttt ttttaccccc tccgcatctg ccgctacgca   660
ctggtgatcc ttatctttaa aacgcatgtt gatcatcata aatacagcgc caaatagcga   720
gaccaaccag aagttgatat ggggactgat actaaaaaat atgccggcaa agaacgcgcc   780
aatagcatag ccaaaagatc cccaggcgcg cgctgttcca tattcgaaat gaaaatttcg   840
```

```
cgccattttt tcggtgaagc tatcaagcaa accgcatccc gccagatacc caagccaaa      900 aaatagcgcc cccagaatta gacctacaga aaaattgctt tgcagtaacg gttcataaac     960
gtaaatcata aacggtccgg tcaagaccag gatgaaactc atacaccaga tgagcggttt    1020
cttcagaccg agtttatcct gaacgatgcc gtagaacatc ataaatagaa tgctggtaaa    1080
ctggttgacc gaataaagtg tacctaattc cgtccctgtc aacctagat gtcctttcag     1140 ccaaatagcg tataacgacc accacagcga ccaggaaata aaaagagaa atgagtaact     1200 ggatgcaaaa cgatagtacg catttctgaa tggaatattc agtgccataa ttacctgcct    1260
gtcgttaaaa aattcacgtc ctatttagag ataagagcga cttcgccgtt tacttctcac    1320
tattccagtt cttgtcgaca tggcagcgct gtcattgccc cttttcgccgt tactgcaagc    1380 gctccgcaac gttgagcgag atcgataatt cgtcgcattt ctctctcatc tgtagataat    1440
cccgtagagg acagacctgt gagtaacccg gcaacgaacg catctcccgc cccgtgcta     1500 tcgacacaat tcagagacat tccagcaaaa tggtgaactt gtcctcgata acagaccacc    1560 acccccttctg caccttttagt caccaacagc atggcgatct catactcttt tgccagggcg   1620
catatatcct gatcgttctg tgtttttcca ctgataagtc gccattcttc ttccgagagc    1680
ttgacgacat ccgccagttg tagcgcctgc cgcaaacaca agcggagcaa atgctcgtct    1740
tgccatagat cttcacgaat attaggatcg aagctgacaa aacctccggc atgccggatc    1800
gccgtcatcg cagtaaatgc gctggtacgc gaaggctcgg cagacaacgc aattgaacag    1860
agatgtaacc attcgccatg tcgccagcag ggcaagtctg tcgtctctaa aaaaagatcg    1920
gcactggggc ggaccataaa cgtaaatgaa cgttccccctt gatcgttcag atcgacaagc    1980
accgtggatg tccggtgcca ttcatcttgc ttcagatacg tgatatcgac tccctcagtt    2040
agcagcgttc tttgcattaa cgcaccaaaa ggatcatccc ccacccgacc tataaaccca    2100
cttgttccgc ctaatctggc gattcccacc gcaacgttag ctggcgcgcc gccaggacaa    2160
ggcagtaggc gcccgtctga ttctggcaag agatctacga ccgcatcccc taaaacccat    2220
actttggctg acattttttt cccttaaatt catctgagtt acgcatagtg ataaacctct    2280
ttttcgcaaa atcgtcatgg atttactaaa acatgcatat tcgatcacaa aacgtcatag    2340
ttaacgttaa catttgtgat attcatcgca tttatgaaag taagggactt tattttata     2400 aaagttaacg ttaacaattc accaaatttg cttaaccagg atgattaaaa tgacgcaatc    2460
tcgattgcat gcggcgcaaa acgccctagc aaaacttcat gagcaccggg gtaacacttt    2520
ctatccccat tttcacctcg cgcctcctgc cgggtggatg aacgatccaa acggcctgat    2580
ctggtttaac gatcgttatc acgcgtttta tcaacatcat ccgatgagcg aacactgggg    2640
gccaatgcac tggggacatg ccaccagcga cgatatgatc cactggcagc atgagcctat    2700
tgcgctagcg ccaggagacg ataatgacaa agacgggtgt ttttcaggta gtgctgtcga    2760
tgacaatggt gtcctctcac ttatctacac cggacacgtc tggctcgatg gtgcaggtaa    2820
tgacgatgca attcgcgaag tacaatgtct ggctaccagt cgggatggta ttcatttcga    2880
gaaacagggt gtgatcctca ctccaccaga aggaatcatg cacttccgcg atcctaaagt    2940
gtggcgtgaa gccgacacat ggtggatggt agtcggggcg aaagatccag gcaacacggg    3000
gcagatcctg ctttatcgcg gcagttcgtt gcgtgaatgg accttcgatc gcgtactggc    3060
ccacgctgat gcgggtgaaa gctatatgtg ggaatgtccg gacttttttca gccttggcga    3120 tcagcattat ctgatgtttt ccccgcaggg aatgaatgcc gagggataca gttaccgaaa    3180
```

```
tcgctttcaa agtggcgtaa tacccggaat gtggtcgcca ggacgacttt ttgcacaatc    3240
cgggcatttt actgaacttg ataacgggca tgacttttat gcaccacaaa gcttttttagc   3300 gaaggatggt cggcgtattg ttatcggctg gatggatatg tgggaatcgc caatgccctc    3360
aaaacgtgaa ggatgggcag gctgcatgac gctggcgcgc gagctatcag agagcaatgg   3420
caaacttcta caacgcccgg tacacgaagc tgagtcgtta cgccagcagc atcaatctgt    3480
ctctccccgc acaatcagca ataaatatgt tttgcaggaa aacgcgcaag cagttgagat    3540
tcagttgcag tgggcgctga agaacagtga tgccgaacat tacggattac agctcggcac    3600
tggaatgcgg ctgtatattg ataccaatc tgagcgactt gttttgtggc ggtattaccc     3660
acacgagaat ttagacggct accgtagtat tcccctcccg cagcgtgaca cgctcgccct    3720
aaggatattt atcgatacat catccgtgga agtatttatt aacgacgggg aagcggtgat    3780
gagtagtcga atctatccgc agccagaaga acgggaactg tcgctttatg cctcccacgg    3840
agtggctgtg ctgcaacatg gagcactctg gctactgggt taa                     3883
```

```
<210> SEQ ID NO 40
<211> LENGTH: 19
<212> TYPE: DNA
<213> ORGANISM: Artificial Sequence
<220> FEATURE:
<223> OTHER INFORMATION: Primer N130SeqF1

<400> SEQUENCE: 40
tgttccaacc tgatcaccg                                                    19

<210> SEQ ID NO 41
<211> LENGTH: 18
<212> TYPE: DNA
<213> ORGANISM: Artificial Sequence
<220> FEATURE:
<223> OTHER INFORMATION: Primer N130SeqF2

<400> SEQUENCE: 41
ggaaaacagc aaggcgct                                                     18

<210> SEQ ID NO 42
<211> LENGTH: 18
<212> TYPE: DNA
<213> ORGANISM: Artificial Sequence
<220> FEATURE:
<223> OTHER INFORMATION: Primer N130SeqF3

<400> SEQUENCE: 42
cagctgaacc agtttgcc                                                     18

<210> SEQ ID NO 43
<211> LENGTH: 19
<212> TYPE: DNA
<213> ORGANISM: Artificial Sequence
<220> FEATURE:
<223> OTHER INFORMATION: Primer N130SeqF4

<400> SEQUENCE: 43
aaaataccag cgcctgtcc                                                    19

<210> SEQ ID NO 44
<211> LENGTH: 18
<212> TYPE: DNA
<213> ORGANISM: Artificial Sequence
<220> FEATURE:
<223> OTHER INFORMATION: Primer N130SeqR1
```

```
<400> SEQUENCE: 44
tgaatggcca ccatgttg                                              18

<210> SEQ ID NO 45
<211> LENGTH: 18
<212> TYPE: DNA
<213> ORGANISM: Artificial Sequence
<220> FEATURE:
<223> OTHER INFORMATION: Primer N130SeqR2

<400> SEQUENCE: 45
gaggatctcc gccgcctg                                              18

<210> SEQ ID NO 46
<211> LENGTH: 18
<212> TYPE: DNA
<213> ORGANISM: Artificial Sequence
<220> FEATURE:
<223> OTHER INFORMATION: Primer N130SeqR3

<400> SEQUENCE: 46
aggccgagca ggaagatc                                              18

<210> SEQ ID NO 47
<211> LENGTH: 19
<212> TYPE: DNA
<213> ORGANISM: Artificial Sequence
<220> FEATURE:
<223> OTHER INFORMATION: Primer N130SeqR4

<400> SEQUENCE: 47
tgatcaggtt ggaacagcc                                             19

<210> SEQ ID NO 48
<211> LENGTH: 19
<212> TYPE: DNA
<213> ORGANISM: Artificial Sequence
<220> FEATURE:
<223> OTHER INFORMATION: Primer N131SeqF1

<400> SEQUENCE: 48
aagaactgat cccacaggc                                             19

<210> SEQ ID NO 49
<211> LENGTH: 19
<212> TYPE: DNA
<213> ORGANISM: Artificial Sequence
<220> FEATURE:
<223> OTHER INFORMATION: Primer N131SeqF2

<400> SEQUENCE: 49
atcctgtgcg gtatgttgc                                             19

<210> SEQ ID NO 50
<211> LENGTH: 18
<212> TYPE: DNA
<213> ORGANISM: Artificial Sequence
<220> FEATURE:
<223> OTHER INFORMATION: Primer N131Seqf3

<400> SEQUENCE: 50
attgcgatgg tgaaagcg                                              18

<210> SEQ ID NO 51
```

```
<210> SEQ ID NO 51
<211> LENGTH: 19
<212> TYPE: DNA
<213> ORGANISM: Artificial Sequence
<220> FEATURE:
<223> OTHER INFORMATION: Primer N131SeqR1

<400> SEQUENCE: 51
atggtgttgg caatcagcg                                            19

<210> SEQ ID NO 52
<211> LENGTH: 18
<212> TYPE: DNA
<213> ORGANISM: Artificial Sequence
<220> FEATURE:
<223> OTHER INFORMATION: Primer N131SeqR2

<400> SEQUENCE: 52
gtgcttcggt gatggttt                                             18

<210> SEQ ID NO 53
<211> LENGTH: 19
<212> TYPE: DNA
<213> ORGANISM: Artificial Sequence
<220> FEATURE:
<223> OTHER INFORMATION: Primer N131SeqR3

<400> SEQUENCE: 53
ttgaaaccgt gcgagtagc                                            19

<210> SEQ ID NO 54
<211> LENGTH: 19
<212> TYPE: DNA
<213> ORGANISM: Artificial Sequence
<220> FEATURE:
<223> OTHER INFORMATION: Primer N132SeqF1

<400> SEQUENCE: 54
tattcactgc catctcgcg                                            19

<210> SEQ ID NO 55
<211> LENGTH: 18
<212> TYPE: DNA
<213> ORGANISM: Artificial Sequence
<220> FEATURE:
<223> OTHER INFORMATION: Primer N132SeqF2

<400> SEQUENCE: 55
ccgtaagcag ctgttcct                                             18

<210> SEQ ID NO 56
<211> LENGTH: 20
<212> TYPE: DNA
<213> ORGANISM: Artificial Sequence
<220> FEATURE:
<223> OTHER INFORMATION: Primer N132SeqF3

<400> SEQUENCE: 56
gctggaacaa tacgacgtta                                           20

<210> SEQ ID NO 57
<211> LENGTH: 20
<212> TYPE: DNA
<213> ORGANISM: Artificial Sequence
<220> FEATURE:
<223> OTHER INFORMATION: Primer N132SeqF4

<400> SEQUENCE: 57
```

```
tgctctaccc aaccagcttc                                              20

<210> SEQ ID NO 58
<211> LENGTH: 20
<212> TYPE: DNA
<213> ORGANISM: Artificial Sequence
<220> FEATURE:
<223> OTHER INFORMATION: Primer N132SeqR1

<400> SEQUENCE: 58
atggaaagac cagaggtgcc                                              20

<210> SEQ ID NO 59
<211> LENGTH: 18
<212> TYPE: DNA
<213> ORGANISM: Artificial Sequence
<220> FEATURE:
<223> OTHER INFORMATION: Primer N132SeqR2

<400> SEQUENCE: 59
tgcctgtgtg gtacgaat                                                18

<210> SEQ ID NO 60
<211> LENGTH: 19
<212> TYPE: DNA
<213> ORGANISM: Artificial Sequence
<220> FEATURE:
<223> OTHER INFORMATION: Primer N132SeqR3

<400> SEQUENCE: 60
tattacgcgg cagtgcact                                               19

<210> SEQ ID NO 61
<211> LENGTH: 22
<212> TYPE: DNA
<213> ORGANISM: Artificial Sequence
<220> FEATURE:
<223> OTHER INFORMATION: Primer N132SeqR4

<400> SEQUENCE: 61
ggtgattttg tcgcagttag ag                                           22

<210> SEQ ID NO 62
<211> LENGTH: 18
<212> TYPE: DNA
<213> ORGANISM: Artificial Sequence
<220> FEATURE:
<223> OTHER INFORMATION: Primer N133SeqF1

<400> SEQUENCE: 62
tcgaaattgt tgggtcgc                                                18

<210> SEQ ID NO 63
<211> LENGTH: 22
<212> TYPE: DNA
<213> ORGANISM: Artificial Sequence
<220> FEATURE:
<223> OTHER INFORMATION: Primer N133SeqF2

<400> SEQUENCE: 63
ggtcacgcag ttcatttcta ag                                           22

<210> SEQ ID NO 64
<211> LENGTH: 18
<212> TYPE: DNA
```

```
<213> ORGANISM: Artificial Sequence
<220> FEATURE:
<223> OTHER INFORMATION: Primer N133SeqF3

<400> SEQUENCE: 64
tgtggcaagc cgtagaaa                                                 18

<210> SEQ ID NO 65
<211> LENGTH: 19
<212> TYPE: DNA
<213> ORGANISM: Artificial Sequence
<220> FEATURE:
<223> OTHER INFORMATION: Primer N133SeqF4

<400> SEQUENCE: 65
aggatcgcgt ggtgagtaa                                                19

<210> SEQ ID NO 66
<211> LENGTH: 20
<212> TYPE: DNA
<213> ORGANISM: Artificial Sequence
<220> FEATURE:
<223> OTHER INFORMATION: Primer N133SeqR1

<400> SEQUENCE: 66
gtagccgtcg ttattgatga                                               20

<210> SEQ ID NO 67
<211> LENGTH: 22
<212> TYPE: DNA
<213> ORGANISM: Artificial Sequence
<220> FEATURE:
<223> OTHER INFORMATION: Primer N133SeqR2

<400> SEQUENCE: 67
gcagcgaact aatcagagat tc                                            22

<210> SEQ ID NO 68
<211> LENGTH: 19
<212> TYPE: DNA
<213> ORGANISM: Artificial Sequence
<220> FEATURE:
<223> OTHER INFORMATION: Primer N133SeqR3

<400> SEQUENCE: 68
tggtccgatg tattggagg                                                19

<210> SEQ ID NO 69
<211> LENGTH: 19
<212> TYPE: DNA
<213> ORGANISM: Artificial Sequence
<220> FEATURE:
<223> OTHER INFORMATION: Primer N133SeqR4

<400> SEQUENCE: 69
tctgccatat agctcgcgt                                                19

<210> SEQ ID NO 70
<211> LENGTH: 42
<212> TYPE: DNA
<213> ORGANISM: Artificial Sequence
<220> FEATURE:
<223> OTHER INFORMATION: Promoter 1.6GI Variant

<400> SEQUENCE: 70
gcccttgaca atgccacatc ctgagcaaat aattcaacca ct                      42
```

<210> SEQ ID NO 71
<211> LENGTH: 42
<212> TYPE: DNA
<213> ORGANISM: Artificial Sequence
<220> FEATURE:
<223> OTHER INFORMATION: Promoter 1.5GI

<400> SEQUENCE: 71
gcccttgact atgccacatc ctgagcaaat aattcaacca ct                42

<210> SEQ ID NO 72
<211> LENGTH: 18
<212> TYPE: DNA
<213> ORGANISM: Artificial Sequence
<220> FEATURE:
<223> OTHER INFORMATION: Primer Scr1

<400> SEQUENCE: 72
cctttctttg tgaatcgg                                           18

<210> SEQ ID NO 73
<211> LENGTH: 18
<212> TYPE: DNA
<213> ORGANISM: Artificial Sequence
<220> FEATURE:
<223> OTHER INFORMATION: Primer Scr2

<400> SEQUENCE: 73
agaaacaggg tgtgatcc                                           18

<210> SEQ ID NO 74
<211> LENGTH: 20
<212> TYPE: DNA
<213> ORGANISM: Artificial Sequence
<220> FEATURE:
<223> OTHER INFORMATION: Primer Scr3

<400> SEQUENCE: 74
agtgatcatc acctgttgcc                                         20

<210> SEQ ID NO 75
<211> LENGTH: 20
<212> TYPE: DNA
<213> ORGANISM: Artificial Sequence
<220> FEATURE:
<223> OTHER INFORMATION: Primer Scr4

<400> SEQUENCE: 75
agcacggcga gagtcgacgg                                         20

<210> SEQ ID NO 76
<211> LENGTH: 672
<212> TYPE: DNA
<213> ORGANISM: Saccharomyces cerevisiae

<400> SEQUENCE: 76
agttcgagtt tatcattatc aatactgcca tttcaaagaa tacgtaaata attaatagta    60
gtgattttcc taactttatt tagtcaaaaa attagccttt taattctgct gtaacccgta   120
catgcccaaa ataggggggcg ggttacacag aatatataac atcgtaggtg tctgggtgaa   180
cagtttattc ctggcatcca ctaaatataa tggagcccgc tttttaagct ggcatccaga   240
aaaaaaaaga atcccagcac caaaatattg ttttcttcac caaccatcag ttcataggtc   300

```
cattctctta gcgcaactac agagaacagg ggcacaaaca ggcaaaaaac gggcacaacc      360
tcaatggagt gatgcaacct gcctggagta aatgatgaca caaggcaatt gacccacgca      420
tgtatctatc tcattttctt acaccttcta ttaccttctg ctctctctga tttggaaaaa      480
gctgaaaaaa aaggttgaaa ccagttccct gaaattattc ccctacttga ctaataagta      540
tataaagacg gtaggtattg attgtaattc tgtaaatcta tttcttaaac ttcttaaatt      600
ctacttttat agttagtctt tttttagtt ttaaaacacc aagaacttag tttcgaataa       660
acacacataa ac                                                         672

<210> SEQ ID NO 77
<211> LENGTH: 270
<212> TYPE: DNA
<213> ORGANISM: Saccharomyces cerevisiae

<400> SEQUENCE: 77
gacctcgagt catgtaatta gttatgtcac gcttacattc acgccctccc cccacatccg      60
ctctaaccga aaaggaagga gttagacaac ctgaagtcta ggtccctatt tattttttta     120
tagttatgtt agtattaaga acgttattta tatttcaaat ttttcttttt tttctgtaca     180
gacgcgtgta cgcatgtaac attatactga aaaccttgct tgagaaggtt ttgggacgct     240
cgaaggcttt aatttgcggc cggtacccaa                                      270

<210> SEQ ID NO 78
<211> LENGTH: 1716
<212> TYPE: DNA
<213> ORGANISM: Bacillus subtilis

<400> SEQUENCE: 78
atgttgacaa aagcaacaaa agaacaaaaa tcccttgtga aaaacagagg ggcggagctt      60
gttgttgatt gcttagtgga gcaaggtgtc acacatgtat ttggcattcc aggtgcaaaa     120
attgatgcgg tatttgacgc tttacaagat aaaggacctg aaattatcgt tgcccggcac     180
gaacaaaacg cagcattcat ggcccaagca gtcggccgtt aactggaaa ccgggagtc      240 gtgttagtca catcaggacc gggtgcctct aacttggcaa caggcctgct gacagcgaac     300
actgaaggag accctgtcgt tgcgcttgct ggaaacgtga tccgtgcaga tcgtttaaaa     360
cggacacatc aatctttgga taatgcggcg ctattccagc cgattacaaa atacagtgta     420
gaagttcaag atgtaaaaaa tataccggaa gctgttacaa atgcatttag gatagcgtca     480
gcagggcagg ctggggccgc ttttgtgagc tttccgcaag atgttgtgaa tgaagtcaca     540
aatacgaaaa acgtgcgtgc tgttgcagcg ccaaaactcg gtcctgcagc agatgatgca     600
atcagtgcgg ccatagcaaa aatccaaaca gcaaaacttc ctgtcgtttt ggtcggcatg     660
aaaggcggaa gaccggaagc aattaaagcg gttcgcaagc ttttgaaaaa ggttcagctt     720
ccatttgttg aaacatatca agctgccggt accctttcta gagatttaga ggatcaatat     780
tttggccgta tcggtttgtt ccgcaaccag cctggcgatt tactgctaga gcaggcagat     840
gttgttctga cgatcggcta tgacccgatt gaatatgatc cgaaattctg gaatatcaat     900
ggagaccgga caattatcca tttagacgag attatcgctg acattgatca tgcttaccag     960
cctgatcttg aattgatcgg tgacattccg tccacgatca atcatatcga acacgatgct    1020
gtgaaagtgg aatttgcaga gcgtgagcag aaaatccttt ctgatttaaa acaatatatg    1080
catgaaggtg agcaggtgcc tgcagattgg aaatcagaca gagcgcaccc tcttgaaatc    1140
gttaaagagt tgcgtaatgc agtcgatgat catgttacag taacttgcga tatcggttcg    1200
```

```
cacgccattt ggatgtcacg ttatttccgc agctacgagc cgttaacatt aatgatcagt    1260
aacggtatgc aaacactcgg cgttgcgctt ccttgggcaa tcggcgcttc attggtgaaa    1320
ccgggagaaa aagtggtttc tgtctctggt gacggcggtt tcttattctc agcaatggaa    1380
ttagagacag cagttcgact aaaagcacca attgtacaca ttgtatggaa cgacagcaca    1440
tatgacatgg ttgcattcca gcaattgaaa aaatataacc gtacatctgc ggtcgatttc    1500
ggaaatatcg atatcgtgaa atatgcgaaa gcttcggag caactggctt gcgcgtagaa    1560
tcaccagacc agctggcaga tgttctgcgt caaggcatga acgctgaagg tcctgtcatc    1620
atcgatgtcc cggttgacta cagtgataac attaatttag caagtgacaa gcttccgaaa    1680
gaattcgggg aactcatgaa acgaaagct ctctag                              1716
```

<210> SEQ ID NO 79
<211> LENGTH: 643
<212> TYPE: DNA
<213> ORGANISM: Saccharomyces cerevisiae

<400> SEQUENCE: 79

```
gaaatgaata acaatactga cagtactaaa taattgccta cttggcttca catacgttgc      60
atacgtcgat atagataata atgataatga cagcaggatt atcgtaatac gtaatagttg     120
aaaatctcaa aaatgtgtgg gtcattacgt aaataatgat aggaatggga ttcttctatt     180 tttcctttt ccattctagc agccgtcggg aaaacgtggc atcctctctt tcgggctcaa      240
ttggagtcac gctgccgtga gcatcctctc tttccatatc taacaactga gcacgtaacc     300
aatggaaaag catgagctta gcgttgctcc aaaaaagtat tggatggtta ataccatttg     360
tctgttctct tctgactttg actcctcaaa aaaaaaaaat ctacaatcaa cagatcgctt     420
caattacgcc ctcacaaaaa ctttttttcct tcttcttcgc ccacgttaaa ttttatccct    480
catgttgtct aacggatttc tgcacttgat ttattataaa aagacaaaga cataatactt    540
ctctatcaat ttcagttatt gttcttcctt gcgttattct tctgttcttc ttttttctttt    600 gtcatatata accataacca agtaatacat attcaaatct aga                      643
```

<210> SEQ ID NO 80
<211> LENGTH: 1188
<212> TYPE: DNA
<213> ORGANISM: Saccharomyces cerevisiae

<400> SEQUENCE: 80

```
atgttgagaa ctcaagccgc cagattgatc tgcaactccc gtgtcatcac tgctaagaga      60
acctttgctt tggccacccg tgctgctgct tacagcagac cagctgcccg tttcgttaag     120
ccaatgatca ctacccgtgg tttgaagcaa atcaacttcg gtggtactgt tgaaaccgtc     180
tacgaaagag ctgactggcc aagagaaaag ttgttggact acttcaagaa cgacactttt     240
gctttgatcg gttacggttc ccaaggttac ggtcaaggtt gaacttgag agacaacggt      300 ttgaacgtta tcattggtgt ccgtaaagat ggtgcttctt ggaaggctgc catcgaagac     360
ggttgggttc caggcaagaa cttgttcact gttgaagatg ctatcaagag aggtagttac     420
gttatgaact tgttgtccga tgccgctcaa tcagaaacct ggcctgctat caagccattg     480
ttgaccaagg gtaagacttt gtacttctcc cacggtttct ccccagtctt caaggacttg     540
actcacgttg aaccaccaaa ggacttagat gttatcttgg ttgctccaaa gggttccggt     600
agaactgtca gatctttgtt caaggaaggt cgtggtatta actcttctta cgccgtctgg     660
```

```
aacgatgtca ccggtaaggc tcacgaaaag gcccaagctt tggccgttgc cattggttcc      720
ggttacgttt accaaaccac tttcgaaaga gaagtcaact ctgacttgta cggtgaaaga      780
ggttgtttaa tgggtggtat ccacggtatg ttcttggctc aatacgacgt cttgagagaa      840
aacggtcact ccccatctga agctttcaac gaaaccgtcg aagaagctac ccaatctcta      900
tacccattga tcggtaagta cggtatggat tacatgtacg atgcttgttc caccaccgcc      960
agaagaggtg ctttggactg gtacccaatc ttcaagaatg ctttgaagcc tgttttccaa     1020
gacttgtacg aatctaccaa gaacggtacc gaaaccaaga gatctttgga attcaactct     1080
caacctgact acagagaaaa gctagaaaag gaattagaca ccatcagaaa catggaaatc     1140
tggaaggttg gtaaggaagt cagaaagttg agaccagaaa accaataa                  1188
```

<210> SEQ ID NO 81
<211> LENGTH: 760
<212> TYPE: DNA
<213> ORGANISM: Saccharomyces cerevisiae

<400> SEQUENCE: 81

```
tcttttccga ttttttttcta aaccgtggaa tatttcggat atcctttttgt tgtttccggg     60 tgtacaatat ggacttcctc tttttctggca accaaaccca tacatcggga ttcctataat    120
accttcgttg gtctccctaa catgtaggtg gcggagggga gatatacaat agaacagata    180
ccagacaaga cataatgggc taaacaagac tacaccaatt acactgcctc attgatggtg    240
gtacataacg aactaatact gtagccctag acttgatagc catcatcata tcgaagtttc    300
actacccttt ttccatttgc catctattga agtaataata ggcgcatgca acttcttttc    360 ttttttttc ttttctctct cccccgttgt tgtctcacca tatccgcaat gacaaaaaaa     420
tgatggaaga cactaaagga aaaaattaac gacaaagaca gcaccaacag atgtcgttgt    480
tccagagctg atgagggta tctcgaagca cacgaaactt ttttccttcct tcattcacgc    540 acactactct ctaatgagca acggtatacg gccttccttc cagttacttg aatttgaaat    600 aaaaaaagt ttgctgtctt gctatcaagt ataaatagac ctgcaattat taatcttttg    660
tttcctcgtc attgttctcg ttcccttttct tccttgtttc tttttctgca caatatttca    720
agctatacca agcatacaat caactatctc atatacaatg                           760
```

<210> SEQ ID NO 82
<211> LENGTH: 316
<212> TYPE: DNA
<213> ORGANISM: Saccharomyces cerevisiae

<400> SEQUENCE: 82

```
gagtaagcga atttcttatg atttatgatt tttattatta aataagttat aaaaaaaata      60
agtgtataca aattttaaag tgactcttag gttttaaaac gaaaattctt attcttgagt    120
aactctttcc tgtaggtcag gttgctttct caggtatagc atgaggtcgc tcttattgac    180
cacacctcta ccggcatgcc gagcaaatgc ctgcaaatcg ctccccattt cacccaattg    240
tagatatgct aactccagca atgagttgat gaatctcggt gtgtattta tgtcctcaga    300 ggacaacacc tgtggt                                                     316
```

<210> SEQ ID NO 83
<211> LENGTH: 1758
<212> TYPE: DNA
<213> ORGANISM: Saccharomyces cerevisiae

<400> SEQUENCE: 83

```
atgggcttgt taacgaaagt tgctacatct agacaattct ctacaacgag atgcgttgca    60
aagaagctca acaagtactc gtatatcatc actgaaccta agggccaagg tgcgtcccag   120
gccatgcttt atgccaccgg tttcaagaag gaagatttca agaagcctca agtcggggtt   180
ggttcctgtt ggtggtccgg taacccatgt aacatgcatc tattggactt gaataacaga   240
tgttctcaat ccattgaaaa agcgggtttg aaagctatgc agttcaacac catcggtgtt   300
tcagacggta tctctatggg tactaaaggt atgagatact cgttacaaag tagagaaatc   360
attgcagact cctttgaaac catcatgatg gcacaacact acgatgctaa catcgccatc   420
ccatcatgtg acaaaaacat gcccggtgtc atgatggcca tgggtagaca taacagacct   480
tccatcatgg tatatggtgg tactatcttg cccggtcatc aacatgtgg ttcttcgaag    540 atctctaaaa acatcgatat cgtctctgcg ttccaatcct acggtgaata tatttccaag   600
caattcactg aagaagaaag agaagatgtt gtggaacatg catgcccagg tcctggttct   660
tgtggtggta tgtatactgc caacacaatg gcttctgccg ctgaagtgct aggttttgacc  720 attccaaact cctcttcctt cccagccgtt tccaaggaga agttagctga gtgtgacaac   780
attggtgaat acatcaagaa gacaatggaa ttgggtattt acctcgtga tatcctcaca    840 aaagaggctt ttgaaaacgc cattacttat gtcgttgcaa ccggtgggtc cactaatgct   900
gttttgcatt tggtggctgt tgctcactct gcgggtgtca agttgtcacc agatgatttc   960
caaagaatca gtgatactac accattgatc ggtgacttca accttctgg taaatacgtc   1020 atggccgatt tgattaacgt tggtggtacc caatctgtga ttaagtatct atatgaaaac  1080
aacatgttgc acggtaacac aatgactgtt accggtgaca ctttggcaga acgtgcaaag  1140
aaagcaccaa gcctacctga aggacaagag attattaagc cactctccca cccaatcaag  1200
gccaacggtc acttgcaaat tctgtacggt tcattggcac caggtggagc tgtgggtaaa  1260
attaccggta aggaaggtac ttacttcaag ggtagagcac gtgtgttcga agaggaaggt  1320
gcctttattg aagccttgga aagaggtgaa atcaagaagg gtgaaaaaac cgttgttgtt  1380
atcagatatg aaggtccaag aggtgcacca ggtatgcctg aaatgctaaa gccttcctct  1440
gctctgatgg gttacggttt gggtaaagat gttgcattgt tgactgatgg tagattctct  1500
ggtggttctc acgggttctt aatcggccac attgttcccg aagccgctga aggtggtcct  1560
atcgggttgg tcagagacgg cgatgagatt atcattgatg ctgataataa caagattgac  1620
ctattagtct ctgataagga aatggctcaa cgtaaacaaa gttgggttgc acctccacct  1680
cgttacacaa gaggtactct atccaagtat gctaagttgg tttccaacgc ttccaacggt  1740
tgtgttttag atgcttga                                                 1758
```

```
<210> SEQ ID NO 84
<211> LENGTH: 753
<212> TYPE: DNA
<213> ORGANISM: Saccharomyces cerevisiae

<400> SEQUENCE: 84
```

```
gcatgcttgc atttagtcgt gcaatgtatg actttaagat ttgtgagcag gaagaaaagg    60
gagaatcttc taacgataaa cccttgaaaa actgggtaga ctacgctatg ttgagttgct   120
acgcaggctg cacaattaca cgagaatgct cccgcctagg atttaaggct aagggacgtg   180
caatgcagac gacagatcta aatgaccgtg tcggtgaagt gttcgccaaa ctttcggtt    240 aacacatgca gtgatgcacg cgcgatggtg ctaagttaca tatatatata tatagccata   300
```

```
gtgatgtcta agtaaccttt atggtatatt tcttaatgtg gaaagatact agcgcgcgca    360
cccacacaca agcttcgtct tttcttgaag aaaagaggaa gctcgctaaa tgggattcca    420
ctttccgttc cctgccagct gatggaaaaa ggttagtgga acgatgaaga ataaaaagag    480
agatccactg aggtgaaatt tcagctgaca gcgagtttca tgatcgtgat gaacaatggt    540
aacgagttgt ggctgttgcc agggagggtg gttctcaact tttaatgtat ggccaaatcg    600
ctacttgggt tgttatata acaaagaaga aataatgaac tgattctctt cctccttctt    660
gtcctttctt aattctgttg taattacctt cctttgtaat ttttttttgta attattcttc    720 ttaataatcc aaacaaacac acatattaca ata                                  753
```

```
<210> SEQ ID NO 85
<211> LENGTH: 20
<212> TYPE: DNA
<213> ORGANISM: Artificial Sequence
<220> FEATURE:
<223> OTHER INFORMATION: Primer N98SeqF1

<400> SEQUENCE: 85
cgtgttagtc acatcaggac                                                  20

<210> SEQ ID NO 86
<211> LENGTH: 24
<212> TYPE: DNA
<213> ORGANISM: Artificial Sequence
<220> FEATURE:
<223> OTHER INFORMATION: Primer N98SeqF2

<400> SEQUENCE: 86
ggccatagca aaatccaaa cagc                                              24

<210> SEQ ID NO 87
<211> LENGTH: 24
<212> TYPE: DNA
<213> ORGANISM: Artificial Sequence
<220> FEATURE:
<223> OTHER INFORMATION: Primer N98SeqF3

<400> SEQUENCE: 87
ccacgatcaa tcatatcgaa cacg                                             24

<210> SEQ ID NO 88
<211> LENGTH: 20
<212> TYPE: DNA
<213> ORGANISM: Artificial Sequence
<220> FEATURE:
<223> OTHER INFORMATION: Primer N98SeqF4

<400> SEQUENCE: 88
ggtttctgtc tctggtgacg                                                  20

<210> SEQ ID NO 89
<211> LENGTH: 22
<212> TYPE: DNA
<213> ORGANISM: Artificial Sequence
<220> FEATURE:
<223> OTHER INFORMATION: Primer N99SeqR1

<400> SEQUENCE: 89
gtctggtgat tctacgcgca ag                                               22

<210> SEQ ID NO 90
<211> LENGTH: 22
```

```
<212> TYPE: DNA
<213> ORGANISM: Artificial Sequence
<220> FEATURE:
<223> OTHER INFORMATION: Primer N99SeqR2

<400> SEQUENCE: 90
catcgactgc attacgcaac tc                                              22

<210> SEQ ID NO 91
<211> LENGTH: 22
<212> TYPE: DNA
<213> ORGANISM: Artificial Sequence
<220> FEATURE:
<223> OTHER INFORMATION: Primer N99SeqR3

<400> SEQUENCE: 91
cgatcgtcag aacaacatct gc                                              22

<210> SEQ ID NO 92
<211> LENGTH: 20
<212> TYPE: DNA
<213> ORGANISM: Artificial Sequence
<220> FEATURE:
<223> OTHER INFORMATION: Primer N99SeqR4

<400> SEQUENCE: 92
ccttcagtgt tcgctgtcag                                                 20

<210> SEQ ID NO 93
<211> LENGTH: 36
<212> TYPE: DNA
<213> ORGANISM: Artificial Sequence
<220> FEATURE:
<223> OTHER INFORMATION: Primer N136

<400> SEQUENCE: 93
ccgcggatag atctgaaatg aataacaata ctgaca                               36

<210> SEQ ID NO 94
<211> LENGTH: 65
<212> TYPE: DNA
<213> ORGANISM: Artificial Sequence
<220> FEATURE:
<223> OTHER INFORMATION: Primer N137

<400> SEQUENCE: 94
taccaccgaa gttgatttgc ttcaacatcc tcagctctag atttgaatat gtattacttg     60
gttat                                                                 65

<210> SEQ ID NO 95
<211> LENGTH: 28
<212> TYPE: DNA
<213> ORGANISM: Artificial Sequence
<220> FEATURE:
<223> OTHER INFORMATION: Primer N138

<400> SEQUENCE: 95
atgttgaagc aaatcaactt cggtggta                                        28

<210> SEQ ID NO 96
<211> LENGTH: 22
<212> TYPE: DNA
<213> ORGANISM: Artificial Sequence
<220> FEATURE:
<223> OTHER INFORMATION: Primer N139
```

```
<400> SEQUENCE: 96
ttattggttt tctggtctca ac                                          22

<210> SEQ ID NO 97
<211> LENGTH: 57
<212> TYPE: DNA
<213> ORGANISM: Artificial Sequence
<220> FEATURE:
<223> OTHER INFORMATION: Primer N140

<400> SEQUENCE: 97
aagttgagac cagaaaacca ataattaatt aatcatgtaa ttagttatgt cacgctt    57

<210> SEQ ID NO 98
<211> LENGTH: 30
<212> TYPE: DNA
<213> ORGANISM: Artificial Sequence
<220> FEATURE:
<223> OTHER INFORMATION: Primer N141

<400> SEQUENCE: 98
gcggccgccc gcaaattaaa gccttcgagc                                  30

<210> SEQ ID NO 99
<211> LENGTH: 28
<212> TYPE: DNA
<213> ORGANISM: Artificial Sequence
<220> FEATURE:
<223> OTHER INFORMATION: Primer N142

<400> SEQUENCE: 99
ggatccgcat gcttgcattt agtcgtgc                                    28

<210> SEQ ID NO 100
<211> LENGTH: 56
<212> TYPE: DNA
<213> ORGANISM: Artificial Sequence
<220> FEATURE:
<223> OTHER INFORMATION: N143

<400> SEQUENCE: 100
caggtaatcc cccacagtat acatcctcag ctattgtaat atgtgtgttt gtttgg     56

<210> SEQ ID NO 101
<211> LENGTH: 22
<212> TYPE: DNA
<213> ORGANISM: Artificial Sequence
<220> FEATURE:
<223> OTHER INFORMATION: Primer N144

<400> SEQUENCE: 101
atgtatactg tgggggatta cc                                          22

<210> SEQ ID NO 102
<211> LENGTH: 22
<212> TYPE: DNA
<213> ORGANISM: Artificial Sequence
<220> FEATURE:
<223> OTHER INFORMATION: Primer N145

<400> SEQUENCE: 102
ttagctttta ttttgctccg ca                                          22

<210> SEQ ID NO 103
<211> LENGTH: 57
```

```
<212> TYPE: DNA
<213> ORGANISM: Artificial Sequence
<220> FEATURE:
<223> OTHER INFORMATION: Primer N146

<400> SEQUENCE: 103
tttgcggagc aaaataaaag ctaattaatt aagagtaagc gaatttctta tgattta        57

<210> SEQ ID NO 104
<211> LENGTH: 28
<212> TYPE: DNA
<213> ORGANISM: Artificial Sequence
<220> FEATURE:
<223> OTHER INFORMATION: Primer N147

<400> SEQUENCE: 104
actagtacca caggtgttgt cctctgag                                         28

<210> SEQ ID NO 105
<211> LENGTH: 22
<212> TYPE: DNA
<213> ORGANISM: Artificial Sequence
<220> FEATURE:
<223> OTHER INFORMATION: Primer N151

<400> SEQUENCE: 105
ctagagagct ttcgttttca tg                                               22

<210> SEQ ID NO 106
<211> LENGTH: 57
<212> TYPE: DNA
<213> ORGANISM: Artificial Sequence
<220> FEATURE:
<223> OTHER INFORMATION: Primer N152

<400> SEQUENCE: 106
ctcatgaaaa cgaaagctct ctagttaatt aatcatgtaa ttagttatgt cacgctt        57

<210> SEQ ID NO 107
<211> LENGTH: 25
<212> TYPE: DNA
<213> ORGANISM: Artificial Sequence
<220> FEATURE:
<223> OTHER INFORMATION: Primer N155

<400> SEQUENCE: 107
atggcaaaga agctcaacaa gtact                                            25

<210> SEQ ID NO 108
<211> LENGTH: 22
<212> TYPE: DNA
<213> ORGANISM: Artificial Sequence
<220> FEATURE:
<223> OTHER INFORMATION: Primer N156

<400> SEQUENCE: 108
tcaagcatct aaaacacaac cg                                               22

<210> SEQ ID NO 109
<211> LENGTH: 57
<212> TYPE: DNA
<213> ORGANISM: Artificial Sequence
<220> FEATURE:
<223> OTHER INFORMATION: Primer N157

<400> SEQUENCE: 109
```
aacggttgtg ttttagatgc ttgattaatt aagagtaagc gaatttctta tgattta    57

<210> SEQ ID NO 110
<211> LENGTH: 28
<212> TYPE: DNA
<213> ORGANISM: Artificial Sequence
<220> FEATURE:
<223> OTHER INFORMATION: Primer N158

<400> SEQUENCE: 110
ggatcctttt ctggcaacca aacccata    28

<210> SEQ ID NO 111
<211> LENGTH: 56
<212> TYPE: DNA
<213> ORGANISM: Artificial Sequence
<220> FEATURE:
<223> OTHER INFORMATION: Primer N159

<400> SEQUENCE: 111
cgagtacttg ttgagcttct ttgccatcct cagcgagata gttgattgta tgcttg    56

<210> SEQ ID NO 112
<211> LENGTH: 19
<212> TYPE: DNA
<213> ORGANISM: Artificial Sequence
<220> FEATURE:
<223> OTHER INFORMATION: Primer N160SeqF1

<400> SEQUENCE: 112
gaaaacgtgg catcctctc    19

<210> SEQ ID NO 113
<211> LENGTH: 19
<212> TYPE: DNA
<213> ORGANISM: Artificial Sequence
<220> FEATURE:
<223> OTHER INFORMATION: Primer N160SeqF2

<400> SEQUENCE: 113
gctgactggc caagagaaa    19

<210> SEQ ID NO 114
<211> LENGTH: 20
<212> TYPE: DNA
<213> ORGANISM: Artificial Sequence
<220> FEATURE:
<223> OTHER INFORMATION: Primer N160SeqF3

<400> SEQUENCE: 114
tgtacttctc ccacggtttc    20

<210> SEQ ID NO 115
<211> LENGTH: 22
<212> TYPE: DNA
<213> ORGANISM: Artificial Sequence
<220> FEATURE:
<223> OTHER INFORMATION: Primer N160SeqF4

<400> SEQUENCE: 115
agctacccaa tctctatacc ca    22

<210> SEQ ID NO 116
<211> LENGTH: 22
<212> TYPE: DNA
<213> ORGANISM: Artificial Sequence

```
<220> FEATURE:
<223> OTHER INFORMATION: Primer N160SeqF5

<400> SEQUENCE: 116
cctgaagtct aggtccctat tt                                              22

<210> SEQ ID NO 117
<211> LENGTH: 19
<212> TYPE: DNA
<213> ORGANISM: Artificial Sequence
<220> FEATURE:
<223> OTHER INFORMATION: N160SeqR1

<400> SEQUENCE: 117
gcgtgaatgt aagcgtgac                                                  19

<210> SEQ ID NO 118
<211> LENGTH: 20
<212> TYPE: DNA
<213> ORGANISM: Artificial Sequence
<220> FEATURE:
<223> OTHER INFORMATION: Primer N160SeqR2

<400> SEQUENCE: 118
cgtcgtattg agccaagaac                                                 20

<210> SEQ ID NO 119
<211> LENGTH: 20
<212> TYPE: DNA
<213> ORGANISM: Artificial Sequence
<220> FEATURE:
<223> OTHER INFORMATION: Primer N160SeqR3

<400> SEQUENCE: 119
gcatcggaca acaagttcat                                                 20

<210> SEQ ID NO 120
<211> LENGTH: 22
<212> TYPE: DNA
<213> ORGANISM: Artificial Sequence
<220> FEATURE:
<223> OTHER INFORMATION: Primer N160SeqR4

<400> SEQUENCE: 120
tcgttcttga agtagtccaa ca                                              22

<210> SEQ ID NO 121
<211> LENGTH: 19
<212> TYPE: DNA
<213> ORGANISM: Artificial Sequence
<220> FEATURE:
<223> OTHER INFORMATION: Primer N160SeqR5

<400> SEQUENCE: 121
tgagcccgaa agagaggat                                                  19

<210> SEQ ID NO 122
<211> LENGTH: 19
<212> TYPE: DNA
<213> ORGANISM: Artificial Sequence
<220> FEATURE:
<223> OTHER INFORMATION: Primer N161SeqF1

<400> SEQUENCE: 122
acggtatacg gccttcctt                                                  19
```

<210> SEQ ID NO 123
<211> LENGTH: 20
<212> TYPE: DNA
<213> ORGANISM: Artificial Sequence
<220> FEATURE:
<223> OTHER INFORMATION: Primer N161SeqF2

<400> SEQUENCE: 123
gggtttgaaa gctatgcagt                                              20

<210> SEQ ID NO 124
<211> LENGTH: 22
<212> TYPE: DNA
<213> ORGANISM: Artificial Sequence
<220> FEATURE:
<223> OTHER INFORMATION: Primer N161SeqF3

<400> SEQUENCE: 124
ggtggtatgt atactgccaa ca                                           22

<210> SEQ ID NO 125
<211> LENGTH: 22
<212> TYPE: DNA
<213> ORGANISM: Artificial Sequence
<220> FEATURE:
<223> OTHER INFORMATION: Primer N161SeqF4

<400> SEQUENCE: 125
ggtggtaccc aatctgtgat ta                                           22

<210> SEQ ID NO 126
<211> LENGTH: 20
<212> TYPE: DNA
<213> ORGANISM: Artificial Sequence
<220> FEATURE:
<223> OTHER INFORMATION: Primer N161SeqF5

<400> SEQUENCE: 126
cggtttgggt aaagatgttg                                              20

<210> SEQ ID NO 127
<211> LENGTH: 22
<212> TYPE: DNA
<213> ORGANISM: Artificial Sequence
<220> FEATURE:
<223> OTHER INFORMATION: Primer N161SeqF6

<400> SEQUENCE: 127
aaacgaaaat tcttattctt ga                                           22

<210> SEQ ID NO 128
<211> LENGTH: 22
<212> TYPE: DNA
<213> ORGANISM: Artificial Sequence
<220> FEATURE:
<223> OTHER INFORMATION: Primer N161SeqR1

<400> SEQUENCE: 128
tcgttttaaa acctaagagt ca                                           22

<210> SEQ ID NO 129
<211> LENGTH: 19
<212> TYPE: DNA
<213> ORGANISM: Artificial Sequence
<220> FEATURE:
<223> OTHER INFORMATION: Primer N161SeqR2

```
<400> SEQUENCE: 129
ccaaaccgta acccatcag                                                19

<210> SEQ ID NO 130
<211> LENGTH: 19
<212> TYPE: DNA
<213> ORGANISM: Artificial Sequence
<220> FEATURE:
<223> OTHER INFORMATION: Primer N161SeqR3

<400> SEQUENCE: 130
cacagattgg gtaccacca                                                19

<210> SEQ ID NO 131
<211> LENGTH: 20
<212> TYPE: DNA
<213> ORGANISM: Artificial Sequence
<220> FEATURE:
<223> OTHER INFORMATION: Primer N161Seqr4

<400> SEQUENCE: 131
accacaagaa ccaggacctg                                               20

<210> SEQ ID NO 132
<211> LENGTH: 19
<212> TYPE: DNA
<213> ORGANISM: Artificial Sequence
<220> FEATURE:
<223> OTHER INFORMATION: Primer N161SeqR5

<400> SEQUENCE: 132
catagctttc aaacccgct                                                19

<210> SEQ ID NO 133
<211> LENGTH: 22
<212> TYPE: DNA
<213> ORGANISM: Artificial Sequence
<220> FEATURE:
<223> OTHER INFORMATION: Primer N161SeqR6

<400> SEQUENCE: 133
cgtataccgt tgctcattag ag                                            22

<210> SEQ ID NO 134
<211> LENGTH: 23
<212> TYPE: DNA
<213> ORGANISM: Artificial Sequence
<220> FEATURE:
<223> OTHER INFORMATION: Primer N162

<400> SEQUENCE: 134
atgttgacaa aagcaacaaa aga                                           23

<210> SEQ ID NO 135
<211> LENGTH: 38
<212> TYPE: DNA
<213> ORGANISM: Artificial Sequence
<220> FEATURE:
<223> OTHER INFORMATION: Primer N189

<400> SEQUENCE: 135
atccgcggat agatctagtt cgagtttatc attatcaa                           38

<210> SEQ ID NO 136
```

```
<211> LENGTH: 53
<212> TYPE: DNA
<213> ORGANISM: Artificial Sequence
<220> FEATURE:
<223> OTHER INFORMATION: Primer N190.1

<400> SEQUENCE: 136
ttcttttgtt gcttttgtca acatcctcag cgtttatgtg tgtttattcg aaa          53

<210> SEQ ID NO 137
<211> LENGTH: 38
<212> TYPE: DNA
<213> ORGANISM: Artificial Sequence
<220> FEATURE:
<223> OTHER INFORMATION: Primer N176

<400> SEQUENCE: 137
atccgcggat agatctatta gaagccgccg agcgggcg                           38

<210> SEQ ID NO 138
<211> LENGTH: 31
<212> TYPE: DNA
<213> ORGANISM: Artificial Sequence
<220> FEATURE:
<223> OTHER INFORMATION: Primer N177

<400> SEQUENCE: 138
atcctcagct tttctccttg acgttaaagt a                                  31

<210> SEQ ID NO 139
<211> LENGTH: 477
<212> TYPE: PRT
<213> ORGANISM: Escherichia coli

<400> SEQUENCE: 139
```

| Met | Thr | Gln | Ser | Arg | Leu | His | Ala | Ala | Gln | Asn | Ala | Leu | Ala | Lys | Leu |
|---|---|---|---|---|---|---|---|---|---|---|---|---|---|---|---|
| 1 | | | | 5 | | | | | 10 | | | | | 15 | |

| His | Glu | His | Arg | Gly | Asn | Thr | Phe | Tyr | Pro | His | Phe | His | Leu | Ala | Pro |
|---|---|---|---|---|---|---|---|---|---|---|---|---|---|---|---|
| | | | 20 | | | | | 25 | | | | | 30 | | |

| Pro | Ala | Gly | Trp | Met | Asn | Asp | Pro | Asn | Gly | Leu | Ile | Trp | Phe | Asn | Asp |
|---|---|---|---|---|---|---|---|---|---|---|---|---|---|---|---|
| | | 35 | | | | | 40 | | | | | 45 | | | |

| Arg | Tyr | His | Ala | Phe | Tyr | Gln | His | His | Pro | Met | Ser | Glu | His | Trp | Gly |
|---|---|---|---|---|---|---|---|---|---|---|---|---|---|---|---|
| | 50 | | | | | 55 | | | | | 60 | | | | |

| Pro | Met | His | Trp | Gly | His | Ala | Thr | Ser | Asp | Asp | Met | Ile | His | Trp | Gln |
|---|---|---|---|---|---|---|---|---|---|---|---|---|---|---|---|
| 65 | | | | | 70 | | | | | 75 | | | | | 80 |

| His | Glu | Pro | Ile | Ala | Leu | Ala | Pro | Gly | Asp | Asp | Asn | Asp | Lys | Asp | Gly |
|---|---|---|---|---|---|---|---|---|---|---|---|---|---|---|---|
| | | | | 85 | | | | | 90 | | | | | 95 | |

| Cys | Phe | Ser | Gly | Ser | Ala | Val | Asp | Asp | Asn | Gly | Val | Leu | Ser | Leu | Ile |
|---|---|---|---|---|---|---|---|---|---|---|---|---|---|---|---|
| | | | | 100 | | | | | 105 | | | | | 110 | |

| Tyr | Thr | Gly | His | Val | Trp | Leu | Asp | Gly | Ala | Gly | Asn | Asp | Asp | Ala | Ile |
|---|---|---|---|---|---|---|---|---|---|---|---|---|---|---|---|
| | | | 115 | | | | | 120 | | | | | 125 | | |

| Arg | Glu | Val | Gln | Cys | Leu | Ala | Thr | Ser | Arg | Asp | Gly | Ile | His | Phe | Glu |
|---|---|---|---|---|---|---|---|---|---|---|---|---|---|---|---|
| | 130 | | | | | 135 | | | | | 140 | | | | |

| Lys | Gln | Gly | Val | Ile | Leu | Thr | Pro | Pro | Glu | Gly | Ile | Met | His | Phe | Arg |
|---|---|---|---|---|---|---|---|---|---|---|---|---|---|---|---|
| 145 | | | | | 150 | | | | | 155 | | | | | 160 |

| Asp | Pro | Lys | Val | Trp | Arg | Glu | Ala | Asp | Thr | Trp | Met | Val | Val | Gly |
|---|---|---|---|---|---|---|---|---|---|---|---|---|---|---|
| | | | | 165 | | | | | 170 | | | | | 175 |

| Ala | Lys | Asp | Pro | Gly | Asn | Thr | Gly | Gln | Ile | Leu | Leu | Tyr | Arg | Gly | Ser |
|---|---|---|---|---|---|---|---|---|---|---|---|---|---|---|---|
| | | | 180 | | | | | 185 | | | | | 190 | | |

Ser Leu Arg Glu Trp Thr Phe Asp Arg Val Leu Ala His Ala Asp Ala

```
              195                 200                 205
Gly Glu Ser Tyr Met Trp Glu Cys Pro Asp Phe Phe Ser Leu Gly Asp
210                 215                 220

Gln His Tyr Leu Met Phe Ser Pro Gln Gly Met Asn Ala Glu Gly Tyr
225                 230                 235                 240

Ser Tyr Arg Asn Arg Phe Gln Ser Gly Val Ile Pro Gly Met Trp Ser
                245                 250                 255

Pro Gly Arg Leu Phe Ala Gln Ser Gly His Phe Thr Glu Leu Asp Asn
            260                 265                 270

Gly His Asp Phe Tyr Ala Pro Gln Ser Phe Leu Ala Lys Asp Gly Arg
        275                 280                 285

Arg Ile Val Ile Gly Trp Met Asp Met Trp Glu Ser Pro Met Pro Ser
    290                 295                 300

Lys Arg Glu Gly Trp Ala Gly Cys Met Thr Leu Ala Arg Glu Leu Ser
305                 310                 315                 320

Glu Ser Asn Gly Lys Leu Leu Gln Arg Pro Val His Glu Ala Glu Ser
                325                 330                 335

Leu Arg Gln Gln His Gln Ser Val Ser Pro Arg Thr Ile Ser Asn Lys
            340                 345                 350

Tyr Val Leu Gln Glu Asn Ala Gln Ala Val Glu Ile Gln Leu Gln Trp
        355                 360                 365

Ala Leu Lys Asn Ser Asp Ala Glu His Tyr Gly Leu Gln Leu Gly Thr
    370                 375                 380

Gly Met Arg Leu Tyr Ile Asp Asn Gln Ser Glu Arg Leu Val Leu Trp
385                 390                 395                 400

Arg Tyr Tyr Pro His Glu Asn Leu Asp Gly Tyr Arg Ser Ile Pro Leu
                405                 410                 415

Pro Gln Arg Asp Thr Leu Ala Leu Arg Ile Phe Ile Asp Thr Ser Ser
            420                 425                 430

Val Glu Val Phe Ile Asn Asp Gly Glu Ala Val Met Ser Ser Arg Ile
        435                 440                 445

Tyr Pro Gln Pro Glu Glu Arg Glu Leu Ser Leu Tyr Ala Ser His Gly
    450                 455                 460

Val Ala Val Leu Gln His Gly Ala Leu Trp Leu Leu Gly
465                 470                 475

<210> SEQ ID NO 140
<211> LENGTH: 304
<212> TYPE: PRT
<213> ORGANISM: Escherichia coli

<400> SEQUENCE: 140

Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95
```

```
Phe Thr Phe Met Val Arg Pro Ser Ala Asp Leu Phe Leu Glu Thr Thr
                100                 105                 110

Asp Leu Pro Cys Trp Arg His Gly Glu Trp Leu His Leu Cys Ser Ile
            115                 120                 125

Ala Leu Ser Ala Glu Pro Ser Arg Thr Ser Ala Phe Thr Ala Met Thr
        130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Trp Arg
            180                 185                 190

Leu Ile Ser Gly Lys Thr Gln Asn Asp Gln Asp Ile Cys Ala Leu Ala
            195                 200                 205

Lys Glu Tyr Glu Ile Ala Met Leu Leu Val Thr Lys Gly Ala Glu Gly
210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
            245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
            275                 280                 285

Thr Ala Lys Gly Ala Met Thr Ala Leu Pro Cys Arg Gln Glu Leu Glu
290                 295                 300

<210> SEQ ID NO 141
<211> LENGTH: 415
<212> TYPE: PRT
<213> ORGANISM: Escherichia coli

<400> SEQUENCE: 141

Met Ala Leu Asn Ile Pro Phe Arg Asn Ala Tyr Tyr Arg Phe Ala Ser
1               5                   10                  15

Ser Tyr Ser Phe Leu Phe Ile Ser Trp Ser Leu Trp Trp Ser Leu
                20                  25                  30

Tyr Ala Ile Trp Leu Lys Gly His Leu Gly Leu Thr Gly Thr Glu Leu
            35                  40                  45

Gly Thr Leu Tyr Ser Val Asn Gln Phe Thr Ser Ile Leu Phe Met Met
        50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
                100                 105                 110

Gly Ala Leu Phe Phe Gly Leu Gly Tyr Leu Ala Gly Cys Gly Leu Leu
            115                 120                 125

Asp Ser Phe Thr Glu Lys Met Ala Arg Asn Phe His Phe Glu Tyr Gly
        130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175
```

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
            195                 200                 205

Asp Phe Ile Ala Val Phe Lys Asp Arg Asn Phe Trp Val Phe Val Ile
210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
            245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
            275                 280                 285

Ala Leu Leu Ile Gly Val Val Ile Met Ala Leu Arg Ile Leu Ser Cys
            290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
            325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
            355                 360                 365

Ile Leu Phe Asp His Ala Gly Tyr Gln Thr Val Phe Phe Ala Ile Ser
            370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
            405                 410                 415

<210> SEQ ID NO 142
<211> LENGTH: 6341
<212> TYPE: DNA
<213> ORGANISM: Artificial Sequence
<220> FEATURE:
<223> OTHER INFORMATION: Plasmid pFP988DssPspac

<400> SEQUENCE: 142
gatccaagtt taaactgtac actagatatt tcttctccgc ttaaatcatc aaagaaatct     60
ttatcacttg taaccagtcc gtccacatgt cgaattgcat ctgaccgaat tttacgtttc    120
cctgaataat tctcatcaat cgtttcatca attttatctt tatactttat attttgtgcg    180
ttaatcaaat cataattttt atatgtttcc tcatgattta tgtctttatt attatagttt    240
ttattctctc tttgattatg tctttgtatc ccgtttgtat tacttgatcc tttaactctg    300
gcaaccctca aaattgaatg agacatgcta cacctccgga ataaatat atataaacgt    360 atatagattt cataaagtct aacacactag acttatttac ttcgtaatta agtcgttaaa    420
ccgtgtgctc tacgaccaaa actataaaac ctttaagaac tttctttttt tacaagaaaa    480
aagaaattag ataaatctct catatctttt attcaataat cgcatccgat tgcagtataa    540
atttaacgat cactcatcat gttcatattt atcagagctc gtgctataat tatactaatt    600
ttataaggag gaaaaatat gggcatttt agtattttg taatcagcac agttcattat    660
caaccaaaca aaaataagt ggttataatg aatcgttaat aagcaaaatt catataacca    720

```
aattaaagag ggttataatg aacgagaaaa atataaaaca cagtcaaaac tttattactt      780
caaaacataa tatagataaa ataatgacaa atataagatt aaatgaacat gataatatct      840
ttgaaatcgg ctcaggaaaa ggccatttta cccttgaatt agtaaagagg tgtaatttcg      900
taactgccat tgaaatagac cataaattat gcaaaactac agaaaataaa cttgttgatc      960
acgataattt ccaagtttta aacaaggata tattgcagtt taaatttcct aaaaaccaat     1020
cctataaaat atatggtaat ataccttata acataagtac ggatataata cgcaaaattg     1080
tttttgatag tatagctaat gagatttatt taatcgtgga atacgggttt gctaaaagat     1140
tattaaatac aaaacgctca ttggcattac ttttaatggc agaagttgat atttctatat     1200
taagtatggt tccaagagaa tattttcatc ctaaacctaa agtgaatagc tcacttatca     1260
gattaagtag aaaaaaatca agaatatcac acaaagataa acaaaagtat aattatttcg     1320
ttatgaaatg ggttaacaaa gaatacaaga aaatatttac aaaaaatcaa tttaacaatt     1380
ccttaaaaca tgcaggaatt gacgatttaa acaatattag ctttgaacaa ttcttatctc     1440
ttttcaatag ctataaatta tttaataagt aagttaaggg atgcagttca tcgatgaagg     1500 caactcagc tcaggcgaca accatacgct gagagatcct cactacgtag aagataaagg     1560
ccacaaatac ttagtatttg aagcaaacac tggaactgaa gatggctacc aaggcgaaga     1620
atctttattt aacaaagcat actatggcaa aagcacatca ttcttccgtc aagaaagtca     1680
aaaacttctg caaagcgata aaaaacgcac ggctgagtta gcaaacggcg ctctcggtat     1740
gattgagcta aacgatgatt acacactgaa aaaagtgatg aaaccgctga ttgcatctaa     1800
cacagtaaca gatgaaattg aacgcgcgaa cgtctttaaa atgaacggca aatggtacct     1860
gttcactgac tcccgcggat caaaaatgac gattgacggc attacgtcta acgatattta     1920
catgcttggt tatgtttcta attctttaac tggcccatac aagccgctga acaaaactgg     1980
ccttgtgtta aaaatggatc ttgatcctaa cgatgtaacc tttacttact cacacttcgc     2040
tgtacctcaa gcgaaaggaa acaatgtcgt gattacaagc tatatgacaa acagaggatt     2100
ctacgcagac aaacaatcaa cgtttgcgcc aagcttgcat gcgagagtag ggaactgcca     2160
ggcatcaaat aaaacgaaag gctcagtcga aagactgggc ctttcgtttt atctgttgtt     2220
tgtcggtgaa cgctctcctg agtaggacaa atccgccggg agcggatttg aacgttgcga     2280
agcaacggcc cggagggtgg cgggcaggac gcccgccata aactgccagg catcaaatta     2340
agcagaaggc catcctgacg gatggccttt ttgcgtttct acaaactctt tttgtttatt     2400
tttctaaata cattcaaata tgtatccgct catgctccgg atctgcatcg caggatgctg     2460
ctggctaccc tgtggaacac ctacatctgt attaacgaag cgctggcatt gaccctgagt     2520
gatttttctc tggtcccgcc gcatccatac cgccagttgt ttaccctcac aacgttccag     2580
taaccgggca tgttcatcat cagtaacccg tatcgtgagc atcctctctc gtttcatcgg     2640
tatcattacc cccatgaaca gaaattcccc cttacacgga ggcatcaagt gaccaaacag     2700
gaaaaaaccg cccttaacat ggcccgcttt atcagaagcc agacattaac gcttctggag     2760
aaactcaacg agctggacgc ggatgaacag gcagacatct gtgaatcgct tcacgaccac     2820
gctgatgagc tttaccgcag ctgcctcgcg cgtttcggtg atgacggtga aaacctctga     2880
cacatgcagc tcccggagac ggtcacagct tgtctgtaag cggatgccgg gagcagacaa     2940
gcccgtcagg gcgcgtcagc gggtgttggc gggtgtcggg gcgcagccat gacccagtca     3000
cgtagcgata gcggagtgta tactggctta actatgcggc atcagagcag attgtactga     3060
```

```
gagtgcacca tatgcggtgt gaaataccgc acagatgcgt aaggagaaaa taccgcatca    3120
ggcgctcttc cgcttcctcg ctcactgact cgctgcgctc ggtcgttcgg ctgcggcgag    3180
cggtatcagc tcactcaaag gcggtaatac ggttatccac agaatcaggg gataacgcag    3240
gaaagaacat gtgagcaaaa ggccagcaaa aggccaggaa ccgtaaaaag gccgcgttgc    3300
tggcgttttt ccataggctc cgcccccctg acgagcatca caaaaatcga cgctcaagtc    3360
agaggtggcg aaacccgaca ggactataaa gataccaggc gtttccccct ggaagctccc    3420
tcgtgcgctc tcctgttccg accctgccgc ttaccggata cctgtccgcc tttctccctt    3480
cgggaagcgt ggcgctttct caatgctcac gctgtaggta tctcagttcg gtgtaggtcg    3540
ttcgctccaa gctgggctgt gtgcacgaac cccccgttca gcccgaccgc tgcgccttat    3600
ccggtaacta tcgtcttgag tccaacccgg taagacacga cttatcgcca ctggcagcag    3660
ccactggtaa caggattagc agagcgaggt atgtaggcgg tgctacagag ttcttgaagt    3720
ggtggcctaa ctacggctac actagaagga cagtatttgg tatctgcgct ctgctgaagc    3780
cagttacctt cggaaaaaga gttggtagct cttgatccgg caaacaaacc accgctggta    3840
gcggtggttt ttttgtttgc aagcagcaga ttacgcgcag aaaaaaagga tctcaagaag    3900
atcctttgat cttttctacg gggtctgacg ctcagtggaa cgaaaactca cgttaaggga    3960
ttttggtcat gagattatca aaaggatct tcacctagat ccttttaaat taaaaatgaa    4020
gttttaaatc aatctaaagt atatatgagt aaacttggtc tgacagttac caatgcttaa    4080
tcagtgaggc acctatctca gcgatctgtc tatttcgttc atccatagtt gcctgactcc    4140
ccgtcgtgta gataactacg atacgggagg gcttaccatc tggccccagt gctgcaatga    4200
taccgcgaga cccacgctca ccggctccag atttatcagc aataaaccag ccagccggaa    4260
gggccgagcg cagaagtggt cctgcaactt tatccgcctc catccagtct attaattgtt    4320
gccgggaagc tagagtaagt agttcgccag ttaatagttt gcgcaacgtt gttgccattg    4380
ctgcaggcat cgtggtgtca cgctcgtcgt ttggtatggc ttcattcagc tccgttcc     4440 aacgatcaag gcgagttaca tgatccccca tgttgtgcaa aaaagcggtt agctccttcg    4500
gtcctccgat cgttgtcaga agtaagttgg ccgcagtgtt atcactcatg gttatggcag    4560
cactgcataa ttctcttact gtcatgccat ccgtaagatg cttttctgtg actggtgagt    4620
actcaaccaa gtcattctga gaatagtgta tgcggcgacc gagttgctct tgcccggcgt    4680
caatacggga taataccgcg ccacatagca gaactttaaa agtgctcatc attggaaaac    4740
gttcttcggg gcgaaaactc tcaaggatct taccgctgtt gagatccagt tcgatgtaac    4800
ccactcgtgc acccaactga tcttcagcat cttttacttt caccagcgtt tctgggtgag    4860
caaaaacagg aaggcaaaat gccgcaaaaa agggaataag ggcgacacgg aaatgttgaa    4920
tactcatact cttcctttt caatattatt gaagcattta tcagggttat tgtctcatga    4980
gcggatacat atttgaatgt atttagaaaa ataaacaaat aggggttccg cgcacatttc    5040
cccgaaaagt gccacctgac gtctaagaaa ccattattat catgacatta acctataaaa    5100
ataggcgtat cacgaggccc tttcgtctcg cgcgtttcgg tgatgacggt gaaaacctct    5160
gacacatgca gctcccggag acggtcacag cttgtctgta gcggatgcc gggagcagac    5220 aagcccgtca gggcgcgtca gcgggtgttc atgtgcgtaa ctaacttgcc atcttcaaac    5280
aggagggctg gaagaagcag accgctaaca cagtacataa aaaaggagac atgaacgatg    5340
aacatcaaaa agtttgcaaa acaagcaaca gtattaacct ttactaccgc actgctggca    5400
ggaggcgcaa ctcaagcgtt tgcgaaagaa acgaaccaaa agccatataa ggaaacatac    5460
```

```
ggcatttccc atattacacg ccatgatatg ctgcaaatcc ctgaacagca aaaaaatgaa    5520
aaatatcaag ttcctgaatt cgattcgtcc acaattaaaa atatctcttc tgcaaaaggc    5580
ctggacgttt gggacagctg gccattacaa aacgctgacg gcactgtcgc aaactatcac    5640
ggctaccaca tcgtctttgc attagccgga gatcctaaaa atgcggatga cacatcgatt    5700
tacatgttct atcaaaaagt cggcgaaact tctattgaca gctggaaaaa cgctggccgc    5760
gtctttaaag acagcgacaa attcgatgca atgattccta tcctaaaaga ccaaacacaa    5820
gaatggtcag gttcagccac atttacatct gacggaaaaa tccgtttatt ctacactgat    5880
ttctccggta acattacgg caaacaaaca ctgacaactg cacaagttaa cgtatcagca    5940
tcagacagct ctttgaacat caacggtgta gaggattata atcaatctt tgacggtgac    6000 ggaaaaacgt atcaaaatgt acagaattcg agctctcgag taattctaca gcccagtc     6060 cagactattc ggcactgaaa ttatgggtga agtggtcaag acctcactag cgaccttaaa   6120
aatagcgcac cctgaagaag atttatttga ggtagcccct gcctacctag cttccaagaa   6180
agatatccta acagcacaag agcggaaaga tgttttgttc tacatccaga acaacctctg   6240
ctaaaattcc tgaaaaattt tgcaaaaagt tgttgacttt atctacaagg tgtggcataa   6300
tgtgtggaat tgtgagcgct cacaattaag cttgaattcc c                       6341
```

<210> SEQ ID NO 143
<211> LENGTH: 6221
<212> TYPE: DNA
<213> ORGANISM: Artificial Sequence
<220> FEATURE:
<223> OTHER INFORMATION: Plasmid pFP988DssPgroE

<400> SEQUENCE: 143

```
tcgagagcta ttgtaacata atcggtacgg gggtgaaaaa gctaacggaa aagggagcgg     60
aaaagaatga tgtaagcgtg aaaaattttt tatcttatca cttgaaattg gaagggagat    120
tctttattat aagaattgtg gaattgtgag cggataacaa ttcccaatta aaggaggaaa    180
ctagtggatc caagtttaaa ctgtacacta gatatttctt ctccgcttaa atcatcaaag    240
aaatctttat cacttgtaac cagtccgtcc acatgtcgaa ttgcatctga ccgaatttta    300
cgtttccctg aataattctc atcaatcgtt tcatcaattt tatctttata ctttatattt    360
tgtgcgttaa tcaaatcata ttttttatat gtttcctcat gatttatgtc tttattatta    420
tagtttttat tctctctttg attatgtctt tgtatcccgt tgtattact tgatccttta    480 actctggcaa ccctcaaaat tgaatgagac atgctacacc tccggataat aaatatatat    540
aaacgtatat agatttcata agtctaaca cactagactt attacttcg taattaagtc     600 gttaaccgt gtgctctacg accaaaacta taaaacctt aagaactttc ttttttaca     660 agaaaaaga aattagataa atctctcata tcttttattc aataatcgca tccgattgca    720
gtataaattt aacgatcact catcatgttc atatttatca gagctcgtgc tataattata    780
ctaattttat aaggaggaaa aaatatgggc attttttagta tttttgtaat cagcacagtt   840
cattatcaac caaacaaaaa ataagtggtt ataatgaatc gttaataagc aaaattcata    900
taaccaaatt aaagagggtt ataatgaacg agaaaaatat aaaacacagt caaaacttta    960
ttacttcaaa acataatata gataaaataa tgacaaatat aagattaaat gaacatgata   1020
atatctttga aatcggctca ggaaaaggcc attttacccc tgaattagta aagaggtgta   1080
atttcgtaac tgccattgaa atagaccata aattatgcaa aactacagaa ataaacttg     1140
```

```
ttgatcacga taatttccaa gttttaaaca aggatatatt gcagtttaaa tttcctaaaa    1200
accaatccta taaaatatat ggtaatatac cttataacat aagtacggat ataatacgca    1260
aaattgtttt tgatagtata gctaatgaga tttatttaat cgtggaatac gggtttgcta    1320
aaagattatt aaatacaaaa cgctcattgg cattactttt aatggcagaa gttgatattt    1380
ctatattaag tatggttcca agagaatatt ttcatcctaa acctaaagtg aatagctcac    1440
ttatcagatt aagtagaaaa aaatcaagaa tatcacacaa agataaacaa aagtataatt    1500
atttcgttat gaaatgggtt aacaaagaat acaagaaaat atttacaaaa aatcaattta    1560
acaattcctt aaaacatgca ggaattgacg atttaaacaa tattagcttt gaacaattct    1620
tatctctttt caatagctat aaattattta ataagtaagt taagggatgc agttcatcga    1680
tgaaggcaac tacagctcag gcgacaacca tacgctgaga gatcctcact acgtagaaga    1740
taaaggccac aaatacttag tatttgaagc aaacactgga actgaagatg ctaccaagg    1800 cgaagaatct ttatttaaca aagcatacta tggcaaaagc acatcattct tccgtcaaga    1860
aagtcaaaaa cttctgcaaa gcgataaaaa acgcacggct gagttagcaa acggcgctct    1920
cggtatgatt gagctaaacg atgattacac actgaaaaaa gtgatgaaac cgctgattgc    1980
atctaacaca gtaacagatg aaattgaacg cgcgaacgtc tttaaaatga acggcaaatg    2040
gtacctgttc actgactccc gcggatcaaa aatgacgatt gacggcatta cgtctaacga    2100
tatttacatg cttggttatg tttctaattc tttaactggc ccatacaagc cgctgaacaa    2160
aactggcctt gtgttaaaaa tggatcttga tcctaacgat gtaacctta cttactcaca    2220 cttcgctgta cctcaagcga aaggaaacaa tgtcgtgatt acaagctata tgacaaacag    2280
aggattctac gcagacaaac aatcaacgtt tgcgccaagc ttgcatgcga gagtagggaa    2340
ctgccaggca tcaaataaaa cgaaaggctc agtcgaaaga ctgggccttt cgttttatct    2400
gttgtttgtc ggtgaacgct ctcctgagta ggacaaatcc gccgggagcg gatttgaacg    2460
ttgcgaagca acgccccgga gggtggcggg caggacgccc gccataaact gccaggcatc    2520
aaattaagca gaaggccatc ctgacggatg ccttttttgc gtttctacaa actcttttg    2580 tttattttc taaatacatt caaatatgta tccgctcatg ctccggatct gcatcgcagg    2640
atgctgctgg ctaccctgtg gaacacctac atctgtatta acgaagcgct ggcattgacc    2700
ctgagtgatt tttctctggt cccgccgcat ccataccgcc agttgtttac cctcacaacg    2760
ttccagtaac cgggcatgtt catcatcagt aacccgtatc gtgagcatcc tctctcgttt    2820
catcggtatc attacccccca tgaacagaaa ttccccctta cacggaggca tcaagtgacc    2880
aaacaggaaa aaaccgccct taacatggcc cgctttatca gaagccagac attaacgctt    2940
ctggagaaac tcaacgagct ggacgcggat gaacaggcag acatctgtga atcgcttcac    3000
gaccacgctg atgagcttta ccgcagctgc ctcgcgcgtt tcggtgatga cggtgaaaac    3060
ctctgacaca tgcagctccc ggagacggtc acagcttgtc tgtaagcgga tgccgggagc    3120
agacaagccc gtcagggcgc gtcagcgggt gttggcgggt gtcggggcgc agccatgacc    3180
cagtcacgta gcgatagcgg agtgtatact ggcttaacta tgcggcatca gagcagattg    3240
tactgagagt gcaccatatg cggtgtgaaa taccgcacag atgcgtaagg agaaaatacc    3300
gcatcaggcg ctcttccgct tcctcgctca ctgactcgct gcgctcggtc gttcggctgc    3360
ggcgagcggt atcagctcac tcaaaggcgg taatacggtt atccacagaa tcaggggata    3420
acgcaggaaa gaacatgtga gcaaaaggcc agcaaaaggc caggaaccgt aaaaaggccg    3480
cgttgctggc gtttttccat aggctccgcc cccctgacga gcatcacaaa aatcgacgct    3540
```

```
caagtcagag gtggcgaaac ccgacaggac tataaagata ccaggcgttt ccccctggaa    3600
gctccctcgt gcgctctcct gttccgaccc tgccgcttac cggatacctg tccgcctttc    3660
tcccttcggg aagcgtggcg ctttctcaat gctcacgctg taggtatctc agttcggtgt    3720
aggtcgttcg ctccaagctg ggctgtgtgc acgaaccccc cgttcagccc gaccgctgcg    3780
ccttatccgg taactatcgt cttgagtcca acccggtaag acacgactta tcgccactgg    3840
cagcagccac tggtaacagg attagcagag cgaggtatgt aggcggtgct acagagttct    3900
tgaagtggtg gcctaactac ggctacacta aaggacagt atttggtatc tgcgctctgc     3960
tgaagccagt taccttcgga aaaagagttg gtagctcttg atccggcaaa caaccaccg     4020
ctggtagcgg tggttttttt gtttgcaagc agcagattac gcgcagaaaa aaggatctc     4080
aagaagatcc tttgatcttt tctacggggt ctgacgctca gtggaacgaa aactcacgtt    4140
aagggatttt ggtcatgaga ttatcaaaaa ggatcttcac ctagatcctt ttaaattaaa    4200
aatgaagttt taaatcaatc taaagtatat atgagtaaac ttggtctgac agttaccaat    4260
gcttaatcag tgaggcacct atctcagcga tctgtctatt tcgttcatcc atagttgcct    4320
gactccccgt cgtgtagata actacgatac gggagggctt accatctggc cccagtgctg    4380
caatgatacc gcgagaccca cgctcaccgg ctccagattt atcagcaata aaccagccag    4440
ccggaagggc cgagcgcaga agtggtcctg caactttatc cgcctccatc cagtctatta    4500
attgttgccg ggaagctaga gtaagtagtt cgccagttaa tagtttgcgc aacgttgttg    4560
ccattgctgc aggcatcgtg gtgtcacgct cgtcgtttgg tatggcttca ttcagctccg    4620
gttcccaacg atcaaggcga gttacatgat cccccatgtt gtgcaaaaaa gcggttagct    4680
ccttcggtcc tccgatcgtt gtcagaagta agttggccgc agtgttatca ctcatggtta    4740
tggcagcact gcataattct cttactgtca tgccatccgt aagatgcttt tctgtgactg    4800
gtgagtactc aaccaagtca ttctgagaat agtgtatgcg gcgaccgagt tgctcttgcc    4860
cggcgtcaat acgggataat accgcgccac atagcagaac tttaaaagtg ctcatcattg    4920
gaaaacgttc ttcggggcga aaactctcaa ggatcttacc gctgttgaga tccagttcga    4980
tgtaacccac tcgtgcaccc aactgatctt cagcatcttt tactttcacc agcgtttctg    5040
ggtgagcaaa aacaggaagg caaaatgccg caaaaaaggg aataagggcg acacggaaat    5100
gttgaatact catactcttc ctttttcaat attattgaag catttatcag ggttattgtc    5160
tcatgagcgg atacatattt gaatgtattt agaaaaataa acaaataggg gttccgcgca    5220
catttccccg aaaagtgcca cctgacgtct aagaaaccat tattatcatg acattaacct    5280
ataaaaatag gcgtatcacg aggccctttc gtctcgcgcg tttcggtgat gacggtgaaa    5340
acctctgaca catgcagctc ccggagacgg tcacagcttg tctgtaagcg gatgccggga    5400
gcagacaagc ccgtcagggc gcgtcagcgg gtgttcatgt gcgtaactaa cttgccatct    5460
tcaaacagga gggctggaag aagcagaccg ctaacacagt acataaaaaa ggagacatga    5520
acgatgaaca tcaaaaagtt tgcaaaacaa gcaacagtat taaccttac taccgcactg     5580
ctggcaggag gcgcaactca agcgtttgcg aaagaaacga accaaaagcc atataaggaa    5640
acatacggca tttcccatat tacacgccat gatatgctgc aaatccctga acagcaaaaa    5700
aatgaaaaat atcaagttcc tgaattcgat tcgtccacaa ttaaaaatat ctcttctgca    5760
aaaggcctgg acgtttggga cagctggcca ttacaaaacg ctgacggcac tgtcgcaaac    5820
tatcacggct accacatcgt ctttgcatta gccggagatc ctaaaaatgc ggatgacaca    5880
```

```
tcgatttaca tgttctatca aaaagtcggc gaaacttcta ttgacagctg gaaaaacgct      5940
ggccgcgtct ttaaagacag cgacaaattc gatgcaaatg attctatcct aaaagaccaa      6000
acacaagaat ggtcaggttc agccacattt acatctgacg gaaaaatccg tttattctac      6060
actgatttct ccggtaaaca ttacggcaaa caaacactga caactgcaca agttaacgta      6120
tcagcatcag acagctcttt gaacatcaac ggtgtagagg attataaatc aatctttgac      6180
ggtgacggaa aaacgtatca aaatgtacag aattcgagct c                          6221

<210> SEQ ID NO 144
<211> LENGTH: 40
<212> TYPE: DNA
<213> ORGANISM: Artificial Sequence
<220> FEATURE:
<223> OTHER INFORMATION: Primer T-budB (BamHI)

<400> SEQUENCE: 144
agatagatgg atccggaggt gggtcacatg gacaaacagt                            40

<210> SEQ ID NO 145
<211> LENGTH: 29
<212> TYPE: DNA
<213> ORGANISM: Artificial Sequence
<220> FEATURE:
<223> OTHER INFORMATION: Primer B-kivD (BamHI)

<400> SEQUENCE: 145
ctctagagga tccagactcc taggacatg                                        29

<210> SEQ ID NO 146
<211> LENGTH: 6039
<212> TYPE: DNA
<213> ORGANISM: Artificial Sequence
<220> FEATURE:
<223> OTHER INFORMATION: Vector fragment pFP988Dss

<400> SEQUENCE: 146
gatccaagtt taaactgtac actagatatt tcttctccgc ttaaatcatc aaagaaatct      60
ttatcacttg taaccagtcc gtccacatgt cgaattgcat ctgaccgaat ttacgtttc       120 cctgaataat tctcatcaat cgtttcatca atttatctt tatactttat attttgtgcg      180
ttaatcaaat cataattttt atatgttccc tcatgattta tgtctttatt attatagttt     240
ttattctctc tttgattatg tctttgtatc ccgtttgtat tacttgatcc tttaactctg     300
gcaaccctca aaattgaatg agacatgcta cacctccgga taataatat atataaacgt     360 atatagattt cataaagtct aacacactag acttatttac ttcgtaatta agtcgttaaa     420
ccgtgtgctc tacgaccaaa actataaaac ctttaagaac tttctttttt tacaagaaaa     480
aagaaattag ataaatctct catatctttt attcaataat cgcatccgat tgcagtataa     540
atttaacgat cactcatcat gttcatattt atcagagctc gtgctataat tatactaatt     600
ttataaggag gaaaaaatat gggcattttt agtattttg taatcagcac agttcattat     660
caaccaaaca aaaataagt ggttataatg aatcgttaat aagcaaaatt catataacca     720
aattaaagag ggttataatg aacgagaaaa atataaaaca cagtcaaaac tttattactt     780
caaaacataa tatagataaa ataatgacaa atataagatt aaatgaacat gataatatct     840
ttgaaatcgg ctcaggaaaa ggccatttta cccttgaatt agtaaagagg tgtaatttcg     900
taactgccat tgaaatagac cataaattat gcaaaactac agaaaataaa cttgttgatc     960
acgataattt ccaagtttta aacaaggata tattgcagtt taaatttcct aaaaaccaat    1020
```

```
cctataaaat atatggtaat ataccttata acataagtac ggatataata cgcaaaattg   1080
tttttgatag tatagctaat gagatttatt taatcgtgga atacgggttt gctaaaagat   1140
tattaaatac aaaacgctca ttggcattac ttttaatggc agaagttgat atttctatat   1200
taagtatggt tccaagagaa tattttcatc ctaaacctaa agtgaatagc tcacttatca   1260
gattaagtag aaaaaaatca agaatatcac acaaagataa acaaaagtat aattatttcg   1320
ttatgaaatg ggttaacaaa gaatacaaga aaatatttac aaaaaatcaa tttaacaatt   1380
ccttaaaaca tgcaggaatt gacgatttaa acaatattag ctttgaacaa ttcttatctc   1440
ttttcaatag ctataaatta tttaataagt aagttaaggg atgcagttca tcgatgaagg   1500
caactacagc tcaggcgaca accatacgct gagagatcct cactacgtag aagataaagg   1560
ccacaaatac ttagtatttg aagcaaacac tggaactgaa gatggctacc aaggcgaaga   1620
atctttattt aacaaagcat actatggcaa aagcacatca ttcttccgtc aagaaagtca   1680
aaaacttctg caaagcgata aaaacgcac ggctgagtta gcaaacgcg ctctcggtat   1740 gattgagcta aacgatgatt acacactgaa aaaagtgatg aaaccgctga ttgcatctaa   1800
cacagtaaca gatgaaattg aacgcgcgaa cgtcttaaa atgaacggca aatggtacct   1860
gttcactgac tcccgcggat caaaaatgac gattgacggc attacgtcta acgatattta   1920
catgcttggt tatgtttcta attctttaac tggcccatac aagccgctga acaaaactgg   1980
ccttgtgtta aaaatggatc ttgatcctaa cgatgtaacc tttacttact cacacttcgc   2040
tgtacctcaa gcgaaaggaa acaatgtcgt gattacaagc tatatgacaa acagaggatt   2100
ctacgcagac aaacaatcaa cgtttgcgcc aagcttgcat gcgagagtag ggaactgcca   2160
ggcatcaaat aaaacgaaag gctcagtcga aagactgggc ctttcgtttt atctgttgtt   2220
tgtcggtgaa cgctctcctg agtaggacaa atccgccggg agcggatttg aacgttgcga   2280
agcaacggcc cggagggtgg cgggcaggac gcccgccata aactgccagg catcaaatta   2340
agcagaaggc catcctgacg gatggccttt ttgcgtttct acaaactctt tttgttatt    2400 tttctaaata cattcaaata tgtatccgct catgctccgg atctgcatcg caggatgctg   2460
ctggctaccc tgtggaacac ctacatcgt attaacgaag cgctggcatt gaccctgagt    2520 gattttctc tggtcccgcc gcatccatac cgccagttgt ttaccctcac aacgttccag   2580
taaccgggca tgttcatcat cagtaacccg tatcgtgagc atcctctctc gtttcatcgg   2640
tatcattacc cccatgaaca gaaattcccc cttacacgga ggcatcaagt gaccaaacag   2700
gaaaaaaccg cccttaacat ggcccgcttt atcagaagcc agacattaac gcttctggag   2760
aaactcaacg agctggacgc ggatgaacag gcagacatct gtgaatcgct tcacgaccac   2820
gctgatgagc tttaccgcag ctgcctcgcg cgtttcggtg atgacggtga aaacctctga   2880
cacatgcagc tcccggagac ggtcacagct tgtctgtaag cggatgccgg gagcagacaa   2940
gcccgtcagg gcgcgtcagc gggtgttggc gggtgtcggg gcgcagccat gacccagtca   3000
cgtagcgata gcggagtgta tactggctta actatgcggc atcagagcag attgtactga   3060
gagtgcacca tatgcggtgt gaaataccgc acagatgcgt aaggagaaaa taccgcatca   3120
ggcgctcttc cgcttcctcg ctcactgact cgctgcgctc ggtcgttcgg ctgcggcgag   3180
cggtatcagc tcactcaaag gcggtaatac ggttatccac agaatcaggg gataacgcag   3240
gaaagaacat gtgagcaaaa ggccagcaaa aggccaggaa ccgtaaaaag gccgcgttgc   3300
tggcgttttt ccataggctc cgcccccctg acgagcatca caaaaatcga cgctcaagtc   3360
```

-continued

```
agaggtggcg aaacccgaca ggactataaa gataccaggc gtttcccct ggaagctccc    3420 tcgtgcgctc tcctgttccg accctgccgc ttaccggata cctgtccgcc tttctccctt    3480
cgggaagcgt ggcgctttct caatgctcac gctgtaggta tctcagttcg gtgtaggtcg    3540
ttcgctccaa gctgggctgt gtgcacgaac cccccgttca gcccgaccgc tgcgccttat    3600
ccggtaacta tcgtcttgag tccaacccgg taagacacga cttatcgcca ctggcagcag    3660
ccactggtaa caggattagc agagcgaggt atgtaggcgg tgctacagag ttcttgaagt    3720
ggtggcctaa ctacggctac actagaagga cagtatttgg tatctgcgct ctgctgaagc    3780
cagttacctt cggaaaaaga gttggtagct cttgatccgg caaacaaacc accgctggta    3840
gcggtggttt ttttgtttgc aagcagcaga ttacgcgcag aaaaaaagga tctcaagaag    3900
atcctttgat cttttctacg gggtctgacg ctcagtggaa cgaaaactca cgttaaggga    3960
ttttggtcat gagattatca aaaaggatct tcacctagat ccttttaaat taaaaatgaa    4020
gttttaaatc aatctaaagt atatatgagt aaacttggtc tgacagttac caatgcttaa    4080
tcagtgaggc acctatctca gcgatctgtc tatttcgttc atccatagtt gcctgactcc    4140
ccgtcgtgta gataactacg atacgggagg gcttaccatc tggccccagt gctgcaatga    4200
taccgcgaga cccacgctca ccggctccag atttatcagc aataaaccag ccagccggaa    4260
gggccgagcg cagaagtggt cctgcaactt tatccgcctc catccagtct attaattgtt    4320
gccgggaagc tagagtaagt agttcgccag ttaatagttt gcgcaacgtt gttgccattg    4380
ctgcaggcat cgtggtgtca cgctcgtcgt ttggtatggc ttcattcagc tccggttccc    4440
aacgatcaag gcgagttaca tgatccccca tgttgtgcaa aaaagcggtt agctccttcg    4500
gtcctccgat cgttgtcaga agtaagttgg ccgcagtgtt atcactcatg gttatggcag    4560
cactgcataa ttctcttact gtcatgccat ccgtaagatg cttttctgtg actggtgagt    4620
actcaaccaa gtcattctga atagtgta tgcggcgacc gagttgctct tgcccggcgt    4680
caatacggga taataccgcg ccacatagca gaactttaaa agtgctcatc attggaaaac    4740
gttcttcggg gcgaaaactc tcaaggatct taccgctgtt gagatccagt tcgatgtaac    4800
ccactcgtgc acccaactga tcttcagcat cttttacttt caccagcgtt tctgggtgag    4860
caaaaacagg aaggcaaaat gccgcaaaaa agggaataag ggcgacacgg aaatgttgaa    4920
tactcatact cttcctttt caatattatt gaagcattta tcagggttat tgtctcatga    4980
gcggatacat atttgaatgt atttagaaaa ataaacaaat aggggttccg cgcacatttc    5040
cccgaaaagt gccacctgac gtctaagaaa ccattattat catgacatta acctataaaa    5100
ataggcgtat cacgaggccc tttcgtctcg cgcgtttcgg tgatgacggt gaaaacctct    5160
gacacatgca gctcccggag acggtcacag cttgtctgta agcggatgcc gggagcagac    5220
aagcccgtca gggcgcgtca gcgggtgttc atgtgcgtaa ctaacttgcc atcttcaaac    5280
aggagggctg gaagaagcag accgctaaca cagtacataa aaaaggagac atgaacgatg    5340
aacatcaaaa agtttgcaaa acaagcaaca gtattaacct ttactaccgc actgctggca    5400
ggaggcgcaa ctcaagcgtt gcgaaagaa acgaaccaaa agccatataa ggaaacatac    5460
ggcatttccc atattacacg ccatgatatg ctgcaaatcc ctgaacagca aaaaatgaa    5520 aaatatcaag ttcctgaatt cgattcgtcc acaattaaaa atatctcttc tgcaaaaggc    5580
ctggacgttt gggacagctg gccattacaa aacgctgacg gcactgtcgc aaactatcac    5640
ggctaccaca tcgtctttgc attagccgga gatcctaaaa atgcggatga cacatcgatt    5700
tacatgttct atcaaaaagt cggcgaaact tctattgaca gctggaaaaa cgctggccgc    5760
```

```
gtctttaaag acagcgacaa attcgatgca aatgattcta tcctaaaaga ccaaacacaa      5820
gaatggtcag gttcagccac atttacatct gacggaaaaa tccgtttatt ctacactgat      5880
ttctccggta acattacgg caaacaaaca ctgacaactg cacaagttaa cgtatcagca       5940
tcagacagct ctttgaacat caacggtgta gaggattata aatcaatctt tgacggtgac      6000
ggaaaaacgt atcaaaatgt acagaattcg agctctcga                            6039
```

```
<210> SEQ ID NO 147
<211> LENGTH: 44
<212> TYPE: DNA
<213> ORGANISM: Artificial Sequence
<220> FEATURE:
<223> OTHER INFORMATION: Primer T-groE(XhoI)

<400> SEQUENCE: 147
agatagatct cgagagctat tgtaacataa tcggtacggg ggtg                      44

<210> SEQ ID NO 148
<211> LENGTH: 51
<212> TYPE: DNA
<213> ORGANISM: Artificial Sequence
<220> FEATURE:
<223> OTHER INFORMATION: Primer B-groEL (SpeI BamH1)

<400> SEQUENCE: 148
attatgtcag gatccactag tttcctcctt taattgggaa ttgttatccg c              51

<210> SEQ ID NO 149
<211> LENGTH: 30
<212> TYPE: DNA
<213> ORGANISM: Artificial Sequence
<220> FEATURE:
<223> OTHER INFORMATION: Primer T-groEL

<400> SEQUENCE: 149
agctattgta acataatcgg tacggggtg                                       30

<210> SEQ ID NO 150
<211> LENGTH: 45
<212> TYPE: DNA
<213> ORGANISM: Artificial Sequence
<220> FEATURE:
<223> OTHER INFORMATION: Primer T-ilvCB.s.(BamHI)

<400> SEQUENCE: 150
acattgatgg atcccataac aagggagaga ttgaaatggt aaaag                     45

<210> SEQ ID NO 151
<211> LENGTH: 47
<212> TYPE: DNA
<213> ORGANISM: Artificial Sequence
<220> FEATURE:
<223> OTHER INFORMATION: Primer B-ilvCB.s.(SpeIBamHI)

<400> SEQUENCE: 151
tagacaacgg atccactagt ttaattttgc gcaacggaga ccaccgc                   47

<210> SEQ ID NO 152
<211> LENGTH: 47
<212> TYPE: DNA
<213> ORGANISM: Artificial Sequence
<220> FEATURE:
<223> OTHER INFORMATION: Primer T-BD64 (DraIII)
```

<400> SEQUENCE: 152
ttaccgtgga ctcaccgagt gggtaactag cctcgccgga aagagcg                47

<210> SEQ ID NO 153
<211> LENGTH: 48
<212> TYPE: DNA
<213> ORGANISM: Artificial Sequence
<220> FEATURE:
<223> OTHER INFORMATION: Primer B-BD64 (DraIII)

<400> SEQUENCE: 153
tcacagttaa gacacctggt gccgttaatg cgccatgaca gccatgat              48

<210> SEQ ID NO 154
<211> LENGTH: 49
<212> TYPE: DNA
<213> ORGANISM: Artificial Sequence
<220> FEATURE:
<223> OTHER INFORMATION: Primer T-lacIq (DraIII)

<400> SEQUENCE: 154
acagatagat caccaggtgc aagctaattc cggtggaaac gaggtcatc             49

<210> SEQ ID NO 155
<211> LENGTH: 48
<212> TYPE: DNA
<213> ORGANISM: Artificial Sequence
<220> FEATURE:
<223> OTHER INFORMATION: Primer B-lacIq (DraIII)

<400> SEQUENCE: 155
acagtacgat acacggggtg tcactgcccg ctttccagtc gggaaacc              48

<210> SEQ ID NO 156
<211> LENGTH: 49
<212> TYPE: DNA
<213> ORGANISM: Artificial Sequence
<220> FEATURE:
<223> OTHER INFORMATION: Primer T-groE (DraIII)

<400> SEQUENCE: 156
tcggattacg cacccgtga gctattgtaa cataatcggt acggggtg               49

<210> SEQ ID NO 157
<211> LENGTH: 48
<212> TYPE: DNA
<213> ORGANISM: Artificial Sequence
<220> FEATURE:
<223> OTHER INFORMATION: Primer B-B.s.ilvC (DraIII)

<400> SEQUENCE: 157
ctgctgatct cacaccgtgt gttaattttg cgcaacggag accaccgc              48

<210> SEQ ID NO 158
<211> LENGTH: 1221
<212> TYPE: DNA
<213> ORGANISM: Clostridium acetobutylicum

<400> SEQUENCE: 158
cacacggtgt aaataataat ctaaacagga ggggttaaaa tggttgattt cgaatattca    60
ataccaacta gaattttttt cggtaaagat aagataaatg tacttggaag agagcttaaa   120
aaatatggtt ctaaagtgct tatagtttat ggtggaggaa gtataaagag aaatggaata   180
tatgataaag ctgtaagtat acttgaaaaa aacagtatta aattttatga acttgcagga   240

```
gtagagccaa atccaagagt aactacagtt gaaaaaggag ttaaaatatg tagagaaaat         300
ggagttgaag tagtactagc tataggtgga ggaagtgcaa tagattgcgc aaaggttata         360
gcagcagcat gtgaatatga tggaaatcca tgggatattg tgttagatgg ctcaaaaata         420
aaaagggtgc ttcctatagc tagtatatta accattgctg caacaggatc agaaatggat         480
acgtgggcag taataaataa tatggataca aacgaaaaac taattgcggc acatccagat         540
atggctccta agttttctat attagatcca acgtatacgt ataccgtacc taccaatcaa         600
acagcagcag gaacagctga tattatgagt catatatttg aggtgtattt tagtaataca         660
aaaacagcat atttgcagga tagaatgcga gaagcgttat taagaacttg tattaaatat         720
ggaggaatag ctcttgagaa gccggatgat tatgaggcaa gagccaatct aatgtgggct         780
tcaagtcttg cgataaatgg acttttaaca tatggtaaag cactaattg gagtgtacac          840 ttaatggaac atgaattaag tgcttattac gacataacac acggcgtagg gcttgcaatt         900
ttaacaccta attggatgga gtatatttta aataatgata cagtgtacaa gtttgttgaa         960
tatggtgtaa atgtttgggg aatagacaaa gaaaaaaatc actatgacat agcacatcaa        1020
gcaatacaaa aaacaagaga ttactttgta aatgtactag gtttaccatc tagactgaga        1080
gatgttggaa ttgaagaaga aaaattggac ataatggcaa aggaatcagt aaagcttaca        1140
ggaggaacca taggaaacct aagaccagta acgcctccg aagtcctaca aatattcaaa         1200
aaatctgtgt aacaccgagt g                                                  1221

<210> SEQ ID NO 159
<211> LENGTH: 54
<212> TYPE: DNA
<213> ORGANISM: Artificial Sequence
<220> FEATURE:
<223> OTHER INFORMATION: Primer T-bdhB (DraIII)

<400> SEQUENCE: 159
tcgatagcat acacacggtg gttaacaaag gagggggttaa aatggttgat ttcg             54

<210> SEQ ID NO 160
<211> LENGTH: 91
<212> TYPE: DNA
<213> ORGANISM: Artificial Sequence
<220> FEATURE:
<223> OTHER INFORMATION: Primer B-bdhB (rrnBT1DraIII)

<400> SEQUENCE: 160
atctacgcac tcggtgataa aacgaaaggc ccagtctttc gactgagcct ttcgttttat         60
cttacacaga ttttttgaat atttgtagga c                                       91

<210> SEQ ID NO 161
<211> LENGTH: 29
<212> TYPE: DNA
<213> ORGANISM: Artificial Sequence
<220> FEATURE:
<223> OTHER INFORMATION: Primer LDH EcoRV F

<400> SEQUENCE: 161
gacgtcatga ccacccgccg atccctttt                                          29

<210> SEQ ID NO 162
<211> LENGTH: 30
<212> TYPE: DNA
<213> ORGANISM: Artificial Sequence
<220> FEATURE:
```

<223> OTHER INFORMATION: Primer LDH AatIIR

<400> SEQUENCE: 162
gatatccaac accagcgacc gacgtattac                                30

<210> SEQ ID NO 163
<211> LENGTH: 47
<212> TYPE: DNA
<213> ORGANISM: Artificial Sequence
<220> FEATURE:
<223> OTHER INFORMATION: Primer Cm F

<400> SEQUENCE: 163
atttaaatct cgagtagagg atcccaacaa acgaaaattg gataaag             47

<210> SEQ ID NO 164
<211> LENGTH: 29
<212> TYPE: DNA
<213> ORGANISM: Artificial Sequence
<220> FEATURE:
<223> OTHER INFORMATION: Primer Cm R

<400> SEQUENCE: 164
acgcgttatt ataaaagcca gtcattagg                                 29

<210> SEQ ID NO 165
<211> LENGTH: 58
<212> TYPE: DNA
<213> ORGANISM: Artificial Sequence
<220> FEATURE:
<223> OTHER INFORMATION: Primer P11 F-StuI

<400> SEQUENCE: 165
cctagcgcta tagttgttga cagaatggac atactatgat atattgttgc tatagcga   58

<210> SEQ ID NO 166
<211> LENGTH: 62
<212> TYPE: DNA
<213> ORGANISM: Artificial Sequence
<220> FEATURE:
<223> OTHER INFORMATION: Primer P11 R-SpeI

<400> SEQUENCE: 166
ctagtcgcta tagcaacaat atatcatagt atgtccattc tgtcaacaac tatagcgcta   60
gg                                                              62

<210> SEQ ID NO 167
<211> LENGTH: 38
<212> TYPE: DNA
<213> ORGANISM: Artificial Sequence
<220> FEATURE:
<223> OTHER INFORMATION: Primer PldhL F-HindIII

<400> SEQUENCE: 167
aagcttgtcg acaaaccaac attatgacgt gtctgggc                       38

<210> SEQ ID NO 168
<211> LENGTH: 28
<212> TYPE: DNA
<213> ORGANISM: Artificial Sequence
<220> FEATURE:
<223> OTHER INFORMATION: Primer PldhL R-BamHI

<400> SEQUENCE: 168
ggatcctcat cctctcgtag tgaaaatt                                  28

<210> SEQ ID NO 169
<211> LENGTH: 36
<212> TYPE: DNA
<213> ORGANISM: Artificial Sequence
<220> FEATURE:
<223> OTHER INFORMATION: Primer F-bdhB-AvrII

<400> SEQUENCE: 169
ttcctaggaa ggaggtggtt aaaatggttg atttcg                    36

<210> SEQ ID NO 170
<211> LENGTH: 29
<212> TYPE: DNA
<213> ORGANISM: Artificial Sequence
<220> FEATURE:
<223> OTHER INFORMATION: Primer R-bdhB-BamHI

<400> SEQUENCE: 170
ttggatcctt acacagattt tttgaatat                            29

<210> SEQ ID NO 171
<211> LENGTH: 39
<212> TYPE: DNA
<213> ORGANISM: Artificial Sequence
<220> FEATURE:
<223> OTHER INFORMATION: Primer F-ilvC(B.s.)-AflII

<400> SEQUENCE: 171
aacttaagaa ggaggtgatt gaaatggtaa aagtatatt                 39

<210> SEQ ID NO 172
<211> LENGTH: 32
<212> TYPE: DNA
<213> ORGANISM: Artificial Sequence
<220> FEATURE:
<223> OTHER INFORMATION: Primer R-ilvC(B.s.)-NotI

<400> SEQUENCE: 172
aagcggccgc ttaattttgc gcaacggaga cc                        32

<210> SEQ ID NO 173
<211> LENGTH: 30
<212> TYPE: DNA
<213> ORGANISM: Artificial Sequence
<220> FEATURE:
<223> OTHER INFORMATION: Primer F-PnisA(HindIII)

<400> SEQUENCE: 173
ttaagcttga catacttgaa tgacctagtc                           30

<210> SEQ ID NO 174
<211> LENGTH: 39
<212> TYPE: DNA
<213> ORGANISM: Artificial Sequence
<220> FEATURE:
<223> OTHER INFORMATION: Primer R-PnisA(SpeI BamHI)

<400> SEQUENCE: 174
ttggatccaa actagtataa tttattttgt agttccttc                 39

<210> SEQ ID NO 175
<211> LENGTH: 38
<212> TYPE: DNA
<213> ORGANISM: Artificial Sequence
<220> FEATURE:

<223> OTHER INFORMATION: Primer N191

<400> SEQUENCE: 175
atccgcggat agatctccca ttaccgacat ttgggcgc        38

<210> SEQ ID NO 176
<211> LENGTH: 31
<212> TYPE: DNA
<213> ORGANISM: Artificial Sequence
<220> FEATURE:
<223> OTHER INFORMATION: Primer N192

<400> SEQUENCE: 176
atcctcagcg atgattgatt gattgattgt a        31

<210> SEQ ID NO 177
<211> LENGTH: 6509
<212> TYPE: DNA
<213> ORGANISM: Artificial Sequence
<220> FEATURE:
<223> OTHER INFORMATION: Vector pFP988

<400> SEQUENCE: 177
tcgaggcccc gcacatacga aaagactggc tgaaaacatt gagcctttga tgactgatga        60
tttggctgaa gaagtggatc gattgtttga gaaagaaga agaccataaa ataccttgt        120 ctgtcatcag acagggtatt ttttatgctg tccagactgt ccgctgtgta aaaatagga        180 ataaaggggg gttgttatta ttttactgat atgtaaaata aatttgtat aaggaattgt        240 gagcggataa caattcctac gaaaatgaga gggagaggaa acatgattca aaaacgaaag        300
cggacagttt cgttcagact tgtgcttatg tgcacgctgt tatttgtcag tttgccgatt        360
acaaaaacat cagccggatc ccaccatcac catcaccatt aagaattcct agaaactcca        420
agctatcttt aaaaaatcta gtaaatgcac gagcaacatc ttttgttgct cagtgcattt        480 tttatttgt acactagata tttcttctcc gcttaaatca tcaaagaaat ctttatcact        540
tgtaaccagt ccgtccacat gtcgaattgc atctgaccga attttacgtt tccctgaata        600
attctcatca atcgtttcat caatttatc tttatacttt atattttgtg cgttaatcaa        660
atcataattt ttatatgttt cctcatgatt tatgtcttta ttattatagt ttttattctc        720
tctttgatta tgtctttgta tcccgtttgt attacttgat cctttaactc tggcaaccct        780
caaaattgaa tgagacatgc tacacctccg gataataaat atatataaac gtatatagat        840
ttcataaagt ctaacacact agacttattt acttcgtaat taagtcgtta aaccgtgtgc        900
tctacgacca aaactataaa acctttaaga actttctttt tttacaagaa aaaagaaatt        960
agataaatct ctcatatctt ttattcaata atcgcatccg attgcagtat aaatttaacg        1020
atcactcatc atgttcatat ttatcagagc tcgtgctata attatactaa ttttataagg        1080
aggaaaaaat atgggcattt ttagtatttt tgtaatcagc acagttcatt atcaaccaaa        1140
caaaaaataa gtggttataa tgaatcgtta ataagcaaaa ttcatataac caaattaaag        1200
agggttataa tgaacgagaa aaatataaaa cacagtcaaa actttattac ttcaaaacat        1260
aatatagata aaataatgac aaatataaga ttaaatgaac atgataatat ctttgaaatc        1320
ggctcaggaa aaggccattt taccccttgaa ttagtaaaga ggtgtaattt cgtaactgcc        1380
attgaaatag accataaatt atgcaaaact acagaaaata aacttgttga tcacgataat        1440
ttccaagttt taacaagga tatattgcag tttaaatttc ctaaaaacca atcctataaa        1500
atatatggta atataccttta aacataagt acggatataa tacgcaaaat tgttttttgat        1560

```
agtatagcta atgagattta tttaatcgtg aatacgggt ttgctaaaag attattaaat   1620
acaaaacgct cattggcatt acttttaatg gcagaagttg atatttctat attaagtatg   1680
gttccaagag aatattttca tcctaaacct aaagtgaata gctcacttat cagattaagt   1740
agaaaaaaat caagaatatc acacaaagat aaacaaaagt ataattattt cgttatgaaa   1800
tgggttaaca aagaatacaa gaaatatttt acaaaaaatc aatttaacaa ttccttaaaa   1860
catgcaggaa ttgacgattt aaacaatatt agctttgaac aattcttatc tcttttcaat   1920
agctataaat tatttaataa gtaagttaag ggatgcagtt catcgatgaa ggcaactaca   1980
gctcaggcga caaccatacg ctgagagatc ctcactacgt agaagataaa ggccacaaat   2040
acttagtatt tgaagcaaac actggaactg aagatggcta ccaaggcgaa gaatctttat   2100
ttaacaaagc atactatggc aaaagcacat cattcttccg tcaagaaagt caaaaacttc   2160
tgcaaagcga taaaaacgc acggctgagt tagcaaacgg cgctctcggt atgattgagc   2220
taaacgatga ttcacactg aaaaaagtga tgaaaccgct gattgcatct aacacagtaa   2280
cagatgaaat tgaacgcgcg aacgtcttta aaatgaacgg caaatggtac ctgttcactg   2340
actcccgcgg atcaaaaatg acgattgacg gcattacgtc taacgatatt tacatgcttg   2400
gttatgtttc taattcttta actggcccat acaagccgct gaacaaaact ggccttgtgt   2460
taaaaatgga tcttgatcct aacgatgtaa cctttactta ctcacacttc gctgtacctc   2520
aagcgaaagg aaacaatgtc gtgattacaa gctatatgac aaacagagga ttctacgcag   2580
acaaacaatc aacgtttgcg ccaagcttgc atgcgagagt agggaactgc caggcatcaa   2640
ataaaacgaa aggctcagtc gaaagactgg gcctttcgtt ttatctgttg tttgtcggtg   2700
aacgctctcc tgagtaggac aaatccgccg ggagcggatt tgaacgttgc gaagcaacgg   2760
cccggagggt ggcgggcagg acgcccgcca taaactgcca ggcatcaaat taagcagaag   2820
gccatcctga cggatggcct ttttgcgttt ctacaaactc ttttttgttta tttttctaaa   2880
tacattcaaa tatgtatccg ctcatgctcc ggatctgcat cgcaggatgc tgctggctac   2940
cctgtggaac acctacatct gtattaacga agcgctggca ttgaccctga gtgatttttc   3000
tctggtcccg ccgcatccat accgccagtt gtttaccctc acaacgttcc agtaaccggg   3060
catgttcatc atcagtaacc cgtatcgtga gcatcctctc tcgtttcatc ggtatcatta   3120
cccccatgaa cagaaattcc cccttacacg gaggcatcaa gtgaccaaac aggaaaaaac   3180
cgcccttaac atggcccgct ttatcagaag ccagacatta acgcttctgg agaaactcaa   3240
cgagctggac gcggatgaac aggcagacat ctgtgaatcg cttcacgacc acgctgatga   3300
gctttaccgc agctgcctcg cgcgtttcgg tgatgacggt gaaaacctct gacacatgca   3360
gctcccggag acgtcacag cttgtctgta gcggatgcc gggagcagac aagcccgtca   3420
gggcgcgtca gcgggtgttg gcgggtgtcg gggcgcagcc atgacccagt cacgtagcga   3480
tagcggagtg tatactggct taactatgcg gcatcagagc agattgtact gagagtgcac   3540
catatgcggt gtgaaatacc gcacagatgc gtaaggagaa ataccgcat caggcgctct   3600
tccgcttcct cgctcactga ctcgctgcgc tcggtcgttc ggctgcggcg agcggtatca   3660
gctcactcaa aggcggtaat acggttatcc acagaatcag gggataacgc aggaaagaac   3720
atgtgagcaa aaggccagca aaaggccagg aaccgtaaaa aggccgcgtt gctggcgttt   3780
ttccataggc tccgcccccc tgacgagcat cacaaaaatc gacgctcaag tcagaggtgg   3840
cgaaacccga caggactata aagataccag gcgtttcccc ctggaagctc cctcgtgcgc   3900
```

```
tctcctgttc cgaccctgcc gcttaccgga tacctgtccg cctttctccc ttcgggaagc     3960
gtggcgcttt ctcaatgctc acgctgtagg tatctcagtt cggtgtaggt cgttcgctcc     4020
aagctgggct gtgtgcacga acccccgtt cagcccgacc gctgcgcctt atccggtaac      4080
tatcgtcttg agtccaaccc ggtaagacac gacttatcgc cactggcagc agccactggt     4140
aacaggatta gcagagcgag gtatgtaggc ggtgctacag agttcttgaa gtggtggcct     4200
aactacggct acactagaag gacagtattt ggtatctgcg ctctgctgaa gccagttacc     4260
ttcggaaaaa gagttggtag ctcttgatcc ggcaaacaaa ccaccgctgg tagcggtggt     4320 tttttgttt gcaagcagca gattacgcgc agaaaaaaag gatctcaaga agatcctttg      4380
atcttttcta cggggtctga cgctcagtgg aacgaaaact cacgttaagg gattttggtc     4440
atgagattat caaaaggat cttcacctag atccttttaa attaaaaatg aagttttaaa      4500
tcaatctaaa gtatatatga gtaaacttgg tctgacagtt accaatgctt aatcagtgag     4560
gcacctatct cagcgatctg tctatttcgt tcatccatag ttgcctgact ccccgtcgtg     4620
tagataacta cgatacggga gggcttacca tctggcccca gtgctgcaat gataccgcga     4680
gacccacgct caccggctcc agatttatca gcaataaacc agccagccgg aagggccgag     4740
cgcagaagtg gtcctgcaac tttatccgcc tccatccagt ctattaattg ttgccgggaa     4800
gctagagtaa gtagttcgcc agttaatagt ttgcgcaacg ttgttgccat tgctgcaggc     4860
atcgtggtgt cacgctcgtc gtttggtatg gcttcattca gctccggttc ccaacgatca     4920
aggcgagtta catgatcccc catgttgtgc aaaaaagcgg ttagctcctt cggtcctccg     4980
atcgttgtca gaagtaagtt ggccgcagtg ttatcactca tggttatggc agcactgcat     5040
aattctctta ctgtcatgcc atccgtaaga tgcttttctg tgactggtga gtactcaacc     5100
aagtcattct gagaatagtg tatgcggcga ccgagttgct cttgcccggc gtcaatacgg     5160
gataataccg cgccacatag cagaacttta aaagtgctca tcattggaaa acgttcttcg     5220
gggcgaaaac tctcaaggat cttaccgctg ttgagatcca gttcgatgta acccactcgt     5280
gcacccaact gatcttcagc atcttttact ttcaccagcg tttctgggtg agcaaaaaca     5340
ggaaggcaaa atgccgcaaa aaagggaata agggcgacac ggaaatgttg aatactcata     5400
ctcttccttt ttcaatatta ttgaagcatt tatcagggtt attgtctcat gagcggatac     5460
atatttgaat gtatttagaa aaataaacaa ataggggttc cgcgcacatt tccccgaaaa     5520
gtgccacctg acgtctaaga accattatt atcatgacat taacctataa aaataggcgt     5580
atcacgaggc cctttcgtct cgcgcgtttc ggtgatgacg gtgaaaacct ctgacacatg     5640
cagctcccgg agacggtcac agcttgtctg taagcggatg ccgggagcag acaagcccgt     5700
cagggcgcgt cagcgggtgt tcatgtgcgt aactaacttg ccatcttcaa acaggagggc     5760
tggaagaagc agaccgctaa cacagtacat aaaaaaggag acatgaacga tgaacatcaa     5820
aaagtttgca aaacaagcaa cagtattaac ctttactacc gcactgctgg caggaggcgc     5880
aactcaagcg tttgcgaaag aaacgaacca aaagccatat aaggaaacat acggcatttc     5940
ccatattaca cgccatgata tgctgcaaat ccctgaacag caaaaaaatg aaaaatatca     6000
agttcctgaa ttcgattcgt ccacaattaa aaatatctct tctgcaaaag gcctggacgt     6060
ttgggacagc tggccattac aaaacgctga cggcactgtc gcaaactatc acggctacca     6120
catcgtcttt gcattagccg gagatcctaa aaatgcggat gacacatcga tttacatgtt     6180
ctatcaaaaa gtcggcgaaa cttctattga cagctggaaa aacgctggcc gcgtctttaa     6240
agacagcgac aaattcgatg caaatgattc tatcctaaaa gaccaaacac aagaatggtc     6300
```

-continued

```
aggttcagcc acatttacat ctgacggaaa aatccgttta ttctacactg atttctccgg    6360
taaacattac ggcaaacaaa cactgacaac tgcacaagtt aacgtatcag catcagacag    6420
ctctttgaac atcaacggtg tagaggatta taaatcaatc tttgacggtg acggaaaaac    6480
gtatcaaaat gtacagcatg ccacgcgtc                                      6509
```

<210> SEQ ID NO 178
<211> LENGTH: 571
<212> TYPE: PRT
<213> ORGANISM: Bacillus subtilis

<400> SEQUENCE: 178

```
Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335
```

```
Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 179
<211> LENGTH: 1665
<212> TYPE: DNA
<213> ORGANISM: Lactococcus lactis

<400> SEQUENCE: 179
atgtctgaga acaatttggg ggcgaacttg gttgtcgata gtttgattaa ccataaagtg     60
aagtatgtat ttgggattcc aggagcaaaa attgaccggg tttttgattt attagaaaat    120
gaagaaggcc ctcaaatggt cgtgactcgt catgagcaag agctgctttc atggctcaa    180 gctgtcggtc gtttaactgg cgaacctggt gtagtagttg ttacgagtgg gcctggtgta    240
tcaaaccttg cgactccgct tttgaccgcg acatcagaag gtgatgctat tttggctatc    300
ggtggacaag ttaaacgaag tgaccgtctt aaacgtgcgc accaatcaat ggataatgct    360
ggaatgatgc aatcagcaac aaaatattca gcagaagttc ttgaccctaa tacactttct    420
gaatcaattg ccaacgctta tcgtattgca aaatcaggac atccaggtgc aactttctta    480
tcaatccccc aagatgtaac ggatgccgaa gtatcaatca agccattca accactttca    540 gaccctaaaa tggggaatgc ctctattgat gacattaatt atttagcaca agcaattaaa    600
aatgctgtat tgccagtaat tttggttgga gctggtgctt cagatgctaa agtcgcttca    660
tccttgcgta atctattgac tcatgttaat attcctgtcg ttgaaacatt ccaaggtgca    720
ggggttattt cacatgattt agaacatact ttttatggac gtatcggtct tttccgcaat    780
```

```
caaccaggcg atatgcttct gaaacgttct gaccttgtta ttgctgttgg ttatgaccca    840
attgaatatg aagctcgtaa ctggaatgca gaaattgata gtcgaattat cgttattgat    900
aatgccattg ctgaaattga tacttactac caaccagagc gtgaattaat tggtgatatc    960
gcagcaacat tggataatct tttaccagct gttcgtggct acaaaattcc aaaaggaaca   1020
aaagattatc tcgatggcct tcatgaagtt gctgagcaac acgaatttga tactgaaaat   1080
actgaagaag gtagaatgca ccctcttgat tggtcagca ctttccaaga aatcgtcaag   1140
gatgatgaaa cagtaaccgt tgacgtaggt tcactctaca tttggatggc acgtcatttc   1200
aaatcatacg aaccacgtca tctcctcttc tcaaacggaa tgcaaacact cggagttgca   1260
cttccttggg caattacagc cgcattgttg cgcccaggta aaaaagttta ttcacactct   1320
ggtgatggag gcttcctttt cacagggcaa gaattggaaa cagctgtacg tttgaatctt   1380
ccaatcgttc aaattatctg gaatgacggc cattatgata tggttaaatt ccaagaagaa   1440
atgaaatatg gtcgttcagc agccgttgat tttggctatg ttgattacgt aaaatatgct   1500
gaagcaatga gagcaaaagg ttaccgtgca cacagcaaag aagaacttgc tgaaattctc   1560
aaatcaatcc cagatactac tggaccggtg gtaattgacg ttcctttgga ctattctgat   1620
aacattaaat tagcagaaaa attattgcct gaagagtttt attga                   1665
```

<210> SEQ ID NO 180
<211> LENGTH: 554
<212> TYPE: PRT
<213> ORGANISM: Lactococcus lactis

<400> SEQUENCE: 180

```
Met Ser Glu Lys Gln Phe Gly Ala Asn Leu Val Val Asp Ser Leu Ile
1               5                   10                  15

Asn His Lys Val Lys Tyr Val Phe Gly Ile Pro Gly Ala Lys Ile Asp
            20                  25                  30

Arg Val Phe Asp Leu Leu Glu Asn Glu Gly Pro Gln Met Val Val
        35                  40                  45

Thr Arg His Glu Gln Gly Ala Ala Phe Met Ala Gln Ala Val Gly Arg
    50                  55                  60

Leu Thr Gly Glu Pro Gly Val Val Val Thr Ser Gly Pro Gly Val
65                  70                  75                  80

Ser Asn Leu Ala Thr Pro Leu Leu Thr Ala Thr Ser Glu Gly Asp Ala
                85                  90                  95

Ile Leu Ala Ile Gly Gly Gln Val Lys Arg Ser Asp Arg Leu Lys Arg
            100                 105                 110

Ala His Gln Ser Met Asp Asn Ala Gly Met Met Gln Ser Ala Thr Lys
        115                 120                 125

Tyr Ser Ala Glu Val Leu Asp Pro Asn Thr Leu Ser Glu Ser Ile Ala
    130                 135                 140

Asn Ala Tyr Arg Ile Ala Lys Ser Gly His Pro Gly Ala Thr Phe Leu
145                 150                 155                 160

Ser Ile Pro Gln Asp Val Thr Asp Ala Glu Val Ser Ile Lys Ala Ile
                165                 170                 175

Gln Pro Leu Ser Asp Pro Lys Met Gly Asn Ala Ser Ile Asp Asp Ile
            180                 185                 190

Asn Tyr Leu Ala Gln Ala Ile Lys Asn Ala Val Leu Pro Val Ile Leu
        195                 200                 205

Val Gly Ala Gly Ala Ser Asp Ala Lys Val Ala Ser Ser Leu Arg Asn
```

```
                210                 215                 220
Leu Leu Thr His Val Asn Ile Pro Val Glu Thr Phe Gln Gly Ala
225                 230                 235                 240

Gly Val Ile Ser His Asp Leu Glu His Thr Phe Tyr Gly Arg Ile Gly
                245                 250                 255

Leu Phe Arg Asn Gln Pro Gly Asp Met Leu Leu Lys Arg Ser Asp Leu
                260                 265                 270

Val Ile Ala Val Gly Tyr Asp Pro Ile Glu Tyr Glu Ala Arg Asn Trp
                275                 280                 285

Asn Ala Glu Ile Asp Ser Arg Ile Ile Val Ile Asp Asn Ala Ile Ala
                290                 295                 300

Glu Ile Asp Thr Tyr Tyr Gln Pro Glu Arg Glu Leu Ile Gly Asp Ile
305                 310                 315                 320

Ala Ala Thr Leu Asp Asn Leu Leu Pro Ala Val Arg Gly Tyr Lys Ile
                325                 330                 335

Pro Lys Gly Thr Lys Asp Tyr Leu Asp Gly Leu His Glu Val Ala Glu
                340                 345                 350

Gln His Glu Phe Asp Thr Glu Asn Thr Glu Glu Gly Arg Met His Pro
                355                 360                 365

Leu Asp Leu Val Ser Thr Phe Gln Glu Ile Val Lys Asp Asp Glu Thr
370                 375                 380

Val Thr Val Asp Val Gly Ser Leu Tyr Ile Trp Met Ala Arg His Phe
385                 390                 395                 400

Lys Ser Tyr Glu Pro Arg His Leu Leu Phe Ser Asn Gly Met Gln Thr
                405                 410                 415

Leu Gly Val Ala Leu Pro Trp Ala Ile Thr Ala Ala Leu Leu Arg Pro
                420                 425                 430

Gly Lys Lys Val Tyr Ser His Ser Gly Asp Gly Phe Leu Phe Thr
                435                 440                 445

Gly Gln Glu Leu Glu Thr Ala Val Arg Leu Asn Leu Pro Ile Val Gln
450                 455                 460

Ile Ile Trp Asn Asp Gly His Tyr Asp Met Val Lys Phe Gln Glu Glu
465                 470                 475                 480

Met Lys Tyr Gly Arg Ser Ala Ala Val Asp Phe Gly Tyr Val Asp Tyr
                485                 490                 495

Val Lys Tyr Ala Glu Ala Met Arg Ala Lys Gly Tyr Arg Ala His Ser
                500                 505                 510

Lys Glu Glu Leu Ala Glu Ile Leu Lys Ser Ile Pro Asp Thr Thr Gly
                515                 520                 525

Pro Val Val Ile Asp Val Pro Leu Asp Tyr Ser Asp Asn Ile Lys Leu
530                 535                 540

Ala Glu Lys Leu Leu Pro Glu Glu Phe Tyr
545                 550

<210> SEQ ID NO 181
<211> LENGTH: 395
<212> TYPE: PRT
<213> ORGANISM: Saccharomyces cerevisiae

<400> SEQUENCE: 181

Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
                20                  25                  30
```

Arg Pro Ala Ala Arg Phe Val Lys Pro Met Ile Thr Thr Arg Gly Leu
                35                  40                  45

Lys Gln Ile Asn Phe Gly Gly Thr Val Glu Thr Val Tyr Glu Arg Ala
 50                  55                  60

Asp Trp Pro Arg Glu Lys Leu Leu Asp Tyr Phe Lys Asn Asp Thr Phe
 65                  70                  75                  80

Ala Leu Ile Gly Tyr Gly Ser Gln Gly Tyr Gly Gln Gly Leu Asn Leu
                 85                  90                  95

Arg Asp Asn Gly Leu Asn Val Ile Gly Val Arg Lys Asp Gly Ala
                100                 105                 110

Ser Trp Lys Ala Ala Ile Glu Asp Gly Trp Val Pro Gly Lys Asn Leu
                115                 120                 125

Phe Thr Val Glu Asp Ala Ile Lys Arg Gly Ser Tyr Val Met Asn Leu
                130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
                180                 185                 190

Leu Val Ala Pro Lys Gly Ser Gly Arg Thr Val Arg Ser Leu Phe Lys
                195                 200                 205

Glu Gly Arg Gly Ile Asn Ser Ser Tyr Ala Val Trp Asn Asp Val Thr
                210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
                260                 265                 270

Ala Gln Tyr Asp Val Leu Arg Glu Asn Gly His Ser Pro Ser Glu Ala
                275                 280                 285

Phe Asn Glu Thr Val Glu Glu Ala Thr Gln Ser Leu Tyr Pro Leu Ile
                290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
                340                 345                 350

Lys Arg Ser Leu Glu Phe Asn Ser Gln Pro Asp Tyr Arg Glu Lys Leu
                355                 360                 365

Glu Lys Glu Leu Asp Thr Ile Arg Asn Met Glu Ile Trp Lys Val Gly
                370                 375                 380

Lys Glu Val Arg Lys Leu Arg Pro Glu Asn Gln
385                 390                 395

<210> SEQ ID NO 182
<211> LENGTH: 993
<212> TYPE: DNA
<213> ORGANISM: Methanococcus maripaludis

<400> SEQUENCE: 182
atgaaggtat tctatgactc agattttaaa ttagatgctt taaagaaaaa aacaattgca       60

```
gtaatcggtt atggaagtca aggtagggca cagtccttaa acatgaaaga cagcggatta    120
aacgttgttg ttggtttaag aaaaaacggt gcttcatgga acaacgctaa agcagacggt    180
cacaatgtaa tgaccattga agaagctgct gaaaaagcgg acatcatcca catcttaata    240
cctgatgaat acaggcaga agtttatgaa agccagataa aaccatacct aaaagaagga    300
aaaacactaa gcttttcaca tggttttaac atccactatg gattcattgt tccaccaaaa    360
ggagttaacg tggttttagt tgctccaaaa tcacctggaa aaatggttag aagaacatac    420
gaagaaggtt tcggtgttcc aggtttaatc tgtattgaaa ttgatgcaac aaacaacgca    480
tttgatattg tttcagcaat ggcaaaagga atcggtttat caagagctgg agttatccag    540
acaactttca agaagaaac agaaactgac cttttcggtg aacaagctgt tttatgcggt    600
ggagttaccg aattaatcaa ggcaggattt gaaacactcg ttgaagcagg atacgcacca    660
gaaatggcat actttgaaac ctgccacgaa ttgaaattaa tcgttgactt aatctaccaa    720
aaaggattca aaacatgtg gaacgatgta agtaacactg cagaatacgg cggacttaca    780
agaagaagca gaatcgttac agctgattca aaagctgcaa tgaaagaaat cttaagagaa    840
atccaagatg gaagattcac aaaagaattc cttctcgaaa aacaggtaag ctatgctcat    900
ttaaaatcaa tgagaagact cgaaggagac ttacaaatcg aagaagtcgg cgcaaaatta    960
agaaaaatgt gcggtcttga aaagaagaa taa                                  993
```

<210> SEQ ID NO 183
<211> LENGTH: 330
<212> TYPE: PRT
<213> ORGANISM: Methanococcus maripaludis

<400> SEQUENCE: 183

```
Met Lys Val Phe Tyr Asp Ser Asp Phe Lys Leu Asp Ala Leu Lys Glu
1               5                   10                  15

Lys Thr Ile Ala Val Ile Gly Tyr Gly Ser Gln Gly Arg Ala Gln Ser
                20                  25                  30

Leu Asn Met Lys Asp Ser Gly Leu Asn Val Val Gly Leu Arg Lys
            35                  40                  45

Asn Gly Ala Ser Trp Asn Asn Ala Lys Ala Asp Gly His Asn Val Met
        50                  55                  60

Thr Ile Glu Glu Ala Ala Glu Lys Ala Asp Ile Ile His Ile Leu Ile
65                  70                  75                  80

Pro Asp Glu Leu Gln Ala Glu Val Tyr Glu Ser Gln Ile Lys Pro Tyr
                85                  90                  95

Leu Lys Glu Gly Lys Thr Leu Ser Phe Ser His Gly Phe Asn Ile His
                100                 105                 110

Tyr Gly Phe Ile Val Pro Pro Lys Gly Val Asn Val Val Leu Val Ala
            115                 120                 125

Pro Lys Ser Pro Gly Lys Met Val Arg Arg Thr Tyr Glu Glu Gly Phe
        130                 135                 140

Gly Val Pro Gly Leu Ile Cys Ile Glu Ile Asp Ala Thr Asn Asn Ala
145                 150                 155                 160

Phe Asp Ile Val Ser Ala Met Ala Lys Gly Ile Gly Leu Ser Arg Ala
                165                 170                 175

Gly Val Ile Gln Thr Thr Phe Lys Glu Glu Thr Glu Thr Asp Leu Phe
            180                 185                 190

Gly Glu Gln Ala Val Leu Cys Gly Gly Val Thr Glu Leu Ile Lys Ala
        195                 200                 205
```

```
Gly Phe Glu Thr Leu Val Glu Ala Gly Tyr Ala Pro Glu Met Ala Tyr
210                 215                 220

Phe Glu Thr Cys His Glu Leu Lys Leu Ile Val Asp Leu Ile Tyr Gln
225                 230                 235                 240

Lys Gly Phe Lys Asn Met Trp Asn Asp Val Ser Asn Thr Ala Glu Tyr
                245                 250                 255

Gly Gly Leu Thr Arg Arg Ser Arg Ile Val Thr Ala Asp Ser Lys Ala
                260                 265                 270

Ala Met Lys Glu Ile Leu Arg Glu Ile Gln Asp Gly Arg Phe Thr Lys
                275                 280                 285

Glu Phe Leu Leu Glu Lys Gln Val Ser Tyr Ala His Leu Lys Ser Met
290                 295                 300

Arg Arg Leu Glu Gly Asp Leu Gln Ile Glu Glu Val Gly Ala Lys Leu
305                 310                 315                 320

Arg Lys Met Cys Gly Leu Glu Lys Glu Glu
                325                 330
```

<210> SEQ ID NO 184
<211> LENGTH: 1476
<212> TYPE: DNA
<213> ORGANISM: Bacillus subtilis

<400> SEQUENCE: 184

```
atggctaact acttcaatac actgaatctg cgccagcagc tggcacagct gggcaaatgt      60
cgctttatgg ccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
ctgatgaaag acgcgcggc gctgggctac tcgcacggtt tcaacatcgt cgaagtgggc     420
gagcagatcc gtaaagatat caccgtagtg atggttgcgc gaaatgccc aggcaccgaa     480
gtgcgtgaag agtacaaacg tgggttcggc gtaccgacgc tgattgccgt tcacccggaa     540
aacgatccga aggcgaagg catggcgatt gccaaagcct gggcggctgc aaccggtggt     600
caccgtgcgg gtgtgctgga atcgtccttc gttgcggaag tgaaatctga cctgatgggc     660
gagcaaacca tcctgtgcgg tatgttgcag gctggctctc tgctgtgctt cgacaagctg     720
gtggaagaag gtaccgatcc agcatacgca gaaaaactga ttcagttcgg ttgggaaacc     780
atcaccgaag cactgaaaca gggcggcatc accctgatga tggaccgtct ctctaacccg     840
gcgaaactgc gtgcttatgc gctttctgaa cagctgaaag agatcatggc accctgttc     900
cagaaacata tggacgacat catctccggc gaattctctt ccggtatgat ggcggactgg     960
gccaacgatg ataagaaact gctgacctgg cgtgaagaga ccggcaaaac gcgtttgaa    1020
accgcgccgc agtatgaagg caaaatcggc gagcaggagt acttcgataa ggcgtactg    1080
atgattgcga tggtgaaagc gggcgttgaa ctggcgttcg aaaccatggt cgattccggc    1140
atcattgaag agtctgcata ttatgaatca ctgcacgagc tgccgctgat tgccaacacc    1200
atcgcccgta agcgtctgta cgaaatgaac gtggttatct ctgataccgc tgagtacggt    1260
aactatctgt tctcttacgc ttgtgtgccg ttgctgaaac cgtttatggc agagctgcaa    1320
ccgggcgacc tgggtaaagc tattccgaa ggcgcggtag ataacgggca actgcgtgat    1380
gtgaacgaag cgattcgcag ccatgcgatt gagcaggtag gtaagaaact gcgcggctat    1440
```

```
atgacagata tgaaacgtat tgctgttgcg ggttaa                                    1476
```

<210> SEQ ID NO 185
<211> LENGTH: 342
<212> TYPE: PRT
<213> ORGANISM: Bacillus subtilis

<400> SEQUENCE: 185

```
Met Val Lys Val Tyr Tyr Asn Gly Asp Ile Lys Glu Asn Val Leu Ala
1               5                   10                  15

Gly Lys Thr Val Ala Val Ile Gly Tyr Gly Ser Gln Gly His Ala His
            20                  25                  30

Ala Leu Asn Leu Lys Glu Ser Gly Val Asp Val Ile Val Gly Val Arg
        35                  40                  45

Gln Gly Lys Ser Phe Thr Gln Ala Gln Glu Asp Gly His Lys Val Phe
    50                  55                  60

Ser Val Lys Glu Ala Ala Ala Gln Ala Glu Ile Ile Met Val Leu Leu
65                  70                  75                  80

Pro Asp Glu Gln Gln Gln Lys Val Tyr Glu Ala Glu Ile Lys Asp Glu
                85                  90                  95

Leu Thr Ala Gly Lys Ser Leu Val Phe Ala His Gly Phe Asn Val His
            100                 105                 110

Phe His Gln Ile Val Pro Pro Ala Asp Val Asp Val Phe Leu Val Ala
        115                 120                 125

Pro Lys Gly Pro Gly His Leu Val Arg Arg Thr Tyr Glu Gln Gly Ala
    130                 135                 140

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Gly Ala Arg Ala
                165                 170                 175

Gly Val Leu Glu Thr Thr Phe Lys Glu Glu Thr Glu Thr Asp Leu Phe
            180                 185                 190

Gly Glu Gln Ala Val Leu Cys Gly Gly Leu Ser Ala Leu Val Lys Ala
        195                 200                 205

Gly Phe Glu Thr Leu Thr Glu Ala Gly Tyr Gln Pro Glu Leu Ala Tyr
    210                 215                 220

Phe Glu Cys Leu His Glu Leu Lys Leu Ile Val Asp Leu Met Tyr Glu
225                 230                 235                 240

Glu Gly Leu Ala Gly Met Arg Tyr Ser Ile Ser Asp Thr Ala Gln Trp
                245                 250                 255

Gly Asp Phe Val Ser Gly Pro Arg Val Val Asp Ala Lys Val Lys Glu
            260                 265                 270

Ser Met Lys Glu Val Leu Lys Asp Ile Gln Asn Gly Thr Phe Ala Lys
        275                 280                 285

Glu Trp Ile Val Glu Asn Gln Val Asn Arg Pro Arg Phe Asn Ala Ile
    290                 295                 300

Asn Ala Ser Glu Asn Glu His Gln Ile Glu Val Val Gly Arg Lys Leu
305                 310                 315                 320

Arg Glu Met Met Pro Phe Val Lys Gln Gly Lys Lys Glu Ala Val
                325                 330                 335

Val Ser Val Ala Gln Asn
            340
```

<210> SEQ ID NO 186

```
<211> LENGTH: 585
<212> TYPE: PRT
<213> ORGANISM: Saccharomyces cerevisiae

<400> SEQUENCE: 186
```

| Met | Gly | Leu | Leu | Thr | Lys | Val | Ala | Thr | Ser | Arg | Gln | Phe | Ser | Thr | Thr |
|---|---|---|---|---|---|---|---|---|---|---|---|---|---|---|---|
| 1 | | | | 5 | | | | | 10 | | | | | 15 | |

| Arg | Cys | Val | Ala | Lys | Lys | Leu | Asn | Lys | Tyr | Ser | Tyr | Ile | Ile | Thr | Glu |
|---|---|---|---|---|---|---|---|---|---|---|---|---|---|---|---|
| | | | 20 | | | | | 25 | | | | | 30 | | |

| Pro | Lys | Gly | Gln | Gly | Ala | Ser | Gln | Ala | Met | Leu | Tyr | Ala | Thr | Gly | Phe |
|---|---|---|---|---|---|---|---|---|---|---|---|---|---|---|---|
| | | 35 | | | | | 40 | | | | | 45 | | | |

| Lys | Lys | Glu | Asp | Phe | Lys | Lys | Pro | Gln | Val | Gly | Val | Gly | Ser | Cys | Trp |
|---|---|---|---|---|---|---|---|---|---|---|---|---|---|---|---|
| 50 | | | | | 55 | | | | | 60 | | | | | |

| Trp | Ser | Gly | Asn | Pro | Cys | Asn | Met | His | Leu | Leu | Asp | Leu | Asn | Asn | Arg |
|---|---|---|---|---|---|---|---|---|---|---|---|---|---|---|---|
| 65 | | | | | 70 | | | | | 75 | | | | | 80 |

| Cys | Ser | Gln | Ser | Ile | Glu | Lys | Ala | Gly | Leu | Lys | Ala | Met | Gln | Phe | Asn |
|---|---|---|---|---|---|---|---|---|---|---|---|---|---|---|---|
| | | | | 85 | | | | | 90 | | | | | 95 | |

| Thr | Ile | Gly | Val | Ser | Asp | Gly | Ile | Ser | Met | Gly | Thr | Lys | Gly | Met | Arg |
|---|---|---|---|---|---|---|---|---|---|---|---|---|---|---|---|
| | | | 100 | | | | | 105 | | | | | 110 | | |

| Tyr | Ser | Leu | Gln | Ser | Arg | Glu | Ile | Ile | Ala | Asp | Ser | Phe | Glu | Thr | Ile |
|---|---|---|---|---|---|---|---|---|---|---|---|---|---|---|---|
| | | 115 | | | | | 120 | | | | | 125 | | | |

| Met | Met | Ala | Gln | His | Tyr | Asp | Ala | Asn | Ile | Ala | Ile | Pro | Ser | Cys | Asp |
|---|---|---|---|---|---|---|---|---|---|---|---|---|---|---|---|
| 130 | | | | | 135 | | | | | 140 | | | | | |

| Lys | Asn | Met | Pro | Gly | Val | Met | Met | Ala | Met | Gly | Arg | His | Asn | Arg | Pro |
|---|---|---|---|---|---|---|---|---|---|---|---|---|---|---|---|
| 145 | | | | | 150 | | | | | 155 | | | | | 160 |

| Ser | Ile | Met | Val | Tyr | Gly | Gly | Thr | Ile | Leu | Pro | Gly | His | Pro | Thr | Cys |
|---|---|---|---|---|---|---|---|---|---|---|---|---|---|---|---|
| | | | | 165 | | | | | 170 | | | | | 175 | |

| Gly | Ser | Ser | Lys | Ile | Ser | Lys | Asn | Ile | Asp | Ile | Val | Ser | Ala | Phe | Gln |
|---|---|---|---|---|---|---|---|---|---|---|---|---|---|---|---|
| | | | 180 | | | | | 185 | | | | | 190 | | |

| Ser | Tyr | Gly | Glu | Tyr | Ile | Ser | Lys | Gln | Phe | Thr | Glu | Glu | Glu | Arg | Glu |
|---|---|---|---|---|---|---|---|---|---|---|---|---|---|---|---|
| | | 195 | | | | | 200 | | | | | 205 | | | |

| Asp | Val | Val | Glu | His | Ala | Cys | Pro | Gly | Pro | Gly | Ser | Cys | Gly | Gly | Met |
|---|---|---|---|---|---|---|---|---|---|---|---|---|---|---|---|
| 210 | | | | | 215 | | | | | 220 | | | | | |

| Tyr | Thr | Ala | Asn | Thr | Met | Ala | Ser | Ala | Ala | Glu | Val | Leu | Gly | Leu | Thr |
|---|---|---|---|---|---|---|---|---|---|---|---|---|---|---|---|
| 225 | | | | | 230 | | | | | 235 | | | | | 240 |

| Ile | Pro | Asn | Ser | Ser | Ser | Phe | Pro | Ala | Val | Ser | Lys | Glu | Lys | Leu | Ala |
|---|---|---|---|---|---|---|---|---|---|---|---|---|---|---|---|
| | | | | 245 | | | | | 250 | | | | | 255 | |

| Glu | Cys | Asp | Asn | Ile | Gly | Glu | Tyr | Ile | Lys | Lys | Thr | Met | Glu | Leu | Gly |
|---|---|---|---|---|---|---|---|---|---|---|---|---|---|---|---|
| | | | 260 | | | | | 265 | | | | | 270 | | |

| Ile | Leu | Pro | Arg | Asp | Ile | Leu | Thr | Lys | Glu | Ala | Phe | Glu | Asn | Ala | Ile |
|---|---|---|---|---|---|---|---|---|---|---|---|---|---|---|---|
| | | 275 | | | | | 280 | | | | | 285 | | | |

| Thr | Tyr | Val | Val | Ala | Thr | Gly | Gly | Ser | Thr | Asn | Ala | Val | Leu | His | Leu |
|---|---|---|---|---|---|---|---|---|---|---|---|---|---|---|---|
| 290 | | | | | 295 | | | | | 300 | | | | | |

| Val | Ala | Val | Ala | His | Ser | Ala | Gly | Val | Lys | Leu | Ser | Pro | Asp | Asp | Phe |
|---|---|---|---|---|---|---|---|---|---|---|---|---|---|---|---|
| 305 | | | | | 310 | | | | | 315 | | | | | 320 |

| Gln | Arg | Ile | Ser | Asp | Thr | Thr | Pro | Leu | Ile | Gly | Asp | Phe | Lys | Pro | Ser |
|---|---|---|---|---|---|---|---|---|---|---|---|---|---|---|---|
| | | | | 325 | | | | | 330 | | | | | 335 | |

| Gly | Lys | Tyr | Val | Met | Ala | Asp | Leu | Ile | Asn | Val | Gly | Gly | Thr | Gln | Ser |
|---|---|---|---|---|---|---|---|---|---|---|---|---|---|---|---|
| | | | 340 | | | | | 345 | | | | | 350 | | |

| Val | Ile | Lys | Tyr | Leu | Tyr | Glu | Asn | Asn | Met | Leu | His | Gly | Asn | Thr | Met |
|---|---|---|---|---|---|---|---|---|---|---|---|---|---|---|---|
| | | 355 | | | | | 360 | | | | | 365 | | | |

| Thr | Val | Thr | Gly | Asp | Thr | Leu | Ala | Glu | Arg | Ala | Lys | Lys | Ala | Pro | Ser |
|---|---|---|---|---|---|---|---|---|---|---|---|---|---|---|---|
| 370 | | | | | 375 | | | | | 380 | | | | | |

| Leu | Pro | Glu | Gly | Gln | Glu | Ile | Ile | Lys | Pro | Leu | Ser | His | Pro | Ile | Lys |

```
                385                 390                 395                 400
Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
                420                 425                 430

Ala Arg Val Phe Glu Glu Gly Ala Phe Ile Glu Ala Leu Glu Arg
            435                 440                 445

Gly Glu Ile Lys Lys Gly Glu Lys Thr Val Val Ile Arg Tyr Glu
        450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
                500                 505                 510

Pro Glu Ala Ala Glu Gly Gly Pro Ile Gly Leu Val Arg Asp Gly Asp
                515                 520                 525

Glu Ile Ile Ile Asp Ala Asp Asn Asn Lys Ile Asp Leu Leu Val Ser
        530                 535                 540

Asp Lys Glu Met Ala Gln Arg Lys Gln Ser Trp Val Ala Pro Pro Pro
545                 550                 555                 560

Arg Tyr Thr Arg Gly Thr Leu Ser Lys Tyr Ala Lys Leu Val Ser Asn
                565                 570                 575

Ala Ser Asn Gly Cys Val Leu Asp Ala
                580                 585

<210> SEQ ID NO 187
<211> LENGTH: 1653
<212> TYPE: DNA
<213> ORGANISM: Methanococcus maripaludis

<400> SEQUENCE: 187
atgataagtg ataacgtcaa aaagggagtt ataagaactc aaaccgagc tcttttaaag      60
gcttgcggat atacagacga agacatggaa aaaccattta ttggaattgt aaacagcttt     120
acagaagttg ttcccggcca cattcactta agaacattat cagaagcggc taaacatggt     180
gtttatgcaa acgtggaaac accatttgaa tttaatacca ttggaatttg cgacggtatt     240
gcaatgggcc acgaaggtat gaaatactct ttaccttcaa gagaaattat tgcagacgct     300
gttgaatcaa tggcaagagc acatggattt gatggtcttg ttttaattcc tacgtgtgat     360
aaaatcgttc ctggaatgat aatgggtgct ttaagactaa acattccatt tattgtagtt     420
actggaggac caatgcttcc cggagaattc caaggtaaaa aatacgaact tatcagcctt     480
tttgaaggtg tcggagaata ccaagttgga aaaattactg aagaagagtt aaagtgcatt     540
gaagactgtg catgttcagg tgctggaagt tgtgcagggc tttacactgc aaacagtatg     600
gcctgcctta cagaagcttt gggactctct cttccaatgt gtgcaacaac gcatgcagtt     660
gatgcccaaa aagttaggct tgctaaaaaa agtggctcaa aaattgttga tatggtaaaa     720
gaagacctaa aaccaacaga catattaaca aaagaagctt tgaaaatgc tattttagtt     780
gaccttgcac ttggtggatc aacaaacaca acattacaca ttcctgcaat tgcaaatgaa     840
attgaaaata aattcataac tctcgatgac tttgacaggt taagcgatga agttccacac     900
attgcatcaa tcaaaccagg tggagaacac tacatgattg atttcacaa tgctggaggt     960
attcctgcgg tattgaacgt tttaaaagaa aaaattagag atacaaaaac agttgatgga    1020
```

-continued

```
agaagcattt tggaaatcgc agaatctgtt aaatacataa attacgacgt tataagaaaa    1080
gtggaagctc cggttcacga aactgctggt ttaagggttt taaagggaaa tcttgctcca    1140
aacggttgcg ttgtaaaaat cggtgcagta catccgaaaa tgtacaaaca cgatggacct    1200
gcaaaagttt acaattccga agatgaagca atttctgcga tacttggcgg aaaaattgta    1260
gaagggacg ttatagtaat cagatacgaa ggaccatcag gaggccctgg aatgagagaa    1320
atgctctccc caacttcagc aatctgtgga atgggtcttg atgacagcgt tgcattgatt    1380
actgatggaa gattcagtgg tggaagtagg ggcccatgta tcggacacgt ttctccagaa    1440
gctgcagctg gcggagtaat tgctgcaatt gaaaacgggg atatcatcaa aatcgacatg    1500
attgaaaaag aaataaatgt tgatttagat gaatcagtca ttaaagaaag actctcaaaa    1560
ctgggagaat tgagcctaa aatcaaaaaa ggctatttat caagatactc aaaacttgtc    1620
tcatctgctg acgaagggc agttttaaaa taa                                  1653
```

<210> SEQ ID NO 188
<211> LENGTH: 550
<212> TYPE: PRT
<213> ORGANISM: Methanococcus maripaludis

<400> SEQUENCE: 188

```
Met Ile Ser Asp Asn Val Lys Lys Gly Val Ile Arg Thr Pro Asn Arg
1               5                   10                  15

Ala Leu Leu Lys Ala Cys Gly Tyr Thr Asp Glu Asp Met Glu Lys Pro
            20                  25                  30

Phe Ile Gly Ile Val Asn Ser Phe Thr Glu Val Pro Gly His Ile
        35                  40                  45

His Leu Arg Thr Leu Ser Glu Ala Ala Lys His Gly Val Tyr Ala Asn
    50                  55                  60

Gly Gly Thr Pro Phe Glu Phe Asn Thr Ile Gly Ile Cys Asp Gly Ile
65                  70                  75                  80

Ala Met Gly His Glu Gly Met Lys Tyr Ser Leu Pro Ser Arg Glu Ile
                85                  90                  95

Ile Ala Asp Ala Val Glu Ser Met Ala Arg Ala His Gly Phe Asp Gly
            100                 105                 110

Leu Val Leu Ile Pro Thr Cys Asp Lys Ile Val Pro Gly Met Ile Met
        115                 120                 125

Gly Ala Leu Arg Leu Asn Ile Pro Phe Ile Val Val Thr Gly Gly Pro
    130                 135                 140

Met Leu Pro Gly Glu Phe Gln Gly Lys Lys Tyr Glu Leu Ile Ser Leu
145                 150                 155                 160

Phe Glu Gly Val Gly Glu Tyr Gln Val Gly Lys Ile Thr Glu Glu
                165                 170                 175

Leu Lys Cys Ile Glu Asp Cys Ala Cys Ser Gly Ala Gly Ser Cys Ala
            180                 185                 190

Gly Leu Tyr Thr Ala Asn Ser Met Ala Cys Leu Thr Glu Ala Leu Gly
        195                 200                 205

Leu Ser Leu Pro Met Cys Ala Thr Thr His Ala Val Asp Ala Gln Lys
    210                 215                 220

Val Arg Leu Ala Lys Lys Ser Gly Ser Lys Ile Val Asp Met Val Lys
225                 230                 235                 240

Glu Asp Leu Lys Pro Thr Asp Ile Leu Thr Lys Glu Ala Phe Glu Asn
                245                 250                 255
```

```
Ala Ile Leu Val Asp Leu Ala Leu Gly Gly Ser Thr Asn Thr Thr Leu
            260                 265                 270

His Ile Pro Ala Ile Ala Asn Glu Ile Glu Asn Lys Phe Ile Thr Leu
        275                 280                 285

Asp Asp Phe Asp Arg Leu Ser Asp Glu Val Pro His Ile Ala Ser Ile
    290                 295                 300

Lys Pro Gly Gly Glu His Tyr Met Ile Asp Leu His Asn Ala Gly Gly
305                 310                 315                 320

Ile Pro Ala Val Leu Asn Val Leu Lys Glu Lys Ile Arg Asp Thr Lys
                325                 330                 335

Thr Val Asp Gly Arg Ser Ile Leu Glu Ile Ala Glu Ser Val Lys Tyr
            340                 345                 350

Ile Asn Tyr Asp Val Ile Arg Lys Val Glu Ala Pro Val His Glu Thr
        355                 360                 365

Ala Gly Leu Arg Val Leu Lys Gly Asn Leu Ala Pro Asn Gly Cys Val
    370                 375                 380

Val Lys Ile Gly Ala Val His Pro Lys Met Tyr Lys His Asp Gly Pro
385                 390                 395                 400

Ala Lys Val Tyr Asn Ser Glu Asp Glu Ala Ile Ser Ala Ile Leu Gly
                405                 410                 415

Gly Lys Ile Val Glu Gly Asp Val Ile Val Ile Arg Tyr Glu Gly Pro
            420                 425                 430

Ser Gly Gly Pro Gly Met Arg Glu Met Leu Ser Pro Thr Ser Ala Ile
        435                 440                 445

Cys Gly Met Gly Leu Asp Asp Ser Val Ala Leu Ile Thr Asp Gly Arg
    450                 455                 460

Phe Ser Gly Gly Ser Arg Gly Pro Cys Ile Gly His Val Ser Pro Glu
465                 470                 475                 480

Ala Ala Ala Gly Gly Val Ile Ala Ala Ile Glu Asn Gly Asp Ile Ile
                485                 490                 495

Lys Ile Asp Met Ile Glu Lys Glu Ile Asn Val Asp Leu Asp Glu Ser
            500                 505                 510

Val Ile Lys Glu Arg Leu Ser Lys Leu Gly Glu Phe Glu Pro Lys Ile
        515                 520                 525

Lys Lys Gly Tyr Leu Ser Arg Tyr Ser Lys Leu Val Ser Ser Ala Asp
    530                 535                 540

Glu Gly Ala Val Leu Lys
545                 550

<210> SEQ ID NO 189
<211> LENGTH: 1677
<212> TYPE: DNA
<213> ORGANISM: Bacillus subtilis

<400> SEQUENCE: 189
atggcagaat tacgcagtaa tatgatcaca caaggaatcg atagagctcc gcaccgcagt      60
ttgcttcgtg cagcaggggt aaaagaagag gatttcggca agccgtttat tgcggtgtgt     120
aattcataca ttgatatcgt tcccggtcat gttcacttgc aggagtttgg gaaaatcgta     180
aaagaagcaa tcagagaagc aggggcgtt ccgtttgaat taataccat ggggtagat       240 gatggcatcg caatggggca tatcggtatg agatattcgc tgccaagccg tgaaattatc     300
gcagactctg tggaaacggt tgtatccgca cactggtttg acggaatggt ctgtattccg     360
aactgcgaca aaatcacacc gggaatgctt atggcggcaa tgcgcatcaa cattccgacg     420
```

```
atttttgtca gcggcggacc gatggcggca ggaagaacaa gttacgggcg aaaaatctcc      480
ctttcctcag tattcgaagg ggtaggcgcc taccaagcag ggaaaatcaa cgaaaacgag      540
cttcaagaac tagagcagtt cggatgccca acgtgcgggt cttgctcagg catgtttacg      600
gcgaactcaa tgaactgtct gtcagaagca cttggtcttg ctttgccggg taatggaacc      660
attctggcaa catctccgga acgcaaagag tttgtgagaa aatcggctgc gcaattaatg      720
gaaacgattc gcaaagatat caaaccgcgt gatattgtta cagtaaaagc gattgataac      780
gcgtttgcac tcgatatggc gctcggaggt tctacaaata ccgttcttca taccct tgcc      840 cttgcaaacg aagccggcgt tgaatactct ttagaacgca ttaacgaagt cgctgagcgc      900
gtgccgcact ggctaagct ggcgcctgca tcggatgtgt ttattgaaga tcttcacgaa       960
gcgggcggcg tttcagcggc tctgaatgag ctttcgaaga aagaaggagc gcttcattta      1020
gatgcgctga ctgttacagg aaaaactctt ggagaaacca ttgccggaca tgaagtaaag      1080
gattatgacg tcattcaccc gctggatcaa ccattcactg aaaagggagg ccttgctgtt      1140
ttattcggta atctagctcc ggacggcgct atcattaaaa caggcggcgt acagaatggg      1200
attacaagac acgaagggcc ggctgtcgta ttcgattctc aggacgaggc gcttgacggc      1260
attatcaacc gaaaagtaaa agaaggcgac gttgtcatca tcagatacga agggccaaaa      1320
ggcggacctg gcatgccgga aatgctggcg ccaacatccc aaatcgttgg aatgggactc      1380
gggccaaaag tggcattgat tacgacgga cgttttttccg gagcctcccg tggcctctca      1440
atcggccacg tatcacctga ggccgctgag ggcgggccgc ttgcctttgt tgaaaacgga      1500
gaccatatta tcgttgatat tgaaaaacgc atcttggatg tacaagtgcc agaagaagag      1560
tgggaaaaac gaaaagcgaa ctggaaaggt tttgaaccga aagtgaaaac cggctacctg      1620
gcacgttatt ctaaacttgt gacaagtgcc aacaccggcg gtattatgaa aatctag       1677
```

<210> SEQ ID NO 190
<211> LENGTH: 558
<212> TYPE: PRT
<213> ORGANISM: Bacillus subtilis

<400> SEQUENCE: 190

```
Met Ala Glu Leu Arg Ser Asn Met Ile Thr Gln Gly Ile Asp Arg Ala
1               5                   10                  15

Pro His Arg Ser Leu Leu Arg Ala Ala Gly Val Lys Glu Glu Asp Phe
            20                  25                  30

Gly Lys Pro Phe Ile Ala Val Cys Asn Ser Tyr Ile Asp Ile Val Pro
        35                  40                  45

Gly His Val His Leu Gln Glu Phe Gly Lys Ile Val Lys Glu Ala Ile
    50                  55                  60

Arg Glu Ala Gly Gly Val Pro Phe Glu Phe Asn Thr Ile Gly Val Asp
65                  70                  75                  80

Asp Gly Ile Ala Met Gly His Ile Gly Met Arg Tyr Ser Leu Pro Ser
                85                  90                  95

Arg Glu Ile Ile Ala Asp Ser Val Glu Thr Val Val Ser Ala His Trp
            100                 105                 110

Phe Asp Gly Met Val Cys Ile Pro Asn Cys Asp Lys Ile Thr Pro Gly
        115                 120                 125

Met Leu Met Ala Ala Met Arg Ile Asn Ile Pro Thr Ile Phe Val Ser
    130                 135                 140

Gly Gly Pro Met Ala Ala Gly Arg Thr Ser Tyr Gly Arg Lys Ile Ser
145                 150                 155                 160
```

Leu Ser Ser Val Phe Glu Gly Val Gly Ala Tyr Gln Ala Gly Lys Ile
                165                 170                 175

Asn Glu Asn Glu Leu Gln Glu Leu Glu Gln Phe Gly Cys Pro Thr Cys
            180                 185                 190

Gly Ser Cys Ser Gly Met Phe Thr Ala Asn Ser Met Asn Cys Leu Ser
        195                 200                 205

Glu Ala Leu Gly Leu Ala Leu Pro Gly Asn Gly Thr Ile Leu Ala Thr
    210                 215                 220

Ser Pro Glu Arg Lys Glu Phe Val Arg Lys Ser Ala Ala Gln Leu Met
225                 230                 235                 240

Glu Thr Ile Arg Lys Asp Ile Lys Pro Arg Asp Ile Val Thr Val Lys
                245                 250                 255

Ala Ile Asp Asn Ala Phe Ala Leu Asp Met Ala Leu Gly Gly Ser Thr
            260                 265                 270

Asn Thr Val Leu His Thr Leu Ala Leu Ala Asn Glu Ala Gly Val Glu
        275                 280                 285

Tyr Ser Leu Glu Arg Ile Asn Glu Val Ala Glu Arg Val Pro His Leu
    290                 295                 300

Ala Lys Leu Ala Pro Ala Ser Asp Val Phe Ile Glu Asp Leu His Glu
305                 310                 315                 320

Ala Gly Gly Val Ser Ala Ala Leu Asn Glu Leu Ser Lys Lys Glu Gly
                325                 330                 335

Ala Leu His Leu Asp Ala Leu Thr Val Thr Gly Lys Thr Leu Gly Glu
            340                 345                 350

Thr Ile Ala Gly His Glu Val Lys Asp Tyr Asp Val Ile His Pro Leu
        355                 360                 365

Asp Gln Pro Phe Thr Glu Lys Gly Gly Leu Ala Val Leu Phe Gly Asn
    370                 375                 380

Leu Ala Pro Asp Gly Ala Ile Ile Lys Thr Gly Gly Val Gln Asn Gly
385                 390                 395                 400

Ile Thr Arg His Glu Gly Pro Ala Val Val Phe Asp Ser Gln Asp Glu
                405                 410                 415

Ala Leu Asp Gly Ile Ile Asn Arg Lys Val Lys Glu Gly Asp Val Val
            420                 425                 430

Ile Ile Arg Tyr Glu Gly Pro Lys Gly Gly Pro Gly Met Pro Glu Met
        435                 440                 445

Leu Ala Pro Thr Ser Gln Ile Val Gly Met Gly Leu Gly Pro Lys Val
    450                 455                 460

Ala Leu Ile Thr Asp Gly Arg Phe Ser Gly Ala Ser Arg Gly Leu Ser
465                 470                 475                 480

Ile Gly His Val Ser Pro Glu Ala Ala Glu Gly Gly Pro Leu Ala Phe
                485                 490                 495

Val Glu Asn Gly Asp His Ile Ile Val Asp Ile Glu Lys Arg Ile Leu
            500                 505                 510

Asp Val Gln Val Pro Glu Glu Trp Glu Lys Arg Lys Ala Asn Trp
        515                 520                 525                 Trp

Lys Gly Phe Glu Pro Lys Val Lys Thr Gly Tyr Leu Ala Arg Tyr Ser
    530                 535                 540

Lys Leu Val Thr Ser Ala Asn Thr Gly Gly Ile Met Lys Ile
545                 550                 555

<210> SEQ ID NO 191
<211> LENGTH: 1647

```
<212> TYPE: DNA
<213> ORGANISM: Lactococcus lactis

<400> SEQUENCE: 191
atgtatacag taggagatta cctattagac cgattacacg agttaggaat tgaagaaatt     60
tttggagtcc ctggagacta aacttacaa tttttagatc aaattatttc ccacaaggat    120
atgaaatggg tcggaaatgc taatgaatta aatgcttcat atatggctga tggctatgct    180
cgtactaaaa aagctgccgc atttcttaca acctttggag taggtgaatt gagtgcagtt    240
aatggattag caggaagtta cgccgaaaat ttaccagtag tagaaatagt gggatcacct    300
acatcaaaag ttcaaaatga aggaaaattt gttcatcata cgctggctga cggtgatttt    360
aaacacttta tgaaaatgca cgaacctgtt acagcagctc gaactttact gacagcagaa    420
aatgcaaccg ttgaaattga ccgagtactt tctgcactat aaaagaaag aaaacctgtc    480
tatatcaact taccagttga tgttgctgct gcaaaagcag agaaaccctc actcccttg     540
aaaaaggaaa actcaacttc aaatacaagt gaccaagaaa ttttgaacaa aattcaagaa    600
agcttgaaaa atgccaaaaa accaatcgtg attacaggac atgaaataat tagttttggc    660
ttagaaaaaa cagtcactca atttatttca aagacaaaac tacctattac gacattaaac    720
tttggtaaaa gttcagttga tgaagccctc ccttcatttt taggaatcta taatggtaca    780
ctctcagagc ctaatcttaa agaattcgtg gaatcagccg acttcatctt gatgcttgga    840
gttaaactca cagactcttc aacaggagcc ttcactcatc atttaaatga aaataaaatg    900
atttcactga atatagatga aggaaaaata tttaacgaaa gaatccaaaa ttttgatttt    960
gaatccctca tctcctctct cttagaccta agcgaaatag aatacaaagg aaaatatatc   1020
gataaaaagc aagaagactt tgttccatca aatgcgcttt tatcacaaga ccgcctatgg   1080
caagcagttg aaaacctaac tcaaagcaat gaaacaatcg ttgctgaaca agggacatca   1140
ttctttggcg cttcatcaat tttcttaaaa tcaaagagtc attttattgg tcaacccta    1200
tggggatcaa ttggatatac attcccagca gcattaggaa gccaaattgc agataaagaa   1260
agcagacacc ttttatttat tggtgatggt tcacttcaac ttacagtgca agaattagga   1320
ttagcaatca gagaaaaaat taatccaatt tgctttatta tcaataatga tggttataca   1380
gtcgaaagag aaattcatgg accaaatcaa agctacaatg atattccaat gtggaattac   1440
tcaaaattac cagaatcgtt tggagcaaca gaagatcgag tagtctcaaa aatcgttaga   1500
actgaaaatg aatttgtgtc tgtcatgaaa gaagctcaag cagatccaaa tagaatgtac   1560
tggattgagt taatttttggc aaaagaaggt gcaccaaaag tactgaaaaa aatgggcaaa   1620
ctatttgctg aacaaaataa atcataa                                        1647

<210> SEQ ID NO 192
<211> LENGTH: 1644
<212> TYPE: DNA
<213> ORGANISM: Lactococcus lactis

<400> SEQUENCE: 192
atgtatacag taggagatta cctgttagac cgattacacg agttgggaat tgaagaaatt     60
tttggagttc ctggtgacta aacttacaa tttttagatc aaattatttc acgcgaagat    120
atgaaatgga ttggaaatgc taatgaatta aatgcttctt atatggctga tggttatgct    180
cgtactaaaa aagctgccgc atttctcacc acatttggag tcggcgaatt gagtgcgatc    240
aatggactgg caggaagtta tgccgaaaat ttaccagtag tagaaattgt tggttcacca    300
```

```
acttcaaaag tacaaaatga cggaaaattt gtccatcata cactagcaga tggtgatttt    360
aaacacttta tgaagatgca tgaacctgtt acagcagcgc ggactttact gacagcagaa    420
aatgccacat atgaaattga ccgagtactt tctcaattac taaaagaaag aaaaccagtc    480
tatattaact taccagtcga tgttgctgca gcaaaagcag agaagcctgc attatcttta    540 gaaaagaaa gctctacaac aaatacaact gaacaagtga ttttgagtaa gattgaagaa    600
agtttgaaaa atgcccaaaa accagtagtg attgcaggac acgaagtaat tagttttggt    660
ttagaaaaaa cggtaactca gtttgtttca gaaacaaaac taccgattac gacactaaat    720
tttggtaaaa gtgctgttga tgaatctttg ccctcatttt taggaatata taacgggaaa    780
ctttcagaaa tcagtcttaa aaattttgtg gagtccgcag actttatcct aatgcttgga    840
gtgaagctta cggactcctc aacaggtgca ttcacacatc atttagatga aaataaaatg    900
atttcactaa acatagatga aggaataatt ttcaataaag tggtagaaga ttttgatttt    960
agagcagtgg tttcttcttt atcagaatta aaaggaatag aatatgaagg acaatatatt   1020
gataagcaat atgaagaatt tattccatca agtgctccct tatcacaaga ccgtctatgg   1080
caggcagttg aaagtttgac tcaaagcaat gaaacaatcg ttgctgaaca aggaacctca   1140
ttttttggag cttcaacaat tttcttaaaa tcaaatagtc gttttattgg acaaccttta   1200
tggggttcta ttggatatac ttttccagcg gctttaggaa gccaaattgc ggataaagag   1260
agcagacacc tttatttat tggtgatggt tcacttcaac ttaccgtaca agaattagga   1320
ctatcaatca gagaaaaact caatccaatt tgttttatca taaataatga tggttataca   1380
gttgaaagag aaatccacgg acctactcaa agttataacg acattccaat gtggaattac   1440
tcgaaattac cagaaacatt tggagcaaca gaagatcgtg tagtatcaaa aattgttaga   1500
acagagaatg aatttgtgtc tgtcatgaaa gaagcccaag cagatgtcaa tagaatgtat   1560
tggatagaac tagttttgga aaaagaagat gcgccaaaat tactgaaaaa atgggtaaa   1620 ttatttgctg agcaaaataa atag                                           1644
```

<210> SEQ ID NO 193
<211> LENGTH: 547
<212> TYPE: PRT
<213> ORGANISM: Lactococcus lactis

<400> SEQUENCE: 193

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
```

```
            130                 135                 140
Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
                180                 185                 190

Val Ile Leu Ser Lys Ile Glu Glu Ser Leu Lys Asn Ala Gln Lys Pro
                195                 200                 205

Val Val Ile Ala Gly His Glu Val Ile Ser Phe Gly Leu Glu Lys Thr
                210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
                260                 265                 270

Ala Asp Phe Ile Leu Met Leu Gly Val Lys Leu Thr Asp Ser Ser Thr
                275                 280                 285

Gly Ala Phe Thr His His Leu Asp Glu Asn Lys Met Ile Ser Leu Asn
                290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Glu Phe Ile Pro Ser Ser Ala
                340                 345                 350

Pro Leu Ser Gln Asp Arg Leu Trp Gln Ala Val Glu Ser Leu Thr Gln
                355                 360                 365

Ser Asn Glu Thr Ile Val Ala Glu Gln Gly Thr Ser Phe Phe Gly Ala
                370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ser Ile Arg Glu Lys Leu Asn
                435                 440                 445

Pro Ile Cys Phe Ile Ile Asn Asn Asp Gly Tyr Thr Val Glu Arg Glu
                450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Val Asn Arg Met Tyr Trp Ile Glu Leu Val Leu Glu Lys
                515                 520                 525

Glu Asp Ala Pro Lys Leu Leu Lys Lys Met Gly Lys Leu Phe Ala Glu
                530                 535                 540

Gln Asn Lys
545
```

<210> SEQ ID NO 194
<211> LENGTH: 1653
<212> TYPE: DNA
<213> ORGANISM: Salmonella typhimurium

<400> SEQUENCE: 194

```
ttatccccg ttgcgggctt ccagcgcccg ggtcacggta cgcagtaatt ccggcagatc      60
ggcttttggc aacatcactt caataaatga cagacgttgt gggcgcgcca accgttcgag     120
gacctctgcc agttggatag cctgcgtcac ccgccagcac tccgcctgtt gcgccgcgtt     180
tagcgccggt ggtatctgcg tccagttcca gctcgcgatg tcgttatacc gctgggccgc     240
gccgtgaatg gcgcgctcta cggtatagcc gtcattgttg agcagcagga tgaccggcgc     300
ctgcccgtcg cgtaacatcg agcccatctc tgaatcgtg agctgcgccg cgccatcgcc      360
gataatcaga atcacccgcc gatcgggaca ggcggtttgc gcgccaaacg cggcgggcaa     420
ggaatagccg atagaccccc acagcggctg taacacaact tccgcgccgt caggaagcga     480
cagcgcggca gcgccaaaag ctgctgtccc ctggtcgaca aggataatat ctccgggttt     540
gagatactgc tgtaaggttt gccagaagct ttcctgggtc agttctcctt tatcaatccg     600
cactggctgt ccggcggaac gcgtcggcgg cggcgcaaaa gcgcattcca ggcacagttc     660
gcgcagcgta gacaccgcct gcgccatcgg gaggttgaac caggtttcgc cgatgcgcga     720
cgcgtaaggc tgaatctcca gcgtgcgttc cgccggtaat tgttgggtaa atccggccgt     780
aagggtatcg acaaaacggg tgccgacgca gataaccta tcggcgtcct ctatggcctg      840
acgcacttct tgctgctgg cgccagcgct ataggtgcca acgaagttcg ggtgctgttc      900
atcaaaaagc cccttcccca tcagtagtgt cgcatgagcg atgggcgttt ccgccatcca     960
gcgctgcaac agtggtcgta aaccaaaacg cccggcaaga aagtcggcca atagcgcaat    1020
gcgccgactg ttcatcaggc actgacgggc gtgataacga aaggccgtct ccacgccgct    1080
ttgcgcttca tgcacgggca acgccagcgc ctgcgtaggt gggatggccg tttttttcgc    1140
cacatcggcg gcaacatga tgtatcctgg cctgcgtgcg gcaagcattt cacccaacac    1200
gcggtcaatc tcgaaacagg cgttctgttc atctaatatt gcgctggcag cggatatcgc    1260
ctgactcatg cgataaaaat gacgaaaatc gccgtcaccg agggtatggt gcatcaattc    1320
gccacgctgc tgcgcagcgc tacagggcgc gccgacgata tgcaagaccg ggacatattc    1380
cgcgtaactg cccgcgatac cgttaatagc gctaagttct cccacgccaa aggtggtgag    1440
tagcgctcca gcgcccgaca tgcgcgcata gccgtccgcg gcataagcgg cgttcagctc    1500
attggcgcat cccacccaac gcagggtcgg gtggtcaatc acatggtcaa gaaactgcaa    1560
gttataatcg cccggtacgc caaaaagatg gccaatgccg catcctgcca gtctgtccag    1620
caaatagtcg gccacggtat aggggttttg cat                                 1653
```

<210> SEQ ID NO 195
<211> LENGTH: 550
<212> TYPE: PRT
<213> ORGANISM: Salmonella typhimurium

<400> SEQUENCE: 195

```
Met Gln Asn Pro Tyr Thr Val Ala Asp Tyr Leu Leu Asp Arg Leu Ala
1               5                   10                  15

Gly Cys Gly Ile Gly His Leu Phe Gly Val Pro Gly Asp Tyr Asn Leu
            20                  25                  30
```

```
Gln Phe Leu Asp His Val Ile Asp His Pro Thr Leu Arg Trp Val Gly
         35                  40                  45

Cys Ala Asn Glu Leu Asn Ala Ala Tyr Ala Ala Asp Gly Tyr Ala Arg
 50                  55                  60

Met Ser Gly Ala Gly Ala Leu Leu Thr Thr Phe Gly Val Gly Glu Leu
 65                  70                  75                  80

Ser Ala Ile Asn Gly Ile Ala Gly Ser Tyr Ala Glu Tyr Val Pro Val
                 85                  90                  95

Leu His Ile Val Gly Ala Pro Cys Ser Ala Ala Gln Arg Gly Glu
                100                 105                 110

Leu Met His His Thr Leu Gly Asp Gly Asp Phe Arg His Phe Tyr Arg
            115                 120                 125

Met Ser Gln Ala Ile Ser Ala Ala Ser Ala Ile Leu Asp Glu Gln Asn
130                 135                 140

Ala Cys Phe Glu Ile Asp Arg Val Leu Gly Glu Met Leu Ala Ala Arg
145                 150                 155                 160

Arg Pro Gly Tyr Ile Met Leu Pro Ala Asp Val Ala Lys Lys Thr Ala
                165                 170                 175

Ile Pro Pro Thr Gln Ala Leu Ala Leu Pro Val His Glu Ala Gln Ser
                180                 185                 190

Gly Val Glu Thr Ala Phe Arg Tyr His Ala Arg Gln Cys Leu Met Asn
            195                 200                 205

Ser Arg Arg Ile Ala Leu Leu Ala Asp Phe Leu Ala Gly Arg Phe Gly
        210                 215                 220

Leu Arg Pro Leu Leu Gln Arg Trp Met Ala Glu Thr Pro Ile Ala His
225                 230                 235                 240

Ala Thr Leu Leu Met Gly Lys Gly Leu Phe Asp Glu Gln His Pro Asn
                245                 250                 255

Phe Val Gly Thr Tyr Ser Ala Gly Ala Ser Ser Lys Glu Val Arg Gln
                260                 265                 270

Ala Ile Glu Asp Ala Asp Arg Val Ile Cys Val Gly Thr Arg Phe Val
            275                 280                 285

Asp Thr Leu Thr Ala Gly Phe Thr Gln Gln Leu Pro Ala Glu Arg Thr
        290                 295                 300

Leu Glu Ile Gln Pro Tyr Ala Ser Arg Ile Gly Glu Thr Trp Phe Asn
305                 310                 315                 320

Leu Pro Met Ala Gln Ala Val Ser Thr Leu Arg Glu Leu Cys Leu Glu
                325                 330                 335

Cys Ala Phe Ala Pro Pro Thr Arg Ser Ala Gly Gln Pro Val Arg
                340                 345                 350

Ile Asp Lys Gly Glu Leu Thr Gln Glu Ser Phe Trp Gln Thr Leu Gln
            355                 360                 365

Gln Tyr Leu Lys Pro Gly Asp Ile Ile Leu Val Asp Gln Gly Thr Ala
        370                 375                 380

Ala Phe Gly Ala Ala Ala Leu Ser Leu Pro Asp Gly Ala Glu Val Val
385                 390                 395                 400

Leu Gln Pro Leu Trp Gly Ser Ile Gly Tyr Ser Leu Pro Ala Ala Phe
                405                 410                 415

Gly Ala Gln Thr Ala Cys Pro Asp Arg Arg Val Ile Leu Ile Ile Gly
            420                 425                 430

Asp Gly Ala Ala Gln Leu Thr Ile Gln Glu Met Gly Ser Met Leu Arg
        435                 440                 445

Asp Gly Gln Ala Pro Val Ile Leu Leu Leu Asn Asn Asp Gly Tyr Thr
```

| | | 450 | | | 455 | | | 460 | | | |
|---|---|---|---|---|---|---|---|---|---|---|---|

Val Glu Arg Ala Ile His Gly Ala Ala Gln Arg Tyr Asn Asp Ile Ala
465             470             475             480

Ser Trp Asn Trp Thr Gln Ile Pro Pro Ala Leu Asn Ala Ala Gln Gln
            485             490             495

Ala Glu Cys Trp Arg Val Thr Gln Ala Ile Gln Leu Ala Glu Val Leu
        500             505             510

Glu Arg Leu Ala Arg Pro Gln Arg Leu Ser Phe Ile Glu Val Met Leu
    515             520             525

Pro Lys Ala Asp Leu Pro Glu Leu Leu Arg Thr Val Thr Arg Ala Leu
530             535             540

Glu Ala Arg Asn Gly Gly
545             550

<210> SEQ ID NO 196
<211> LENGTH: 1665
<212> TYPE: DNA
<213> ORGANISM: Clostridium acetobutylicum

<400> SEQUENCE: 196

```
ttgaagagtg aatacacaat tggaagatat ttgttagacc gtttatcaga gttgggtatt      60
cggcatatct ttggtgtacc tggagattac aatctatcct ttttagacta tataatggag     120
tacaaaggga tagattgggt tggaaattgc aatgaattga atgctgggta tgctgctgat     180
ggatatgcaa gaataaatgg aattggagcc atacttacaa catttggtgt tggagaatta     240
agtgccatta cgcaattgc tggggcatac gctgagcaag ttccagttgt taaaattaca     300
ggtatcccca cagcaaaagt tagggacaat ggattatatg tacaccacac attaggtgac     360
ggaaggtttg atcactttt tgaaatgttt agagaagtaa cagttgctga ggcattacta     420
agcgaagaaa atgcagcaca agaaattgat cgtgttctta tttcatgctg agacaaaaa      480
cgtcctgttc ttataaattt accgattgat gtatatgata aaccaattaa caaaccatta     540
aagccattac tcgattatac tatttcaagt aacaaagagg ctgcatgtga atttgttaca     600
gaaatagtac ctataataaa tagggcaaaa agcctgtta ttcttgcaga ttatggagta      660
tatcgttacc aagttcaaca tgtgcttaaa acttggccg aaaaaaccgg atttcctgtg      720
gctacactaa gtatgggaaa aggtgttttc aatgaagcac accctcaatt tattggtgtt     780
tataatggtg atgtaagttc tccttattta aggcagcgag ttgatgaagc agactgcatt     840
attagcgttg gtgtaaaatt gacggattca accacagggg gatttttctca tggatttttct     900
aaaaggaatg taattcacat tgatcctttt tcaataaagg caaaaggtaa aaaatatgca     960
cctattacga tgaaagatgc tttaacagaa ttaacaagta aaattgagca tagaaacttt    1020
gaggattag atataaagcc ttacaaatca gataatcaaa agtattttgc aaaagagaag    1080
ccaattacac aaaaacgttt ttttgagcgt attgctcact ttataaaaga aaaagatgta    1140
ttattagcag aacagggtac atgctttttt ggtgcgtcaa ccatacaact acccaaagat    1200
gcaacttta ttggtcaacc tttatgggga tctattggat acacacttcc tgctttatta     1260
ggttcacaat tagctgatca aaaaaggcgt aatattcttt taattgggga tggtgcattt    1320
caaatgacag cacaagaaat ttcaacaatg cttcgtttac aaatcaaacc tattattttt    1380
ttaattaata cgatggtta tacaattgaa cgtgctattc atggtagaga acaagtatat    1440
aacaatattc aaatgtggcg atatcataat gttccaaagg ttttaggtcc taagaatgc      1500
agcttaaccct ttaaagtaca aagtgaaact gaacttgaaa aggctctttt agtggcagat    1560
```

-continued

```
aaggattgtg aacatttgat ttttatagaa gttgttatgg atcgttatga taaacccgag    1620
cctttagaac gtctttcgaa acgttttgca aatcaaaata attag                    1665
```

<210> SEQ ID NO 197
<211> LENGTH: 554
<212> TYPE: PRT
<213> ORGANISM: Clostridium acetobutylicum

<400> SEQUENCE: 197

| | | | | | | | | | | | | | | |
|---|---|---|---|---|---|---|---|---|---|---|---|---|---|---|
| Met | Lys | Ser | Glu | Tyr | Thr | Ile | Gly | Arg | Tyr | Leu | Leu | Asp | Arg | Leu | Ser |
| 1 | | | | 5 | | | | | 10 | | | | | 15 | |
| Glu | Leu | Gly | Ile | Arg | His | Ile | Phe | Gly | Val | Pro | Gly | Asp | Tyr | Asn | Leu |
| | | | 20 | | | | | 25 | | | | | 30 | | |
| Ser | Phe | Leu | Asp | Tyr | Ile | Met | Glu | Tyr | Lys | Gly | Ile | Asp | Trp | Val | Gly |
| | | 35 | | | | | 40 | | | | | 45 | | | |
| Asn | Cys | Asn | Glu | Leu | Asn | Ala | Gly | Tyr | Ala | Ala | Asp | Gly | Tyr | Ala | Arg |
| | 50 | | | | | 55 | | | | | 60 | | | | |
| Ile | Asn | Gly | Ile | Gly | Ala | Ile | Leu | Thr | Thr | Phe | Gly | Val | Gly | Glu | Leu |
| 65 | | | | | 70 | | | | | 75 | | | | | 80 |
| Ser | Ala | Ile | Asn | Ala | Ile | Ala | Gly | Ala | Tyr | Ala | Glu | Gln | Val | Pro | Val |
| | | | | 85 | | | | | 90 | | | | | 95 | |
| Val | Lys | Ile | Thr | Gly | Ile | Pro | Thr | Ala | Lys | Val | Arg | Asp | Asn | Gly | Leu |
| | | | 100 | | | | | 105 | | | | | 110 | | |
| Tyr | Val | His | His | Thr | Leu | Gly | Asp | Gly | Arg | Phe | Asp | His | Phe | Phe | Glu |
| | | 115 | | | | | 120 | | | | | 125 | | | |
| Met | Phe | Arg | Glu | Val | Thr | Val | Ala | Glu | Ala | Leu | Leu | Ser | Glu | Glu | Asn |
| | 130 | | | | | 135 | | | | | 140 | | | | |
| Ala | Ala | Gln | Glu | Ile | Asp | Arg | Val | Leu | Ile | Ser | Cys | Trp | Arg | Gln | Lys |
| 145 | | | | | 150 | | | | | 155 | | | | | 160 |
| Arg | Pro | Val | Leu | Ile | Asn | Leu | Pro | Ile | Asp | Val | Tyr | Asp | Lys | Pro | Ile |
| | | | | 165 | | | | | 170 | | | | | 175 | |
| Asn | Lys | Pro | Leu | Lys | Pro | Leu | Leu | Asp | Tyr | Thr | Ile | Ser | Ser | Asn | Lys |
| | | | 180 | | | | | 185 | | | | | 190 | | |
| Glu | Ala | Ala | Cys | Glu | Phe | Val | Thr | Glu | Ile | Val | Pro | Ile | Ile | Asn | Arg |
| | | 195 | | | | | 200 | | | | | 205 | | | |
| Ala | Lys | Lys | Pro | Val | Ile | Leu | Ala | Asp | Tyr | Gly | Val | Tyr | Arg | Tyr | Gln |
| | 210 | | | | | 215 | | | | | 220 | | | | |
| Val | Gln | His | Val | Leu | Lys | Asn | Leu | Ala | Glu | Lys | Thr | Gly | Phe | Pro | Val |
| 225 | | | | | 230 | | | | | 235 | | | | | 240 |
| Ala | Thr | Leu | Ser | Met | Gly | Lys | Gly | Val | Phe | Asn | Glu | Ala | His | Pro | Gln |
| | | | | 245 | | | | | 250 | | | | | 255 | |
| Phe | Ile | Gly | Val | Tyr | Asn | Gly | Asp | Val | Ser | Ser | Pro | Tyr | Leu | Arg | Gln |
| | | | 260 | | | | | 265 | | | | | 270 | | |
| Arg | Val | Asp | Glu | Ala | Asp | Cys | Ile | Ile | Ser | Val | Gly | Val | Lys | Leu | Thr |
| | | 275 | | | | | 280 | | | | | 285 | | | |
| Asp | Ser | Thr | Thr | Gly | Gly | Phe | Ser | His | Gly | Phe | Ser | Lys | Arg | Asn | Val |
| | 290 | | | | | 295 | | | | | 300 | | | | |
| Ile | His | Ile | Asp | Pro | Phe | Ser | Ile | Lys | Ala | Lys | Gly | Lys | Lys | Tyr | Ala |
| 305 | | | | | 310 | | | | | 315 | | | | | 320 |
| Pro | Ile | Thr | Met | Lys | Asp | Ala | Leu | Thr | Glu | Leu | Thr | Ser | Lys | Ile | Glu |
| | | | | 325 | | | | | 330 | | | | | 335 | |
| His | Arg | Asn | Phe | Glu | Asp | Leu | Asp | Ile | Lys | Pro | Tyr | Lys | Ser | Asp | Asn |
| | | | 340 | | | | | 345 | | | | | 350 | | |

Gln Lys Tyr Phe Ala Lys Glu Lys Pro Ile Thr Gln Lys Arg Phe Phe
355                 360                 365

Glu Arg Ile Ala His Phe Ile Lys Glu Lys Asp Val Leu Leu Ala Glu
        370                 375                 380

Gln Gly Thr Cys Phe Phe Gly Ala Ser Thr Ile Gln Leu Pro Lys Asp
385                 390                 395                 400

Ala Thr Phe Ile Gly Gln Pro Leu Trp Gly Ser Ile Gly Tyr Thr Leu
                405                 410                 415

Pro Ala Leu Leu Gly Ser Gln Leu Ala Asp Gln Lys Arg Arg Asn Ile
            420                 425                 430

Leu Leu Ile Gly Asp Gly Ala Phe Gln Met Thr Ala Gln Glu Ile Ser
        435                 440                 445

Thr Met Leu Arg Leu Gln Ile Lys Pro Ile Ile Phe Leu Ile Asn Asn
450                 455                 460

Asp Gly Tyr Thr Ile Glu Arg Ala Ile His Gly Arg Glu Gln Val Tyr
465                 470                 475                 480

Asn Asn Ile Gln Met Trp Arg Tyr His Asn Val Pro Lys Val Leu Gly
                485                 490                 495

Pro Lys Glu Cys Ser Leu Thr Phe Lys Val Gln Ser Glu Thr Glu Leu
            500                 505                 510

Glu Lys Ala Leu Leu Val Ala Asp Lys Asp Cys Glu His Leu Ile Phe
        515                 520                 525

Ile Glu Val Val Met Asp Arg Tyr Asp Lys Pro Glu Pro Leu Glu Arg
        530                 535                 540

Leu Ser Lys Arg Phe Ala Asn Gln Asn Asn
545                 550

<210> SEQ ID NO 198
<211> LENGTH: 939
<212> TYPE: DNA
<213> ORGANISM: Saccharomyces cerevisiae

<400> SEQUENCE: 198
atgcctgcta cgttaaagaa ttcttctgct acattaaaac taaatactgg tgcctccatt      60
ccagtgttgg gtttcggcac ttggcgttcc gttgacaata acggttacca ttctgtaatt     120
gcagctttga agctggata cagacacatt gatgctgcgg ctatctattt gaatgaagaa      180
gaagttggca gggctattaa agattccgga gtccctcgtg aggaaatttt tattactact     240
aagctttggg gtacggaaca acgtgatccg gaagctgctc taaacaagtc tttgaaaaga     300
ctaggcttgg attatgttga cctatatctg atgcattggc cagtgccttt gaaaaccgac     360
agagttactg atggtaacgt tctgtgcatt ccaacattag aagatggcac tgttgacatc     420
gatactaaga atggaatttt atcaagacg tgggagttga tgcaagagtt gccaaagacg      480
ggcaaaacta agccgttgg tgtctctaat ttttctatta caacattaa agaattatta      540 gaatctccaa ataacaaggt ggtaccagct actaatcaaa ttgaaattca tccattgcta     600
ccacaagacg aattgattgc cttttgtaag gaaaagggta ttgttgttga agcctactca     660
ccatttggga gtgctaatgc tccttttacta aaagagcaag caattattga tatggctaaa     720
aagcacggcg ttgagccagc acagcttatt atcagttgga gtattcaaag aggctacgtt     780
gttctggcca aatcggttaa tcctgaaaga attgtatcca atttaagat tttcactctg      840 cctgaggatg atttcaagac tattagtaac ctatccaaag tgcatggtac aaagagagtc     900
gttgatatga agtggggatc cttcccaatt ttccaatga                            939

<210> SEQ ID NO 199
<211> LENGTH: 312
<212> TYPE: PRT
<213> ORGANISM: Saccharomyces cerevisiae

<400> SEQUENCE: 199

```
Met Pro Ala Thr Leu Lys Asn Ser Ser Ala Thr Leu Lys Leu Asn Thr
1               5                   10                  15

Gly Ala Ser Ile Pro Val Leu Gly Phe Gly Thr Trp Arg Ser Val Asp
                20                  25                  30

Asn Asn Gly Tyr His Ser Val Ile Ala Ala Leu Lys Ala Gly Tyr Arg
            35                  40                  45

His Ile Asp Ala Ala Ile Tyr Leu Asn Glu Glu Glu Val Gly Arg
50                  55                  60

Ala Ile Lys Asp Ser Gly Val Pro Arg Glu Glu Ile Phe Ile Thr Thr
65                  70                  75                  80

Lys Leu Trp Gly Thr Glu Gln Arg Asp Pro Glu Ala Ala Leu Asn Lys
                85                  90                  95

Ser Leu Lys Arg Leu Gly Leu Asp Tyr Val Asp Leu Tyr Leu Met His
            100                 105                 110

Trp Pro Val Pro Leu Lys Thr Asp Arg Val Thr Asp Gly Asn Val Leu
        115                 120                 125

Cys Ile Pro Thr Leu Glu Asp Gly Thr Val Asp Ile Asp Thr Lys Glu
130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Ile
                165                 170                 175

Lys Glu Leu Leu Glu Ser Pro Asn Asn Lys Val Val Pro Ala Thr Asn
            180                 185                 190

Gln Ile Glu Ile His Pro Leu Leu Pro Gln Asp Glu Leu Ile Ala Phe
        195                 200                 205

Cys Lys Glu Lys Gly Ile Val Val Glu Ala Tyr Ser Pro Phe Gly Ser
210                 215                 220

Ala Asn Ala Pro Leu Leu Lys Glu Gln Ala Ile Ile Asp Met Ala Lys
225                 230                 235                 240

Lys His Gly Val Glu Pro Ala Gln Leu Ile Ile Ser Trp Ser Ile Gln
                245                 250                 255

Arg Gly Tyr Val Val Leu Ala Lys Ser Val Asn Pro Glu Arg Ile Val
            260                 265                 270

Ser Asn Phe Lys Ile Phe Thr Leu Pro Glu Asp Asp Phe Lys Thr Ile
        275                 280                 285

Ser Asn Leu Ser Lys Val His Gly Thr Lys Arg Val Val Asp Met Lys
290                 295                 300

Trp Gly Ser Phe Pro Ile Phe Gln
305                 310
```

<210> SEQ ID NO 200
<211> LENGTH: 1083
<212> TYPE: DNA
<213> ORGANISM: Saccharomyces cerevisiae

<400> SEQUENCE: 200

```
ctagtctgaa aattctttgt cgtagccgac taaggtaaat ctatatctaa cgtcacccct      60
ttccatcctt tcgaaggctt catggacgcc ggcttcacca acaggtaatg tttccaccca     120
```

-continued

```
aattttgata tcttttcag agactaattt caagagttgg ttcaattctt tgatggaacc        180
taaagcactg taagaaatgg agacagcctt taagccatat ggctttagcg ataacatttc        240
gtgttgttct ggtatagaga ttgagacaat tctaccacca accttcatag cctttggcat        300
aatgttgaag tcaatgtcgg taagggagga agcacagact acaatcaggt cgaaggtgtc        360
aaagtacttt tcaccccaat caccttcttc taatgtagca atgtagtgat cggcgcccat        420
cttcattgca tcttctcttt ttctcgaaga acgagaaata acatacgtct ctgccccat         480 ggctttggaa atcaatgtac ccatactgcc gataccacca agaccaacta taccaactt         540 tttacctgga ccgcaaccgt tacgaaccaa tggagagtac acagtcaaac caccacataa        600
tagtggagca gccaaatgtg atggaatatt ctctgggata ggcaccacaa aatgttcatg        660
aactctgacg tagtttgcat agccaccctg cgacacatag ccgtcttcat aaggctgact        720
gtatgtggta acaaacttgg tgcagtatgg ttcattatca ttcttacaac ggtcacattc        780
caagcatgaa aagacttgag cacctacacc aacacgttga ccgactttca acccactgtt        840
tgacttgggc cctagcttga caactttacc aacgatttca tgaccaacga ctagcggcat        900
cttcatattg ccccaatgac cagctgcaca atgaatatca ctaccgcaga caccacatgc        960
ttcgatctta atgtcaatgt catgatcgta aaatggtttt gggtcatact ttgtcttctt       1020 tgggttttc caatcttcgt gtgattgaat agcgatacct tcaaatttct caggataaga       1080
cat                                                                     1083
```

<210> SEQ ID NO 201
<211> LENGTH: 360
<212> TYPE: PRT
<213> ORGANISM: Saccharomyces cerevisiae

<400> SEQUENCE: 201

```
Met Ser Tyr Pro Glu Lys Phe Glu Gly Ile Ala Ile Gln Ser His Glu
 1               5                  10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
         35                  40                  45

Asp Ile His Cys Ala Ala Gly His Trp Gly Asn Met Lys Met Pro Leu
     50                  55                  60

Val Val Gly His Glu Ile Val Gly Lys Val Val Lys Leu Gly Pro Lys
 65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190
```

```
Ser Met Gly Thr Leu Ile Ser Lys Ala Met Gly Ala Glu Thr Tyr Val
            195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
                260                 265                 270

Val Ser Ile Ser Ile Pro Glu Gln His Glu Met Leu Ser Leu Lys Pro
    275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
                340                 345                 350

Gly Tyr Asp Lys Glu Phe Ser Asp
    355                 360

<210> SEQ ID NO 202
<211> LENGTH: 1170
<212> TYPE: DNA
<213> ORGANISM: Clostridium acetobutylicum

<400> SEQUENCE: 202
ttaataagat tttttaaata tctcaagaac atcctctgca tttattggtc ttaaacttcc      60
tattgttcct ccagaatttc taacagcttg ctttgccatt agttctagtt tatcttttcc    120
tattccaact tctctaagct tgaaggaat  acccaatgaa ttaaagtatt ctctcgtatt    180
tttaatagcc tctcgtgcta tttcatagtt atctttgttc ttgtctattc cccaaacatt    240
tattccataa gaaacaaatt tatgaagtgt atcgtcattt agaatatatt ccatccaatt    300
aggtgttaaa attgcaagtc ctacaccatg tgttatatca taatatgcac ttaactcgtg    360
ttccatagga tgacaactcc attttctatc cttaccaagt gataatagac catttatagc    420
taaacttgaa gcccacatca aattagctct agcctcgtaa tcatcagtct tctccattgc    480
tatttttcca tactttatac atgttcttaa gattgcttct gctataccgt cctgcacata    540
agcaccttca acaccactaa agtaagattc aaaggtgtga ctcataatgt cagctgttcc    600
cgctgctgtt tgattttag  gtactgtaaa agtatatgta ggatctaaca ctgaaaattt    660
aggtctcata tcatcatgtc ctactccaag cttttcatta gtctccatat ttgaaattac    720
tgcaatttga tccatttcag accctgttgc tgaaagagta agtatacttg caattggaag    780
aactttagtt attttagatg gatctttaac catgtcccat gtatcgccat cataataaac    840
tccagctgca attaccttag aacagtctat tgcacttcct cccccctattg ctaatactaa    900 atccacatta ttttctctac atatttctat gccttttttt actgttgtta tcctaggatt    960
tggctctact cctgaaagtt catagaaagc tatattgttt tctttttaata gctgttgc    1020 tctatcatat ataccgttcc ttttttatact tcctccgcca taaactataa gcactcttga   1080
gccatatttc ttaatttctt ctccaattac gtctattttt ccttttccaa aaaaaacttt    1140
```
agttggtatt gaataatcaa aacttagcat     1170

<210> SEQ ID NO 203
<211> LENGTH: 389
<212> TYPE: PRT
<213> ORGANISM: Clostridium acetobutylicum

<400> SEQUENCE: 203

```
Met Leu Ser Phe Asp Tyr Ser Ile Pro Thr Lys Val Phe Gly Lys
 1               5                  10                  15

Gly Lys Ile Asp Val Ile Gly Glu Glu Ile Lys Lys Tyr Gly Ser Arg
             20                  25                  30

Val Leu Ile Val Tyr Gly Gly Gly Ser Ile Lys Arg Asn Gly Ile Tyr
             35                  40                  45

Asp Arg Ala Thr Ala Ile Leu Lys Glu Asn Asn Ile Ala Phe Tyr Glu
         50                  55                  60

Leu Ser Gly Val Glu Pro Asn Pro Arg Ile Thr Val Lys Lys Gly
 65              70                  75                  80

Ile Glu Ile Cys Arg Glu Asn Asn Val Asp Leu Val Leu Ala Ile Gly
                 85                  90                  95

Gly Gly Ser Ala Ile Asp Cys Ser Lys Val Ile Ala Ala Gly Val Tyr
                100                 105                 110

Tyr Asp Gly Asp Thr Trp Asp Met Val Lys Asp Pro Ser Lys Ile Thr
            115                 120                 125

Lys Val Leu Pro Ile Ala Ser Ile Leu Thr Leu Ser Ala Thr Gly Ser
130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asp Asp Thr Leu His Lys
    290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365
```

Thr Ile Gly Ser Leu Arg Pro Ile Asn Ala Glu Asp Val Leu Glu Ile
    370                 375                 380

Phe Lys Lys Ser Tyr
385

<210> SEQ ID NO 204
<211> LENGTH: 390
<212> TYPE: PRT
<213> ORGANISM: Clostridium acetobutylicum

<400> SEQUENCE: 204

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

```
Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390

<210> SEQ ID NO 205
<211> LENGTH: 993
<212> TYPE: DNA
<213> ORGANISM: Bacillus subtilis

<400> SEQUENCE: 205
atgagtacaa accgacatca agcactaggg ctgactgatc aggaagccgt tgatatgtat      60
agaaccatgc tgttagcaag aaaaatcgat gaaagaatgt ggctgttaaa ccgttctggc     120
aaaattccat ttgtaatctc ttgtcaagga caggaagcag cacaggtagg agcggctttc     180
gcacttgacc gtgaaatgga ttatgtattg ccgtactaca gagacatggg tgtcgtgctc     240
gcgtttggca tgacagcaaa ggacttaatg atgtccgggt ttgcaaaagc agcagatccg     300
aactcaggag gccgccagat gccgggacat ttcggacaaa agaaaaaccg cattgtgacg     360
ggatcatctc cggttacaac gcaagtgccg cacgcagtcg gtattgcgct gcgggacgt      420
atggagaaaa aggatatcgc agcctttgtt acattcgggg aagggtcttc aaaccaaggc     480
gatttccatg aaggggcaaa ctttgccgct gtccataagc tgccggttat tttcatgtgt     540
gaaaacaaca atacgcaat ctcagtgcct acgataagc aagtcgcatg tgagaacatt      600
tccgaccgtg ccataggcta tgggatgcct ggcgtaactg tgaatggaaa tgatccgctg     660
gaagtttatc aagcggttaa agaagcacgc gaaagggcac gcagaggaga aggcccgaca     720
ttaattgaaa cgatttctta ccgccttaca ccacattcca gtgatgacga tgacagcagc     780
tacagaggcc gtgaagaagt agaggaagcg aaaaaaagtg atccccctgct tacttatcaa     840
gcttacttaa aggaaacagg cctgctgtcc gatgagatag aacaaaccat gctggatgaa     900
attatggcaa tcgtaaatga agcgacggat gaagcggaga cgccccata tgcagctcct      960
gagtcagcgc ttgattatgt ttatgcgaag tag                                   993

<210> SEQ ID NO 206
<211> LENGTH: 330
<212> TYPE: PRT
<213> ORGANISM: Bacillus subtilis

<400> SEQUENCE: 206

Met Ser Thr Asn Arg His Gln Ala Leu Gly Leu Thr Asp Gln Glu Ala
1               5                   10                  15

Val Asp Met Tyr Arg Thr Met Leu Leu Ala Arg Lys Ile Asp Glu Arg
            20                  25                  30

Met Trp Leu Leu Asn Arg Ser Gly Lys Ile Pro Phe Val Ile Ser Cys
        35                  40                  45

Gln Gly Gln Glu Ala Ala Gln Val Gly Ala Ala Phe Ala Leu Asp Arg
    50                  55                  60

Glu Met Asp Tyr Val Leu Pro Tyr Tyr Arg Asp Met Gly Val Val Leu
65                  70                  75                  80

Ala Phe Gly Met Thr Ala Lys Asp Leu Met Met Ser Gly Phe Ala Lys
                85                  90                  95

Ala Ala Asp Pro Asn Ser Gly Gly Arg Gln Met Pro Gly His Phe Gly
```

```
            100                 105                 110
Gln Lys Lys Asn Arg Ile Val Thr Gly Ser Ser Pro Val Thr Thr Gln
        115                 120                 125

Val Pro His Ala Val Gly Ile Ala Leu Ala Gly Arg Met Glu Lys Lys
    130                 135                 140

Asp Ile Ala Ala Phe Val Thr Phe Gly Glu Gly Ser Ser Asn Gln Gly
145                 150                 155                 160

Asp Phe His Glu Gly Ala Asn Phe Ala Ala Val His Lys Leu Pro Val
                165                 170                 175

Ile Phe Met Cys Glu Asn Asn Lys Tyr Ala Ile Ser Val Pro Tyr Asp
            180                 185                 190

Lys Gln Val Ala Cys Glu Asn Ile Ser Asp Arg Ala Ile Gly Tyr Gly
        195                 200                 205

Met Pro Gly Val Thr Val Asn Gly Asn Asp Pro Leu Glu Val Tyr Gln
    210                 215                 220

Ala Val Lys Glu Ala Arg Glu Arg Ala Arg Gly Glu Gly Pro Thr
225                 230                 235                 240

Leu Ile Glu Thr Ile Ser Tyr Arg Leu Thr Pro His Ser Ser Asp Asp
                245                 250                 255

Asp Asp Ser Ser Tyr Arg Gly Arg Glu Val Glu Glu Ala Lys Lys
            260                 265                 270

Ser Asp Pro Leu Leu Thr Tyr Gln Ala Tyr Leu Lys Gly Thr Gly Leu
        275                 280                 285

Leu Ser Asp Glu Ile Glu Gln Thr Met Leu Asp Glu Ile Met Ala Ile
    290                 295                 300

Val Asn Glu Ala Thr Asp Glu Ala Glu Asn Ala Pro Tyr Ala Ala Pro
305                 310                 315                 320

Glu Ser Ala Leu Asp Tyr Val Tyr Ala Lys
                325                 330

<210> SEQ ID NO 207
<211> LENGTH: 984
<212> TYPE: DNA
<213> ORGANISM: Bacillus subtilis

<400> SEQUENCE: 207
atgtcagtaa tgtcatatat tgatgcaatc aatttggcga tgaaagaaga aatggaacga      60
gattctcgcg ttttcgtcct tggggaagat gtaggaagaa aaggcggtgt gtttaaagcg     120
acagcgggac tctatgaaca atttggggaa gagcgcgtta tggatacgcc gcttgctgaa     180
tctgcaatcg caggagtcgg tatcggagcg gcaatgtacg gaatgagacc gattgctgaa     240
atgcagtttg ctgatttcat tatgccggca gtcaaccaaa ttatttctga agcggctaaa     300
atccgctacc gcagcaacaa tgactggagc tgtccgattg tcgtcagagc gccatacggc     360
ggaggcgtgc acgagcccct gtatcattct caatcagtcg aagcaatttt cgccaaccag     420
cccggactga aaattgtcat gccatcaaca ccatatgacg cgaaagggct cttaaaagcc     480
gcagttcgtg acgaagaccc cgtgctgttt tttgagcaca agcgggcata ccgtctgata     540
aagggcgagg ttccggctga tgattatgtc ctgccaatcg gcaaggcgga cgtaaaaagg     600
gaaggcgacg acatcacagt gatcacatac ggcctgtgtg tccacttcgc cttacaagct     660
gcagaacgtc tcgaaaaaga tggcatttca gcgcatgtgg tggatttaag aacagtttac     720
ccgcttgata agaagccat catcgaagct gcgtccaaaa ctggaaaggt tcttttggtc     780
acagaagata caaaagaagg cagcatcatg agcgaagtag ccgcaattat atccgagcat     840
```

-continued

```
tgtctgttcg acttagacgc gccgatcaaa cggcttgcag gtcctgatat tccggctatg    900
ccttatgcgc cgacaatgga aaatacttt atggtcaacc ctgataaagt ggaagcggcg    960
atgagagaat tagcggagtt ttaa                                           984
```

<210> SEQ ID NO 208
<211> LENGTH: 327
<212> TYPE: PRT
<213> ORGANISM: Bacillus subtilis

<400> SEQUENCE: 208

```
Met Ser Val Met Ser Tyr Ile Asp Ala Ile Asn Leu Ala Met Lys Glu
1               5                   10                  15

Glu Met Glu Arg Asp Ser Arg Val Phe Val Leu Gly Glu Asp Val Gly
            20                  25                  30

Arg Lys Gly Gly Val Phe Lys Ala Thr Ala Gly Leu Tyr Glu Gln Phe
        35                  40                  45

Gly Glu Glu Arg Val Met Asp Thr Pro Leu Ala Glu Ser Ala Ile Ala
    50                  55                  60

Gly Val Gly Ile Gly Ala Ala Met Tyr Gly Met Arg Pro Ile Ala Glu
65                  70                  75                  80

Met Gln Phe Ala Asp Phe Ile Met Pro Ala Val Asn Gln Ile Ile Ser
                85                  90                  95

Glu Ala Ala Lys Ile Arg Tyr Arg Ser Asn Asn Asp Trp Ser Cys Pro
            100                 105                 110

Ile Val Val Arg Ala Pro Tyr Gly Gly Gly Val His Gly Ala Leu Tyr
        115                 120                 125

His Ser Gln Ser Val Glu Ala Ile Phe Ala Asn Gln Pro Gly Leu Lys
    130                 135                 140

Ile Val Met Pro Ser Thr Pro Tyr Asp Ala Lys Gly Leu Leu Lys Ala
145                 150                 155                 160

Ala Val Arg Asp Glu Asp Pro Val Leu Phe Phe Glu His Lys Arg Ala
                165                 170                 175

Tyr Arg Leu Ile Lys Gly Glu Val Pro Ala Asp Asp Tyr Val Leu Pro
            180                 185                 190

Ile Gly Lys Ala Asp Val Lys Arg Glu Gly Asp Asp Ile Thr Val Ile
        195                 200                 205

Thr Tyr Gly Leu Cys Val His Phe Ala Leu Gln Ala Ala Glu Arg Leu
    210                 215                 220

Glu Lys Asp Gly Ile Ser Ala His Val Val Asp Leu Arg Thr Val Tyr
225                 230                 235                 240

Pro Leu Asp Lys Glu Ala Ile Ile Glu Ala Ala Ser Lys Thr Gly Lys
                245                 250                 255

Val Leu Leu Val Thr Glu Asp Thr Lys Glu Gly Ser Ile Met Ser Glu
            260                 265                 270

Val Ala Ala Ile Ile Ser Glu His Cys Leu Phe Asp Leu Asp Ala Pro
        275                 280                 285

Ile Lys Arg Leu Ala Gly Pro Asp Ile Pro Ala Met Pro Tyr Ala Pro
    290                 295                 300

Thr Met Glu Lys Tyr Phe Met Val Asn Pro Asp Lys Val Glu Ala Ala
305                 310                 315                 320

Met Arg Glu Leu Ala Glu Phe
                325
```

<210> SEQ ID NO 209
<211> LENGTH: 1275
<212> TYPE: DNA
<213> ORGANISM: Bacillus subtilis

<400> SEQUENCE: 209

```
atggcaattg aacaaatgac gatgccgcag cttggagaaa gcgtaacaga ggggacgatc      60
agcaaatggc ttgtcgcccc cggtgataaa gtgaacaaat acgatccgat cgcggaagtc     120
atgacagata aggtaaatgc agaggttccg tcttctttta ctggtacgat aacagagctt     180
gtgggagaag aaggccaaac cctgcaagtc ggagaaatga tttgcaaaat tgaaacagaa     240
ggcgcgaatc cggctgaaca aaaacaagaa cagccagcag catcagaagc cgctgagaac     300
cctgttgcaa aaagtgctgg agcagccgat cagcccaata aaagcgcta ctcgccagct     360
gttctccgtt tggccggaga gcacggcatt gacctcgatc aagtgacagg aactggtgcc     420
ggcgggcgca tcacacgaaa agatattcag cgcttaattg aaacaggcgg cgtgcaagaa     480
cagaatcctg aggagctgaa acagcagct cctgcaccga gtctgcatc aaaacctgag     540
ccaaaagaag agacgtcata tcctgcgtct gcagccggtg ataaagaaat ccctgtcaca     600
ggtgtaagaa aagcaattgc ttccaatatg aagcgaagca aaacagaaat tccgcatgct     660
tggacgatga tggaagtcga cgtcacaaat atggttgcat atcgcaacag tataaaagat     720
tcttttaaga agacagaagg ctttaattta acgttcttcg cctttttgt aaaagcggtc     780
gctcaggcgt taaagaatt cccgcaaatg aatagcatgt gggcggggga caaaattatt     840
cagaaaaagg atatcaatat ttcaattgca gttgccacag aggattcttt atttgttccg     900
gtgattaaaa acgctgatga aaaaacaatt aaaggcattg cgaaagacat taccggccta     960
gctaaaaaag taagagacgg aaaactcact gcagatgaca tgcagggagg cacgtttacc    1020
gtcaacaaca caggttcgtt cgggtctgtt cagtcgatgg gcattatcaa ctaccctcag    1080
gctgcgattc ttcaagtaga atccatcgtc aaacgcccgg ttgtcatgga caatggcatg    1140
attgctgtca gagacatggt taatctgtgc ctgtcattag atcacagagt gcttgacggt    1200
ctcgtgtgcg gacgattcct cggacgagtg aaacaaattt tagaatcgat tgacgagaag    1260
acatctgttt actaa                                                     1275
```

<210> SEQ ID NO 210
<211> LENGTH: 424
<212> TYPE: PRT
<213> ORGANISM: Bacillus subtilis

<400> SEQUENCE: 210

```
Met Ala Ile Glu Gln Met Thr Met Pro Gln Leu Gly Glu Ser Val Thr
1               5                   10                  15

Glu Gly Thr Ile Ser Lys Trp Leu Val Ala Pro Gly Asp Lys Val Asn
            20                  25                  30

Lys Tyr Asp Pro Ile Ala Glu Val Met Thr Asp Lys Val Asn Ala Glu
        35                  40                  45

Val Pro Ser Ser Phe Thr Gly Thr Ile Thr Glu Leu Val Gly Glu Glu
    50                  55                  60

Gly Gln Thr Leu Gln Val Gly Glu Met Ile Cys Lys Ile Glu Thr Glu
65                  70                  75                  80

Gly Ala Asn Pro Ala Glu Gln Lys Gln Glu Gln Pro Ala Ala Ser Glu
                85                  90                  95

Ala Ala Glu Asn Pro Val Ala Lys Ser Ala Gly Ala Ala Asp Gln Pro
            100                 105                 110
```

```
Asn Lys Lys Arg Tyr Ser Pro Ala Val Leu Arg Leu Ala Gly Glu His
        115                 120                 125

Gly Ile Asp Leu Asp Gln Val Thr Gly Thr Gly Ala Gly Gly Arg Ile
    130                 135                 140

Thr Arg Lys Asp Ile Gln Arg Leu Ile Glu Thr Gly Gly Val Gln Glu
145                 150                 155                 160

Gln Asn Pro Glu Glu Leu Lys Thr Ala Ala Pro Ala Pro Lys Ser Ala
                165                 170                 175

Ser Lys Pro Glu Pro Lys Glu Glu Thr Ser Tyr Pro Ala Ser Ala Ala
                180                 185                 190

Gly Asp Lys Glu Ile Pro Val Thr Gly Val Arg Lys Ala Ile Ala Ser
            195                 200                 205

Asn Met Lys Arg Ser Lys Thr Glu Ile Pro His Ala Trp Thr Met Met
    210                 215                 220

Glu Val Asp Val Thr Asn Met Val Ala Tyr Arg Asn Ser Ile Lys Asp
225                 230                 235                 240

Ser Phe Lys Lys Thr Glu Gly Phe Asn Leu Thr Phe Phe Ala Phe Phe
                245                 250                 255

Val Lys Ala Val Ala Gln Ala Leu Lys Glu Phe Pro Gln Met Asn Ser
            260                 265                 270

Met Trp Ala Gly Asp Lys Ile Ile Gln Lys Lys Asp Ile Asn Ile Ser
    275                 280                 285

Ile Ala Val Ala Thr Glu Asp Ser Leu Phe Val Pro Val Ile Lys Asn
    290                 295                 300

Ala Asp Glu Lys Thr Ile Lys Gly Ile Ala Lys Asp Ile Thr Gly Leu
305                 310                 315                 320

Ala Lys Lys Val Arg Asp Gly Lys Leu Thr Ala Asp Asp Met Gln Gly
                325                 330                 335

Gly Thr Phe Thr Val Asn Asn Thr Gly Ser Phe Gly Ser Val Gln Ser
            340                 345                 350

Met Gly Ile Ile Asn Tyr Pro Gln Ala Ala Ile Leu Gln Val Glu Ser
    355                 360                 365

Ile Val Lys Arg Pro Val Val Met Asp Asn Gly Met Ile Ala Val Arg
    370                 375                 380

Asp Met Val Asn Leu Cys Leu Ser Leu Asp His Arg Val Leu Asp Gly
385                 390                 395                 400

Leu Val Cys Gly Arg Phe Leu Gly Arg Val Lys Gln Ile Leu Glu Ser
                405                 410                 415

Ile Asp Glu Lys Thr Ser Val Tyr
            420

<210> SEQ ID NO 211
<211> LENGTH: 1374
<212> TYPE: DNA
<213> ORGANISM: Bacillus subtilis

<400> SEQUENCE: 211
atggcaactg agtatgacgt agtcattctg gcggcggta  ccggcggtta tgttgcggcc      60
atcagagccg ctcagctcgg cttaaaaaca gccgttgtgg aaaaggaaaa actcggggga    120
acatgtctgc ataaaggctg tatcccgagt aaagcgctgc ttagaagcgc agaggtatac    180
cggacagctc gtgaagccga tcaattcgga gtggaaacgg ctggcgtgtc cctcaacttt    240
gaaaaagtgc agcagcgtaa gcaagccgtt gttgataagc ttgcagcggg tgtaaatcat    300
```

```
ttaatgaaaa aaggaaaaat tgacgtgtac accggatatg acgtatcct tggaccgtca      360
atcttctctc cgctgccggg aacaatttct gttgagcggg gaaatggcga agaaaatgac     420
atgctgatcc cgaaacaagt gatcattgca acaggatcaa gaccgagaat gcttccgggt    480
cttgaagtgg acggtaagtc tgtactgact tcagatgagg cgctccaaat ggaggagctg    540
ccacagtcaa tcatcattgt cggcggaggg gttatcggta tcgaatgggc gtctatgctt   600
catgattttg cgttaaggt aacggttatt gaatacgcgg atcgcatatt gccgactgaa    660
gatctagaga tttcaaaaga aatggaaagt cttcttaaga aaaaaggcat ccagttcata    720
acaggggcaa aagtgctgcc tgacacaatg acaaaaacat cagacgatat cagcatacaa    780
gcggaaaaag acggagaaac cgttacctat tctgctgaga aaatgcttgt ttccatcggc   840
agacaggcaa atatcgaagg catcggccta gagaacaccg atattgttac tgaaaatggc   900
atgatttcag tcaatgaaag ctgccaaacg aaggaatctc atatttatgc aatcggagac   960
gtaatcggtg gcctgcagtt agctcacgtt gcttcacatg agggaattat tgctgttgag  1020
cattttgcag gtctcaatcc gcatccgctt gatccgacgc ttgtgccgaa gtgcatttac  1080
tcaagccctg aagctgccag tgtcggctta accgaagacg aagcaaaggc gaacgggcat  1140
aatgtcaaaa tcggcaagtt cccatttatg gcgattggaa aagcgcttgt atacggtgaa  1200
agcgacggtt ttgtcaaaat cgtggctgac cgagatacag atgatattct cggcgttcat  1260
atgattggcc gcatgtcac cgacatgatt tctgaagcgg tcttgccaa agtgctggac   1320
gcaacaccgt gggaggtcgg gcaaacgatt tcacccgcat ccaacgcttt ctga         1374

<210> SEQ ID NO 212
<211> LENGTH: 457
<212> TYPE: PRT
<213> ORGANISM: Bacillus subtilis

<400> SEQUENCE: 212

Met Ala Thr Glu Tyr Asp Val Val Ile Leu Gly Gly Gly Thr Gly Gly
1               5                   10                  15

Tyr Val Ala Ala Ile Arg Ala Ala Gln Leu Gly Leu Lys Thr Ala Val
                20                  25                  30

Val Glu Lys Glu Lys Leu Gly Gly Thr Cys Leu His Lys Gly Cys Ile
            35                  40                  45

Pro Ser Lys Ala Leu Leu Arg Ser Ala Glu Val Tyr Arg Thr Ala Arg
        50                  55                  60

Glu Ala Asp Gln Phe Gly Val Glu Thr Ala Gly Val Ser Leu Asn Phe
65                  70                  75                  80

Glu Lys Val Gln Gln Arg Lys Gln Ala Val Val Asp Lys Leu Ala Ala
                85                  90                  95

Gly Val Asn His Leu Met Lys Lys Gly Lys Ile Asp Val Tyr Thr Gly
            100                 105                 110

Tyr Gly Arg Ile Leu Gly Pro Ser Ile Phe Ser Pro Leu Pro Gly Thr
        115                 120                 125

Ile Ser Val Glu Arg Gly Asn Gly Glu Glu Asn Asp Met Leu Ile Pro
    130                 135                 140

Lys Gln Val Ile Ile Ala Thr Gly Ser Arg Pro Arg Met Leu Pro Gly
145                 150                 155                 160

Leu Glu Val Asp Gly Lys Ser Val Leu Thr Ser Asp Glu Ala Leu Gln
                165                 170                 175

Met Glu Glu Leu Pro Gln Ser Ile Ile Ile Val Gly Gly Gly Val Ile
            180                 185                 190
```

Gly Ile Glu Trp Ala Ser Met Leu His Asp Phe Gly Val Lys Val Thr
            195                 200                 205

Val Ile Glu Tyr Ala Asp Arg Ile Leu Pro Thr Glu Asp Leu Glu Ile
210                 215                 220

Ser Lys Glu Met Glu Ser Leu Leu Lys Lys Gly Ile Gln Phe Ile
225                 230                 235                 240

Thr Gly Ala Lys Val Leu Pro Asp Thr Met Thr Lys Thr Ser Asp Asp
                245                 250                 255

Ile Ser Ile Gln Ala Glu Lys Asp Gly Glu Thr Val Thr Tyr Ser Ala
                260                 265                 270

Glu Lys Met Leu Val Ser Ile Gly Arg Gln Ala Asn Ile Glu Gly Ile
            275                 280                 285

Gly Leu Glu Asn Thr Asp Ile Val Thr Glu Asn Gly Met Ile Ser Val
            290                 295                 300

Asn Glu Ser Cys Gln Thr Lys Glu Ser His Ile Tyr Ala Ile Gly Asp
305                 310                 315                 320

Val Ile Gly Gly Leu Gln Leu Ala His Val Ala Ser His Glu Gly Ile
                325                 330                 335

Ile Ala Val Glu His Phe Ala Gly Leu Asn Pro His Pro Leu Asp Pro
            340                 345                 350

Thr Leu Val Pro Lys Cys Ile Tyr Ser Ser Pro Glu Ala Ala Ser Val
            355                 360                 365

Gly Leu Thr Glu Asp Glu Ala Lys Ala Asn Gly His Asn Val Lys Ile
            370                 375                 380

Gly Lys Phe Pro Phe Met Ala Ile Gly Lys Ala Leu Val Tyr Gly Glu
385                 390                 395                 400

Ser Asp Gly Phe Val Lys Ile Val Ala Asp Arg Asp Thr Asp Ile
                405                 410                 415

Leu Gly Val His Met Ile Gly Pro His Val Thr Asp Met Ile Ser Glu
                420                 425                 430

Ala Gly Leu Ala Lys Val Leu Asp Ala Thr Pro Trp Glu Val Gly Gln
            435                 440                 445

Thr Ile Ser Pro Ala Ser Asn Ala Phe
            450                 455

<210> SEQ ID NO 213
<211> LENGTH: 1233
<212> TYPE: DNA
<213> ORGANISM: Pseudomonas putida

<400> SEQUENCE: 213
atgaacgagt acgcccccct gcgtttgcat gtgcccgagc ccaccggccg gccaggctgc      60
cagaccgatt tttcctacct gcgcctgaac gatgcaggtc aagcccgtaa accccctgtc     120
gatgtcgacg ctgccgacac cgccgacctg tcctacagcc tggtccgcgt gctcgacgag     180
caaggcgacg cccaaggccc gtgggctgaa gacatcgacc gcagatcct gcgccaaggc     240 atgcgcgcca tgctcaagac gcggatcttc gacagccgca tggtggttgc ccagcgccag     300
aagaagatgt ccttctacat gcagagcctg ggcgaagaag ccatcggcag cggccaggcg     360
ctggcgctta accgcaccga catgtgcttc cccacctacc gtcagcaaag catcctgatg     420
gcccgcgacg tgtcgctggt ggagatgatc tgccagttgc tgtccaacga acgcgacccc     480
ctcaagggcc gccagctgcc gatcatgtac tcggtacgcg aggccggctt cttcaccatc     540
agcggcaacc tggcgaccca gttcgtgcag gcggtcggct gggccatggc ctcggcgatc     600

```
aagggcgata ccaagattgc ctcggcctgg atcggcgacg gcgccactgc cgaatcggac      660
ttccacaccg ccctcacctt tgcccacgtt taccgcgccc cggtgatcct caacgtggtc      720
aacaaccagt gggccatctc aaccttccag gccatcgccg gtggcgagtc gaccaccttc      780
gccggccgtg gcgtgggctg cggcatcgct tcgctgcggg tggacggcaa cgacttcgtc      840
gccgtttacg ccgcttcgcg ctgggctgcc gaacgtgccc gccgtggttt gggcccgagc      900
ctgatcgagt gggtcaccta ccgtgccggc ccgcactcga cctcggacga cccgtccaag      960
taccgccctg ccgatgactg gagccacttc ccgctgggtg acccgatcgc ccgcctgaag     1020
cagcacctga tcaagatcgg ccactggtcc gaagaagaac accaggccac acggccgag      1080 ttcgaagcgg ccgtgattgc tgcgcaaaaa gaagccgagc agtacggcac cctggccaac     1140
ggtcacatcc cgagcgccgc ctcgatgttc gaggacgtgt acaaggagat gcccgaccac     1200
ctgcgccgcc aacgccagga actgggggtt tga                                   1233

<210> SEQ ID NO 214
<211> LENGTH: 410
<212> TYPE: PRT
<213> ORGANISM: Pseudomonas putida

<400> SEQUENCE: 214

Met Asn Glu Tyr Ala Pro Leu Arg Leu His Val Pro Glu Pro Thr Gly
  1               5                  10                  15

Arg Pro Gly Cys Gln Thr Asp Phe Ser Tyr Leu Arg Leu Asn Asp Ala
             20                  25                  30

Gly Gln Ala Arg Lys Pro Pro Val Asp Val Asp Ala Ala Asp Thr Ala
         35                  40                  45

Asp Leu Ser Tyr Ser Leu Val Arg Val Leu Asp Glu Gln Gly Asp Ala
     50                  55                  60

Gln Gly Pro Trp Ala Glu Asp Ile Asp Pro Gln Ile Leu Arg Gln Gly
 65                  70                  75                  80

Met Arg Ala Met Leu Lys Thr Arg Ile Phe Asp Ser Arg Met Val Val
                 85                  90                  95

Ala Gln Arg Gln Lys Lys Met Ser Phe Tyr Met Gln Ser Leu Gly Glu
            100                 105                 110

Glu Ala Ile Gly Ser Gly Gln Ala Leu Ala Leu Asn Arg Thr Asp Met
        115                 120                 125

Cys Phe Pro Thr Tyr Arg Gln Gln Ser Ile Leu Met Ala Arg Asp Val
    130                 135                 140

Ser Leu Val Glu Met Ile Cys Gln Leu Leu Ser Asn Glu Arg Asp Pro
145                 150                 155                 160

Leu Lys Gly Arg Gln Leu Pro Ile Met Tyr Ser Val Arg Glu Ala Gly
                165                 170                 175

Phe Phe Thr Ile Ser Gly Asn Leu Ala Thr Gln Phe Val Gln Ala Val
            180                 185                 190

Gly Trp Ala Met Ala Ser Ala Ile Lys Gly Asp Thr Lys Ile Ala Ser
        195                 200                 205

Ala Trp Ile Gly Asp Gly Ala Thr Ala Glu Ser Asp Phe His Thr Ala
    210                 215                 220

Leu Thr Phe Ala His Val Tyr Arg Ala Pro Val Ile Leu Asn Val Val
225                 230                 235                 240

Asn Asn Gln Trp Ala Ile Ser Thr Phe Gln Ala Ile Ala Gly Gly Glu
                245                 250                 255
```

```
Ser Thr Thr Phe Ala Gly Arg Gly Val Gly Cys Gly Ile Ala Ser Leu
            260                 265                 270

Arg Val Asp Gly Asn Asp Phe Val Ala Val Tyr Ala Ala Ser Arg Trp
        275                 280                 285

Ala Ala Glu Arg Ala Arg Arg Gly Leu Gly Pro Ser Leu Ile Glu Trp
    290                 295                 300

Val Thr Tyr Arg Ala Gly Pro His Ser Thr Ser Asp Asp Pro Ser Lys
305                 310                 315                 320

Tyr Arg Pro Ala Asp Asp Trp Ser His Phe Pro Leu Gly Asp Pro Ile
                325                 330                 335

Ala Arg Leu Lys Gln His Leu Ile Lys Ile Gly His Trp Ser Glu Glu
            340                 345                 350

Glu His Gln Ala Thr Thr Ala Glu Phe Glu Ala Ala Val Ile Ala Ala
        355                 360                 365

Gln Lys Glu Ala Glu Gln Tyr Gly Thr Leu Ala Asn Gly His Ile Pro
    370                 375                 380

Ser Ala Ala Ser Met Phe Glu Asp Val Tyr Lys Glu Met Pro Asp His
385                 390                 395                 400

Leu Arg Arg Gln Arg Gln Glu Leu Gly Val
                405                 410

<210> SEQ ID NO 215
<211> LENGTH: 1059
<212> TYPE: DNA
<213> ORGANISM: Pseudomonas putida

<400> SEQUENCE: 215
atgaacgacc acaacaacag catcaacccg aaaccgcca tggccaccac taccatgacc      60
atgatccagg ccctgcgctc ggccatggat gtcatgcttg agcgcgacga caatgtggtg    120
gtgtacggcc aggacgtcgg ctacttcggc ggcgtgttcc gctgcaccga aggcctgcag    180
accaagtacg gcaagtcccg cgtgttcgac gcgcccatct ctgaaagcgg catcgtcggc    240
accgccgtgg gcatgggtgc ctacggcctg cgcccggtgg tggaaatcca gttcgctgac    300
tacttctacc cggcctccga ccagatcgtt tctgaaatgg cccgcctgcg ctaccgttcg    360
gccggcgagt tcatcgcccc gctgaccctg cgtatgccct gcggtggcgg tatctatggc    420
ggccagacac acagccagag cccggaagcg atgttcactc aggtgtgcgg cctgcgcacc    480
gtaatgccat ccaacccgta cgacgccaaa ggcctgctga ttgcctcgat cgaatgcgac    540
gacccggtga tcttcctgga gcccaagcgc ctgtacaacg gccgttcga cggccaccat    600
gaccgcccgg ttacgccgtg gtcgaaacac ccgcacagcg ccgtgcccga tggctactac    660
accgtgccac tggacaaggc cgccatcacc cgcccgggca atgacgtgag cgtgctcacc    720
tatggcacca ccgtgtacgt ggcccaggtg gccgccgaag aaagtggcgt ggatgccgaa    780
gtgatcgacc tgcgcagcct gtggccgcta gacctggaca ccatcgtcga gtcggtgaaa    840
aagaccggcc gttgcgtggt agtacacgag gccacccgta cttgtggctt tggcgcagaa    900
ctggtgtcgc tggtgcagga gcactgcttc caccacctgg aggcgccgat cgagcgcgtc    960
accggttggg acaccccta ccctcacgcg caggaatggg cttacttccc agggccttcg   1020
cgggtaggtg cggcattgaa aaaggtcatg gaggtctga                           1059

<210> SEQ ID NO 216
<211> LENGTH: 352
<212> TYPE: PRT
<213> ORGANISM: Pseudomonas putida
```

<400> SEQUENCE: 216

```
Met Asn Asp His Asn Asn Ser Ile Asn Pro Glu Thr Ala Met Ala Thr
1               5                   10                  15

Thr Thr Met Thr Met Ile Gln Ala Leu Arg Ser Ala Met Asp Val Met
            20                  25                  30

Leu Glu Arg Asp Asp Asn Val Val Tyr Gly Gln Asp Val Gly Tyr
        35                  40                  45

Phe Gly Gly Val Phe Arg Cys Thr Glu Gly Leu Gln Thr Lys Tyr Gly
50                  55                  60

Lys Ser Arg Val Phe Asp Ala Pro Ile Ser Glu Ser Gly Ile Val Gly
65                  70                  75                  80

Thr Ala Val Gly Met Gly Ala Tyr Gly Leu Arg Pro Val Val Glu Ile
                85                  90                  95

Gln Phe Ala Asp Tyr Phe Tyr Pro Ala Ser Asp Gln Ile Val Ser Glu
            100                 105                 110

Met Ala Arg Leu Arg Tyr Arg Ser Ala Gly Glu Phe Ile Ala Pro Leu
        115                 120                 125

Thr Leu Arg Met Pro Cys Gly Gly Ile Tyr Gly Gly Gln Thr His
130                 135                 140

Ser Gln Ser Pro Glu Ala Met Phe Thr Gln Val Cys Gly Leu Arg Thr
145                 150                 155                 160

Val Met Pro Ser Asn Pro Tyr Asp Ala Lys Gly Leu Leu Ile Ala Ser
                165                 170                 175

Ile Glu Cys Asp Asp Pro Val Ile Phe Leu Glu Pro Lys Arg Leu Tyr
            180                 185                 190

Asn Gly Pro Phe Asp Gly His His Asp Arg Pro Val Thr Pro Trp Ser
        195                 200                 205

Lys His Pro His Ser Ala Val Pro Asp Gly Tyr Tyr Thr Val Pro Leu
210                 215                 220

Asp Lys Ala Ala Ile Thr Arg Pro Gly Asn Asp Val Ser Val Leu Thr
225                 230                 235                 240

Tyr Gly Thr Thr Val Tyr Val Ala Gln Val Ala Ala Glu Ser Gly
                245                 250                 255

Val Asp Ala Glu Val Ile Asp Leu Arg Ser Leu Trp Pro Leu Asp Leu
            260                 265                 270

Asp Thr Ile Val Glu Ser Val Lys Lys Thr Gly Arg Cys Val Val Val
        275                 280                 285

His Glu Ala Thr Arg Thr Cys Gly Phe Gly Ala Glu Leu Val Ser Leu
290                 295                 300

Val Gln Glu His Cys Phe His His Leu Glu Ala Pro Ile Glu Arg Val
305                 310                 315                 320

Thr Gly Trp Asp Thr Pro Tyr Pro His Ala Gln Glu Trp Ala Tyr Phe
                325                 330                 335

Pro Gly Pro Ser Arg Val Gly Ala Ala Leu Lys Lys Val Met Glu Val
            340                 345                 350
```

<210> SEQ ID NO 217
<211> LENGTH: 1272
<212> TYPE: DNA
<213> ORGANISM: Pseudomonas putida

<400> SEQUENCE: 217

```
atgggcacgc acgtcatcaa gatgccggac attggcgaag gcatcgcgca ggtcgaattg      60
```

```
gtggaatggt tcgtcaaggt gggcgacatc atcgccgagg accaagtggt agccgacgtc    120
atgaccgaca aggccaccgt ggaaatcccg tcgccggtca gcggcaaggt gctggccctg    180
ggtggccagc caggtgaagt gatggcggtc ggcagtgagc tgatccgcat cgaagtggaa    240
ggcagcggca accatgtgga tgtgccgcaa gccaagccgg ccgaagtgcc tgcggcaccg    300
gtagccgcta aacctgaacc acagaaagac gttaaaccgg cggcgtacca ggcgtcagcc    360
agccacgagg cagcgcccat cgtgccgcgc agccgggcg acaagccgct ggcctcgccg    420
gcggtgcgca acgcgccct cgatgccggc atcgaattgc gttatgtgca cggcagcggc    480
ccggccgggc gcatcctgca cgaagacctc gacgcgttca tgagcaaacc gcaaagcgct    540
gccgggcaaa cccccaatgg ctatgccagg cgcaccgaca gcgagcaggt gccggtgatc    600
ggcctgcgcc gcaagatcgc ccagcgcatg caggacgcca agcgccgggt cgcgcacttc    660
agctatgtgg aagaaatcga cgtcaccgcc ctggaagccc tgcgccagca gctcaacagc    720
aagcacggcg acagccgcgg caagctgaca ctgctgccgt tcctggtgcg cgccctggtc    780
gtggcactgc gtgacttccc gcagataaac gccacctacg atgacgaagc gcagatcatc    840
acccgccatg gcgcggtgca tgtgggcatc gccacccaag gtgacaacgg cctgatggta    900
cccgtgctgc gccacgccga agcgggcagc ctgtgggcca tgccggtga gatttcacgc     960 ctggccaacg ctgcgcgcaa caacaaggcc agccgcgaag agctgtccgg ttcgaccatt    1020
accctgacca gcctcggcgc cctgggcggc atcgtcagca cgccggtggt caacaccccg    1080
gaagtggcga tcgtcggtgt caaccgcatg gttgagcggc ccgtggtgat cgacggccag    1140
atcgtcgtgc gcaagatgat gaacctgtcc agctcgttcg accaccgcgt ggtcgatggc    1200
atggacgccg ccctgttcat ccaggccgtg cgtggcctgc tcgaacaacc cgcctgcctg    1260
ttcgtggagt ga                                                       1272

<210> SEQ ID NO 218
<211> LENGTH: 423
<212> TYPE: PRT
<213> ORGANISM: Pseudomonas putida

<400> SEQUENCE: 218

Met Gly Thr His Val Ile Lys Met Pro Asp Ile Gly Glu Gly Ile Ala
1               5                   10                  15

Gln Val Glu Leu Val Glu Trp Phe Val Lys Val Gly Asp Ile Ile Ala
            20                  25                  30

Glu Asp Gln Val Val Ala Asp Val Met Thr Asp Lys Ala Thr Val Glu
        35                  40                  45

Ile Pro Ser Pro Val Ser Gly Lys Val Leu Ala Leu Gly Gly Gln Pro
    50                  55                  60

Gly Glu Val Met Ala Val Gly Ser Glu Leu Ile Arg Ile Glu Val Glu
65                  70                  75                  80

Gly Ser Gly Asn His Val Asp Val Pro Gln Ala Lys Pro Ala Glu Val
                85                  90                  95

Pro Ala Ala Pro Val Ala Ala Lys Pro Glu Pro Gln Lys Asp Val Lys
            100                 105                 110

Pro Ala Ala Tyr Gln Ala Ser Ala Ser His Glu Ala Ala Pro Ile Val
        115                 120                 125

Pro Arg Gln Pro Gly Asp Lys Pro Leu Ala Ser Pro Ala Val Arg Lys
    130                 135                 140

Arg Ala Leu Asp Ala Gly Ile Glu Leu Arg Tyr Val His Gly Ser Gly
145                 150                 155                 160
```

Pro Ala Gly Arg Ile Leu His Glu Asp Leu Asp Ala Phe Met Ser Lys
            165                 170                 175

Pro Gln Ser Ala Ala Gly Gln Thr Pro Asn Gly Tyr Ala Arg Arg Thr
        180                 185                 190

Asp Ser Glu Gln Val Pro Val Ile Gly Leu Arg Arg Lys Ile Ala Gln
    195                 200                 205

Arg Met Gln Asp Ala Lys Arg Arg Val Ala His Phe Ser Tyr Val Glu
210                 215                 220

Glu Ile Asp Val Thr Ala Leu Glu Ala Leu Arg Gln Gln Leu Asn Ser
225                 230                 235                 240

Lys His Gly Asp Ser Arg Gly Lys Leu Thr Leu Pro Phe Leu Val
                245                 250                 255

Arg Ala Leu Val Val Ala Leu Arg Asp Phe Pro Gln Ile Asn Ala Thr
                260                 265                 270

Tyr Asp Asp Glu Ala Gln Ile Ile Thr Arg His Gly Ala Val His Val
            275                 280                 285

Gly Ile Ala Thr Gln Gly Asp Asn Gly Leu Met Val Pro Val Leu Arg
        290                 295                 300

His Ala Glu Ala Gly Ser Leu Trp Ala Asn Ala Gly Glu Ile Ser Arg
305                 310                 315                 320

Leu Ala Asn Ala Ala Arg Asn Asn Lys Ala Ser Arg Glu Glu Leu Ser
                325                 330                 335

Gly Ser Thr Ile Thr Leu Thr Ser Leu Gly Ala Leu Gly Gly Ile Val
            340                 345                 350

Ser Thr Pro Val Val Asn Thr Pro Glu Val Ala Ile Val Gly Val Asn
        355                 360                 365

Arg Met Val Glu Arg Pro Val Val Ile Asp Gly Gln Ile Val Val Arg
    370                 375                 380

Lys Met Met Asn Leu Ser Ser Ser Phe Asp His Arg Val Val Asp Gly
385                 390                 395                 400

Met Asp Ala Ala Leu Phe Ile Gln Ala Val Arg Gly Leu Leu Glu Gln
                405                 410                 415

Pro Ala Cys Leu Phe Val Glu
            420

<210> SEQ ID NO 219
<211> LENGTH: 1380
<212> TYPE: DNA
<213> ORGANISM: Pseudomonas putida

<400> SEQUENCE: 219
atgcaacaga ctatccagac aaccctgttg atcatcggcg gcggccctgg cggctatgtg      60
gcggccatcc gcgccgggca actgggcatc cctaccgtgc tggtggaagg ccaggcgctg     120
ggcggtacct gcctgaacat cggctgcatt ccgtccaagg cgctgatcca tgtggccgag     180
cagttccacc aggcctcgcg ctttaccgaa ccctcgccgc tgggcatcag cgtggcttcg     240
ccacgcctgg acatcggcca gagcgtggcc tggaaagacg gcatcgtcga tcgcctgacc     300
actggtgtcg ccgccctgct gaaaaagcac ggggtgaagg tggtgcacgg ctgggccaag     360
gtgcttgatg caagcaggt cgaggtggat ggccagcgca tccagtgcga gcacctgttg     420
ctggccacgg gctccagcag tgtcgaactg ccgatgctgc cgttgggtgg gccggtgatt     480
tcctcgacca aggccctggc accgaaagcc ctgccgcaac acctggtggt ggtgggcggt     540
ggctacatcg gcctggagct gggtatcgcc taccgcaagc tcggcgcgca ggtcagcgtg     600

-continued

```
gtggaagcgc gcgagcgcat cctgccgact tacgacagcg aactgaccgc cccggtggcc      660
gagtcgctga aaaagctggg tatcgccctg caccttggcc acagcgtcga aggttacgaa      720
aatggctgcc tgctggccaa cgatggcaag ggcggacaac tgcgcctgga agccgaccgg      780
gtgctggtgg ccgtgggccg ccgcccacgc accaagggct tcaacctgga atgcctggac      840
ctgaagatga atggtgccgc gattgccatc gacgagcgct gccagaccag catgcacaac      900
gtctgggcca tcggcgacgt ggccggcgaa ccgatgctgg cgcaccgggc catggcccag      960
ggcgagatgg tggccgagat catcgccggc aaggcacgcc gcttcgaacc cgctgcgata     1020
gccgccgtgt gcttcaccga cccggaagtg gtcgtggtcg gcaagacgcc ggaacaggcc     1080
agtcagcaag gcctggactg catcgtcgcg cagttcccgt tcgccgccaa cggccgggcc     1140
atgagcctgg agtcgaaaag cggtttcgtg cgcgtggtcg cgcggcgtga caaccacctg     1200
atcctgggct ggcaagcggt tggcgtggcg gtttccgagc tgtccacggc gtttgcccag     1260
tcgctggaga tgggtgcctg cctggaggat gtggccggta ccatccatgc ccacccgacc     1320
ctgggtgaag cggtacagga agcggcactg cgtgccctgg ccacgccct gcatatctga     1380
```

<210> SEQ ID NO 220
<211> LENGTH: 459
<212> TYPE: PRT
<213> ORGANISM: Pseudomonas putida

<400> SEQUENCE: 220

```
Met Gln Gln Thr Ile Gln Thr Thr Leu Leu Ile Ile Gly Gly Gly Pro
1               5                   10                  15

Gly Gly Tyr Val Ala Ala Ile Arg Ala Gly Gln Leu Gly Ile Pro Thr
                20                  25                  30

Val Leu Val Glu Gly Gln Ala Leu Gly Gly Thr Cys Leu Asn Ile Gly
            35                  40                  45

Cys Ile Pro Ser Lys Ala Leu Ile His Val Ala Glu Gln Phe His Gln
        50                  55                  60

Ala Ser Arg Phe Thr Glu Pro Ser Pro Leu Gly Ile Ser Val Ala Ser
65                  70                  75                  80

Pro Arg Leu Asp Ile Gly Gln Ser Val Ala Trp Lys Asp Gly Ile Val
                85                  90                  95

Asp Arg Leu Thr Thr Gly Val Ala Ala Leu Leu Lys Lys His Gly Val
            100                 105                 110

Lys Val Val His Gly Trp Ala Lys Val Leu Asp Gly Lys Gln Val Glu
        115                 120                 125

Val Asp Gly Gln Arg Ile Gln Cys Glu His Leu Leu Leu Ala Thr Gly
    130                 135                 140

Ser Ser Ser Val Glu Leu Pro Met Leu Pro Leu Gly Gly Pro Val Ile
145                 150                 155                 160

Ser Ser Thr Glu Ala Leu Ala Pro Lys Ala Leu Pro Gln His Leu Val
                165                 170                 175

Val Val Gly Gly Gly Tyr Ile Gly Leu Glu Leu Gly Ile Ala Tyr Arg
            180                 185                 190

Lys Leu Gly Ala Gln Val Ser Val Val Glu Ala Arg Glu Arg Ile Leu
        195                 200                 205

Pro Thr Tyr Asp Ser Glu Leu Thr Ala Pro Val Ala Glu Ser Leu Lys
    210                 215                 220

Lys Leu Gly Ile Ala Leu His Leu Gly His Ser Val Glu Gly Tyr Glu
225                 230                 235                 240
```

```
Asn Gly Cys Leu Leu Ala Asn Asp Gly Lys Gly Gln Leu Arg Leu
            245                 250                 255

Glu Ala Asp Arg Val Leu Val Ala Val Gly Arg Arg Pro Arg Thr Lys
        260                 265                 270

Gly Phe Asn Leu Glu Cys Leu Asp Leu Lys Met Asn Gly Ala Ala Ile
            275                 280                 285

Ala Ile Asp Glu Arg Cys Gln Thr Ser Met His Asn Val Trp Ala Ile
290                 295                 300

Gly Asp Val Ala Gly Glu Pro Met Leu Ala His Arg Ala Met Ala Gln
305                 310                 315                 320

Gly Glu Met Val Ala Glu Ile Ile Ala Gly Lys Ala Arg Arg Phe Glu
            325                 330                 335

Pro Ala Ala Ile Ala Ala Val Cys Phe Thr Asp Pro Glu Val Val Val
            340                 345                 350

Val Gly Lys Thr Pro Glu Gln Ala Ser Gln Gln Gly Leu Asp Cys Ile
            355                 360                 365

Val Ala Gln Phe Pro Phe Ala Ala Asn Gly Arg Ala Met Ser Leu Glu
            370                 375                 380

Ser Lys Ser Gly Phe Val Arg Val Ala Arg Arg Asp Asn His Leu
385                 390                 395                 400

Ile Leu Gly Trp Gln Ala Val Gly Val Ala Val Ser Glu Leu Ser Thr
            405                 410                 415

Ala Phe Ala Gln Ser Leu Glu Met Gly Ala Cys Leu Glu Asp Val Ala
            420                 425                 430

Gly Thr Ile His Ala His Pro Thr Leu Gly Glu Ala Val Gln Glu Ala
            435                 440                 445

Ala Leu Arg Ala Leu Gly His Ala Leu His Ile
        450                 455

<210> SEQ ID NO 221
<211> LENGTH: 1407
<212> TYPE: DNA
<213> ORGANISM: Clostridium beijerinckii

<400> SEQUENCE: 221
atgaataaag acacactaat acctacaact aaagatttaa aattaaaaac aaatgttgaa      60
aacattaatt taaagaacta caaggataat tcttcatgtt tcggagtatt cgaaaatgtt     120
gaaaatgcta taaacagcgc tgtacacgcg caaaagatat tatcccttca ttatacaaaa     180
gaacaaagag aaaaaatcat aactgagata agaaggccg cattagaaaa taagagggtt     240
ttagctacca tgattctgga agaaacacat atgggaaggt atgaagataa aatattaaag     300
catgaattag tagctaaata tactcctggt acagaagatt taactactac tgcttggtca     360
ggtgataatg gtcttacagt tgtagaaatg tctccatatg gcgttatagg tgcaataact     420
ccttctacga atccaactga aactgtaata tgtaatagca tcggcatgat agctgctgga     480
aatgctgtag tatttaacgg acacccaggc gctaaaaaat gtgttgcttt tgctattgaa     540
atgataaata aagcaattat ttcatgtggc ggtcctgaga atttagtaac aactataaaa     600
aatccaacta tggaatccct agatgcaatt attaagcatc tttaataaaa acttctttgc     660
ggaactggag gtccaggaat ggtaaaaacc ctcttaaatt ctggcaagaa agctataggt     720
gctggtgctg gaaatccacc agttattgta gatgataccg ctgatataga aaaggctggt     780
aagagtatca ttgaaggctg ttcttttgat aataatttac cttgtattgc agaaaaagaa     840
```

```
gtatttgttt ttgagaatgt tgcagatgat ttaatatcta acatgctaaa aaataatgct     900
gtaattataa atgaagatca agtatcaaaa ttaatagatt tagtattaca aaaaaataat     960
gaaactcaag aatactttat aaacaaaaaa tgggtaggaa aagatgcaaa attattctca    1020
gatgaaatag atgttgagtc tccttcaaat attaaatgca tagtctgcga agtaaatgca    1080
aatcatccat ttgtcatgac agaactcatg atgccaatat taccaattgt aagagttaaa    1140
gatatagatg aagctgttaa atatacaaag atagcagaac aaaatagaaa acatagtgcc    1200
tatatttatt ctaaaaatat agacaaccta aatagatttg aaagagaaat tgatactact    1260 attttttgtaa agaatgctaa atcttttgct ggtgttggtt atgaagctga aggatttaca    1320
actttcacta ttgctggatc tactggtgaa ggcataacct ctgcaagaaa ttttacaaga    1380
caaagaagat gtgtacttgc cggctaa                                        1407
```

<210> SEQ ID NO 222
<211> LENGTH: 468
<212> TYPE: PRT
<213> ORGANISM: Clostridium beijerinckii

<400> SEQUENCE: 222

```
Met Asn Lys Asp Thr Leu Ile Pro Thr Thr Lys Asp Leu Lys Leu Lys
1               5                  10                  15

Thr Asn Val Glu Asn Ile Asn Leu Lys Asn Tyr Lys Asp Asn Ser Ser
            20                  25                  30

Cys Phe Gly Val Phe Glu Asn Val Glu Asn Ala Ile Asn Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Gly Ala Lys Lys Cys Val Ala
                165                 170                 175

Phe Ala Ile Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Leu Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270
```

```
Leu Pro Cys Ile Ala Glu Lys Glu Val Phe Val Phe Glu Asn Val Ala
            275                 280                 285

Asp Asp Leu Ile Ser Asn Met Leu Lys Asn Asn Ala Val Ile Ile Asn
        290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Ser Asp Glu Ile Asp Val Glu Ser Pro Ser Asn Ile Lys
            340                 345                 350

Cys Ile Val Cys Glu Val Asn Ala Asn His Pro Phe Val Met Thr Glu
            355                 360                 365

Leu Met Met Pro Ile Leu Pro Ile Val Arg Val Lys Asp Ile Asp Glu
        370                 375                 380

Ala Val Lys Tyr Thr Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
        450                 455                 460

Val Leu Ala Gly
465

<210> SEQ ID NO 223
<211> LENGTH: 2589
<212> TYPE: DNA
<213> ORGANISM: Clostridium acetobutylicum

<400> SEQUENCE: 223
atgaaagtca  caacagtaaa  ggaattagat  gaaaaactca  aggtaattaa  agaagctcaa     60
aaaaaattct  cttgttactc  gcaagaaatg  gttgatgaaa  tctttagaaa  tgcagcaatg    120
gcagcaatcg  acgcaaggat  agagctagca  aaagcagctg  ttttggaaac  cggtatgggc    180
ttagttgaag  acaaggttat  aaaaaatcat  tttgcaggcg  aatacatcta  taacaaatat    240
aaggatgaaa  aaacctgcgg  tataattgaa  cgaaatgaac  cctacggaat  tacaaaaata    300
gcagaaccta  taggagttgt  agctgctata  atccctgtaa  caaacccac   atcaacaaca    360 atatttaaat  ccttaatatc  ccttaaaact  agaaatggaa  ttttctttc   gcctcaccca    420 agggcaaaaa  aatccacaat  actagcagct  aaaacaatac  ttgatgcagc  cgttaagagt    480
ggtgccccgg  aaaatataat  aggttggata  gatgaacctt  caattgaact  aactcaatat    540
ttaatgcaaa  aagcagatat  aaccccttgca actggtggtc  cctcactagt  taaatctgct    600
tattcttccg  gaaaccagc   aataggtgtt  ggtccgggta  cacccccagt  aataattgat    660
gaatctgctc  atataaaaat  ggcagtaagt  tcaattatat  atccaaaaac  ctatgataat    720
ggtgttatat  gtgcttctga  acaatctgta  atagtcttaa  atccatata   taacaaggta    780 aaagatgagt  tccaagaaag  aggagcttat  ataataaaga  aaacgaatt   ggataaagtc    840 cgtgaagtga  ttttaaaga   tggatccgta  aaccctaaaa  tagtcggaca  gtcagcttat    900
actatagcag  ctatggctgg  cataaaagta  cctaaaacca  aagaatatt   aataggagaa    960
```

```
gttacctcct taggtgaaga agaaccttt gcccacgaaa actatctcc tgttttggct      1020
atgtatgagg ctgacaattt tgatgatgct taaaaaaag cagtaactct aataaactta     1080
ggaggcctcg gccataccte aggaatatat gcagatgaaa taaaagcacg agataaaata    1140
gatagattta gtagtgccat gaaaaccgta agaaccttg taaatatccc aacctcacaa     1200
ggtgcaagtg gagatctata taattttaga ataccacctt ctttcacgct ggctgcgga     1260
ttttggggag gaaattctgt ttccgagaat gttggtccaa acatctttt gaatattaaa     1320
accgtagctg aaggagaga aacatgctt tggtttagag ttccacataa agtatatttt      1380
aagttcggtt gtcttcaatt tgctttaaaa gatttaaaag atctaaagaa aaaaagagcc   1440
tttatagtta ctgatagtga ccctataat ttaaactatg ttgattcaat aataaaaata    1500
cttgagcacc tagatattga ttttaaagta tttaataagg ttggaagaga agctgatctt   1560
aaaaccataa aaaagcaac tgaagaaatg tcctcctta tgccagacac tataatagct     1620
ttaggtggta ccctgaaat gagctctgca agctaatgt gggtactata tgaacatcca    1680
gaagtaaaat tgaagatct tgcaataaaa tttatggaca taagaaagag aatatatact   1740
ttcccaaaac tcggtaaaaa ggctatgtta gttgcaatta caacttctgc tggttccggt   1800
tctgaggtta ctccttttgc tttagtaact gacaataaca ctggaaataa gtacatgtta   1860
gcagattatg aaatgacacc aaatatggca attgtagatg cagaacttat gatgaaaatg   1920
ccaaagggat taaccgctta ttcaggtata gatgcactag taaatagtat agaagcatac   1980
acatccgtat atgcttcaga atacacaaac ggactagcac tagaggcaat acgattaata   2040
tttaaatatt tgcctgaggc ttacaaaaac ggaagaacca atgaaaaagc aagagagaaa   2100
atggctcacg cttcaactat ggcaggtatg gcatccgcta atgcatttct aggtctatgt   2160
cattccatgg caataaaatt aagttcagaa cacaatattc ctagtggcat tgccaatgca   2220
ttactaatag aagaagtaat aaaatttaac gcagttgata atcctgtaaa acaagcccct   2280
tgcccacaat ataagtatcc aaacaccata ttagatatg ctcgaattgc agattatata    2340
aagcttggag gaaatactga tgaggaaaag gtagatctct taattaacaa atacatgaa    2400
ctaaaaaaag ctttaaatat accaacttca ataaaggatg caggtgtttt ggaggaaaac   2460
ttctattcct cccttgatag aatatctgaa cttgcactag atgatcaatg cacaggcgct   2520
aatcctagat ttcctcttac aagtgagata aagaaatgt atataaattg ttttaaaaaa   2580
caaccttaa                                                            2589
```

<210> SEQ ID NO 224
<211> LENGTH: 862
<212> TYPE: PRT
<213> ORGANISM: Clostridium acetobutylicum

<400> SEQUENCE: 224

Met Lys Val Thr Thr Val Lys Glu Leu Asp Glu Lys Leu Lys Val Ile
1               5                   10                  15

Lys Glu Ala Gln Lys Lys Phe Ser Cys Tyr Ser Gln Glu Met Val Asp
            20                  25                  30

Glu Ile Phe Arg Asn Ala Ala Met Ala Ala Ile Asp Ala Arg Ile Glu
        35                  40                  45

Leu Ala Lys Ala Ala Val Leu Glu Thr Gly Met Gly Leu Val Glu Asp
    50                  55                  60

Lys Val Ile Lys Asn His Phe Ala Gly Glu Tyr Ile Tyr Asn Lys Tyr
65                  70                  75                  80

```
Lys Asp Glu Lys Thr Cys Gly Ile Ile Glu Arg Asn Glu Pro Tyr Gly
                85                  90                  95
Ile Thr Lys Ile Ala Glu Pro Ile Gly Val Val Ala Ala Ile Ile Pro
            100                 105                 110
Val Thr Asn Pro Thr Ser Thr Thr Ile Phe Lys Ser Leu Ile Ser Leu
        115                 120                 125
Lys Thr Arg Asn Gly Ile Phe Phe Ser Pro His Pro Arg Ala Lys Lys
    130                 135                 140
Ser Thr Ile Leu Ala Ala Lys Thr Ile Leu Asp Ala Ala Val Lys Ser
145                 150                 155                 160
Gly Ala Pro Glu Asn Ile Ile Gly Trp Ile Asp Glu Pro Ser Ile Glu
                165                 170                 175
Leu Thr Gln Tyr Leu Met Gln Lys Ala Asp Ile Thr Leu Ala Thr Gly
            180                 185                 190
Gly Pro Ser Leu Val Lys Ser Ala Tyr Ser Ser Gly Lys Pro Ala Ile
        195                 200                 205
Gly Val Gly Pro Gly Asn Thr Pro Val Ile Ile Asp Glu Ser Ala His
    210                 215                 220
Ile Lys Met Ala Val Ser Ser Ile Ile Leu Ser Lys Thr Tyr Asp Asn
225                 230                 235                 240
Gly Val Ile Cys Ala Ser Glu Gln Ser Val Ile Val Leu Lys Ser Ile
                245                 250                 255
Tyr Asn Lys Val Lys Asp Glu Phe Gln Glu Arg Gly Ala Tyr Ile Ile
            260                 265                 270
Lys Lys Asn Glu Leu Asp Lys Val Arg Glu Val Ile Phe Lys Asp Gly
        275                 280                 285
Ser Val Asn Pro Lys Ile Val Gly Gln Ser Ala Tyr Thr Ile Ala Ala
    290                 295                 300
Met Ala Gly Ile Lys Val Pro Lys Thr Thr Arg Ile Leu Ile Gly Glu
305                 310                 315                 320
Val Thr Ser Leu Gly Glu Glu Pro Phe Ala His Glu Lys Leu Ser
                325                 330                 335
Pro Val Leu Ala Met Tyr Glu Ala Asp Asn Phe Asp Asp Ala Leu Lys
            340                 345                 350
Lys Ala Val Thr Leu Ile Asn Leu Gly Gly Leu Gly His Thr Ser Gly
        355                 360                 365
Ile Tyr Ala Asp Glu Ile Lys Ala Arg Asp Lys Ile Asp Arg Phe Ser
    370                 375                 380
Ser Ala Met Lys Thr Val Arg Thr Phe Val Asn Ile Pro Thr Ser Gln
385                 390                 395                 400
Gly Ala Ser Gly Asp Leu Tyr Asn Phe Arg Ile Pro Pro Ser Phe Thr
                405                 410                 415
Leu Gly Cys Gly Phe Trp Gly Gly Asn Ser Val Ser Glu Asn Val Gly
            420                 425                 430
Pro Lys His Leu Leu Asn Ile Lys Thr Val Ala Glu Arg Arg Glu Asn
        435                 440                 445
Met Leu Trp Phe Arg Val Pro His Lys Val Tyr Phe Lys Phe Gly Cys
    450                 455                 460
Leu Gln Phe Ala Leu Lys Asp Leu Lys Asp Leu Lys Lys Lys Arg Ala
465                 470                 475                 480
Phe Ile Val Thr Asp Ser Asp Pro Tyr Asn Leu Asn Tyr Val Asp Ser
                485                 490                 495
Ile Ile Lys Ile Leu Glu His Leu Asp Ile Asp Phe Lys Val Phe Asn
```

```
                500             505             510
Lys Val Gly Arg Glu Ala Asp Leu Lys Thr Ile Lys Lys Ala Thr Glu
            515                 520             525

Glu Met Ser Ser Phe Met Pro Asp Thr Ile Ile Ala Leu Gly Gly Thr
            530                 535             540

Pro Glu Met Ser Ser Ala Lys Leu Met Trp Val Leu Tyr Glu His Pro
545             550             555                 560

Glu Val Lys Phe Glu Asp Leu Ala Ile Lys Phe Met Asp Ile Arg Lys
            565                 570             575

Arg Ile Tyr Thr Phe Pro Lys Leu Gly Lys Lys Ala Met Leu Val Ala
            580                 585             590

Ile Thr Thr Ser Ala Gly Ser Gly Ser Glu Val Thr Pro Phe Ala Leu
            595                 600             605

Val Thr Asp Asn Asn Thr Gly Asn Lys Tyr Met Leu Ala Asp Tyr Glu
            610                 615             620

Met Thr Pro Asn Met Ala Ile Val Asp Ala Glu Leu Met Met Lys Met
625             630             635                 640

Pro Lys Gly Leu Thr Ala Tyr Ser Gly Ile Asp Ala Leu Val Asn Ser
            645                 650             655

Ile Glu Ala Tyr Thr Ser Val Tyr Ala Ser Glu Tyr Thr Asn Gly Leu
            660                 665             670

Ala Leu Glu Ala Ile Arg Leu Ile Phe Lys Tyr Leu Pro Glu Ala Tyr
            675                 680             685

Lys Asn Gly Arg Thr Asn Glu Lys Ala Arg Glu Lys Met Ala His Ala
            690                 695             700

Ser Thr Met Ala Gly Met Ala Ser Ala Asn Ala Phe Leu Gly Leu Cys
705             710             715                 720

His Ser Met Ala Ile Lys Leu Ser Ser Glu His Asn Ile Pro Ser Gly
            725                 730             735

Ile Ala Asn Ala Leu Leu Ile Glu Glu Val Ile Lys Phe Asn Ala Val
            740                 745             750

Asp Asn Pro Val Lys Gln Ala Pro Cys Pro Gln Tyr Lys Tyr Pro Asn
            755                 760             765

Thr Ile Phe Arg Tyr Ala Arg Ile Ala Asp Tyr Ile Lys Leu Gly Gly
            770                 775             780

Asn Thr Asp Glu Glu Lys Val Asp Leu Leu Ile Asn Lys Ile His Glu
785             790             795                 800

Leu Lys Lys Ala Leu Asn Ile Pro Thr Ser Ile Lys Asp Ala Gly Val
            805                 810             815

Leu Glu Glu Asn Phe Tyr Ser Ser Leu Asp Arg Ile Ser Glu Leu Ala
            820                 825             830

Leu Asp Asp Gln Cys Thr Gly Ala Asn Pro Arg Phe Pro Leu Thr Ser
            835                 840             845

Glu Ile Lys Glu Met Tyr Ile Asn Cys Phe Lys Lys Gln Pro
850             855             860
```

<210> SEQ ID NO 225
<211> LENGTH: 2577
<212> TYPE: DNA
<213> ORGANISM: Clostridium acetobutylicum

<400> SEQUENCE: 225
atgaaagtta caaatcaaaa agaactaaaa caaaagctaa atgaattgag agaagcgcaa    60
aagaagtttg caacctatac tcaagagcaa gttgataaaa ttttaaaaca atgtgccata    120

```
gccgcagcta aagaaagaat aaacttagct aaattagcag tagaagaaac aggaataggt      180
cttgtagaag ataaaattat aaaaaatcat tttgcagcag aatatatata caataaatat      240
aaaaatgaaa aaacttgtgg cataatagac catgacgatt ctttaggcat aacaaaggtt      300
gctgaaccaa ttggaattgt tgcagccata gttcctacta ctaatccaac ttccacagca      360
attttcaaat cattaatttc tttaaaaaca agaaacgcaa tattctttc accacatcca       420 cgtgcaaaaa aatctacaat tgctgcagca aaattaattt tagatgcagc tgttaaagca      480
ggagcaccta aaatataat aggctggata gatgagccat caatagaact ttctcaagat       540
ttgatgagtg aagctgatat aatattagca acaggaggtc cttcaatggt taaagcggcc      600
tattcatctg gaaaacctgc aattggtgtt ggagcaggaa atacaccagc aataatagat      660
gagagtgcag atatagatat ggcagtaagc tccataattt tatcaaagac ttatgacaat      720
ggagtaatat gcgcttctga acaatcaata ttagttatga attcaatata cgaaaaagtt      780
aaagaggaat ttgtaaaacg aggatcatat atactcaatc aaaatgaaat agctaaaata      840
aaagaaacta tgtttaaaaa tggagctatt aatgctgaca tagttggaaa atctgcttat      900
ataattgcta aaatggcagg aattgaagtt cctcaaacta caaagatact tataggcgaa      960
gtacaatctg ttgaaaaaag cgagctgttc tcacatgaaa aactatcacc agtacttgca     1020
atgtataaag ttaaggattt tgatgaagct ctaaaaaagg cacaaaggct aatagaatta     1080
ggtggaagtg acacacgtc atctttatat atagattcac aaaacaataa ggataaagtt      1140
aaagaatttg gattagcaat gaaaacttca aggacattta ttaacatgcc ttcttcacag     1200
ggagcaagcg gagatttata caattttgcg atagcaccat catttactct tggatgcggc     1260
acttggggag gaaactctgt atcgcaaaat gtagagccta acatttatt aaatattaaa      1320 agtgttgctg aaagaaggga aaatatgctt tggtttaaag tgccacaaaa aatatatttt     1380
aaatatggat gtcttagatt tgcattaaaa gaattaaaag atatgaataa gaaagagcc      1440 tttatagtaa cagataaaga tcttttttaaa cttggatatg ttaataaaat aacaaaggta     1500
ctagatgaga tagatattaa atacagtata tttacagata ttaaatctga tccaactatt     1560
gattcagtaa aaaaaggtgc taaagaaatg cttaactttg aacctgatac tataatctct     1620
attggtggtg gatcgccaat ggatgcagca aaggttatgc acttgttata tgaatatcca     1680
gaagcagaaa ttgaaaatct agctataaac tttatggata taagaaagag aatatgcaat     1740
ttccctaaat taggtacaaa ggcgatttca gtagctattc ctacaactgc tggtaccggt     1800
tcagaggcaa caccttttgc agttataact aatgatgaaa caggaatgaa ataccctta      1860 acttcttatg aattgacccc aaacatggca ataatagata ctgaattaat gttaaatatg     1920
cctagaaaat aacagcagc aactggaata gatgcattag ttcatgctat agaagcatat      1980
gtttcggtta tggctacgga ttatactgat gaattagcct taagagcaat aaaaatgata     2040
tttaaatatt tgcctagagc ctataaaaat gggactaacg acattgaagc aagagaaaaa     2100
atggcacatg cctctaatat tgcggggatg gcatttgcaa atgctttctt aggtgtatgc     2160
cattcaatgg ctcataaact tggggcaatg catcacgttc cacatggaat tgcttgtgct     2220
gtattaatag aagaagttat taaatataac gctacagact gtccaacaaa gcaaacagca     2280
ttccctcaat ataaatctcc taatgctaag agaaaatatg ctgaaattgc agagtatttg     2340
aatttaaagg gtactagcga taccgaaaag gtaacagcct aatagaagc tatttcaaag     2400 ttaaagatag atttgagtat tccacaaaat ataagtgccg ctggaataaa taaaaaagat     2460
```

```
ttttataata cgctagataa aatgtcagag cttgcttttg atgaccaatg tacaacagct      2520
aatcctaggt atccacttat aagtgaactt aaggatatct atataaaatc attttaa        2577

<210> SEQ ID NO 226
<211> LENGTH: 800
<212> TYPE: PRT
<213> ORGANISM: Clostridium acetobutylicum

<400> SEQUENCE: 226

Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
65                  70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
    130                 135                 140

Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
            340                 345                 350

Lys Ala Gln Arg Leu Ile Glu Leu Gly Gly Ser Gly His Thr Ser Ser
```

-continued

```
            355                 360                 365
Leu Tyr Ile Asp Ser Gln Asn Asn Lys Asp Lys Val Lys Glu Phe Gly
370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
                420                 425                 430

Pro Lys His Leu Leu Asn Ile Lys Ser Val Ala Glu Arg Arg Glu Asn
                435                 440                 445

Met Leu Trp Phe Lys Val Pro Gln Lys Ile Tyr Phe Lys Tyr Gly Cys
            450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                485                 490                 495

Ile Thr Lys Val Leu Asp Glu Ile Asp Ile Lys Tyr Ser Ile Phe Thr
                500                 505                 510

Asp Ile Lys Ser Asp Pro Thr Ile Asp Ser Val Lys Lys Gly Ala Lys
                515                 520                 525

Glu Met Leu Asn Phe Glu Pro Asp Thr Ile Ile Ser Ile Gly Gly Gly
                530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
                580                 585                 590

Ile Pro Thr Thr Ala Gly Thr Gly Ser Glu Ala Thr Pro Phe Ala Val
                595                 600                 605

Ile Thr Asn Asp Glu Thr Gly Met Lys Tyr Pro Leu Thr Ser Tyr Glu
                610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
                660                 665                 670

Ala Leu Arg Ala Ile Lys Met Ile Phe Lys Tyr Leu Pro Arg Ala Tyr
                675                 680                 685

Lys Asn Gly Thr Asn Asp Ile Glu Ala Arg Glu Lys Met Ala His Ala
                690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
                740                 745                 750

Asp Cys Pro Thr Lys Gln Thr Ala Phe Pro Gln Tyr Lys Ser Pro Asn
                755                 760                 765

Ala Lys Arg Lys Tyr Ala Glu Ile Ala Glu Tyr Leu Asn Leu Lys Gly
                770                 775                 780
```

Thr Ser Asp Thr Glu Lys Val Thr Ala Leu Ile Glu Ala Ile Ser Lys
785                 790                 795                 800

<210> SEQ ID NO 227
<211> LENGTH: 924
<212> TYPE: DNA
<213> ORGANISM: Pseudomonas putida

<400> SEQUENCE: 227

```
atgagcaaga aactcaaggc ggccatcata ggccccggca atatcggtac cgatctggtg    60
atgaagatgc tccgttccga gtggattgag ccggtgtgga tggtcggcat cgaccccaac   120
tccgacggcc tcaaacgcgc ccgcgatttc ggcatgaaga ccacagccga aggcgtcgac   180
ggcctgctcc cgcacgtgct ggacgacgac atccgcatcg ccttcgacgc cacctcggcc   240
tatgtgcatg ccgagaatag ccgcaagctc aacgcgcttg gcgtgctgat ggtcgacctg   300
accccggcgg ccatcggccc ctactgcgtg ccgccggtca acctcaagca gcatgtcggc   360
cgcctggaaa tgaacgtcaa catggtcacc tgcggcggcc aggccaccat ccccatggtc   420
gccgcggtgt cccgcgtgca gccggtggcc tacgccgaga tcgtcgccac cgtctcctcg   480
cgctcggtcg gcccgggcac gcgcaagaac atcgacgagt tcacccgcac accgccggc    540
gccatcgagc aggtcggcgg cgccagggaa ggcaaggcga tcatcgtcat caacccggcc   600
gagccgccgc tgatgatgcg cgacaccatc cactgcctga ccgacagcga gcggaccag    660
gctgcgatca ccgcttcggt tcacgcgatg atcgccgagg tgcagaaata cgtgcccggc   720
taccgcctga agaacggccc ggtgttcgac ggcaaccgcg tgtcgatctt catggaagtc   780
gaaggcctgg gcgactacct gcccaagtac gccggcaacc tcgacatcat gaccgccgcc   840
gcgctgcgta ccggcgagat gttcgccgag gaaatcgccg ccggcaccat tcaactgccg   900
cgtcgcgaca tcgcgctggc ttga                                          924
```

<210> SEQ ID NO 228
<211> LENGTH: 307
<212> TYPE: PRT
<213> ORGANISM: Pseudomonas putida

<400> SEQUENCE: 228

Met Ser Lys Lys Leu Lys Ala Ala Ile Ile Gly Pro Gly Asn Ile Gly
1               5                   10                  15

Thr Asp Leu Val Met Lys Met Leu Arg Ser Glu Trp Ile Glu Pro Val
            20                  25                  30

Trp Met Val Gly Ile Asp Pro Asn Ser Asp Gly Leu Lys Arg Ala Arg
        35                  40                  45

Asp Phe Gly Met Lys Thr Thr Ala Glu Gly Val Asp Gly Leu Leu Pro
    50                  55                  60

His Val Leu Asp Asp Asp Ile Arg Ile Ala Phe Asp Ala Thr Ser Ala
65                  70                  75                  80

Tyr Val His Ala Glu Asn Ser Arg Lys Leu Asn Ala Leu Gly Val Leu
                85                  90                  95

Met Val Asp Leu Thr Pro Ala Ala Ile Gly Pro Tyr Cys Val Pro Pro
            100                 105                 110

Val Asn Leu Lys Gln His Val Gly Arg Leu Glu Met Asn Val Asn Met
        115                 120                 125

Val Thr Cys Gly Gly Gln Ala Thr Ile Pro Met Val Ala Ala Val Ser
    130                 135                 140

Arg Val Gln Pro Val Ala Tyr Ala Glu Ile Val Ala Thr Val Ser Ser
145                 150                 155                 160

Arg Ser Val Gly Pro Gly Thr Arg Lys Asn Ile Asp Glu Phe Thr Arg
            165                 170                 175

Thr Thr Ala Gly Ala Ile Glu Gln Val Gly Gly Ala Arg Glu Gly Lys
        180                 185                 190

Ala Ile Ile Val Ile Asn Pro Ala Glu Pro Pro Leu Met Met Arg Asp
        195                 200                 205

Thr Ile His Cys Leu Thr Asp Ser Glu Pro Asp Gln Ala Ala Ile Thr
    210                 215                 220

Ala Ser Val His Ala Met Ile Ala Glu Val Gln Lys Tyr Val Pro Gly
225                 230                 235                 240

Tyr Arg Leu Lys Asn Gly Pro Val Phe Asp Gly Asn Arg Val Ser Ile
            245                 250                 255

Phe Met Glu Val Glu Gly Leu Gly Asp Tyr Leu Pro Lys Tyr Ala Gly
        260                 265                 270

Asn Leu Asp Ile Met Thr Ala Ala Ala Leu Arg Thr Gly Glu Met Phe
    275                 280                 285

Ala Glu Glu Ile Ala Ala Gly Thr Ile Gln Leu Pro Arg Arg Asp Ile
290                 295                 300

Ala Leu Ala
305

<210> SEQ ID NO 229
<211> LENGTH: 924
<212> TYPE: DNA
<213> ORGANISM: Thermus thermophilus

<400> SEQUENCE: 229
atgtccgaaa gggttaaggt agccatcctg gctccggca acatcgggac ggacctgatg      60
tacaagctcc tgaagaaccc gggccacatg gagcttgtgg cggtggtggg gatagacccc    120
aagtccgagg gcctggcccg ggcgcgggcc ttagggttag aggcgagcca cgaagggatc    180
gcctacatcc tggagaggcc ggagatcaag atcgtctttg acgccaccag cgccaaggcc    240
cacgtgcgcc acgccaagct cctgaggag gcggggaaga tcgccataga cctcacgccg    300
gcggcccggg gcccttacgt ggtgcccccg gtgaacctga aggaacacct ggacaaggac    360
aacgtgaacc tcatcacctg cggggggcag gccaccatcc cctggtcta cgcggtgcac    420 cgggtggccc ccgtgctcta cgcggagatg gtctccacgg tggcctcccg ctccgcgggc    480
cccggcaccg gcagaacat cgacgagttc accttcacca ccgcccgggg cctgaggcc    540 atcgggggg ccaagaaggg gaaggccatc atcatcctga cccggcgga accccccatc    600 ctcatgacca cacccgtgcg ctgcatcccc gaggacgagg gctttgaccg ggaggccgtg    660
gtggcgagcg tccgggccat ggagcgggag gtccaggcct acgtgcccgg ctaccgcctg    720
aaggcggacc cggtgtttga gaggcttccc accccctggg gggagcgcac cgtggtctcc    780
atgctcctgg aggtggaggg ggcggggac tatttgccca aatacgccgg caacctggac    840
atcatgacgg cttctgcccg gagggtgggg gaggtcttcg cccagcacct cctggggaag    900
cccgtggagg aggtggtggc gtga                                           924

<210> SEQ ID NO 230
<211> LENGTH: 307
<212> TYPE: PRT
<213> ORGANISM: Thermus thermophilus

<400> SEQUENCE: 230

```
Met Ser Glu Arg Val Lys Val Ala Ile Leu Gly Ser Gly Asn Ile Gly
1               5                   10                  15

Thr Asp Leu Met Tyr Lys Leu Leu Lys Asn Pro Gly His Met Glu Leu
            20                  25                  30

Val Ala Val Val Gly Ile Asp Pro Lys Ser Glu Gly Leu Ala Arg Ala
        35                  40                  45

Arg Ala Leu Gly Leu Glu Ala Ser His Glu Gly Ile Ala Tyr Ile Leu
    50                  55                  60

Glu Arg Pro Glu Ile Lys Ile Val Phe Asp Ala Thr Ser Ala Lys Ala
65                  70                  75                  80

His Val Arg His Ala Lys Leu Leu Arg Glu Ala Gly Lys Ile Ala Ile
                85                  90                  95

Asp Leu Thr Pro Ala Ala Arg Gly Pro Tyr Val Val Pro Pro Val Asn
            100                 105                 110

Leu Lys Glu His Leu Asp Lys Asp Asn Val Asn Leu Ile Thr Cys Gly
        115                 120                 125

Gly Gln Ala Thr Ile Pro Leu Val Tyr Ala Val His Arg Val Ala Pro
    130                 135                 140

Val Leu Tyr Ala Glu Met Val Ser Thr Val Ala Ser Arg Ser Ala Gly
145                 150                 155                 160

Pro Gly Thr Arg Gln Asn Ile Asp Glu Phe Thr Phe Thr Thr Ala Arg
                165                 170                 175

Gly Leu Glu Ala Ile Gly Gly Ala Lys Lys Gly Lys Ala Ile Ile Ile
            180                 185                 190

Leu Asn Pro Ala Glu Pro Pro Ile Leu Met Thr Asn Thr Val Arg Cys
        195                 200                 205

Ile Pro Glu Asp Glu Gly Phe Asp Arg Glu Ala Val Val Ala Ser Val
    210                 215                 220

Arg Ala Met Glu Arg Glu Val Gln Ala Tyr Val Pro Gly Tyr Arg Leu
225                 230                 235                 240

Lys Ala Asp Pro Val Phe Glu Arg Leu Pro Thr Pro Trp Gly Glu Arg
                245                 250                 255

Thr Val Val Ser Met Leu Leu Glu Val Glu Gly Ala Gly Asp Tyr Leu
            260                 265                 270

Pro Lys Tyr Ala Gly Asn Leu Asp Ile Met Thr Ala Ser Ala Arg Arg
        275                 280                 285

Val Gly Glu Val Phe Ala Gln His Leu Leu Gly Lys Pro Val Glu Glu
    290                 295                 300

Val Val Ala
305
```

<210> SEQ ID NO 231
<211> LENGTH: 1254
<212> TYPE: DNA
<213> ORGANISM: Escherichia coli

<400> SEQUENCE: 231

```
atgacattct ccctttttgg tgacaaattt acccgccact ccggcattac gctgttgatg      60
gaagatctga cgacggtttt acgcacgcct ggcgcgatta tgctcggcgg cggtaatccg     120
gcgcagatcc cggaaatgca ggactacttc cagacgctac tgaccgacat gctggaaagt     180
ggcaaagcga ctgatgcact gtgtaactac gacggtccac aggggaaaac ggagctactc     240
acactgcttg ccggaatgct gcgcgagaag ttgggttggg atatcgaacc acagaatatt     300
```

```
gcactaacaa acggcagcca gagcgcgttt ttctacttat ttaacctgtt tgccggacgc    360
cgtgccgatg gtcgggtcaa aaagtgctg ttcccgcttg caccggaata cattggctat    420
gctgacgccg gactggaaga agatctgttt gtctctgcgc gtccgaatat tgaactgctg    480
ccggaaggcc agtttaaata ccacgtcgat tttgagcatc tgcatattgg cgaagaaacc    540
gggatgattt cgtctcccg gccgacgaat ccaacaggca atgtgattac tgacgaagag    600
ttgctgaagc ttgacgcgct ggcgaatcaa cacggcattc cgctggtgat tgataacgct    660
tatggcgtcc cgttcccggg tatcatcttc agtgaagcgc gcccgctatg gaatccgaat    720
atcgtgctgt gcatgagtct ttccaagctg ggtctacctg ctcccgctg cggcattatc    780 atcgccaatg aaaaaatcat caccgccatc accaatatga acggcattat cagcctggca    840
cctggcggta ttggtccggc gatgatgtgt gaaatgatta gcgtaacga tctgctgcgc    900 ctgtctgaaa cagtcatcaa accgttttac taccagcgtg ttcaggaaac tatcgccatc    960 attgccgct atttaccgga aaatcgctgc ctgattcata aaccggaagg agccattttc   1020
ctctggctat ggtttaagga tttgcccatt acgaccaagc agctctatca gcgcctgaaa   1080
gcacgcggcg tgctgatggt gccggggcac aacttcttcc cagggctgga taaaccgtgg   1140
ccgcatacgc atcaatgtat gcgcatgaac tacgtaccag agccggagaa aattgaggcg   1200
ggggtgaaga ttctggcgga agagatagaa agagcctggg ctgaaagtca ctaa         1254
```

<210> SEQ ID NO 232
<211> LENGTH: 417
<212> TYPE: PRT
<213> ORGANISM: Escherichia coli

<400> SEQUENCE: 232

```
Met Thr Phe Ser Leu Phe Gly Asp Lys Phe Thr Arg His Ser Gly Ile
1               5                   10                  15

Thr Leu Leu Met Glu Asp Leu Asn Asp Gly Leu Arg Thr Pro Gly Ala
            20                  25                  30

Ile Met Leu Gly Gly Gly Asn Pro Ala Gln Ile Pro Glu Met Gln Asp
        35                  40                  45

Tyr Phe Gln Thr Leu Leu Thr Asp Met Leu Glu Ser Gly Lys Ala Thr
    50                  55                  60

Asp Ala Leu Cys Asn Tyr Asp Gly Pro Gln Gly Lys Thr Glu Leu Leu
65                  70                  75                  80

Thr Leu Leu Ala Gly Met Leu Arg Glu Lys Leu Gly Trp Asp Ile Glu
                85                  90                  95

Pro Gln Asn Ile Ala Leu Thr Asn Gly Ser Gln Ser Ala Phe Phe Tyr
            100                 105                 110

Leu Phe Asn Leu Phe Ala Gly Arg Arg Ala Asp Gly Val Lys Lys
        115                 120                 125

Val Leu Phe Pro Leu Ala Pro Glu Tyr Ile Gly Tyr Ala Asp Ala Gly
    130                 135                 140

Leu Glu Glu Asp Leu Phe Val Ser Ala Arg Pro Asn Ile Glu Leu Leu
145                 150                 155                 160

Pro Glu Gly Gln Phe Lys Tyr His Val Asp Phe Glu His Leu His Ile
                165                 170                 175

Gly Glu Glu Thr Gly Met Ile Cys Val Ser Arg Pro Thr Asn Pro Thr
            180                 185                 190

Gly Asn Val Ile Thr Asp Glu Glu Leu Leu Lys Leu Asp Ala Leu Ala
        195                 200                 205
```

```
Asn Gln His Gly Ile Pro Leu Val Ile Asp Asn Ala Tyr Gly Val Pro
        210                 215                 220
Phe Pro Gly Ile Ile Phe Ser Glu Ala Arg Pro Leu Trp Asn Pro Asn
225                 230                 235                 240
Ile Val Leu Cys Met Ser Leu Ser Lys Leu Gly Leu Pro Gly Ser Arg
                245                 250                 255
Cys Gly Ile Ile Ile Ala Asn Glu Lys Ile Ile Thr Ala Ile Thr Asn
                260                 265                 270
Met Asn Gly Ile Ile Ser Leu Ala Pro Gly Gly Ile Gly Pro Ala Met
            275                 280                 285
Met Cys Glu Met Ile Lys Arg Asn Asp Leu Leu Arg Leu Ser Glu Thr
        290                 295                 300
Val Ile Lys Pro Phe Tyr Tyr Gln Arg Val Gln Glu Thr Ile Ala Ile
305                 310                 315                 320
Ile Arg Arg Tyr Leu Pro Glu Asn Arg Cys Leu Ile His Lys Pro Glu
                325                 330                 335
Gly Ala Ile Phe Leu Trp Leu Trp Phe Lys Asp Leu Pro Ile Thr Thr
                340                 345                 350
Lys Gln Leu Tyr Gln Arg Leu Lys Ala Arg Gly Val Leu Met Val Pro
            355                 360                 365
Gly His Asn Phe Phe Pro Gly Leu Asp Lys Pro Trp Pro His Thr His
        370                 375                 380
Gln Cys Met Arg Met Asn Tyr Val Pro Glu Pro Glu Lys Ile Glu Ala
385                 390                 395                 400
Gly Val Lys Ile Leu Ala Glu Glu Ile Glu Arg Ala Trp Ala Glu Ser
                405                 410                 415
His

<210> SEQ ID NO 233
<211> LENGTH: 1278
<212> TYPE: DNA
<213> ORGANISM: Bacillus licheniformis

<400> SEQUENCE: 233
ttataagtat tcaacctgtt tctcatatac accctcgca attttagcta aaacatcgat       60
tccccttata atatcttcat ccgccgcggt taggctgatt cgtatacact ggtgtgaatg      120
cgccaggcgc cgggattgac ggtgaaagaa agatgatccg ggaacgataa tgactccatc     180
cgctttcata tactcataca gcgctgcatc ggtcaccggc aggtcttcaa accacagcca     240
tccgaaaagc gatccttccc cttgatgcag ataccatttg atgtcttcag gcatcttgca     300
taaaagcgtt tccttgagca gcatgaattt attgcggtaa tatggcctga cttcattcag     360
cgacacgtcg gcgaggcgcc cgtcattcaa tactgatgca gccatatact gccccagcct     420
tgaagaatgg atcgccgcat tcgactgaaa agcttccatt gcctgaatat accgggacgg     480
cccgatggcg attccgatcc tttcgccagg caggccggct tttgaaaggc tcatacagtg     540
aatgatctgc tcgttgaaaa tcggttccat gtcgataaag tgaatcgccg gaaaaggcgg     600
agcatatgcg gaatcaatga acagcggaac attcgcttct cggcatgcgt ctgaaatgaa     660
tgctacatct tctttaggca agatgtttcc gcaaggattg ttcgggcgcg atagcaagac     720
agcaccgatg cgcatcctct ctaaaaaccc cttacggtcg agctcatatc gaaacgtatg     780
atcatccaat ttcgatatga gcggagggat ccctcaatc atctcccgct ccagtgccgc      840
cccgctgtat cccgaatagt caggcagcat cgggatcaag gctttttca tcacagatcc      900
```

```
gcttcccatt ccgcaaaacg aattgatcgc cagaaaaaac agctgctggc ttccggctgt    960
aatcaacacg ttctcttttc gaatgccggc gctataccgc tctgaaaaga agcggacaac   1020
acttgcaatc agttcatcgg ttccatagct cgatccgtat tggccgatca ccgaagaaaa   1080
cctgtcatcg tcaaggagat cggcaagagc cgacttccac atggctgaca cgccgggcaa   1140
aatcatcgga ttgcccgcac ttaaattaat gtatgaccgt tcaccgccgg ccaggacttc   1200
ctgaatatcg ctcatcacag ccctgacccc tgttttctca atcatttct ctccgatttt    1260 gcttaatggc ggcttcac                                                 1278
```

<210> SEQ ID NO 234
<211> LENGTH: 425
<212> TYPE: PRT
<213> ORGANISM: Bacillus licheniformis

<400> SEQUENCE: 234

```
Met Lys Pro Pro Leu Ser Lys Ile Gly Glu Lys Met Ile Glu Lys Thr
1               5                   10                  15

Gly Val Arg Ala Val Met Ser Asp Ile Gln Glu Val Leu Ala Gly Gly
            20                  25                  30

Glu Arg Ser Tyr Ile Asn Leu Ser Ala Gly Asn Pro Met Ile Leu Pro
        35                  40                  45

Gly Val Ser Ala Met Trp Lys Ser Ala Leu Ala Asp Leu Leu Asp Asp
    50                  55                  60

Asp Arg Phe Ser Ser Val Ile Gly Gln Tyr Gly Ser Ser Tyr Gly Thr
65                  70                  75                  80

Asp Glu Leu Ile Ala Ser Val Val Arg Phe Phe Ser Glu Arg Tyr Ser
                85                  90                  95

Ala Gly Ile Arg Lys Glu Asn Val Leu Ile Thr Ala Gly Ser Gln Gln
            100                 105                 110

Leu Phe Phe Leu Ala Ile Asn Ser Phe Cys Gly Met Gly Ser Gly Ser
        115                 120                 125

Val Met Lys Lys Ala Leu Ile Pro Met Leu Pro Asp Tyr Ser Gly Tyr
    130                 135                 140

Ser Gly Ala Ala Leu Glu Arg Glu Met Ile Glu Gly Ile Pro Pro Leu
145                 150                 155                 160

Ile Ser Lys Leu Asp Asp His Thr Phe Arg Tyr Glu Leu Asp Arg Lys
                165                 170                 175

Gly Phe Leu Glu Arg Met Arg Ile Gly Ala Val Leu Leu Ser Arg Pro
            180                 185                 190

Asn Asn Pro Cys Gly Asn Ile Leu Pro Lys Glu Asp Val Ala Phe Ile
        195                 200                 205

Ser Asp Ala Cys Arg Glu Ala Asn Val Pro Leu Phe Ile Asp Ser Ala
    210                 215                 220

Tyr Ala Pro Pro Phe Pro Ala Ile His Phe Ile Asp Met Glu Pro Ile
225                 230                 235                 240

Phe Asn Glu Gln Ile Ile His Cys Met Ser Leu Ser Lys Ala Gly Leu
                245                 250                 255

Pro Gly Glu Arg Ile Gly Ile Ala Ile Gly Pro Ser Arg Tyr Ile Gln
            260                 265                 270

Ala Met Glu Ala Phe Gln Ser Asn Ala Ala Ile His Ser Ser Arg Leu
        275                 280                 285

Gly Gln Tyr Met Ala Ala Ser Val Leu Asn Asp Gly Arg Leu Ala Asp
    290                 295                 300
```

Val Ser Leu Asn Glu Val Arg Pro Tyr Tyr Arg Asn Lys Phe Met Leu
305                 310                 315                 320

Leu Lys Glu Thr Leu Leu Cys Lys Met Pro Glu Asp Ile Lys Trp Tyr
            325                 330                 335

Leu His Gln Gly Glu Gly Ser Leu Phe Gly Trp Leu Trp Phe Glu Asp
        340                 345                 350

Leu Pro Val Thr Asp Ala Ala Leu Tyr Glu Tyr Met Lys Ala Asp Gly
    355                 360                 365

Val Ile Ile Val Pro Gly Ser Ser Phe Phe His Arg Gln Ser Arg Arg
370                 375                 380

Leu Ala His Ser His Gln Cys Ile Arg Ile Ser Leu Thr Ala Ala Asp
385                 390                 395                 400

Glu Asp Ile Ile Arg Gly Ile Asp Val Leu Ala Lys Ile Ala Lys Gly
            405                 410                 415

Val Tyr Glu Lys Gln Val Glu Tyr Leu
        420                 425

<210> SEQ ID NO 235
<211> LENGTH: 930
<212> TYPE: DNA
<213> ORGANISM: Escherichia coli

<400> SEQUENCE: 235
atgaccacga agaaagctga ttacatttgg ttcaatgggg agatggttcg ctgggaagac      60
gcgaaggtgc atgtgatgtc gcacgcgctg cactatggca cttcggtttt tgaaggcatc     120
cgttgctacg actcgcacaa aggaccggtt gtattccgcc atcgtgagca tatgcagcgt     180
ctgcatgact ccgccaaaat ctatcgcttc ccggtttcgc agagcattga tgagctgatg     240
gaagcttgtc gtgacgtgat ccgcaaaaac aatctcacca gcgcctatat ccgtccgctg     300
atcttcgtcg gtgatgttgg catgggagta aacccgccag cgggatactc aaccgacgtg     360
attatcgctg ctttcccgtg gggagcgtat ctgggcgcag aagcgctgga gcaggggatc     420
gatgcgatgg tttcctcctg gaaccgcgca gcaccaaaca ccatcccgac ggcggcaaaa     480
gccggtggta actacctctc ttccctgctg gtgggtagca agcgcgccg ccacggttat     540
caggaaggta tcgcgctgga tgtgaacggt tatatctctg aaggcgcagg cgaaaacctg     600
tttgaagtga agatggtgt gctgttcacc ccaccgttca cctcctccgc gctgccgggt     660
attacccgtg atgccatcat caaactggcg aaagagctgg gaattgaagt acgtgagcag     720
gtgctgtcgc gcgaatccct gtacctggcg gatgaagtgt ttatgtccgg tacgcggca     780
gaaatcacgc cagtgcgcag cgtagacggt attcaggttg gcgaaggccg ttgtggcccg     840
gttaccaaac gcattcagca agccttcttc ggcctcttca ctggcgaaac cgaagataaa     900
tggggctggt tagatcaagt taatcaataa                                      930

<210> SEQ ID NO 236
<211> LENGTH: 309
<212> TYPE: PRT
<213> ORGANISM: Escherichia coli

<400> SEQUENCE: 236

Met Thr Thr Lys Lys Ala Asp Tyr Ile Trp Phe Asn Gly Glu Met Val
1               5                   10                  15

Arg Trp Glu Asp Ala Lys Val His Val Met Ser His Ala Leu His Tyr
            20                  25                  30

Gly Thr Ser Val Phe Glu Gly Ile Arg Cys Tyr Asp Ser His Lys Gly
            35                  40                  45

Pro Val Val Phe Arg His Arg Glu His Met Gln Arg Leu His Asp Ser
 50                  55                  60

Ala Lys Ile Tyr Arg Phe Pro Val Ser Gln Ser Ile Asp Glu Leu Met
 65                  70                  75                  80

Glu Ala Cys Arg Asp Val Ile Arg Lys Asn Asn Leu Thr Ser Ala Tyr
                 85                  90                  95

Ile Arg Pro Leu Ile Phe Val Gly Asp Val Gly Met Gly Val Asn Pro
                100                 105                 110

Pro Ala Gly Tyr Ser Thr Asp Val Ile Ala Ala Phe Pro Trp Gly
            115                 120                 125

Ala Tyr Leu Gly Ala Glu Ala Leu Glu Gln Gly Ile Asp Ala Met Val
            130                 135                 140

Ser Ser Trp Asn Arg Ala Ala Pro Asn Thr Ile Pro Thr Ala Ala Lys
145                 150                 155                 160

Ala Gly Gly Asn Tyr Leu Ser Ser Leu Leu Val Gly Ser Glu Ala Arg
                165                 170                 175

Arg His Gly Tyr Gln Glu Gly Ile Ala Leu Asp Val Asn Gly Tyr Ile
            180                 185                 190

Ser Glu Gly Ala Gly Glu Asn Leu Phe Glu Val Lys Asp Gly Val Leu
    195                 200                 205

Phe Thr Pro Pro Phe Thr Ser Ser Ala Leu Pro Gly Ile Thr Arg Asp
            210                 215                 220

Ala Ile Ile Lys Leu Ala Lys Glu Leu Gly Ile Glu Val Arg Glu Gln
225                 230                 235                 240

Val Leu Ser Arg Glu Ser Leu Tyr Leu Ala Asp Glu Val Phe Met Ser
                245                 250                 255

Gly Thr Ala Ala Glu Ile Thr Pro Val Arg Ser Val Asp Gly Ile Gln
            260                 265                 270

Val Gly Glu Gly Arg Cys Gly Pro Val Thr Lys Arg Ile Gln Gln Ala
    275                 280                 285

Phe Phe Gly Leu Phe Thr Gly Glu Thr Glu Asp Lys Trp Gly Trp Leu
290                 295                 300

Asp Gln Val Asn Gln
305

<210> SEQ ID NO 237
<211> LENGTH: 1131
<212> TYPE: DNA
<213> ORGANISM: Saccharomyces cerevisiae

<400> SEQUENCE: 237

```
atgaccttgg caccsctaga cgcctccaaa gttaagataa ctaccacaca acatgcatct        60
aagccaaaac cgaacagtga gttagtgttt ggcaagagct tcacggacca catgttaact       120
gcggaatgga cagctgaaaa agggtggggt accccagaga ttaaacctta tcaaaatctg       180
tctttagacc cttccgcggt ggttttccat tatgcttttg agctattcga agggatgaag       240
gcttacagaa cggtggacaa caaaattaca atgtttcgtc cagatatgaa tatgaagcgc       300
atgaataagt ctgctcagag aatctgtttg ccaacgttcg acccagaaga gttgattacc       360
ctaattggga aactgatcca gcaagataag tgcttagttc ctgaaggaaa aggttactct       420
ttatatatca ggcctacatt aatcggcact acggccggtt taggggtttc cacgcctgat       480
agagccttgc tatatgtcat ttgctgccct gtgggtcctt attacaaaac tggatttaag       540
```

```
gcggtcagac tggaagccac tgattatgcc acaagagctt ggccaggagg ctgtggtgac      600
aagaaactag gtgcaaacta cgcccctgc gtcctgccac aattgcaagc tgcttcaagg       660
ggttaccaac aaaatttatg gctatttggt ccaaataaca acattactga agtcggcacc     720
atgaatgctt ttttcgtgtt taaagatagt aaaacgggca agaaggaact agttactgct     780
ccactagacg gtaccatttt ggaaggtgtt actagggatt ccattttaaa tcttgctaaa     840
gaaagactcg aaccaagtga atggaccatt agtgaacgct acttcactat aggcgaagtt     900
actgagagat ccaagaacgg tgaactactt gaagcctttg gttctggtac tgctgcgatt     960
gtttctccca ttaaggaaat cggctggaaa ggcgaacaaa ttaatattcc gttgttgccc    1020
ggcgaacaaa ccggtccatt ggccaaagaa gttgcacaat ggattaatgg aatccaatat    1080
ggcgagactg agcatggcaa ttggtcaagg gttgttactg atttgaactg a             1131
```

<210> SEQ ID NO 238
<211> LENGTH: 376
<212> TYPE: PRT
<213> ORGANISM: Saccharomyces cerevisiae

<400> SEQUENCE: 238

```
Met Thr Leu Ala Pro Leu Asp Ala Ser Lys Val Lys Ile Thr Thr Thr
1               5                   10                  15

Gln His Ala Ser Lys Pro Lys Pro Asn Ser Glu Leu Val Phe Gly Lys
            20                  25                  30

Ser Phe Thr Asp His Met Leu Thr Ala Glu Trp Thr Ala Glu Lys Gly
        35                  40                  45

Trp Gly Thr Pro Glu Ile Lys Pro Tyr Gln Asn Leu Ser Leu Asp Pro
    50                  55                  60

Ser Ala Val Val Phe His Tyr Ala Phe Glu Leu Phe Glu Gly Met Lys
65                  70                  75                  80

Ala Tyr Arg Thr Val Asp Asn Lys Ile Thr Met Phe Arg Pro Asp Met
                85                  90                  95

Asn Met Lys Arg Met Asn Lys Ser Ala Gln Arg Ile Cys Leu Pro Thr
            100                 105                 110

Phe Asp Pro Glu Glu Leu Ile Thr Leu Ile Gly Lys Leu Ile Gln Gln
        115                 120                 125

Asp Lys Cys Leu Val Pro Glu Gly Lys Gly Tyr Ser Leu Tyr Ile Arg
    130                 135                 140

Pro Thr Leu Ile Gly Thr Thr Ala Gly Leu Gly Val Ser Thr Pro Asp
145                 150                 155                 160

Arg Ala Leu Leu Tyr Val Ile Cys Cys Pro Val Gly Pro Tyr Tyr Lys
                165                 170                 175

Thr Gly Phe Lys Ala Val Arg Leu Glu Ala Thr Asp Tyr Ala Thr Arg
            180                 185                 190

Ala Trp Pro Gly Gly Cys Gly Asp Lys Lys Leu Gly Ala Asn Tyr Ala
        195                 200                 205

Pro Cys Val Leu Pro Gln Leu Gln Ala Ala Ser Arg Gly Tyr Gln Gln
    210                 215                 220

Asn Leu Trp Leu Phe Gly Pro Asn Asn Ile Thr Glu Val Gly Thr
225                 230                 235                 240

Met Asn Ala Phe Phe Val Phe Lys Asp Ser Lys Thr Gly Lys Lys Glu
                245                 250                 255

Leu Val Thr Ala Pro Leu Asp Gly Thr Ile Leu Glu Gly Val Thr Arg
            260                 265                 270
```

Asp Ser Ile Leu Asn Leu Ala Lys Glu Arg Leu Glu Pro Ser Glu Trp
        275                 280                 285

Thr Ile Ser Glu Arg Tyr Phe Thr Ile Gly Glu Val Thr Glu Arg Ser
        290                 295                 300

Lys Asn Gly Glu Leu Leu Glu Ala Phe Gly Ser Gly Thr Ala Ala Ile
305                 310                 315                 320

Val Ser Pro Ile Lys Glu Ile Gly Trp Lys Gly Glu Gln Ile Asn Ile
                325                 330                 335

Pro Leu Leu Pro Gly Glu Gln Thr Gly Pro Leu Ala Lys Glu Val Ala
            340                 345                 350

Gln Trp Ile Asn Gly Ile Gln Tyr Gly Glu Thr Glu His Gly Asn Trp
        355                 360                 365

Ser Arg Val Val Thr Asp Leu Asn
        370                 375

<210> SEQ ID NO 239
<211> LENGTH: 993
<212> TYPE: DNA
<213> ORGANISM: Methanobacterium thermoautotrophicum

<400> SEQUENCE: 239

```
tcagatgtag gtgagccatc cgaagctgtc ctctgtctct gccctgatta tcctgaagaa    60
ctcatcctgc agcagctttg taacgggacc ccttcgcccg gcacctatct ctataccatc   120
aactgatctg atgggtgtta tctctgcggc tgtacctgtg aagaaggcct catctgcgat   180
gtagagcatc tccctggtta tgggttcctc atgcacggta cacccctcgg tcctggctat   240
ctttattacg gagtcccttg ttatcccct cagaagggat gatgaaacag ggggggtgta   300
aatttcaccc tcactgacga ggaatatgtt ctccccgcta ccctcactta tgtagccatg   360
gtagtccagc attatggcct catcatagcc gtgtctcaca gcctccatct tggcaagctg   420
tgagttgagt agttaccgc cggcctttgc catgttgggc attgtgtttg gtgccatcct   480
ccgccaggtt gaaacaccag catcgacacc aacctcaagg gcctctgcac ccagataggc   540
cccccattcc caggcagcca cagcgacgtc cactgggcag ttaccgggt gaacacccat   600
ctcaccgtat ccctgaata ccacgggtct tatatagcac tcctcaagtc cgttctccct   660
gacggtctca actatggcat cacatatctg ctcctgggtg tagggtatgt ccatccggta   720
tatcttttgca gaatcaaaaa ggcgtttaac atgctcccgc aaacggaaga tggctgaccc   780
cttactgttc ctgtagcacc ttattccctc aaagacagat gatccataat gcacaacatg   840
tgagagtacg tggacggtgg cttcttccca ttcaaccatt tcaccgttta accatatctt   900
tccactggct tcgcatgaca tgataataac ctcaggtgat ttactaggat aggttatggt   960
tggaggccta taatgctctc ccataaccg caa                                  993
```

<210> SEQ ID NO 240
<211> LENGTH: 330
<212> TYPE: PRT
<213> ORGANISM: Methanobacterium thermoautotrophicum

<400> SEQUENCE: 240

Met Arg Leu Trp Arg Ala Leu Tyr Arg Pro Pro Thr Ile Thr Tyr Pro
1               5                   10                  15

Ser Lys Ser Pro Glu Val Ile Ile Met Ser Cys Glu Ala Ser Gly Lys
            20                  25                  30

Ile Trp Leu Asn Gly Glu Met Val Glu Trp Glu Glu Ala Thr Val His 35                  40                  45
Val Leu Ser His Val His Tyr Gly Ser Val Phe Glu Gly Ile
 50                  55                  60

Arg Cys Tyr Arg Asn Ser Lys Gly Ser Ala Ile Phe Arg Leu Arg Glu
 65                  70                  75                  80

His Val Lys Arg Leu Phe Asp Ser Ala Lys Ile Tyr Arg Met Asp Ile
                 85                  90                  95

Pro Tyr Thr Gln Glu Gln Ile Cys Asp Ala Ile Val Glu Thr Val Arg
                100                 105                 110

Glu Asn Gly Leu Glu Glu Cys Tyr Ile Arg Pro Val Val Phe Arg Gly
                115                 120                 125

Tyr Gly Glu Met Gly Val His Pro Val Asn Cys Pro Val Asp Val Ala
                130                 135                 140

Val Ala Ala Trp Glu Trp Gly Ala Tyr Leu Gly Ala Glu Ala Leu Glu
145                 150                 155                 160

Val Gly Val Asp Ala Gly Val Ser Thr Trp Arg Arg Met Ala Pro Asn
                165                 170                 175

Thr Met Pro Asn Met Ala Lys Ala Gly Gly Asn Tyr Leu Asn Ser Gln
                180                 185                 190

Leu Ala Lys Met Glu Ala Val Arg His Gly Tyr Asp Glu Ala Ile Met
                195                 200                 205

Leu Asp Tyr His Gly Tyr Ile Ser Glu Gly Ser Gly Glu Asn Ile Phe
                210                 215                 220

Leu Val Ser Glu Gly Glu Ile Tyr Thr Pro Pro Val Ser Ser Ser Leu
225                 230                 235                 240

Leu Arg Gly Ile Thr Arg Asp Ser Val Ile Lys Ile Ala Arg Thr Glu
                245                 250                 255

Gly Val Thr Val His Glu Glu Pro Ile Thr Arg Glu Met Leu Tyr Ile
                260                 265                 270

Ala Asp Glu Ala Phe Phe Thr Gly Thr Ala Ala Glu Ile Thr Pro Ile
                275                 280                 285

Arg Ser Val Asp Gly Ile Glu Ile Gly Ala Gly Arg Arg Gly Pro Val
                290                 295                 300

Thr Lys Leu Leu Gln Asp Glu Phe Phe Arg Ile Ile Arg Ala Glu Thr
305                 310                 315                 320

Glu Asp Ser Phe Gly Trp Leu Thr Tyr Ile
                325                 330

<210> SEQ ID NO 241
<211> LENGTH: 1095
<212> TYPE: DNA
<213> ORGANISM: Streptomyces coelicolor

<400> SEQUENCE: 241
tcacggccgg ggacgggcct ccgccatccg ctgctcggcg atccggtcgg ccgccgcggc      60
cggcggaata ccgtcctcct tcgcacgtgc gaatatggcc agcgtggtgt cgtagatctt     120
cgaggccttc gccttgcacc ggtcgaagtc gaacccgtgc agctcgtcgg cgacctggat     180
gacaccgccg gcgttcacca catagtccgg cgcgtagagg atcccgccgt cggcgaggtc     240
cttctcgacg cccgggtggg cgagctggtt gttggccgcg ccgcacacca ccttggcggt     300
cagcaccggc acggtgtcgt cgttcagcgc gccgccgagc gcgcagggcg cgtagatgtc     360
caggttctcc acccggatca gcgcgtcggt gtcggcgacg cgaccaccg acgggtgccg     420 ctccgtgatc ccgcgcacca cgtccttgcg cacgtccgtg acgacgacgt gggcgccctc     480

-continued

```
ggcgagcagg tgctcgacca ggtggtggcc gaccttgccg acgcccgcga tgccgacggt      540
gcggtcgcgc agcgtcgggt cgccccacag gtgctgggcg gcggcccgca tgccctggta      600
gacgccgaag gaggtgagca cggaggagtc gcccgcgccg ccgttctccg gggaacgccc      660
ggtcgtccag cggcactcgc gggccacgac gtccatgtcg gcgacgtagg tgccgacgtc      720
gcacgcggtg acgtagcggc cgcccagcga ggcgacgaac cggccgtagg cgaggagcag      780
ctcctcgctc ttgatctgct ccggatcgcc gatgatcacg gccttgccgc accgtggtc       840 cagaccggcc atggcgttct tgtacgacat cccgcgggcg aggttcagcg cgtcggcgac      900
ggcctccgcc tcgctcgcgt acgggtagaa gcgggtaccg ccgagcgccg gcccagggc       960 ggtggagtgg agggcgatca cggccttgag gccgctggca cggtcctggc agagcacgac     1020
ttgctcatgt cccccctgat ccgagtggaa cagggtgtgc agtacatcag caggtgcgcc     1080
gtttacgtcg gtcac                                                     1095
```

<210> SEQ ID NO 242
<211> LENGTH: 364
<212> TYPE: PRT
<213> ORGANISM: Streptomyces coelicolor

<400> SEQUENCE: 242

```
Met Thr Asp Val Asn Gly Ala Pro Ala Asp Val Leu His Thr Leu Phe
1               5                   10                  15

His Ser Asp Gln Gly Gly His Glu Gln Val Val Leu Cys Gln Asp Arg
                20                  25                  30

Ala Ser Gly Leu Lys Ala Val Ile Ala Leu His Ser Thr Ala Leu Gly
            35                  40                  45

Pro Ala Leu Gly Gly Thr Arg Phe Tyr Pro Tyr Ala Ser Glu Ala Glu
        50                  55                  60

Ala Val Ala Asp Ala Leu Asn Leu Ala Arg Gly Met Ser Tyr Lys Asn
65                  70                  75                  80

Ala Met Ala Gly Leu Asp His Gly Gly Gly Lys Ala Val Ile Ile Gly
                85                  90                  95

Asp Pro Glu Gln Ile Lys Ser Glu Glu Leu Leu Leu Ala Tyr Gly Arg
                100                 105                 110

Phe Val Ala Ser Leu Gly Gly Arg Tyr Val Thr Ala Cys Asp Val Gly
            115                 120                 125

Thr Tyr Val Ala Asp Met Asp Val Val Ala Arg Glu Cys Arg Trp Thr
    130                 135                 140

Thr Gly Arg Ser Pro Glu Asn Gly Gly Ala Gly Asp Ser Ser Val Leu
145                 150                 155                 160

Thr Ser Phe Gly Val Tyr Gln Gly Met Arg Ala Ala Gln His Leu
                165                 170                 175

Trp Gly Asp Pro Thr Leu Arg Asp Arg Thr Val Gly Ile Ala Gly Val
            180                 185                 190

Gly Lys Val Gly His His Leu Val Glu His Leu Leu Ala Glu Gly Ala
        195                 200                 205

His Val Val Val Thr Asp Val Arg Lys Asp Val Arg Gly Ile Thr
    210                 215                 220

Glu Arg His Pro Ser Val Val Ala Val Ala Asp Thr Asp Ala Leu Ile
225                 230                 235                 240

Arg Val Glu Asn Leu Asp Ile Tyr Ala Pro Cys Ala Leu Gly Gly Ala
                245                 250                 255
```

```
Leu Asn Asp Asp Thr Val Pro Val Leu Thr Ala Lys Val Val Cys Gly
            260                 265                 270

Ala Ala Asn Asn Gln Leu Ala His Pro Gly Val Glu Lys Asp Leu Ala
        275                 280                 285

Asp Arg Gly Ile Leu Tyr Ala Pro Asp Tyr Val Val Asn Ala Gly Gly
    290                 295                 300

Val Ile Gln Val Ala Asp Glu Leu His Gly Phe Asp Phe Asp Arg Cys
305                 310                 315                 320

Lys Ala Lys Ala Ser Lys Ile Tyr Asp Thr Thr Leu Ala Ile Phe Ala
                325                 330                 335

Arg Ala Lys Glu Asp Gly Ile Pro Pro Ala Ala Ala Asp Arg Ile
            340                 345                 350

Ala Glu Gln Arg Met Ala Glu Ala Arg Pro Arg Pro
            355                 360

<210> SEQ ID NO 243
<211> LENGTH: 1095
<212> TYPE: DNA
<213> ORGANISM: Bacillus subtilis

<400> SEQUENCE: 243 atggaactttt ttaaatatat ggagaaatac gattacgaac aattggtatt ctgccaggat    60
gaacaatctg gattaaaagc gattatcgcc attcatgata caacgcttgg tccggcgctt   120
ggcggaacga gaatgtggac atatgaaaat gaagaagcgg caattgaaga tgcgctcaga   180
ttggcaagag gcatgaccta taagaacgcg gcggcaggct aaaccttggc ggcggaaaa    240 acagtcatta tcggcgatcc gcgcaaagac aaaaatgagg aaatgttccg cgcgtttggc   300
cgctatattc aaggactgaa tgcagatac atcacggctg aagatgtggg cacaacggtc   360
gaggatatgg atatcattca tgatgagaca gactatgtca cagggatttc tcctgctttc   420
ggctcttctg gaaatccgtc cccagtcaca gcgtacgggg tgtacagagg aatgaaggca   480
gcagctaaag ctgcttttcgg aaccgattct cttgaaggaa aaaccattgc tgtacagggt   540
gttgggaacg tagcctataa cctttgccgc caccgtcatg aagaaggagc aaacttaatc   600
gttacggata tcaacaaaca atctgtacag cgtgcagttg aagattttgg cgcccgtgcg   660
gtagatcctg atgacatttta ttcacaagac tgcgatattt atgcgccgtg tgcccttggt   720
gcgactatta cgacgacac cattaaacag ctgaaggcga aagtgatcgc aggtgcggct   780
aacaaccaat taaagagac acgccatggt gatcaaattc acgaaatggg catcgtttat   840
gcaccggatt acgtgattaa cgcgggcggt gtcatcaacg tggcagatga ctttacggc   900 tataatgcag aacgtgcatt gaaaaaagtt gaaggcattt acggcaatat cgagcgtgta   960
cttgagattt ctcagcgtga cggcattcct gcatatttag cggctgaccg cttagcagag  1020
gaacggattg aacgcatgcg ccgctcaaga agccagtttt tgcaaaacgg ccacagtgta  1080
ttaagcagac gttaa                                                    1095

<210> SEQ ID NO 244
<211> LENGTH: 364
<212> TYPE: PRT
<213> ORGANISM: Bacillus subtilis

<400> SEQUENCE: 244

Met Glu Leu Phe Lys Tyr Met Glu Lys Tyr Asp Tyr Glu Gln Leu Val
1               5                   10                  15

Phe Cys Gln Asp Glu Gln Ser Gly Leu Lys Ala Ile Ile Ala Ile His
```

```
            20                  25                  30
Asp Thr Thr Leu Gly Pro Ala Leu Gly Gly Thr Arg Met Trp Thr Tyr
                35                  40                  45

Glu Asn Glu Glu Ala Ala Ile Glu Asp Ala Leu Arg Leu Ala Arg Gly
         50                  55                  60

Met Thr Tyr Lys Asn Ala Ala Gly Leu Asn Leu Gly Gly Gly Lys
 65                  70                  75                  80

Thr Val Ile Ile Gly Asp Pro Arg Lys Asp Lys Asn Glu Glu Met Phe
                 85                  90                  95

Arg Ala Phe Gly Arg Tyr Ile Gln Gly Leu Asn Gly Arg Tyr Ile Thr
                100                 105                 110

Ala Glu Asp Val Gly Thr Thr Val Glu Asp Met Asp Ile Ile His Asp
            115                 120                 125

Glu Thr Asp Tyr Val Thr Gly Ile Ser Pro Ala Phe Gly Ser Ser Gly
        130                 135                 140

Asn Pro Ser Pro Val Thr Ala Tyr Gly Val Tyr Arg Gly Met Lys Ala
145                 150                 155                 160

Ala Ala Lys Ala Ala Phe Gly Thr Asp Ser Leu Glu Gly Lys Thr Ile
                165                 170                 175

Ala Val Gln Gly Val Gly Asn Val Ala Tyr Asn Leu Cys Arg His Leu
            180                 185                 190

His Glu Glu Gly Ala Asn Leu Ile Val Thr Asp Ile Asn Lys Gln Ser
        195                 200                 205

Val Gln Arg Ala Val Glu Asp Phe Gly Ala Arg Ala Val Asp Pro Asp
    210                 215                 220

Asp Ile Tyr Ser Gln Asp Cys Asp Ile Tyr Ala Pro Cys Ala Leu Gly
225                 230                 235                 240

Ala Thr Ile Asn Asp Asp Thr Ile Lys Gln Leu Lys Ala Lys Val Ile
                245                 250                 255

Ala Gly Ala Ala Asn Asn Gln Leu Lys Glu Thr Arg His Gly Asp Gln
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Ala Glu
    290                 295                 300

Arg Ala Leu Lys Lys Val Glu Gly Ile Tyr Gly Asn Ile Glu Arg Val
305                 310                 315                 320

Leu Glu Ile Ser Gln Arg Asp Gly Ile Pro Ala Tyr Leu Ala Ala Asp
                325                 330                 335

Arg Leu Ala Glu Glu Arg Ile Glu Arg Met Arg Arg Ser Arg Ser Gln
            340                 345                 350

Phe Leu Gln Asn Gly His Ser Val Leu Ser Arg Arg
        355                 360

<210> SEQ ID NO 245
<211> LENGTH: 1785
<212> TYPE: DNA
<213> ORGANISM: Streptomyces viridifaciens

<400> SEQUENCE: 245
gtgtcaactt cctccgcttc ttccgggccg gacctcccct cgggcccga ggacacgcca      60 tggcagaagg ccttcagcag gctgcgggcg gtggatggcg tgccgcgcgt caccgcgccg     120
tccagtgatc cgcgtgaggt ctacatggac atcccggaga tccccttctc caaggtccag     180
```

-continued

| | |
|---|---|
| atcccccgg acggaatgga cgagcagcag tacgcagagg ccgagagcct cttccgccgc | 240 |
| tacgtagacg cccagacccg caacttcgcg ggataccagg tcaccagcga cctcgactac | 300 |
| cagcacctca gtcactatct caaccggcat ctgaacaacg tcggcgatcc ctatgagtcc | 360 |
| agctcctaca cgctgaactc caaggtcctt gagcgagccg ttctcgacta cttcgcctcc | 420 |
| ctgtggaacg ccaagtggcc ccatgacgca agcgatccgg aaacgtactg gggttacgtg | 480 |
| ctgaccatgg gctccagcga aggcaacctg tacgggttgt ggaacgcacg ggactatctg | 540 |
| tcgggcaagc tgctgcggcg ccagcaccgg gaggccggcg cgacaaggc ctcggtcgtc | 600 |
| tacacgcaag cgctgcgaca cgaagggcag agtccgcatg cctacgagcc ggtggcgttc | 660 |
| ttctcgcagg acacgcacta ctcgctcacg aaggccgtgc gggttctggg catcgacacc | 720 |
| ttccacagca tcggcagcag tcggtatccg gacgagaacc cgctgggccc cggcactccg | 780 |
| tggccgaccg aagtgccctc ggttgacggt gccatcgatg tcgacaaact cgcctcgttg | 840 |
| gtccgcttct tcgccagcaa gggctacccg atactggtca gcctcaacta cgggtcaacg | 900 |
| ttcaagggcg cctacgacga cgtcccggcc gtggcacagg ccgtgcggga catctgcacg | 960 |
| gaatacggtc tggatcggcg gcgggtatac cacgaccgca gtaaggacag tgacttcgac | 1020 |
| gagcgcagcg gcttctggat ccacatcgat gccgccctgg gggcgggcta cgctccctac | 1080 |
| ctgcagatgg cccgggatgc cggcatggtc gaggaggcgc cgcccgtttt cgacttccgg | 1140 |
| ctcccggagg tgcactcgct gaccatgagc ggccacaagt ggatgggaac accgtgggca | 1200 |
| tgcggtgtct acatgacacg gaccgggctg cagatgaccc cgccgaagtc gtccgagtac | 1260 |
| atcggggcgg ccgacaccac cttcgcgggc tcccgcaacg gcttctcgtc actgctgctg | 1320 |
| tgggactacc tgtcccggca ttcgtatgac gatctggtgc gcctggccgc cgactgcgac | 1380 |
| cggctggccg gctacgccca cgaccggttg ctgaccttgc aggacaaact cggcatggat | 1440 |
| ctgtgggtcg cccgcagccc gcagtccctc acggtgcgct tccgtcagcc atgtgcagac | 1500 |
| atcgtccgca agtactcgct gtcgtgtgag acggtctacg aagacaacga gcaacggacc | 1560 |
| tacgtacatc tctacgccgt tccccacctc actcgggaac tcgtggatga gctcgtgcgc | 1620 |
| gatctgcgcc agcccggagc cttcaccaac gctggtgcac tggaggggga ggcctgggcc | 1680 |
| ggggtgatcg atgccctcgg ccgcccggac cccgacggaa cctatgccgg cgccttgagc | 1740 |
| gctccggctt ccggcccccg ctccgaggac ggcggcggga gctga | 1785 |

<210> SEQ ID NO 246
<211> LENGTH: 594
<212> TYPE: PRT
<213> ORGANISM: Streptomyces viridifaciens

<400> SEQUENCE: 246

Met Ser Thr Ser Ser Ala Ser Ser Gly Pro Asp Leu Pro Phe Gly Pro
1               5                   10                  15

Glu Asp Thr Pro Trp Gln Lys Ala Phe Ser Arg Leu Arg Ala Val Asp
            20                  25                  30

Gly Val Pro Arg Val Thr Ala Pro Ser Ser Asp Pro Arg Glu Val Tyr
        35                  40                  45

Met Asp Ile Pro Glu Ile Pro Phe Ser Lys Val Gln Ile Pro Pro Asp
    50                  55                  60

Gly Met Asp Glu Gln Gln Tyr Ala Glu Ala Glu Ser Leu Phe Arg Arg
65                  70                  75                  80

Tyr Val Asp Ala Gln Thr Arg Asn Phe Ala Gly Tyr Gln Val Thr Ser
                85                  90                  95

```
Asp Leu Asp Tyr Gln His Leu Ser His Tyr Leu Asn Arg His Leu Asn
            100                 105                 110

Asn Val Gly Asp Pro Tyr Glu Ser Ser Tyr Thr Leu Asn Ser Lys
            115                 120                 125

Val Leu Glu Arg Ala Val Leu Asp Tyr Phe Ala Ser Leu Trp Asn Ala
130                 135                 140

Lys Trp Pro His Asp Ala Ser Asp Pro Glu Thr Tyr Trp Gly Tyr Val
145                 150                 155                 160

Leu Thr Met Gly Ser Ser Glu Gly Asn Leu Tyr Gly Leu Trp Asn Ala
            165                 170                 175

Arg Asp Tyr Leu Ser Gly Lys Leu Leu Arg Arg Gln His Arg Glu Ala
            180                 185                 190

Gly Gly Asp Lys Ala Ser Val Val Tyr Thr Gln Ala Leu Arg His Glu
            195                 200                 205

Gly Gln Ser Pro His Ala Tyr Glu Pro Val Ala Phe Phe Ser Gln Asp
            210                 215                 220

Thr His Tyr Ser Leu Thr Lys Ala Val Arg Val Leu Gly Ile Asp Thr
225                 230                 235                 240

Phe His Ser Ile Gly Ser Ser Arg Tyr Pro Asp Glu Asn Pro Leu Gly
            245                 250                 255

Pro Gly Thr Pro Trp Pro Thr Glu Val Pro Ser Val Asp Gly Ala Ile
            260                 265                 270

Asp Val Asp Lys Leu Ala Ser Leu Val Arg Phe Phe Ala Ser Lys Gly
            275                 280                 285

Tyr Pro Ile Leu Val Ser Leu Asn Tyr Gly Ser Thr Phe Lys Gly Ala
            290                 295                 300

Tyr Asp Asp Val Pro Ala Val Ala Gln Ala Val Arg Asp Ile Cys Thr
305                 310                 315                 320

Glu Tyr Gly Leu Asp Arg Arg Val Tyr His Asp Arg Ser Lys Asp
            325                 330                 335

Ser Asp Phe Asp Glu Arg Ser Gly Phe Trp Ile His Ile Asp Ala Ala
            340                 345                 350

Leu Gly Ala Gly Tyr Ala Pro Tyr Leu Gln Met Ala Arg Asp Ala Gly
            355                 360                 365

Met Val Glu Glu Ala Pro Pro Val Phe Asp Phe Arg Leu Pro Glu Val
370                 375                 380

His Ser Leu Thr Met Ser Gly His Lys Trp Met Gly Thr Pro Trp Ala
385                 390                 395                 400

Cys Gly Val Tyr Met Thr Arg Thr Gly Leu Gln Met Thr Pro Pro Lys
            405                 410                 415

Ser Ser Glu Tyr Ile Gly Ala Ala Asp Thr Thr Phe Ala Gly Ser Arg
            420                 425                 430

Asn Gly Phe Ser Ser Leu Leu Leu Trp Asp Tyr Leu Ser Arg His Ser
            435                 440                 445

Tyr Asp Asp Leu Val Arg Leu Ala Ala Asp Cys Asp Arg Leu Ala Gly
            450                 455                 460

Tyr Ala His Asp Arg Leu Leu Thr Leu Gln Asp Lys Leu Gly Met Asp
465                 470                 475                 480

Leu Trp Val Ala Arg Ser Pro Gln Ser Leu Thr Val Arg Phe Arg Gln
            485                 490                 495

Pro Cys Ala Asp Ile Val Arg Lys Tyr Ser Leu Ser Cys Glu Thr Val
            500                 505                 510
```

Tyr Glu Asp Asn Glu Gln Arg Thr Tyr Val His Leu Tyr Ala Val Pro
    515                 520                 525

His Leu Thr Arg Glu Leu Val Asp Glu Leu Val Arg Asp Leu Arg Gln
530                 535                 540

Pro Gly Ala Phe Thr Asn Ala Gly Ala Leu Glu Gly Glu Ala Trp Ala
545                 550                 555                 560

Gly Val Ile Asp Ala Leu Gly Arg Pro Asp Pro Asp Gly Thr Tyr Ala
            565                 570                 575

Gly Ala Leu Ser Ala Pro Ala Ser Gly Pro Arg Ser Glu Asp Gly Gly
            580                 585                 590

Gly Ser

<210> SEQ ID NO 247
<211> LENGTH: 1323
<212> TYPE: DNA
<213> ORGANISM: Alcaligenes denitrificans

<400> SEQUENCE: 247

```
atgagcgctg ccaaactgcc cgacctgtcc cacctctgga tgcccttac cgccaaccgg      60
cagttcaagg cgaaccccg cctgctggcc tcggccaagg gcatgtacta cacgtctttc    120
gacggccgcc agatcctgga cggcacggcc ggcctgtggt gcgtgaacgc cggccactgc    180
cgcgaagaaa tcgtctccgc catcgccagc caggccggcg tcatggacta cgcgccgggg    240
ttccagctcg gccacccgct ggccttcgag gccgccaccg ccgtggccgg cctgatgccg    300
cagggcctgg accgcgtgtt cttcaccaat tcgggctccg aatcggtgga caccgcgctg    360
aagatcgccc tggcctacca ccgcgcgcgc ggcgaggcgc agcgcacccg cctcatcggg    420
cgcgagcgcg gctaccacgg cgtgggcttc ggcggcattt ccgtgggcgg catctcgccc    480
aaccgcaaga ccttctccgg cgcgctgctg ccggccgtgg accacctgcc gcacacccac    540
agcctggaac acaacgcctt cacgcgcggc cagcccgagt ggggcgcgca cctggccgac    600
gagttggaac gcatcatcgc cctgcacgac gcctccacca tcgcggccgt gatcgtcgag    660
cccatggccg gctccaccgg cgtgctcgtc ccgcccaagg gctatctcga aaaactgcgc    720
gaaatcaccg cccgccacgg cattctgctg atcttcgacg aagtcatcac cgcgtacggc    780
cgcctgggcg aggccaccgc cgcggcctat ttcggcgtaa cgcccgacct catcaccatg    840
gccaagggcg tgagcaacgc cgccgttccg gccggcgccg tcgcggtgcg ccgcgaagtg    900
catgacgcca tcgtcaacgg accgcaaggc ggcatcgagt tcttccacgg ctacacctac    960
tcggcccacc cgctggccgc cgccgccgtg ctcgccacgc tggacatcta ccgccgcgaa   1020
gacctgttcg cccgcgcccg caagctgtcg gccgcgttcg aggaagccgc ccacagcctc   1080
aagggcgcgc cgcacgtcat cgacgtgcgc aacatcggcc tggtggccgg catcgagctg   1140
tcgccgcgcg aaggcgcccc gggcgcgcgc gccgccgaag ccttccagaa atgcttcgac   1200
accggcctca tggtgcgcta cacgggcgac atcctcgcgg tgtcgcctcc gctcatcgtc   1260
gacgaaaacc agatcggcca gatcttcgag ggcatcggca aggtgctcaa ggaagtggct   1320
tag                                                                 1323
```

<210> SEQ ID NO 248
<211> LENGTH: 440
<212> TYPE: PRT
<213> ORGANISM: Alcaligenes denitrificans

<400> SEQUENCE: 248

```
Met Ser Ala Ala Lys Leu Pro Asp Leu Ser His Leu Trp Met Pro Phe
1               5                   10                  15

Thr Ala Asn Arg Gln Phe Lys Ala Asn Pro Arg Leu Leu Ala Ser Ala
            20                  25                  30

Lys Gly Met Tyr Tyr Thr Ser Phe Asp Gly Arg Gln Ile Leu Asp Gly
        35                  40                  45

Thr Ala Gly Leu Trp Cys Val Asn Ala Gly His Cys Arg Glu Glu Ile
50                  55                  60

Val Ser Ala Ile Ala Ser Gln Ala Gly Val Met Asp Tyr Ala Pro Gly
65                  70                  75                  80

Phe Gln Leu Gly His Pro Leu Ala Phe Glu Ala Ala Thr Ala Val Ala
                85                  90                  95

Gly Leu Met Pro Gln Gly Leu Asp Arg Val Phe Phe Thr Asn Ser Gly
                100                 105                 110

Ser Glu Ser Val Asp Thr Ala Leu Lys Ile Ala Leu Ala Tyr His Arg
            115                 120                 125

Ala Arg Gly Glu Ala Gln Arg Thr Arg Leu Ile Gly Arg Glu Arg Gly
        130                 135                 140

Tyr His Gly Val Gly Phe Gly Gly Ile Ser Val Gly Gly Ile Ser Pro
145                 150                 155                 160

Asn Arg Lys Thr Phe Ser Gly Ala Leu Leu Pro Ala Val Asp His Leu
                165                 170                 175

Pro His Thr His Ser Leu Glu His Asn Ala Phe Thr Arg Gly Gln Pro
            180                 185                 190

Glu Trp Gly Ala His Leu Ala Asp Glu Leu Glu Arg Ile Ile Ala Leu
        195                 200                 205

His Asp Ala Ser Thr Ile Ala Ala Val Ile Val Glu Pro Met Ala Gly
        210                 215                 220

Ser Thr Gly Val Leu Val Pro Pro Lys Gly Tyr Leu Glu Lys Leu Arg
225                 230                 235                 240

Glu Ile Thr Ala Arg His Gly Ile Leu Leu Ile Phe Asp Glu Val Ile
                245                 250                 255

Thr Ala Tyr Gly Arg Leu Gly Glu Ala Thr Ala Ala Tyr Phe Gly
                260                 265                 270

Val Thr Pro Asp Leu Ile Thr Met Ala Lys Gly Val Ser Asn Ala Ala
            275                 280                 285

Val Pro Ala Gly Ala Val Ala Val Arg Arg Glu Val His Asp Ala Ile
        290                 295                 300

Val Asn Gly Pro Gln Gly Ile Glu Phe Phe His Gly Tyr Thr Tyr
305                 310                 315                 320

Ser Ala His Pro Leu Ala Ala Ala Val Leu Ala Thr Leu Asp Ile
                325                 330                 335

Tyr Arg Arg Glu Asp Leu Phe Ala Arg Ala Arg Lys Leu Ser Ala Ala
            340                 345                 350

Phe Glu Glu Ala Ala His Ser Leu Lys Gly Ala Pro His Val Ile Asp
        355                 360                 365

Val Arg Asn Ile Gly Leu Val Ala Gly Ile Glu Leu Ser Pro Arg Glu
        370                 375                 380

Gly Ala Pro Gly Ala Arg Ala Ala Glu Ala Phe Gln Lys Cys Phe Asp
385                 390                 395                 400

Thr Gly Leu Met Val Arg Tyr Thr Gly Asp Ile Leu Ala Val Ser Pro
                405                 410                 415

Pro Leu Ile Val Asp Glu Asn Gln Ile Gly Gln Ile Phe Glu Gly Ile
```

```
                420              425              430
Gly Lys Val Leu Lys Glu Val Ala
        435              440

<210> SEQ ID NO 249
<211> LENGTH: 1332
<212> TYPE: DNA
<213> ORGANISM: Ralstonia eutropha

<400> SEQUENCE: 249
atggacgccg cgaagaccgt gattcccgat ctcgatgccc tgtggatgcc ctttaccgcg      60
aaccgccagt acaaggcggc gccgcgcctg ctggcctcgg ccagcggcat gtactacacc     120
acccacgacg gacgccagat cctcgacggt tgcgcgggcc tctggtgcgt agcggccggc     180
cactgccgca aggagattgc cgaggccgtg gcccgccagg ccgccacgct cgactacgcg     240
ccgccgttcc agatgggcca tccgctgtcg ttcgaagccg ccaccaaggt ggccgcgatc     300
atgccgcagg gactggaccg catcttcttc acgaattccg gttcggaatc ggtgacacc      360
gcgctgaaga ttgcgctggc ctaccaccgt gcgcgcggcg agggccagcg cacccgcttc     420
atcgggcgcg aacgcggtta ccacggcgtg ggctttggcg gcatggctgt cggtggcatc     480
gggccgaacc gcaaggcgtt ctcggccaac ctgatgccgg gcaccgacca tctgccggcg     540
acgctgaata tcgccgaagc ggcgttctcc aagggtcagc cgacatgggg cgcgcacctt     600
gccgacgaac tcgagcgcat cgtcgcgctg catgatccgt ccacgattgc cgccgtcatc     660
gtggaaccgc tggcgggctc cgccggggtg ctggtgccgc cggtcggcta cctcgacaag     720
ctgcgcgaga tcacgaccaa gcacggcatc ctgctgatct tcgacgaggt catcacggcc     780
tttggtcgcc tgggtaccgc caccgcggcg gaacgcttca aggtcacgcc ggacctgatc     840
accatggcca aggccatcaa caacgccgcc gtgccgatgg tgccgtggc cgtgcgccgc     900
gaagtccatg acaccgtggt caactcggcc gcgccgggcg cgatcgaact cgcgcatggc     960
tacacctact cgggccaccc gctggccgcc gccgctgcca tcgccacgct ggacctgtat    1020
cagcgcgaga acctgttcgg ccgtgccgcg gagctgtcgc cggtgttcga agcggccgtt    1080
cacagcgtac gcacgcgcgcc gcatgtgaag gacatccgca acctcggcat ggtggccggc    1140
atcgagctgg agccgcgtcc gggccagccc ggcgcacgcg cctacgaagc cttcctcaaa    1200
tgccttgagc gtgcgtgct ggtgcgctac accggcgata tcctcgcgtt ctcgccgccg    1260
ctgatcatca gcgaggcgca gattgccgag ctgttcgata cggtcaagca ggccttgcag    1320
gaagtgcagt aa                                                        1332

<210> SEQ ID NO 250
<211> LENGTH: 443
<212> TYPE: PRT
<213> ORGANISM: Ralstonia eutropha

<400> SEQUENCE: 250

Met Asp Ala Ala Lys Thr Val Ile Pro Asp Leu Asp Ala Leu Trp Met
1               5                   10                  15

Pro Phe Thr Ala Asn Arg Gln Tyr Lys Ala Ala Pro Arg Leu Leu Ala
            20                  25                  30

Ser Ala Ser Gly Met Tyr Tyr Thr Thr His Asp Gly Arg Gln Ile Leu
        35                  40                  45

Asp Gly Cys Ala Gly Leu Trp Cys Val Ala Ala Gly His Cys Arg Lys
    50                  55                  60
```

Glu Ile Ala Glu Ala Val Ala Arg Gln Ala Ala Thr Leu Asp Tyr Ala
65                  70                  75                  80

Pro Pro Phe Gln Met Gly His Pro Leu Ser Phe Glu Ala Ala Thr Lys
                85                  90                  95

Val Ala Ala Ile Met Pro Gln Gly Leu Asp Arg Ile Phe Phe Thr Asn
            100                 105                 110

Ser Gly Ser Glu Ser Val Asp Thr Ala Leu Lys Ile Ala Leu Ala Tyr
        115                 120                 125

His Arg Ala Arg Gly Glu Gly Gln Arg Thr Arg Phe Ile Gly Arg Glu
    130                 135                 140

Arg Gly Tyr His Gly Val Gly Phe Gly Gly Met Ala Val Gly Gly Ile
145                 150                 155                 160

Gly Pro Asn Arg Lys Ala Phe Ser Ala Asn Leu Met Pro Gly Thr Asp
                165                 170                 175

His Leu Pro Ala Thr Leu Asn Ile Ala Glu Ala Ala Phe Ser Lys Gly
            180                 185                 190

Gln Pro Thr Trp Gly Ala His Leu Ala Asp Glu Leu Glu Arg Ile Val
        195                 200                 205

Ala Leu His Asp Pro Ser Thr Ile Ala Ala Val Ile Val Glu Pro Leu
    210                 215                 220

Ala Gly Ser Ala Gly Val Leu Val Pro Pro Val Gly Tyr Leu Asp Lys
225                 230                 235                 240

Leu Arg Glu Ile Thr Thr Lys His Gly Ile Leu Leu Ile Phe Asp Glu
                245                 250                 255

Val Ile Thr Ala Phe Gly Arg Leu Gly Thr Ala Thr Ala Ala Glu Arg
            260                 265                 270

Phe Lys Val Thr Pro Asp Leu Ile Thr Met Ala Lys Ala Ile Asn Asn
        275                 280                 285

Ala Ala Val Pro Met Gly Ala Val Ala Val Arg Arg Glu Val His Asp
    290                 295                 300

Thr Val Val Asn Ser Ala Ala Pro Gly Ala Ile Glu Leu Ala His Gly
305                 310                 315                 320

Tyr Thr Tyr Ser Gly His Pro Leu Ala Ala Ala Ala Ile Ala Thr
                325                 330                 335

Leu Asp Leu Tyr Gln Arg Glu Asn Leu Phe Gly Arg Ala Ala Glu Leu
            340                 345                 350

Ser Pro Val Phe Glu Ala Ala Val His Ser Val Arg Ser Ala Pro His
        355                 360                 365

Val Lys Asp Ile Arg Asn Leu Gly Met Val Ala Gly Ile Glu Leu Glu
    370                 375                 380

Pro Arg Pro Gly Gln Pro Gly Ala Arg Ala Tyr Glu Ala Phe Leu Lys
385                 390                 395                 400

Cys Leu Glu Arg Gly Val Leu Val Arg Tyr Thr Gly Asp Ile Leu Ala
                405                 410                 415

Phe Ser Pro Pro Leu Ile Ile Ser Glu Ala Gln Ile Ala Glu Leu Phe
            420                 425                 430

Asp Thr Val Lys Gln Ala Leu Gln Glu Val Gln
        435                 440

<210> SEQ ID NO 251
<211> LENGTH: 1341
<212> TYPE: DNA
<213> ORGANISM: Shewanella oneidensis

<400> SEQUENCE: 251

```
atggccgact cacccaacaa cctcgctcac gaacatcctt cacttgaaca ctattggatg    60 cctttaccg ccaatcgcca attcaaagcg agccctcgtt tactcgccca agctgaaggt   120
atgtattaca cagatatcaa tggcaacaag gtattagact ctacagcggg cttatggtgt   180
tgtaatgctg gccatggtcg ccgtgagatc agtgaagccg tcagcaaaca aattcggcag   240
atggattacg ctccctcctt ccaaatgggc catcccatcg cttttgaact ggccgaacgt   300
ttaaccgaac tcagcccaga aggactcaac aaagtattct ttaccaactc aggctctgag   360
tcggttgata ccgcgctaaa aatggctctt tgctaccata gagccaatgg ccaagcgtca   420
cgcacccgct ttattggccg tgaaatgggt taccatggcg taggatttgg tgggatctcg   480
gtgggtggtt taagcaataa ccgtaaagcc ttcagcggcc agctattgca aggcgtggat   540
cacctgcccc acaccttaga cattcaacat gccgccttta gtcgtggctt accgagcctc   600
ggtgctgaaa aagctgaggt attagaacaa ttagtcacac tccatggcgc cgaaaatatt   660
gccgccgtta ttgttgaacc catgtcaggt tctgcagggg taattttacc acctcaaggc   720
tacttaaaac gcttacgtga atcactaaa aaacacggca tcttattgat tttcgatgaa   780
gtcattaccg catttggccg tgtaggtgca gcattcgcca gccaacgttg gggcgttatt   840
ccagacataa tcaccacggc taaagccatt aataatggcg ccatccccat gggcgcagtg   900
tttgtacagg attatatcca cgatacttgc atgcaagggc caaccgaact gattgaattt   960
ttccacggtt ataccatc gggccaccca gtcgccgcag cagcagcact cgccacgctc  1020
tccatctacc aaaacgagca actgtttgag cgcagttttg agcttgagcg gtatttcgaa  1080
gaagccgttc atagcctcaa agggttaccg aatgtgattg atattcgcaa caccggatta  1140
gtcgcgggtt tccagctagc accgaatagc caaggtgttg gtaaacgcgg atacagcgtg  1200
ttcgagcatt gtttccatca aggcacactc gtgcgggcaa cgggcgatat tatcgccatg  1260
tccccaccac tcattgttga aaacatcag attgaccaaa tggtaaatag ccttagcgat  1320
gcaattcacg ccgttggatg a                                             1341
```

<210> SEQ ID NO 252
<211> LENGTH: 446
<212> TYPE: PRT
<213> ORGANISM: Shewanella oneidensis

<400> SEQUENCE: 252

```
Met Ala Asp Ser Pro Asn Asn Leu Ala His Glu His Pro Ser Leu Glu
1               5                   10                  15

His Tyr Trp Met Pro Phe Thr Ala Asn Arg Gln Phe Lys Ala Ser Pro
            20                  25                  30

Arg Leu Leu Ala Gln Ala Glu Gly Met Tyr Tyr Thr Asp Ile Asn Gly
        35                  40                  45

Asn Lys Val Leu Asp Ser Thr Ala Gly Leu Trp Cys Cys Asn Ala Gly
    50                  55                  60

His Gly Arg Arg Glu Ile Ser Glu Ala Val Ser Lys Gln Ile Arg Gln
65                  70                  75                  80

Met Asp Tyr Ala Pro Ser Phe Gln Met Gly His Pro Ile Ala Phe Glu
                85                  90                  95

Leu Ala Glu Arg Leu Thr Glu Leu Ser Pro Glu Gly Leu Asn Lys Val
            100                 105                 110

Phe Phe Thr Asn Ser Gly Ser Glu Ser Val Asp Thr Ala Leu Lys Met
        115                 120                 125
```

```
Ala Leu Cys Tyr His Arg Ala Asn Gly Gln Ala Ser Arg Thr Arg Phe
    130                 135                 140

Ile Gly Arg Glu Met Gly Tyr His Gly Val Gly Phe Gly Gly Ile Ser
145                 150                 155                 160

Val Gly Gly Leu Ser Asn Asn Arg Lys Ala Phe Ser Gly Gln Leu Leu
                165                 170                 175

Gln Gly Val Asp His Leu Pro His Thr Leu Asp Ile Gln His Ala Ala
            180                 185                 190

Phe Ser Arg Gly Leu Pro Ser Leu Gly Ala Glu Lys Ala Glu Val Leu
        195                 200                 205

Glu Gln Leu Val Thr Leu His Gly Ala Glu Asn Ile Ala Ala Val Ile
    210                 215                 220

Val Glu Pro Met Ser Gly Ser Ala Gly Val Ile Leu Pro Pro Gln Gly
225                 230                 235                 240

Tyr Leu Lys Arg Leu Arg Glu Ile Thr Lys Lys His Gly Ile Leu Leu
                245                 250                 255

Ile Phe Asp Glu Val Ile Thr Ala Phe Gly Arg Val Gly Ala Ala Phe
            260                 265                 270

Ala Ser Gln Arg Trp Gly Val Ile Pro Asp Ile Ile Thr Thr Ala Lys
        275                 280                 285

Ala Ile Asn Asn Gly Ala Ile Pro Met Gly Ala Val Phe Val Gln Asp
    290                 295                 300

Tyr Ile His Asp Thr Cys Met Gln Gly Pro Thr Glu Leu Ile Glu Phe
305                 310                 315                 320

Phe His Gly Tyr Thr Tyr Ser Gly His Pro Val Ala Ala Ala Ala
                325                 330                 335

Leu Ala Thr Leu Ser Ile Tyr Gln Asn Glu Gln Leu Phe Glu Arg Ser
            340                 345                 350

Phe Glu Leu Glu Arg Tyr Phe Glu Glu Ala Val His Ser Leu Lys Gly
        355                 360                 365

Leu Pro Asn Val Ile Asp Ile Arg Asn Thr Gly Leu Val Ala Gly Phe
    370                 375                 380

Gln Leu Ala Pro Asn Ser Gln Gly Val Gly Lys Arg Gly Tyr Ser Val
385                 390                 395                 400

Phe Glu His Cys Phe His Gln Gly Thr Leu Val Arg Ala Thr Gly Asp
                405                 410                 415

Ile Ile Ala Met Ser Pro Pro Leu Ile Val Glu Lys His Gln Ile Asp
            420                 425                 430

Gln Met Val Asn Ser Leu Ser Asp Ala Ile His Ala Val Gly
        435                 440                 445

<210> SEQ ID NO 253
<211> LENGTH: 1347
<212> TYPE: DNA
<213> ORGANISM: Pseudomonas putida

<400> SEQUENCE: 253
atgaacatgc ccgaaactgg tcctgccggt atcgccagcc agctcaagct ggacgcccac     60
tggatgccct acaccgccaa ccgcaacttc agcgcgacc cacgcctgat cgtggcggcc    120
gaaggcaact acctggtcga tgaccacggg cgcaagatct tcgacgccct gtccggcctg    180
tggacctgcg gcgcagggca cactcgcaag gaaatcgctg acgcggtgac cgtcaactg    240 agtacgctgg actactcccc agcgttccag ttcggccacc cgctgtcgtt ccagctggcg    300
gaaaagatcg ccgagctggt tccgggcaat ctgaatcacg tcttctatac caactccggt    360
```

```
tccgagtgcg ccgataccgc actgaagatg gtgcgtgcct actggcgcct gaaaggccag      420
gcaaccaaga ccaagatcat cggccgtgcc cgtggttacc atggcgtgaa catcgccggt      480
accagcctgg gtggcgtcaa cggtaaccgc aagatgtttg ccagctgct ggacgtcgac       540 cacctgcctc acactgtatt gccggtgaac gccttctcga aaggcttgcc ggaagagggc      600
ggtatcgcgc tggctgacga aatgctcaag ctgatcgagc tgcacgatgc ctccaacatc      660
gcagcagtca tcgtcgagcc gctggccggt tcggccggtg tgctgccgcc gccaaagggt      720
tacctgaagc gcctgcgtga atctgcacc cagcacaaca ttctgctgat cttcgacgaa       780
gtgatcacag gcttcggccg catgggcgcg atgaccggct cggaagcctt cggcgttacc      840
ccggacctga tgtgcatcgc caagcaggtg accaacggcg ccatcccgat gggcgcagtg      900
attgccagca gcgagatcta ccagaccttc atgaaccagc cgaccccgga atacgccgtg      960
gaattcccac acggctacac ctattcggcg cacccggtag cctgtgccgc cggtctcgcc     1020
gcgctggacc tgctgcagaa ggaaaaacctg gtgcagtccg cggctgaact ggcgccgcat    1080
ttcgagaagc tgctgcacgg cgtgaagggc accaagaata tcgtcgatat ccgcaactac     1140
ggcctggccg cgccatcca gatcgccgcc cgtgacggtg atgccatcgt tcgcccttac      1200
gaagcggcca tgaagctgtg gaaagcgggc ttctatgtac gctttggtgg cgacaccctg     1260 cagttccggcc caaccttcaa taccaagccg caggaactgg accgcttgtt cgatgctgtt    1320
ggcgaaaccc tgaacctgat cgactga                                         1347
```

<210> SEQ ID NO 254
<211> LENGTH: 448
<212> TYPE: PRT
<213> ORGANISM: Pseudomonas putida

<400> SEQUENCE: 254

```
Met Asn Met Pro Glu Thr Gly Pro Ala Gly Ile Ala Ser Gln Leu Lys
1               5                   10                  15

Leu Asp Ala His Trp Met Pro Tyr Thr Ala Asn Arg Asn Phe Gln Arg
            20                  25                  30

Asp Pro Arg Leu Ile Val Ala Ala Glu Gly Asn Tyr Leu Val Asp Asp
        35                  40                  45

His Gly Arg Lys Ile Phe Asp Ala Leu Ser Gly Leu Trp Thr Cys Gly
    50                  55                  60

Ala Gly His Thr Arg Lys Glu Ile Ala Asp Ala Val Thr Arg Gln Leu
65                  70                  75                  80

Ser Thr Leu Asp Tyr Ser Pro Ala Phe Gln Phe Gly His Pro Leu Ser
                85                  90                  95

Phe Gln Leu Ala Glu Lys Ile Ala Glu Leu Val Pro Gly Asn Leu Asn
            100                 105                 110

His Val Phe Tyr Thr Asn Ser Gly Ser Glu Cys Ala Asp Thr Ala Leu
        115                 120                 125

Lys Met Val Arg Ala Tyr Trp Arg Leu Lys Gly Gln Ala Thr Lys Thr
    130                 135                 140

Lys Ile Ile Gly Arg Ala Arg Gly Tyr His Gly Val Asn Ile Ala Gly
145                 150                 155                 160

Thr Ser Leu Gly Gly Val Asn Gly Asn Arg Lys Met Phe Gly Gln Leu
                165                 170                 175

Leu Asp Val Asp His Leu Pro His Thr Val Leu Pro Val Asn Ala Phe
            180                 185                 190
```

```
Ser Lys Gly Leu Pro Glu Glu Gly Gly Ile Ala Leu Ala Asp Glu Met
            195                 200                 205

Leu Lys Leu Ile Glu Leu His Asp Ala Ser Asn Ile Ala Ala Val Ile
    210                 215                 220

Val Glu Pro Leu Ala Gly Ser Ala Gly Val Leu Pro Pro Lys Gly
225                 230                 235                 240

Tyr Leu Lys Arg Leu Arg Glu Ile Cys Thr Gln His Asn Ile Leu Leu
                245                 250                 255

Ile Phe Asp Glu Val Ile Thr Gly Phe Gly Arg Met Gly Ala Met Thr
                260                 265                 270

Gly Ser Glu Ala Phe Gly Val Thr Pro Asp Leu Met Cys Ile Ala Lys
            275                 280                 285

Gln Val Thr Asn Gly Ala Ile Pro Met Gly Ala Val Ile Ala Ser Ser
        290                 295                 300

Glu Ile Tyr Gln Thr Phe Met Asn Gln Pro Thr Pro Glu Tyr Ala Val
305                 310                 315                 320

Glu Phe Pro His Gly Tyr Thr Tyr Ser Ala His Pro Val Ala Cys Ala
                325                 330                 335

Ala Gly Leu Ala Ala Leu Asp Leu Leu Gln Lys Glu Asn Leu Val Gln
            340                 345                 350

Ser Ala Ala Glu Leu Ala Pro His Phe Glu Lys Leu Leu His Gly Val
        355                 360                 365

Lys Gly Thr Lys Asn Ile Val Asp Ile Arg Asn Tyr Gly Leu Ala Gly
    370                 375                 380

Ala Ile Gln Ile Ala Ala Arg Asp Gly Asp Ala Ile Val Arg Pro Tyr
385                 390                 395                 400

Glu Ala Ala Met Lys Leu Trp Lys Ala Gly Phe Tyr Val Arg Phe Gly
                405                 410                 415

Gly Asp Thr Leu Gln Phe Gly Pro Thr Phe Asn Thr Lys Pro Gln Glu
            420                 425                 430

Leu Asp Arg Leu Phe Asp Ala Val Gly Glu Thr Leu Asn Leu Ile Asp
        435                 440                 445

<210> SEQ ID NO 255
<211> LENGTH: 1701
<212> TYPE: DNA
<213> ORGANISM: Streptomyces cinnamonensis

<400> SEQUENCE: 255
atggacgctg acgcgatcga ggaaggccgc cgacgctggc aggcccgtta cgacaaggcc      60
cgcaagcgcg acgcggactt caccacgctc tccggggacc ccgtcgaccc cgtctacggc     120
ccccggcccg gggacacgta cgacgggttc gagcggatcg gctggccggg ggagtacccc     180
ttcacccgcg ggctctacgc caccgggtac cgcggccgca cctggaccat ccgccagttc     240
gccggcttcg gcaacgccga gcagacgaac gagcgctaca agatgatcct ggccaacggc     300
ggcggcggcc tctccgtcgc cttcgacatg ccgaccctca tgggccgcga ctccgacgac     360
ccgcgctcgc tcggcgaggt cggccactgc ggtgtcgcca tcgactccgc cgccgacatg     420
gaggtcctct tcaaggacat cccgctcggc gacgtcacga cgtccatgac catcagcggg     480
cccgccgtgc ccgtcttctg catgtacctc gtcgcggccg agcgccaggg cgtcgacccg     540
gccgtcctca acggcacgct gcagaccgac atcttcaagg agtacatcgc ccagaaggag     600
tggctcttcc agcccgagcc gcacctgcgc ctcatcggcg acctgatgga gcactgcgcg     660
cgcgacatcc ccgcgtacaa gccgctctcg gtctccggct accacatccg cgaggccggg     720
```

```
gcgacggccg cgcaggagct cgcgtacacc ctcgcggacg gcttcgggta cgtggaactg      780
ggcctctcgc gcggcctgga cgtggacgtc ttcgcgcccg gcctctcctt cttcttcgac      840
gcgcacgtcg acttcttcga ggagatcgcg aagttccgcg ccgcacgccg catctgggcg      900
cgctggctcc gggacgagta cggagcgaag accgagaagg cacagtggct gcgcttccac      960
acgcagaccg cggggggtctc gctcacggcc cagcagccgt acaacaacgt ggtgcggacg     1020
gcggtggagg ccctcgccgc ggtgctcggc ggcacgaact ccctgcacac caacgctctc     1080
gacgagaccc ttgccctccc cagcgagcag gccgcggaga tcgcgctgcg cacccagcag     1140
gtgctgatgg aggagaccgg cgtcgccaac gtcgcggacc cgctgggcgg ctcctggtac     1200
atcgagcagc tcaccgaccg catcgaggcc gacgccgaga agatcttcga gcagatcagg     1260
gagcgggggc ggcgggcctg ccccgacggg cagcacccga tcgggccgat cacctccggc     1320
atcctgcgcg gcatcgagga cggctggttc accggcgaga tcgccgagtc cgccttccag     1380
taccagcggt ccctggagaa gggcgacaag cgggtcgtcg gcgtcaactg cctcgaaggc     1440
tccgtcaccg gcgacctgga gatcctgcgc gtcagccacg aggtcgagcg cgagcaggtg     1500
cgggagcttg cggggcgcaa ggggcggcgt gacgatgcgc gggtgcgggc ctcgctcgac     1560
gcgatgctcg ccgctgcgcg ggacgggtcg aacatgattg ccccccatgct ggaggcggtg     1620 cgggccgagg cgaccctcgg ggagatctgc ggggtgcttc gcgatgagtg ggggggtctac     1680 gtggagccgc ccgggttctg a                                                1701
```

<210> SEQ ID NO 256
<211> LENGTH: 566
<212> TYPE: PRT
<213> ORGANISM: Streptomyces cinnamonensis

<400> SEQUENCE: 256

Met Asp Ala Asp Ala Ile Glu Glu Gly Arg Arg Trp Gln Ala Arg
1               5                   10                  15

Tyr Asp Lys Ala Arg Lys Arg Asp Ala Asp Phe Thr Thr Leu Ser Gly
            20                  25                  30

Asp Pro Val Asp Pro Val Tyr Gly Pro Arg Pro Gly Asp Thr Tyr Asp
        35                  40                  45

Gly Phe Glu Arg Ile Gly Trp Pro Gly Glu Tyr Pro Phe Thr Arg Gly
    50                  55                  60

Leu Tyr Ala Thr Gly Tyr Arg Gly Arg Thr Trp Thr Ile Arg Gln Phe
65                  70                  75                  80

Ala Gly Phe Gly Asn Ala Glu Gln Thr Asn Glu Arg Tyr Lys Met Ile
                85                  90                  95

Leu Ala Asn Gly Gly Gly Leu Ser Val Ala Phe Asp Met Pro Thr
            100                 105                 110

Leu Met Gly Arg Asp Ser Asp Pro Arg Ser Leu Gly Glu Val Gly
        115                 120                 125

His Cys Gly Val Ala Ile Asp Ser Ala Ala Asp Met Glu Val Leu Phe
    130                 135                 140

Lys Asp Ile Pro Leu Gly Asp Val Thr Thr Ser Met Thr Ile Ser Gly
145                 150                 155                 160

Pro Ala Val Pro Val Phe Cys Met Tyr Leu Val Ala Ala Glu Arg Gln
                165                 170                 175

Gly Val Asp Pro Ala Val Leu Asn Gly Thr Leu Gln Thr Asp Ile Phe
            180                 185                 190

Lys Glu Tyr Ile Ala Gln Lys Glu Trp Leu Phe Gln Pro Glu Pro His
            195                 200                 205

Leu Arg Leu Ile Gly Asp Leu Met Glu His Cys Ala Arg Asp Ile Pro
210                 215                 220

Ala Tyr Lys Pro Leu Ser Val Ser Gly Tyr His Ile Arg Glu Ala Gly
225                 230                 235                 240

Ala Thr Ala Ala Gln Glu Leu Ala Tyr Thr Leu Ala Asp Gly Phe Gly
            245                 250                 255

Tyr Val Glu Leu Gly Leu Ser Arg Gly Leu Asp Val Asp Val Phe Ala
            260                 265                 270

Pro Gly Leu Ser Phe Phe Phe Asp Ala His Val Asp Phe Phe Glu Glu
            275                 280                 285

Ile Ala Lys Phe Arg Ala Ala Arg Arg Ile Trp Ala Arg Trp Leu Arg
            290                 295                 300

Asp Glu Tyr Gly Ala Lys Thr Glu Lys Ala Gln Trp Leu Arg Phe His
305                 310                 315                 320

Thr Gln Thr Ala Gly Val Ser Leu Thr Ala Gln Pro Tyr Asn Asn
                    325                 330                 335

Val Val Arg Thr Ala Val Glu Ala Leu Ala Ala Val Leu Gly Gly Thr
                    340                 345                 350

Asn Ser Leu His Thr Asn Ala Leu Asp Glu Thr Leu Ala Leu Pro Ser
            355                 360                 365

Glu Gln Ala Ala Glu Ile Ala Leu Arg Thr Gln Gln Val Leu Met Glu
370                 375                 380

Glu Thr Gly Val Ala Asn Val Ala Asp Pro Leu Gly Gly Ser Trp Tyr
385                 390                 395                 400

Ile Glu Gln Leu Thr Asp Arg Ile Glu Ala Asp Ala Glu Lys Ile Phe
                    405                 410                 415

Glu Gln Ile Arg Glu Arg Gly Arg Arg Ala Cys Pro Asp Gly Gln His
            420                 425                 430

Pro Ile Gly Pro Ile Thr Ser Gly Ile Leu Arg Gly Ile Glu Asp Gly
            435                 440                 445

Trp Phe Thr Gly Glu Ile Ala Glu Ser Ala Phe Gln Tyr Gln Arg Ser
450                 455                 460

Leu Glu Lys Gly Asp Lys Arg Val Gly Val Asn Cys Leu Glu Gly
465                 470                 475                 480

Ser Val Thr Gly Asp Leu Glu Ile Leu Arg Val Ser His Glu Val Glu
                    485                 490                 495

Arg Glu Gln Val Arg Glu Leu Ala Gly Arg Lys Gly Arg Arg Asp Asp
            500                 505                 510

Ala Arg Val Arg Ala Ser Leu Asp Ala Met Leu Ala Ala Arg Asp
            515                 520                 525

Gly Ser Asn Met Ile Ala Pro Met Leu Glu Ala Val Arg Ala Glu Ala
530                 535                 540

Thr Leu Gly Glu Ile Cys Gly Val Leu Arg Asp Glu Trp Gly Val Tyr
545                 550                 555                 560

Val Glu Pro Pro Gly Phe
                565

<210> SEQ ID NO 257
<211> LENGTH: 411
<212> TYPE: DNA
<213> ORGANISM: Streptomyces cinnamonensis

<400> SEQUENCE: 257

-continued

```
atgggtgtgg cagccgggcc gatccgcgtg gtggtcgcca agccggggct cgacgggcac      60
gatcgcgggg ccaaggtgat cgcgcgggcg ttgcgtgacg cgggtatgga ggtcatctac     120
accgggctgc accagacgcc cgagcaggtg gtggacaccg cgatccagga ggacgccgac     180
gcgatcggcc tctccatcct ctccggagcg cacaacacgc tgttcgcgcg cgtgttggag     240
ctcttgaagg agcgggacgc ggaggacatc aaggtgtttg gtggcggcat catcccggag     300
gcggacatcg cgccgctgaa ggagaagggc gtcgcggaga tcttcacgcc cggggccacc     360
accacgtcga tcgtggagtg ggttcggggg aacgtgcgac aggccgtctg a              411
```

<210> SEQ ID NO 258
<211> LENGTH: 136
<212> TYPE: PRT
<213> ORGANISM: Streptomyces cinnamonensis

<400> SEQUENCE: 258

```
Met Gly Val Ala Ala Gly Pro Ile Arg Val Val Ala Lys Pro Gly
1               5                   10                  15
Leu Asp Gly His Asp Arg Gly Ala Lys Val Ile Ala Arg Ala Leu Arg
            20                  25                  30
Asp Ala Gly Met Glu Val Ile Tyr Thr Gly Leu His Gln Thr Pro Glu
        35                  40                  45
Gln Val Val Asp Thr Ala Ile Gln Glu Asp Ala Asp Ala Ile Gly Leu
    50                  55                  60
Ser Ile Leu Ser Gly Ala His Asn Thr Leu Phe Ala Arg Val Leu Glu
65                  70                  75                  80
Leu Leu Lys Glu Arg Asp Ala Glu Asp Ile Lys Val Phe Gly Gly Gly
                85                  90                  95
Ile Ile Pro Glu Ala Asp Ile Ala Pro Leu Lys Glu Lys Gly Val Ala
            100                 105                 110
Glu Ile Phe Thr Pro Gly Ala Thr Thr Thr Ser Ile Val Glu Trp Val
        115                 120                 125
Arg Gly Asn Val Arg Gln Ala Val
    130                 135
```

<210> SEQ ID NO 259
<211> LENGTH: 1701
<212> TYPE: DNA
<213> ORGANISM: Streptomyces coelicolor

<400> SEQUENCE: 259

```
atggacgctc atgccataga ggagggccgc cttcgctggc aggcccggta cgacgcggcg      60
cgcaagcgcg acgcggactt caccacgctc tccggagacc ccgtggagcc ggtgtacggg     120
ccccgccccg gggacgagta cgagggcttc gagcggatcg gctggccggg cgagtacccc     180
ttcacccgcg gcctgtatcc gaccgggtac cggggggcgta cgtggaccat ccggcagttc     240
gccgggttcg gcaacgccga gcagaccaac gagcgctaca gatgatcct ccgcaacggc     300
ggcggcgggc tctcggtcgc cttcgacatg ccgaccctga tgggccgcga ctccgacgac     360
ccgcgctcgc tggcgaggt cgggcactgc ggggtggcca tcgactcggc cgccgacatg     420
gaagtgctgt tcaaggacat cccgctcggg gacgtgacga cctccatgac gatcagcggg     480
cccgccgtgc ccgtgttctg catgtacctc gtcgccgccg agcgccaggg cgtcgacgca     540
tccgtgctca acggcacgct gcagaccgac atcttcaagg agtacatcgc ccagaaggag     600
tggctcttcc agcccgagcc ccacctccgg ctcatcggcg acctcatgga gtactgcgcg     660
```

-continued

```
gccggcatcc ccgcctacaa gccgctctcc gtctccggct accacatccg cgaggcgggc      720
gcgacggccg cgcaggagct ggcgtacacg ctcgccgacg gcttcggata cgtggagctg      780
ggcctcagcc gcgggctcga cgtggacgtc ttcgcgcccg gcctctcctt cttcttcgac      840
gcgcacctcg acttcttcga ggagatcgcc aagttccgcg cggcccgcag gatctgggcc      900
cgctggatgc gcgacgtgta cggcgcgcgg accgacaagg cccagtggct gcggttccac      960
acccagaccg ccggagtctc gctcaccgcg cagcagccgt acaacaacgt cgtacgcacc     1020
gcggtggagg cgctggcggc cgtgctcggc ggcaccaact ccctgcacac caacgcgctc     1080
gacgagaccc tcgccctgcc cagcgagcag gccgccgaga tcgccctgcg cacccagcag     1140
gtgctgatgg aggagaccgg cgtcgccaac gtcgccgacc cgctgggcgg ttcctggttc     1200
atcgagcagc tgaccgaccg catcgaggcc gacgccgaga agatcttcga gcagatcaag     1260
gagcgggggc tgcgcgccca ccccgacggg cagcaccccg tcggaccgat cacctccggc     1320
ctgctgcgcg gcatcgagga cggctggttc accggcgaga tcgccgagtc cgccttccgc     1380
taccagcagt ccttggagaa ggacgacaag aaggtggtcg gcgtcaacgt ccacaccggc     1440
tccgtcaccg gcgacctgga gatcctgcgg gtcagccacg aggtcgagcg cgagcaggtg     1500
cgggtcctgg gcgagcgcaa ggacgcccgg gacgacgccg ccgtgcgcgg cgccctggac     1560
gccatgctgg ccgcggcccg ctccggcggc aacatgatcg gccgatgct ggacgcggtg      1620
cgcgcggagg cgacgctggg cgagatctgc ggtgtgctgc gcgacgagtg ggggtgtac      1680
acggaaccgg cggggttctg a                                                1701
```

<210> SEQ ID NO 260
<211> LENGTH: 566
<212> TYPE: PRT
<213> ORGANISM: Streptomyces coelicolor

<400> SEQUENCE: 260

```
Met Asp Ala His Ala Ile Glu Glu Gly Arg Leu Arg Trp Gln Ala Arg
  1               5                  10                  15
Tyr Asp Ala Ala Arg Lys Arg Asp Ala Asp Phe Thr Thr Leu Ser Gly
             20                  25                  30
Asp Pro Val Glu Pro Val Tyr Gly Pro Arg Pro Gly Asp Glu Tyr Glu
         35                  40                  45
Gly Phe Glu Arg Ile Gly Trp Pro Gly Glu Tyr Pro Phe Thr Arg Gly
     50                  55                  60
Leu Tyr Pro Thr Gly Tyr Arg Gly Arg Thr Trp Thr Ile Arg Gln Phe
 65                  70                  75                  80
Ala Gly Phe Gly Asn Ala Glu Gln Thr Asn Glu Arg Tyr Lys Met Ile
                 85                  90                  95
Leu Arg Asn Gly Gly Gly Gly Leu Ser Val Ala Phe Asp Met Pro Thr
            100                 105                 110
Leu Met Gly Arg Asp Ser Asp Asp Pro Arg Ser Leu Gly Glu Val Gly
        115                 120                 125
His Cys Gly Val Ala Ile Asp Ser Ala Ala Asp Met Glu Val Leu Phe
    130                 135                 140
Lys Asp Ile Pro Leu Gly Asp Val Thr Thr Ser Met Thr Ile Ser Gly
145                 150                 155                 160
Pro Ala Val Pro Val Phe Cys Met Tyr Leu Val Ala Ala Glu Arg Gln
                165                 170                 175
Gly Val Asp Ala Ser Val Leu Asn Gly Thr Leu Gln Thr Asp Ile Phe
```

```
                  180               185               190
Lys Glu Tyr Ile Ala Gln Lys Glu Trp Leu Phe Gln Pro Glu Pro His
            195                 200                 205

Leu Arg Leu Ile Gly Asp Leu Met Glu Tyr Cys Ala Gly Ile Pro
        210                 215                 220

Ala Tyr Lys Pro Leu Ser Val Ser Gly Tyr His Ile Arg Glu Ala Gly
225                 230                 235                 240

Ala Thr Ala Ala Gln Glu Leu Ala Tyr Thr Leu Ala Asp Gly Phe Gly
                245                 250                 255

Tyr Val Glu Leu Gly Leu Ser Arg Gly Leu Asp Val Asp Val Phe Ala
            260                 265                 270

Pro Gly Leu Ser Phe Phe Asp Ala His Leu Asp Phe Glu Glu
        275                 280                 285

Ile Ala Lys Phe Arg Ala Ala Arg Arg Ile Trp Ala Arg Trp Met Arg
                290                 295                 300

Asp Val Tyr Gly Ala Arg Thr Asp Lys Ala Gln Trp Leu Arg Phe His
305                 310                 315                 320

Thr Gln Thr Ala Gly Val Ser Leu Thr Ala Gln Gln Pro Tyr Asn Asn
                325                 330                 335

Val Val Arg Thr Ala Val Glu Ala Leu Ala Ala Val Leu Gly Gly Thr
            340                 345                 350

Asn Ser Leu His Thr Asn Ala Leu Asp Glu Thr Leu Ala Leu Pro Ser
        355                 360                 365

Glu Gln Ala Ala Glu Ile Ala Leu Arg Thr Gln Gln Val Leu Met Glu
        370                 375                 380

Glu Thr Gly Val Ala Asn Val Ala Asp Pro Leu Gly Gly Ser Trp Phe
385                 390                 395                 400

Ile Glu Gln Leu Thr Asp Arg Ile Glu Ala Asp Ala Glu Lys Ile Phe
                405                 410                 415

Glu Gln Ile Lys Glu Arg Gly Leu Arg Ala His Pro Asp Gly Gln His
                420                 425                 430

Pro Val Gly Pro Ile Thr Ser Gly Leu Leu Arg Gly Ile Glu Asp Gly
            435                 440                 445

Trp Phe Thr Gly Glu Ile Ala Glu Ser Ala Phe Arg Tyr Gln Gln Ser
        450                 455                 460

Leu Glu Lys Asp Asp Lys Lys Val Val Gly Val Asn Val His Thr Gly
465                 470                 475                 480

Ser Val Thr Gly Asp Leu Glu Ile Leu Arg Val Ser His Glu Val Glu
                485                 490                 495

Arg Glu Gln Val Arg Val Leu Gly Glu Arg Lys Asp Ala Arg Asp Asp
            500                 505                 510

Ala Ala Val Arg Gly Ala Leu Asp Ala Met Leu Ala Ala Ala Arg Ser
        515                 520                 525

Gly Gly Asn Met Ile Gly Pro Met Leu Asp Ala Val Arg Ala Glu Ala
        530                 535                 540

Thr Leu Gly Glu Ile Cys Gly Val Leu Arg Asp Glu Trp Gly Val Tyr
545                 550                 555                 560

Thr Glu Pro Ala Gly Phe
                565

<210> SEQ ID NO 261
<211> LENGTH: 417
<212> TYPE: DNA
<213> ORGANISM: Streptomyces coelicolor
```

<400> SEQUENCE: 261

```
atgggtgtgg cagccggtcc gatccgcgtg gtggtggcca agccggggct cgacggccac    60
gatcgcgggg ccaaggtgat cgcgagggcc ctgcgtgacg ccggtatgga ggtgatctac   120
accgggctcc accagacgcc cgagcagatc gtcgacaccg cgatccagga ggacgccgac   180
gcgatcgggc tgtccatcct ctccggtgcg cacaacacgc tcttcgccgc cgtgatcgag   240
ctgctccggg agcgggacgc cgcggacatc ctggtcttcg gcggcgggat catccccgag   300
gcggacatcg ccccgctgaa ggagaagggc gtcgcggaga tcttcacgcc cggcgccacc   360
acggcgtcca cgtggactg gtccgggcg aacgtgcggg agcccgcggg agcatag       417
```

<210> SEQ ID NO 262
<211> LENGTH: 138
<212> TYPE: PRT
<213> ORGANISM: Streptomyces coelicolor

<400> SEQUENCE: 262

```
Met Gly Val Ala Ala Gly Pro Ile Arg Val Val Ala Lys Pro Gly
1               5                   10                  15
Leu Asp Gly His Asp Arg Gly Ala Lys Val Ile Ala Arg Ala Leu Arg
            20                  25                  30
Asp Ala Gly Met Glu Val Ile Tyr Thr Gly Leu His Gln Thr Pro Glu
        35                  40                  45
Gln Ile Val Asp Thr Ala Ile Gln Glu Asp Ala Asp Ala Ile Gly Leu
    50                  55                  60
Ser Ile Leu Ser Gly Ala His Asn Thr Leu Phe Ala Ala Val Ile Glu
65                  70                  75                  80
Leu Leu Arg Glu Arg Asp Ala Ala Asp Ile Leu Val Phe Gly Gly Gly
                85                  90                  95
Ile Ile Pro Glu Ala Asp Ile Ala Pro Leu Lys Glu Lys Gly Val Ala
            100                 105                 110
Glu Ile Phe Thr Pro Gly Ala Thr Thr Ala Ser Ile Val Asp Trp Val
        115                 120                 125
Arg Ala Asn Val Arg Glu Pro Ala Gly Ala
    130                 135
```

<210> SEQ ID NO 263
<211> LENGTH: 1701
<212> TYPE: DNA
<213> ORGANISM: Streptomyces avermitilis

<400> SEQUENCE: 263

```
tcagaaaccg gcgggctccg tgtagacccc ccactcctcc ggaggacat cgcagatctc     60
gcccagcgtg gcctccgcgc ggaccgcgtc cagcatcggg gcgatcatgt tcgacccgtc   120
gcgcgcggcg gcgagcatcg cgtccagggc cgcggttacg gcgtgtcgt cgcgccccga    180
cttccgctcg cccagcaccc gcacctgctc gcgctccacc tcgtggctga cgcgcaggat   240
ctccaggtcg cccgtcacgg acccgtggtg gacgttgacg ccgacgaccc gcttgtcgcc   300
cttctccagc gcctgctggt actggaaggc cgactcggcg atctccccgg tgaaccagcc   360
gtcctcgatg ccgcgcagga tgccggaggt gatgggcccg atcgggtgcc gcccgtccgg   420
gtgggcccgc agcccgcgct ccctgatctg ttcgaagatc ttctcggcgt cggcctcgat   480
ccggtcggtc agctgctcca cgtaccagga accgcccagc ggatcggcca cgttggcgac   540
gcccgtctcc tccatcagca cctgctgggt gcgcagggcg atctcggccg cctgctcgga   600
```

```
cggcagggcg agggtctcgt cgagggcgtt ggtgtgcagc gagttcgtcc cgccgagcac    660
cgcggcgagg gcctccacgg ccgtccgtac gacgttgttg tacggctgct gcgcggtgag    720
cgagacgccc gcggtctggg tgtggaagcg cagccactgc gccttctccg acttcgcccc    780
gtacacgtcc cgcagccagc gcgcccagat gcgccgcgcc gcacggaact tggcgatctc    840
ctcgaagaag tcgacgtgcg cgtcgaagaa gaaggagagc ccgggcgcga cacgtccac     900
gtccaggccg cggctcagcc ccagctccac gtatccgaaa ccgtcggcga gggtgtacgc    960
cagctcctgg gcggccgtgg caccggcctc ccggatgtgg tacccggaga cggacagcgg   1020
cttgtacgcg gggatcttcg aggcgcagtg ctccatcagg tcgccgatga ccgcagatg    1080
gggctcgggc tggaagagcc actccttctg cgcgatgtac tccttgaaga tgtcggtctg   1140
gagggtgccg ttgaggacgg aggggtcgac gccctgccgc tcggccgcga ccaggtacat   1200
gcagaagacg ggcacggcgg gcccgctgat cgtcatcgac gtcgtcacgt cacccagcgg   1260
gatgtccttg aacaggacct ccatgtcggc cgccgagtcg atcgcgaccc cgcagtgccc   1320
gacctcgccg agcgcgcggc ggtcgtcgga gtcgcgcccc atgagcgtcg gcatgtcgaa   1380
ggccacggac agcccaccgc cgccgttggc gaggatcttc ttgtagcgct cgttggtctg   1440
ctcggcgttg ccgaacccgg cgaactgccg gatggtccag gtccggcccc ggtagccggt   1500
cggatacaga ccgcgcgtga aggggtactc acccggccag ccgatccgct cgaaaccctc   1560
gtacgcgtcc ccgggccggg gcccgtacgc cggctccacg ggatcgccgg agagcgtggt   1620
gaaatcggcc tcgcgcttgc gtgaggcgtc gtagcgggcc tgccagcgtc ggcggccttc   1680
ctcgatggcg tcagcgtcca t                                             1701
```

<210> SEQ ID NO 264
<211> LENGTH: 566
<212> TYPE: PRT
<213> ORGANISM: Streptomyces avermitilis

<400> SEQUENCE: 264

```
Met Asp Ala Asp Ala Ile Glu Glu Gly Arg Arg Trp Gln Ala Arg
1               5                   10                  15

Tyr Asp Ala Ser Arg Lys Arg Glu Ala Asp Phe Thr Thr Leu Ser Gly
                20                  25                  30

Asp Pro Val Glu Pro Ala Tyr Gly Pro Arg Pro Gly Asp Ala Tyr Glu
            35                  40                  45

Gly Phe Glu Arg Ile Gly Trp Pro Gly Glu Tyr Pro Phe Thr Arg Gly
        50                  55                  60

Leu Tyr Pro Thr Gly Tyr Arg Gly Arg Thr Trp Thr Ile Arg Gln Phe
65                  70                  75                  80

Ala Gly Phe Gly Asn Ala Glu Gln Thr Asn Glu Arg Tyr Lys Lys Ile
                85                  90                  95

Leu Ala Asn Gly Gly Gly Gly Leu Ser Val Ala Phe Asp Met Pro Thr
            100                 105                 110

Leu Met Gly Arg Asp Ser Asp Asp Arg Arg Ala Leu Gly Glu Val Gly
        115                 120                 125

His Cys Gly Val Ala Ile Asp Ser Ala Ala Asp Met Glu Val Leu Phe
    130                 135                 140

Lys Asp Ile Pro Leu Gly Asp Val Thr Thr Ser Met Thr Ile Ser Gly
145                 150                 155                 160

Pro Ala Val Pro Val Phe Cys Met Tyr Leu Val Ala Ala Glu Arg Gln
                165                 170                 175
```

Gly Val Asp Pro Ser Val Leu Asn Gly Thr Leu Gln Thr Asp Ile Phe
            180                 185                 190

Lys Glu Tyr Ile Ala Gln Lys Glu Trp Leu Phe Gln Pro Glu Pro His
            195                 200                 205

Leu Arg Leu Ile Gly Asp Leu Met Glu His Cys Ala Ser Lys Ile Pro
210                 215                 220

Ala Tyr Lys Pro Leu Ser Val Ser Gly Tyr His Ile Arg Glu Ala Gly
225                 230                 235                 240

Ala Thr Ala Ala Gln Glu Leu Ala Tyr Thr Leu Ala Asp Gly Phe Gly
                245                 250                 255

Tyr Val Glu Leu Gly Leu Ser Arg Gly Leu Asp Val Asp Val Phe Ala
            260                 265                 270

Pro Gly Leu Ser Phe Phe Asp Ala His Val Asp Phe Phe Glu Glu
            275                 280                 285

Ile Ala Lys Phe Arg Ala Ala Arg Arg Ile Trp Ala Arg Trp Leu Arg
290                 295                 300

Asp Val Tyr Gly Ala Lys Ser Glu Lys Ala Gln Trp Leu Arg Phe His
305                 310                 315                 320

Thr Gln Thr Ala Gly Val Ser Leu Thr Ala Gln Pro Tyr Asn Asn
                325                 330                 335

Val Val Arg Thr Ala Val Glu Ala Leu Ala Ala Val Leu Gly Gly Thr
            340                 345                 350

Asn Ser Leu His Thr Asn Ala Leu Asp Glu Thr Leu Ala Leu Pro Ser
            355                 360                 365

Glu Gln Ala Ala Glu Ile Ala Leu Arg Thr Gln Gln Val Leu Met Glu
370                 375                 380

Glu Thr Gly Val Ala Asn Val Ala Asp Pro Leu Gly Gly Ser Trp Tyr
385                 390                 395                 400

Val Glu Gln Leu Thr Asp Arg Ile Glu Ala Asp Ala Glu Lys Ile Phe
                405                 410                 415

Glu Gln Ile Arg Glu Arg Gly Leu Arg Ala His Pro Asp Gly Arg His
            420                 425                 430

Pro Ile Gly Pro Ile Thr Ser Gly Ile Leu Arg Gly Ile Glu Asp Gly
            435                 440                 445

Trp Phe Thr Gly Glu Ile Ala Glu Ser Ala Phe Gln Tyr Gln Gln Ala
450                 455                 460

Leu Glu Lys Gly Asp Lys Arg Val Gly Val Asn Val His His Gly
465                 470                 475                 480

Ser Val Thr Gly Asp Leu Glu Ile Leu Arg Val Ser His Glu Val Glu
                485                 490                 495

Arg Glu Gln Val Arg Val Leu Gly Glu Arg Lys Ser Gly Arg Asp Asp
            500                 505                 510

Thr Ala Val Thr Ala Ala Leu Asp Ala Met Leu Ala Ala Arg Asp
            515                 520                 525

Gly Ser Asn Met Ile Ala Pro Met Leu Asp Ala Val Arg Ala Glu Ala
530                 535                 540

Thr Leu Gly Glu Ile Cys Asp Val Leu Arg Glu Glu Trp Gly Val Tyr
545                 550                 555                 560

Thr Glu Pro Ala Gly Phe
                565

<210> SEQ ID NO 265
<211> LENGTH: 417

```
<212> TYPE: DNA
<213> ORGANISM: Streptomyces avermitilis

<400> SEQUENCE: 265
ctacgccccg gcaggctgcc gcacgttcgc ccgcacccac tccacgatcg acgccgtggt    60
cgcccccgga gtgaagatct ccgcgacacc cttctccttc agcggcgcga tgtccgcctc   120
ggggatgatg ccgccaccga acaccttgat gtcctcggca tcgcgctcct tgagcagatc   180
gatgaccgcc gcgaacaacg tgttgtgcgc cccggacagg atcgacagcc cgatcgcgtc   240
ggcgtcctcc tggatggccg tgcccacgat ctgctccggc gtctggtgca gccccgtgta   300
aatgacctcc ataccggcat cgcgcagcgc ccgcgcgatc accttggccc cgcgatcgtg   360
gccatcgagc cccggcttgg ccaccaccac gcggatcgga ccggctgcca cacccat      417

<210> SEQ ID NO 266
<211> LENGTH: 138
<212> TYPE: PRT
<213> ORGANISM: Streptomyces avermitilis

<400> SEQUENCE: 266

Met Gly Val Ala Ala Gly Pro Ile Arg Val Val Ala Lys Pro Gly
1               5                   10                  15

Leu Asp Gly His Asp Arg Gly Ala Lys Val Ile Ala Arg Ala Leu Arg
                20                  25                  30

Asp Ala Gly Met Glu Val Ile Tyr Thr Gly Leu His Gln Thr Pro Glu
            35                  40                  45

Gln Ile Val Gly Thr Ala Ile Gln Glu Asp Ala Asp Ala Ile Gly Leu
        50                  55                  60

Ser Ile Leu Ser Gly Ala His Asn Thr Leu Phe Ala Ala Val Ile Asp
65                  70                  75                  80

Leu Leu Lys Glu Arg Asp Ala Glu Asp Ile Lys Val Phe Gly Gly
                85                  90                  95

Ile Ile Pro Glu Ala Asp Ile Ala Pro Leu Lys Glu Lys Gly Val Ala
            100                 105                 110

Glu Ile Phe Thr Pro Gly Ala Thr Thr Ala Ser Ile Val Glu Trp Val
        115                 120                 125

Arg Ala Asn Val Arg Gln Pro Ala Gly Ala
    130                 135

<210> SEQ ID NO 267
<211> LENGTH: 2910
<212> TYPE: DNA
<213> ORGANISM: Staphylococcus aureus

<400> SEQUENCE: 267
gatcaatttc ttttaagtaa tctaaatccc cattttttaa tttcttttta gcctctttaa    60
ataatcctga ataaactaat acctgtttac ctttaagtga tttataaaat gcatcaaaga   120 cttttttgatt tatttattaa ataatcacta tctttaccag aatacttagc catttcatat   180
aattctttat tattattttg tcttattttt tgaacttgaa cttgtgttat ttctgaaatg   240
cccgttacat cacgccataa atctaaccat tcttgttggc taatataata tcttttatct   300
gtgaaatacg atttatttac tgcaattaac acatgaaaat gaggattata atcatctctt   360
tttttattat atgtaatctc taacttacga acatatccct ttataacact acctactttt   420
tttctcttta taagttttct aaaagaatta ttataacgtt ttatttcatt ttctaattca   480
tcactcatta cattaggtgt agtcaaagtt aaaaagataa actcctttttt ctcttgctgc   540
```

```
ttaatatatt gcatcatcaa agataaaccc aatgcatctt ttctagcttt tctccaagca    600
cagacaggac aaaatcgatt tttacaagaa ttagctttat ataatttctg ttttttctaaa   660 gttttatcag ctacaaaaga cagaaatgta ttgcaatctt caactaaatc catttgattc    720
tctccaatat gacgtttaat aaatttctga aatacttgat ttctttgttt tttctcagta    780
tacttttcca tgttataaca cataaaaaca acttagtttt cacaaactat gacaataaaa    840
aaagttgctt tttccccttt ctatgtatgt ttttactag tcatttaaaa cgatacatta     900
ataggtacga aaaagcaact ttttttgcgc ttaaaaccag tcataccaat aacttaaggg    960
taactagcct cgccggcaat agttacccct attatcaaga taagaaagaa aaggattttt   1020
cgctacgctc aaatccttta aaaaaacaca aaagaccaca tttttttaatg tggtctttat  1080 tcttcaacta aagcacccat tagttcaaca acgaaaaatt ggataaagtg ggatattttt   1140
aaaatatata tttatgttac agtaatattg acttttaaaa aaggattgat tctaatgaag   1200
aaagcagaca agtaagcctc ctaaattcac tttagataaa aatttaggag gcatatcaaa   1260
tgaactttaa taaaattgat ttagacaatt ggaagagaaa agagatattt aatcattatt   1320
tgaaccaaca aacgactttt agtataacca cagaaattga tattagtgtt ttataccgaa   1380
acataaaaca agaaggatat aaattttacc ctgcatttat tttcttagtg acaagggtga   1440
taaactcaaa tacagctttt agaactggtt acaatagcga cggagagtta ggttattggg   1500
ataagttaga gccactttat acaattttttg atggtgtatc taaaacattc tctggtatttt 1560 ggactcctgt aaagaatgac ttcaaagagt tttatgattt atacctttct gatgtagaga   1620
aatataatgg ttcggggaaa ttgtttccca aaacacctat acctgaaaat gcttttctc    1680 tttctattat tccatggact tcatttactg ggtttaactt aaatatcaat aataatagta   1740
attaccttct acccattatt acagcaggaa aattcattaa taaaggtaat tcaatatatt   1800
taccgctatc tttacaggta catcattctg tttgtgatgg ttatcatgca ggattgttta   1860
tgaactctat tcaggaattg tcagataggc ctaatgactg gctttatata tatgagataa   1920
tgccgactgt acttttaca gtcggttttc taatgtcact aacctgcccc gttagttgaa    1980
gaaggttttt atattacagc tccagatcca tatccttctt tttctgaacc gacttctcct   2040
ttttcgcttc tttattccaa ttgctttatt gacgttgagc ctcggaaccc ttaacaatcc   2100
caaaacttgt cgaatggtcg gcttaatagc tcacgctatg ccgacattcg tctgcaagtt   2160
tagttaaggg ttcttctcaa cgcacaataa attttctcgg cataaatgcg tggtctaatt   2220
tttattttta ataaccttga tagcaaaaaa tgccattcca atacaaaacc acataccat    2280 aatcgataac cacataacag tcataaaacc actccttttt aacaaacttt atcacaagaa   2340
atatttaaat tttaaatgcc tttattttga attttaaggg gcattttaaa gatttagggg   2400
taaatcatat agttttatgc ctaaaaacct acagaagctt ttaaaaagca aatatgagcc   2460
aaataaatat attctaattc tacaaacaaa aatttgagca aattcagtgt cgatttttta   2520
agacactgcc cagttacatg caaattaaaa ttttcatgat tttttatagt tcctaacagg   2580
gttaaaattt gtataacgaa agtataatgt ttatataacg ttagtataat aaagcatttt   2640
aacattatac ttttgataat cgtttatcgt cgtcatcaca ataacttta aaatactcgt    2700 gcataattca cgctgacctc ccaataacta catggtgtta tcgggaggtc agctgttagc   2760
acttatattt tgttattgtt cttcctcgat ttcgtctatc attttgtgat taatttctct   2820
```

```
tttttcttgt tctgttaagt cataaagttc actagctaaa tactcttttt gtttccaaat    2880
ataaaaaatt tgatagatat attacggttg                                     2910
```

FERMENTIVE PRODUCTION OF FOUR CARBON ALCOHOLS

CROSS-REFERENCE TO RELATED APPLICATIONS

This application is a continuation of and claims priority to U.S. patent application Ser. No. 12/939,315, filed on Nov. 4, 2010 which is a continuation of and claims priority to U.S. patent application Ser. No. 11/586,315, now U.S. Pat. No. 7,851,188, filed on Oct. 25, 2006, which claims priority under 35 U.S.C. §119 from U.S. Provisional Application Ser. No. 60/730,290, filed Oct. 26, 2005.

FIELD OF THE INVENTION

The invention relates to the field of industrial microbiology and the production of alcohols. More specifically, isobutanol is produced via industrial fermentation of a recombinant microorganism.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Methods for the chemical synthesis of isobutanol are known, such as oxo synthesis, catalytic hydrogenation of carbon monoxide (*Ullmann's Encyclopedia of Industrial Chemistry*, 6$^{th}$ edition, 2003, Wiley-VCHVerlag GmbH and Co., Weinheim, Germany, Vol. 5, pp. 716-719) and Guerbet condensation of methanol with n-propanol (Carlini et al., *J. Mol. Catal. A:Chem.* 220:215-220 (2004)). These processes use starting materials derived from petrochemicals and are generally expensive and are not environmentally friendly. The production of isobutanol from plant-derived raw materials would minimize green house gas emissions and would represent an advance in the art.

Isobutanol is produced biologically as a by-product of yeast fermentation. It is a component of "fusel oil" that forms as a result of incomplete metabolism of amino acids by this group of fungi. Isobutanol is specifically produced from catabolism of L-valine. After the amine group of L-valine is harvested as a nitrogen source, the resulting α-keto acid is decarboxylated and reduced to isobutanol by enzymes of the so-called Ehrlich pathway (Dickinson et al., *J. Biol. Chem.* 273(40):25752-25756 (1998)). Yields of fusel oil and/or its components achieved during beverage fermentation are typically low. For example, the concentration of isobutanol produced in beer fermentation is reported to be less than 16 parts per million (Garcia et al., *Process Biochemistry* 29:303-309 (1994)). Addition of exogenous L-valine to the fermentation increases the yield of isobutanol, as described by Dickinson et al., supra, wherein it is reported that a yield of isobutanol of 3 g/L is obtained by providing L-valine at a concentration of 20 g/L in the fermentation. However, the use of valine as a feed-stock would be cost prohibitive for industrial scale isobutanol production. The biosynthesis of isobutanol directly from sugars would be economically viable and would represent an advance in the art. There have been no reports of a recombinant microorganism designed to produce isobutanol.

There is a need, therefore, for an environmentally responsible, cost-effective process for the production of isobutanol as a single product. The present invention addresses this need by providing a recombinant microbial production host that expresses an isobutanol biosynthetic pathway.

SUMMARY OF THE INVENTION

The invention provides a recombinant microorganism having an engineered isobutanol biosynthetic pathway. The engineered microorganism may be used for the commercial production of isobutanol. Accordingly, in one embodiment the invention provides a recombinant microbial host cell comprising at least one DNA molecule encoding a polypeptide that catalyzes a substrate to product conversion selected from the group consisting of:
  i) pyruvate to acetolactate (pathway step a)
  ii) acetolactate to 2,3-dihydroxyisovalerate (pathway step b)
  iii) 2,3-dihydroxyisovalerate to α-ketoisovalerate (pathway step c)
  iv) α-ketoisovalerate to isobutyraldehyde, (pathway step d), and
  v) isobutyraldehyde to isobutanol; (pathway step e)
wherein the at least one DNA molecule is heterologous to said microbial host cell and wherein said microbial host cell produces isobutanol.

In another embodiment, the invention provides a recombinant microbial host cell comprising at least one DNA molecule encoding a polypeptide that catalyzes a substrate to product conversion selected from the group consisting of:
  i) pyruvate to acetolactate, (pathway step a)
  ii) acetolactate to 2,3-dihydroxyisovalerate, (pathway step b)
  iii) 2,3-dihydroxyisovalerate to α-ketoisovalerate, (pathway step c)
  iv) α-ketoisovalerate to isobutyryl-CoA, (pathway step f)
  v) isobutyryl-CoA to isobutyraldehyde, (pathway step g), and
  vi) isobutyraldehyde to isobutanol; (pathway step e)
wherein the at least one DNA molecule is heterologous to said microbial host cell and wherein said microbial host cell produces isobutanol.

In another embodiment, the invention provides a recombinant microbial host cell comprising at least one DNA molecule encoding a polypeptide that catalyzes a substrate to product conversion selected from the group consisting of:
  i) pyruvate to acetolactate, (pathway step a)
  ii) acetolactate to 2,3-dihydroxyisovalerate, (pathway step b)
  iii) 2,3-dihydroxyisovalerate to α-ketoisovalerate, (pathway step c)
  iv) α-ketoisovalerate to valine, (pathway step h)
  v) valine to isobutylamine, (pathway step i)
  vi) isobutylamine to isobutyraldehyde, (pathway step j), and
  vii) isobutyraldehyde to isobutanol: (pathway step e)
wherein the at least one DNA molecule is heterologous to said microbial host cell and wherein said microbial host cell produces isobutanol.

In another embodiment, the invention provides a method for the production of isobutanol comprising:
  1) providing a recombinant microbial host cell comprising at least one DNA molecule encoding a polypeptide that catalyzes a substrate to product conversion selected from the group consisting of:
    i) pyruvate to acetolactate (pathway step a)
    ii) acetolactate to 2,3-dihydroxyisovalerate (pathway step b)

iii) 2,3-dihydroxyisovalerate to α-ketoisovalerate (pathway step c)
iv) α-ketoisovalerate to isobutyraldehyde, (pathway step d), and
v) isobutyraldehyde to isobutanol; (pathway step e)
wherein the at least one DNA molecule is heterologous to said microbial host cell; and
2) contacting the host cell of (i) with a fermentable carbon substrate in a fermentation medium under conditions whereby isobutanol is produced.

In another embodiment, the invention provides a method for the production of isobutanol comprising:
1) providing a recombinant microbial host cell comprising at least one DNA molecule encoding a polypeptide that catalyzes a substrate to product conversion selected from the group consisting of:
i) pyruvate to acetolactate, (pathway step a)
ii) acetolactate to 2,3-dihydroxyisovalerate, (pathway step b)
iii) 2,3-dihydroxyisovalerate to α-ketoisovalerate, (pathway step c)
iv) α-ketoisovalerate to isobutyryl-CoA, (pathway step f)
v) isobutyryl-CoA to isobutyraldehyde, (pathway step g), and
vi) isobutyraldehyde to isobutanol; (pathway step e)
wherein the at least one DNA molecule is heterologous to said microbial host cell; and
2) contacting the host cell of (i) with a fermentable carbon substrate in a fermentation medium under conditions whereby isobutanol is produced.

In another embodiment, the invention provides a method for the production of isobutanol comprising:
1) providing a recombinant microbial host cell comprising at least one DNA molecule encoding a polypeptide that catalyzes a substrate to product conversion selected from the group consisting of:
i) pyruvate to acetolactate, (pathway step a)
ii) acetolactate to 2,3-dihydroxyisovalerate, (pathway step b)
iii) 2,3-dihydroxyisovalerate to α-ketoisovalerate, (pathway step c)
iv) α-ketoisovalerate to valine, (pathway step h)
v) valine to isobutylamine, (pathway step i)
vi) isobutylamine to isobutyraldehyde, (pathway step j), and
vii) isobutyraldehyde to isobutanol: (pathway step e)
wherein the at least one DNA molecule is heterologous to said microbial host cell; and
2) contacting the host cell of (i) with a fermentable carbon substrate in a fermentation medium under conditions whereby isobutanol is produced.

In an alternate embodiment the invention provides an isobutanol containing fermentation medium produced by the methods of the invention.

BRIEF DESCRIPTION OF THE FIGURES AND SEQUENCE DESCRIPTIONS

The invention can be more fully understood from the following detailed description, FIGURE, and the accompanying sequence descriptions, which form a part of this application.

FIG. 1 shows four different isobutanol biosynthetic pathways. The steps labeled "a", "b", "c", "d", "e", "f", "g", "h", "i", "j" and "k" represent the substrate to product conversions described below.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers

| Description | SEQ ID NO: Nucleic acid | SEQ ID NO: Peptide |
|---|---|---|
| *Klebsiella pneumoniae* budB (acetolactate synthase) | 1 | 2 |
| *Bacillus subtilis* alsS (acetolactate synthase) | 78 | 178 |
| *Lactococcus lactis* als (acetolactate synthase) | 179 | 180 |
| *E. coli* ilvC (acetohydroxy acid reductoisomerase) | 3 | 4 |
| *S. cerevisiae* ILV5 (acetohydroxy acid reductoisomerase) | 80 | 181 |
| *M. maripaludis* ilvC (Ketol-acid reductoisomerase) | 182 | 183 |
| *B. subtilis* ilvC (acetohydroxy acid reductoisomerase) | 184 | 185 |
| *E. coli* ilvD (acetohydroxy acid dehydratase) | 5 | 6 |
| *S. cerevisiae* ILV3 (Dihydroxyacid dehydratase) | 83 | 186 |
| *M. maripaludis* ilvD (Dihydroxy-acid dehydratase) | 187 | 188 |
| *B. subtilis* ilvD (dihydroxy-acid dehydratase) | 189 | 190 |
| *Lactococcus lactis* kivD (branched-chain α-keto acid decarboxylase), codon optimized | 7 | 8 |
| *Lactococcus lactis* kivD (branched-chain α-keto acid decarboxylase), | 191 | 8 |
| *Lactococcus lactis* kdcA (branched-chain alpha-ketoacid decarboxylase) | 192 | 193 |
| *Salmonella typhimurium* (indolepyruvate decarboxylase) | 194 | 195 |
| *Clostridium acetobutylicum* pdc (Pyruvate decarboxylase) | 196 | 197 |
| *E. coli* yqhD (branched-chain alcohol dehydrogenase) | 9 | 10 |
| *S. cerevisiae* YPR1 (2-methylbutyraldehyde reductase) | 198 | 199 |
| *S. cerevisiae* ADH6 (NADPH-dependent cinnamyl alcohol dehydrogenase) | 200 | 201 |
| *Clostridium acetobutylicum* bdhA (NADH-dependent butanol dehydrogenase A) | 202 | 203 |
| *Clostridium acetobutylicum* bdhB Butanol dehydrogenase | 158 | 204 |
| *B. subtilis* bkdAA (branched-chain keto acid dehydrogenase E1 subunit) | 205 | 206 |
| *B. subtilis* bkdAB (branched-chain alpha-keto acid dehydrogenase E1 subunit) | 207 | 208 |
| *B. subtilis* bkdB (branched-chain alpha-keto acid dehydrogenase E2 subunit) | 209 | 210 |
| *B. subtilis* lpdV (branched-chain alpha-keto acid dehydrogenase E3 subunit) | 211 | 212 |
| *P. putida* bkdA1 (keto acid dehydrogenase E1-alpha subunit) | 213 | 214 |

TABLE 1-continued

Summary of Gene and Protein SEQ ID Numbers

| Description | SEQ ID NO: Nucleic acid | SEQ ID NO: Peptide |
|---|---|---|
| *P. putida* bkdA2 (keto acid dehydrogenase E1-beta subunit) | 215 | 216 |
| *P. putida* bkdB (transacylase E2) | 217 | 218 |
| *P. putida* lpdV (lipoamide dehydrogenase) | 219 | 220 |
| *C. beijerinckii* ald (coenzyme A acylating aldehyde dehydrogenase) | 221 | 222 |
| *C. acetobutylicum* adhe1 (aldehyde dehydrogenase) | 223 | 224 |
| *C. acetobutylicum* adhe (alcohol-aldehyde dehydrogenase) | 225 | 226 |
| *P. putida* nahO (acetaldehyde dehydrogenase) | 227 | 228 |
| *T. thermophilus* (acetaldehyde dehydrogenase) | 229 | 230 |
| *E. coli* avtA (valine-pyruvate transaminase) | 231 | 232 |
| *B. licheniformis* avtA (valine-pyruvate transaminase) | 233 | 234 |
| *E. coli* ilvE (branched chain amino acid aminotransferase) | 235 | 236 |
| *S. cerevisiae* BAT2 (branched chain amino acid aminotransferase) | 237 | 238 |
| *M. thermoautotrophicum* (branched chain amino acid aminotransferase) | 239 | 240 |
| *S. coelicolor* (valine dehydrogenase) | 241 | 242 |
| *B.. subtilis* bcd (leucine dehydrogenase) | 243 | 244 |
| *S. viridifaciens* (valine decarboxyase) | 245 | 246 |
| *A. denitrificans* aptA (omega-amino acid:pyruvate transaminase) | 247 | 248 |
| *R. eutropha* (alanine-pyruvate transaminase) | 249 | 250 |
| *S. oneidensis* (beta alanine-pyruvate transaminase) | 251 | 252 |
| *P. putida* (beta alanine-pyruvate transaminase) | 253 | 254 |
| *S. cinnamonensis* icm (isobutyrl-CoA mutase) | 255 | 256 |
| *S. cinnamonensis* icmB (isobutyrl-CoA mutase) | 257 | 258 |
| *S. coelicolor* SCO5415 (isobutyrl-CoA mutase) | 259 | 260 |
| *S. coelicolor* SCO4800 (isobutyrl-CoA mutase) | 261 | 262 |
| *S. avermitilis* icmA (isobutyrl-CoA mutase) | 263 | 264 |
| *S. avermitilis* icmB (isobutyrl-CoA mutase) | 265 | 266 |

SEQ ID NOs:11-38, 40-69, 72-75, 85-138, 144, 145, 147-157, 159-176 are the nucleotide sequences of oligonucleotide cloning, screening or sequencing primers used in the Examples described herein.

SEQ ID NO:39 is the nucleotide sequence of the cscBKA gene cluster described in Example 16.

SEQ ID NO:70 is the nucleotide sequence of the glucose isomerase promoter 1.6GI described in Example 13.

SEQ ID NO:71 is the nucleotide sequence of the 1.5GI promoter described in Example 13.

SEQ ID NO:76 is the nucleotide sequence of the GPD promoter described in Example 17.

SEQ ID NO:77 is the nucleotide sequence of the CYC1 terminator described in Example 17.

SEQ ID NO:79 is the nucleotide sequence of the FBA promoter described in Example 17.

SEQ ID NO:81 is the nucleotide sequence of ADH1 promoter described in Example 17.

SEQW ID NO:82 is the nucleotide sequence of ADH1 terminator described in Example 17.

SEQ ID NO:84 is the nucleotide sequence of GPM promoter described in Example 17.

SEQ ID NO:139 is the amino acid sequence of sucrose hydrolase (CscA).

SEQ ID NO:140 is the amino acid sequence of D-fructokinase (CscK).

SEQ ID NO:141 is the amino acid sequence of sucrose permease (CscB).

SEQ ID NO:142 is the nucleotide sequence of plasmid pFP988DssPspac described in Example 20.

SEQ ID NO:143 is the nucleotide sequence of plasmid pFP988DssPgroE described in Example 20.

SEQ ID NO:146 is the nucleotide sequence of the pFP988Dss vector fragment described in Example 20.

SEQ ID NO:177 is the nucleotide sequence of the pFP988 integration vector described in Example 21.

SEQ ID NO:267 is the nucleotide sequence of plasmid pC194 described in Example 21.

DETAILED DESCRIPTION OF THE INVENTION

The present invention relates to methods for the production of isobutanol using recombinant microorganisms. The present invention meets a number of commercial and industrial needs. Butanol is an important industrial commodity chemical with a variety of applications, where its potential as a fuel or fuel additive is particularly significant. Although only a four-carbon alcohol, butanol has an energy content similar to that of gasoline and can be blended with any fossil fuel. Butanol is favored as a fuel or fuel additive as it yields only $CO_2$ and little or no $SO_X$ or $NO_X$ when burned in the standard internal combustion engine. Additionally butanol is less corrosive than ethanol, the most preferred fuel additive to date.

In addition to its utility as a biofuel or fuel additive, butanol has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or vehicles.

Finally the present invention produces isobutanol from plant derived carbon sources, avoiding the negative environmental impact associated with standard petrochemical processes for butanol production.

The following definitions and abbreviations are to be used for the interpretation of the claims and the specification.

The term "invention" or "present invention" as used herein is a non-limiting term and is not intended to refer to any single embodiment of the particular invention but encompasses all possible embodiments as described in the specification and the claims.

The term "isobutanol biosynthetic pathway" refers to an enzyme pathways to produce isobutanol.

The terms "acetolactate synthase" and "acetolactate synthetase" are used intechangeably herein to refer to an enzyme that catalyzes the conversion of pyruvate to acetolactate and $CO_2$. Preferred acetolactate synthases are known by the EC number 2.2.1.6 (*Enzyme Nomenclature* 1992, Academic Press, San Diego). These enzymes are available from a number of sources, including, but not limited to, *Bacillus subtilis* (GenBank Nos: CAB15618 (SEQ ID NO:178), Z99122 (SEQ ID NO:78), NCBI (National Center for Biotechnology Information) amino acid sequence, NCBI nucleotide sequence, respectively), *Klebsiella pneumoniae* (GenBank Nos: AAA25079 (SEQ ID NO:2), M73842 (SEQ ID NO:1)), and *Lactococcus lactis* (GenBank Nos: AAA25161 (SEQ ID NO:180), L16975 (SEQ ID NO:179)).

The terms "acetohydroxy acid isomeroreductase" and "acetohydroxy acid reductoisomerase" are used interchangeably herein to refer to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:4), NC_000913 (SEQ ID NO:3)), *Saccharomyces cerevisiae* (GenBank Nos: NP_013459 (SEQ ID NO:181), NC_001144 (SEQ ID NO:80)), *Methanococcus maripaludis* (GenBank Nos: CAF30210 (SEQ ID NO:183), BX957220 (SEQ ID NO:182)), and *Bacillus. subtilis* (GenBank Nos: CAB14789 (SEQ ID NO:185), Z99118 (SEQ ID NO:184)).

The term "acetohydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:6), NC_000913 (SEQ ID NO:5)), *S. cerevisiae* (GenBank Nos: NP_012550 (SEQ ID NO:186), NC_001142 (SEQ ID NO:83)), *M. maripaludis* (GenBank Nos: CAF29874 (SEQ ID NO:188), BX957219 (SEQ ID NO:187)), and *B. subtilis* (GenBank Nos: CAB14105 (SEQ ID NO:190), Z99115 (SEQ ID NO:189)).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166 (SEQ ID NO:193), AY548760 (SEQ ID NO:192); CAG34226 (SEQ ID NO:8), AJ746364 (SEQ ID NO:191), *Salmonella typhimurium* (GenBank Nos: NP_461346 (SEQ ID NO:195), NC_003197 (SEQ ID NO:194)), and *Clostridium acetobutylicum* (GenBank Nos: NP_149189 (SEQ ID NO:197), NC_001988 (SEQ ID NO:196)).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656 (SEQ ID NO:199), NC_001136 (SEQ ID NO:198); NP_014051 (SEQ ID NO:201) NC_001145 (SEQ ID NO:200)), *E. coli* (GenBank Nos: NP_417484 (SEQ ID NO:10), NC_000913 (SEQ ID NO:9)), and *C. acetobutylicum* (GenBank Nos: NP_349892 (SEQ ID NO:203), NC_003030 (SEQ ID NO:202); NP_349891 (SEQ ID NO:204), NC_003030 (SEQ ID NO:158)).

The term "branched-chain keto acid dehydrogenase" refers to an enzyme that catalyzes the conversion of α-ketoisovalerate to isobutyryl-CoA (isobutyryl-coenzyme A), using $NAD^+$ (nicotinamide adenine dinucleotide) as electron acceptor. Preferred branched-chain keto acid dehydrogenases are known by the EC number 1.2.4.4. These branched-chain keto acid dehydrogenases are comprised of four subunits and sequences from all subunits are available from a vast array of microorganisms, including, but not limited to, *B. subtilis* (GenBank Nos: CAB14336 (SEQ ID NO:206), Z99116 (SEQ ID NO:205); CAB14335 (SEQ ID NO:208), Z99116 (SEQ ID NO:207); CAB14334 (SEQ ID NO:210), Z99116 (SEQ ID NO:209); and CAB14337 (SEQ ID NO:212), Z99116 (SEQ ID NO:211)) and *Pseudomonas putida* (GenBank Nos: AAA65614 (SEQ ID NO:214), M57613 (SEQ ID NO:213); AAA65615 (SEQ ID NO:216), M57613 (SEQ ID NO:215); AAA65617 (SEQ ID NO:218), M57613 (SEQ ID NO:217); and AAA65618 (SEQ ID NO:220), M57613 (SEQ ID NO:219)).

The term "acylating aldehyde dehydrogenase" refers to an enzyme that catalyzes the conversion of isobutyryl-CoA to isobutyraldehyde, using either NADH or NADPH as electron donor. Preferred acylating aldehyde dehydrogenases are known by the EC numbers 1.2.1.10 and 1.2.1.57. These enzymes are available from multiple sources, including, but not limited to, *Clostridium beijerinckii* (GenBank Nos: AAD31841 (SEQ ID NO:222), AF157306 (SEQ ID NO:221)), *C. acetobutylicum* (GenBank Nos: NP_149325 (SEQ ID NO:224), NC_001988 (SEQ ID NO:223); NP_149199 (SEQ ID NO:226), NC_001988 (SEQ ID NO:225)), *P. putida* (GenBank Nos: AAA89106 (SEQ ID NO:228), U13232 (SEQ ID NO:227)), and *Thermus thermophilus* (GenBank Nos: YP_145486 (SEQ ID NO:230), NC_006461 (SEQ ID NO:229)).

The term "transaminase" refers to an enzyme that catalyzes the conversion of α-ketoisovalerate to L-valine, using either alanine or glutamate as amine donor. Preferred transaminases are known by the EC numbers 2.6.1.42 and 2.6.1.66. These enzymes are available from a number of sources. Examples of sources for alanine-dependent enzymes include, but are not limited to, *E. coli* (GenBank Nos: YP_026231 (SEQ ID NO:232), NC_000913 (SEQ ID NO:231)) and *Bacillus licheniformis* (GenBank Nos: YP_093743 (SEQ ID NO:234), NC_006322 (SEQ ID NO:233)). Examples of sources for glutamate-dependent enzymes include, but are not limited to, *E. coli* (GenBank Nos: YP_026247 (SEQ ID NO:236), NC_000913 (SEQ ID NO:235)), *S. cerevisiae* (GenBank Nos: NP_012682 (SEQ ID NO:238), NC_001142 (SEQ ID NO:237)) and *Methanobacterium thermoautotrophicum* (GenBank Nos: NP_276546 (SEQ ID NO:240), NC_000916 (SEQ ID NO:239)).

The term "valine dehydrogenase" refers to an enzyme that catalyzes the conversion of α-ketoisovalerate to L-valine, using NAD(P)H as electron donor and ammonia as amine donor. Preferred valine dehydrogenases are known by the EC numbers 1.4.1.8 and 1.4.1.9 and are available from a number of sources, including, but not limited to, *Streptomyces coelicolor* (GenBank Nos: NP_628270 (SEQ ID NO:242), NC_003888 (SEQ ID NO:241)) and *B. subtilis* (GenBank Nos: CAB14339 (SEQ ID NO:244), Z99116 (SEQ ID NO:243)).

The term "valine decarboxylase" refers to an enzyme that catalyzes the conversion of L-valine to isobutylamine and $CO_2$. Preferred valine decarboxylases are known by the EC number 4.1.1.14. These enzymes are found in Streptomycetes, such as for example, *Streptomyces viridifaciens* (GenBank Nos: AAN10242 (SEQ ID NO:246), AY116644 (SEQ ID NO:245)).

The term "omega transaminase" refers to an enzyme that catalyzes the conversion of isobutylamine to isobutyraldehyde using a suitable amino acid as amine donor. Preferred omega transaminases are known by the EC number 2.6.1.18 and are available from a number of sources, including, but not limited to, *Alcaligenes denitrificans* (AAP92672 (SEQ ID NO:248), AY330220 (SEQ ID NO:247)), *Ralstonia eutropha* (GenBank Nos: YP_294474 (SEQ ID NO:250), NC_007347 (SEQ ID NO:249)), *Shewanella oneidensis* (GenBank Nos: NP_719046 (SEQ ID NO:252), NC_004347 (SEQ ID NO:251)), and *P. putida* (GenBank Nos: AAN66223 (SEQ ID NO:254), AE016776 (SEQ ID NO:253)).

The term "isobutyryl-CoA mutase" refers to an enzyme that catalyzes the conversion of butyryl-CoA to isobutyryl-CoA. This enzyme uses coenzyme $B_{12}$ as cofactor. Preferred isobutyryl-CoA mutases are known by the EC number 5.4.99.13. These enzymes are found in a number of Streptomycetes, including, but not limited to, *Streptomyces cinnamonensis* (GenBank Nos: AAC08713 (SEQ ID NO:256), U67612 (SEQ ID NO:255); CAB59633 (SEQ ID NO:258), AJ246005 (SEQ ID NO:257)), *S. coelicolor* (GenBank Nos: CAB70645 (SEQ ID NO:260), AL939123 (SEQ ID NO:259); CAB92663 (SEQ ID NO:262), AL939121 (SEQ ID NO:261)), and *Streptomyces avermitilis* (GenBank Nos: NP_824008 (SEQ ID NO:264), NC_003155 (SEQ ID NO:263); NP_824637 (SEQ ID NO:266), NC_003155 (SEQ ID NO:265)).

The term "a facultative anaerobe" refers to a microorganism that can grow in both aerobic and anaerobic environments.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" or "heterologous gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein the term "codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

Standard recombinant DNA and molecular cloning techniques used herein are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987).

Isobutanol Biosynthetic Pathways

Carbohydrate utilizing microorganisms employ the Embden-Meyerhof-Parnas (EMP) pathway, the Entner-Doudoroff pathway and the pentose phosphate cycle as the central, metabolic routes to provide energy and cellular precursors for growth and maintenance. These pathways have in common the intermediate glyceraldehyde-3-phosphate and, ultimately, pyruvate is formed directly or in combination with the EMP pathway. Subsequently, pyruvate is transformed to acetyl-coenzyme A (acetyl-CoA) via a variety of means. Acetyl-CoA serves as a key intermediate, for example, in generating fatty acids, amino acids and secondary metabolites. The combined reactions of sugar conversion to pyruvate produce energy (e.g. adenosine-5'-triphosphate, ATP) and reducing equivalents (e.g. reduced nicotinamide adenine dinucleotide, NADH, and reduced nicotinamide adenine dinucleotide phosphate, NADPH). NADH and NADPH must be recycled to their oxidized forms ($NAD^+$ and $NADP^+$, respectively). In the presence of inorganic electron acceptors (e.g. $O_2$, $NO_3^-$ and $SO_4^{2-}$), the reducing equivalents may be used to augment the energy pool; alternatively, a reduced carbon by-product may be formed.

The invention enables the production of isobutanol from carbohydrate sources with recombinant microorganisms by providing four complete reaction pathways, as shown in FIG. 1. Three of the pathways comprise conversion of pyruvate to isobutanol via a series of enzymatic steps. The preferred isobutanol pathway (FIG. 1, steps a to e), comprises the following substrate to product conversions:
 a) pyruvate to acetolactate, as catalyzed for example by acetolactate synthase,
 b) acetolactate to 2,3-dihydroxyisovalerate, as catalyzed for example by acetohydroxy acid isomeroreductase,
 c) 2,3-dihydroxyisovalerate to α-ketoisovalerate, as catalyzed for example by acetohydroxy acid dehydratase,
 d) α-ketoisovalerate to isobutyraldehyde, as catalyzed for example by a branched-chain keto acid decarboxylase, and
 e) isobutyraldehyde to isobutanol, as catalyzed for example by, a branched-chain alcohol dehydrogenase.

This pathway combines enzymes known to be involved in well-characterized pathways for valine biosynthesis (pyruvate to α-ketoisovalerate) and valine catabolism (α-ketoisovalerate to isobutanol). Since many valine biosynthetic enzymes also catalyze analogous reactions in the isoleucine biosynthetic pathway, substrate specificity is a major consideration in selecting the gene sources. For this reason, the primary genes of interest for the acetolactate synthase enzyme are those from *Bacillus* (alsS) and *Klebsiella* (budB). These particular acetolactate synthases are known to participate in butanediol fermentation in these organisms and show increased affinity for pyruvate over ketobutyrate (Gollop et al., *J. Bacteriol.* 172(6):3444-3449 (1990); Holtzclaw et al., *J. Bacteriol.* 121(3):917-922 (1975)). The second and third pathway steps are catalyzed by acetohydroxy acid reductoisomerase and dehydratase, respectively. These enzymes have been characterized from a number of sources, such as for example, *E. coli* (Chunduru et al., *Biochemistry* 28(2):486-493 (1989); Flint et al., *J. Biol. Chem.* 268(29):14732-14742 (1993)). The final two steps of the preferred isobutanol pathway are known to occur in yeast, which can use valine as a nitrogen source and, in the process, secrete isobutanol. α-Ketoisovalerate can be converted to isobutyraldehyde by a number of keto acid decarboxylase enzymes, such as for example pyruvate decarboxylase. To prevent misdirection of pyruvate away from isobutanol production, a decarboxylase with decreased affinity for pyruvate is desired. So far, there are two such enzymes known in the art (Smit et al., *Appl. Environ. Microbiol.* 71(1):303-311 (2005); de la Plaza et al., *FEMS Microbiol. Lett.* 238(2):367-374 (2004)). Both enzymes are from strains of *Lactococcus lactis* and have a 50-200-fold preference for ketoisovalerate over pyruvate. Finally, a number of aldehyde reductases have been identified in yeast, many with overlapping substrate specificity. Those known to prefer branched-chain substrates over acetaldehyde include, but are not limited to, alcohol dehydrogenase VI (ADH6) and Ypr1p (Larroy et al., *Biochem. J.* 361(Pt 1):163-172 (2002); Ford et al., *Yeast* 19(12):1087-1096 (2002)), both of which use NADPH as electron donor. An NADPH-dependent reductase, YqhD, active with branched-chain substrates has also been recently identified in *E. coli* (Sulzenbacher et al., *J. Mol. Biol.* 342(2):489-502 (2004)).

Another pathway for converting pyruvate to isobutanol comprises the following substrate to product conversions (FIG. 1, steps a, b, c, f, g, e):
 a) pyruvate to acetolactate, as catalyzed for example by acetolactate synthase,
 b) acetolactate to 2,3-dihydroxyisovalerate, as catalyzed for example by acetohydroxy acid isomeroreductase,
 c) 2,3-dihydroxyisovalerate to α-ketoisovalerate, as catalyzed for example by acetohydroxy acid dehydratase,
 f) α-ketoisovalerate to isobutyryl-CoA, as catalyzed for example by a branched-chain keto acid dehydrogenase,
 g) isobutyryl-CoA to isobutyraldehyde, as catalyzed for example by an acylating aldehyde dehydrogenase, and
 e) isobutyraldehyde to isobutanol, as catalyzed for example by, a branched-chain alcohol dehydrogenase.

The first three steps in this pathway (a, b, c) are the same as those described above. The α-ketoisovalerate is converted to isobutyryl-CoA by the action of a branched-chain keto acid dehydrogenase. While yeast can only use valine as a nitrogen source, many other organisms (both eukaryotes and prokaryotes) can use valine as the carbon source as well. These organisms have branched-chain keto acid dehydrogenase (Sokatch et al. *J. Bacteriol.* 148(2):647-652 (1981)), which generates isobutyryl-CoA. Isobutyryl-CoA may be converted to isobutyraldehyde by an acylating aldehyde dehydrogenase. Dehydrogenases active with the branched-chain substrate have been described, but not cloned, in *Leuconostoc* and *Propionibacterium* (Kazahaya et al., *J. Gen. Appl. Microbiol.* 18:43-55 (1972); Hosoi et al., *J. Ferment. Technol.* 57:418-427 (1979)). However, it is also possible that acylating aldehyde dehydrogenases known to function with straight-chain acyl-CoAs (i.e. butyryl-CoA), may also work with isobutyryl-CoA. The isobutyraldehyde is then converted to isobutanol by a branched-chain alcohol dehydrogenase, as described above for the first pathway.

Another pathway for converting pyruvate to isobutanol comprises the following substrate to product conversions (FIG. 1, steps a, b, c, h, i, j, e):
- a) pyruvate to acetolactate, as catalyzed for example by acetolactate synthase,
- b) acetolactate to 2,3-dihydroxyisovalerate, as catalyzed for example by acetohydroxy acid isomeroreductase,
- c) 2,3-dihydroxyisovalerate to α-ketoisovalerate, as catalyzed for example by acetohydroxy acid dehydratase,
- h) α-ketoisovalerate to valine, as catalyzed for example by valine dehydrogenase or transaminase,
- i) valine to isobutylamine, as catalyzed for example by valine decarboxylase,
- j) isobutylamine to isobutyraldehyde, as catalyzed for example by omega transaminase, and
- e) isobutyraldehyde to isobutanol, as catalyzed for example by, a branched-chain alcohol dehydrogenase.

The first three steps in this pathway (a, b, c) are the same as those described above. This pathway requires the addition of a valine dehydrogenase or a suitable transaminase. Valine (and or leucine) dehydrogenase catalyzes reductive amination and uses ammonia; $K_m$ values for ammonia are in the millimolar range (Priestly et al., *Biochem J.* 261(3):853-861 (1989); Vancura et al., *J. Gen. Microbiol.* 134(12):3213-3219 (1988) Zink et al., *Arch. Biochem. Biophys.* 99:72-77 (1962); Sekimoto et al. *J. Biochem* (Japan) 116(1):176-182 (1994)). Transaminases typically use either glutamate or alanine as amino donors and have been characterized from a number of organisms (Lee-Peng et al, *J. Bacteriol.* 139(2):339-345 (1979); Berg et al., *J. Bacteriol.* 155(3):1009-1014 (1983)). An alanine-specific enzyme may be desirable, since the generation of pyruvate from this step could be coupled to the consumption of pyruvate later in the pathway when the amine group is removed (see below). The next step is decarboxylation of valine, a reaction that occurs in valanimycin biosynthesis in *Streptomyces* (Garg et al., *Mol. Microbiol.* 46(2): 505-517 (2002)). The resulting isobutylamine may be converted to isobutyraldehyde in a pyridoxal 5'-phosphate-dependent reaction by, for example, an enzyme of the omega-aminotransferase family. Such an enzyme from *Vibrio fluvialis* has demonstrated activity with isobutylamine (Shin et al., *Biotechnol. Bioeng.* 65(2):206-211 (1999)). Another omega-aminotransferase from *Alcaligenes denitrificans* has been cloned and has some activity with butylamine (Yun et al., *Appl. Environ. Microbiol.* 70(4):2529-2534 (2004)). In this direction, these enzymes use pyruvate as the amino acceptor, yielding alanine. As mentioned above, adverse affects on the pyruvate pool may be offset by using a pyruvate-producing transaminase earlier in the pathway. The isobutyraldehyde is then converted to isobutanol by a branched-chain alcohol dehydrogenase, as described above for the first pathway.

The fourth isobutanol biosynthetic pathway comprises the substrate to product conversions shown as steps k, g, e in FIG. 1. A number of organisms are known to produce butyrate and/or butanol via a butyryl-CoA intermediate (Dürre et al., FEMS *Microbiol. Rev.* 17(3):251-262 (1995); Abbad-Andaloussi et al., *Microbiology* 142(5):1149-1158 (1996)). Isobutanol production may be engineered in these organisms by addition of a mutase able to convert butyryl-CoA to isobutyryl-CoA (FIG. 1, step k). Genes for both subunits of isobutyryl-CoA mutase, a coenzyme $B_{12}$-dependent enzyme, have been cloned from a Streptomycete (Ratnatilleke et al., *J. Biol. Chem.* 274(44):31679-31685 (1999)). The isobutyryl-CoA is converted to isobutyraldehyde (step g in FIG. 1), which is converted to isobutanol (step e in FIG. 1).

Thus, in providing multiple recombinant pathways from pyruvate to isobutanol, there exist a number of choices to fulfill the individual conversion steps, and the person of skill in the art will be able to utilize publicly available sequences to construct the relevant pathways. A listing of a representative number of genes known in the art and useful in the construction of isobutanol biosynthetic pathways are listed below in Table 2.

TABLE 2

Sources of Isobutanol Biosynthetic Pathway Genes

| Gene | GenBank Citation |
|---|---|
| acetolactate synthase | Z99122, *Bacillus subtilis* complete genome (section 19 of 21): from 3608981 to 3809670<br>gi\|32468830\|emb\|Z99122.2\|BSUB0019[32468830]<br>M73842, *Klebsiella pneumoniae* acetolactate synthase (iluk) gene, complete cds<br>gi\|149210\|gb\|M73842.1\|KPNILUK[149210]<br>L16975, *Lactococcus lactis* alpha-acetolactate synthase (als) gene, complete cds<br>gi\|473900\|gb\|L16975.1\|LACALS[473900] |
| acetohydroxy acid isomeroreductase | NC_000913, *Escherichia coli* 12, complete genome<br>gi\|49175990\|ref\|NC_000913.2\|[49175990]<br>NC_001144, *Saccharomyces cerevisiae* chromosome XII, complete chromosome sequence<br>gi\|42742286\|ref\|NC_001144.3\|[42742286]<br>BX957220, *Methanococcus maripaludis* S2 complete genome; segment 2/5<br>gi\|44920669\|emb\|BX957220.1\|[44920669]<br>Z99118, *Bacillus subtilis* complete genome (section 15 of 21): from 2812801 to 3013507<br>gi\|32468802\|emb\|Z99118.2\|BSUB0015[32468802] |
| acetohydroxy acid dehydratase | NC_000913, *Escherichia coli* K12, complete genome<br>gi\|49175990\|ref\|NC_000913.2\|[49175990]<br>NC_001142, *Saccharomyces cerevisiae* chromosome X, complete chromosome sequence<br>gi\|42742252\|ref\|NC_001142.5\|[42742252]<br>BX957219, *Methanococcus maripaludis* S2 complete genome; segment 1/5<br>gi\|45047123\|emb\|BX957219.1\|[45047123] |

TABLE 2-continued

Sources of Isobutanol Biosynthetic Pathway Genes

| Gene | GenBank Citation |
|---|---|
| branched-chain α-keto acid decarboxylase | Z99115, *Bacillus subtilis* complete genome (section 12 of 21): from 2207806 to 2409180<br>gi\|32468778\|emb\|Z99115.2\|BSUB0012[32468778]<br>AY548760, *Lactococcus lactis* branched-chain alpha-ketoacid decarboxylase (kdcA) gene, complete cds<br>gi\|44921616\|gb\|AY548760.1\|[44921616]<br>AJ746364, *Lactococcus lactis* subsp. *lactis* kivd gene for alpha-ketoisovalerate decarboxylase, strain IFPL730<br>gi\|51870501\|emb\|AJ746364.1\|[51870501]<br>NC_003197, *Salmonella typhimurium* LT2, complete genome<br>gi\|16763390\|ref\|NC_003197.1\|[16763390]<br>NC_001988, *Clostridium acetobutylicum* ATCC 824 plasmid pSOL1, complete sequence<br>gi\|15004705\|ref\|NC_001988.2\|[15004705] |
| branched-chain alcohol dehydrogenase | NC_001136, *Saccharomyces cerevisiae* chromosome IV, complete chromosome sequence<br>gi\|50593138\|ref\|NC_001136.6\|[50593138]<br>NC_001145, *Saccharomyces cerevisiae* chromosome XIII, complete chromosome sequence<br>gi\|44829554\|ref\|NC_001145.2\|[44829554]<br>NC_000913, *Escherichia coli* K12, complete genome<br>gi\|49175990\|ref\|NC_000913.2\|[49175990]<br>NC_003030, *Clostridium acetobutylicum* ATCC 824, complete genome<br>gi\|15893298\|ref\|NC_003030.1\|[15893298] |
| branched-chain keto acid dehydrogenase | Z99116, *Bacillus subtilis* complete genome (section 13 of 21): from 2409151 to 2613687<br>gi\|32468787\|emb\|Z99116.2\|BSUB0013[32468787]<br>M57613, *Pseudomonas putida* branched-chain keto acid dehydrogenase operon (bkdA1, bkdA1 and bkdA2), transacylase E2 (bkdB), bkdR and lipoamide dehydrogenase (lpdV) genes, complete cds<br>gi\|790512\|gb\|M57613.1\|PSEBKDPPG2[790512] |
| acylating aldehyde dehydrogenase | AF157306, *Clostridium beijerinckii* strain NRRL B593 hypothetical protein, coenzyme A acylating aldehyde dehydrogenase (ald), acetoacetate:butyrate/acetate coenzyme A transferase (ctfA), acetoacetate:butyrate/acetate coenzyme A transferase (ctfB), and acetoacetate decarboxylase (adc) genes, complete cds<br>gi\|47422980\|gb\|AF157306.2\|[47422980]<br>NC_001988, *Clostridium acetobutylicum* ATCC 824 plasmid pSOL1, complete sequence<br>gi\|15004705\|ref\|NC_001988.2\|[15004705]<br>U13232, *Pseudomonas putida* NCIB9816 acetaldehyde dehydrogenase (nahO) and 4-hydroxy-2-oxovalerate aldolase (nahM) genes, complete cds, and 4-oxalocrotonate decarboxylase (nahK) and 2-oxopent-4-enoate hydratase (nahL) genes, partial cds<br>gi\|595671\|gb\|U13232.1\|PPU13232[595671] |
| transaminase | NC_000913, *Escherichia coli* K12, complete genome<br>gi\|49175990\|ref\|NC_000913.2\|[49175990]<br>NC_006322, *Bacillus licheniformis* TCC 14580, complete genome<br>gi\|52783855\|ref\|NC_006322.1\|[52783855]<br>NC_001142, *Saccharomyces cerevisiae* chromosome X, complete chromosome sequence<br>gi\|42742252\|ref\|NC_001142.5\|[42742252]<br>NC_000916, *Methanothermobacter thermautotrophicus* str. Delta H, complete genome<br>gi\|15678031\|ref\|NC_000916.1\|[15678031] |
| valine dehydrogenase | NC_003888, *Streptomyces coelicolor* A3(2), complete genome<br>gi\|32141095\|ref\|NC_003888.3\|[32141095]<br>Z99116, *Bacillus subtilis* complete genome (section 13 of 21): from 2409151 to 2613687<br>gi\|32468787\|emb\|Z99116.2\|BSUB0013[32468787] |
| valine decarboxylase | AY116644, *Streptomyces viridifaciens* amino acid aminotransferase gene, partial cds; ketol-acid reductoisomerase, acetolactate synthetase small subunit, acetolactate synthetase large subunit, complete cds; azoxy antibiotic valanimycin gene cluster, complete sequence; and putative transferase, and putative secreted protein genes, complete cds<br>gi\|27777548\|gb\|AY116644.1\|[27777548] |

TABLE 2-continued

Sources of Isobutanol Biosynthetic Pathway Genes

| Gene | GenBank Citation |
|---|---|
| omega transaminase | AY330220, *Achromobacter denitrificans* omega-amino acid:pyruvate transaminase (aptA) gene, complete cds gi\|33086797\|gb\|AY330220.1\|[33086797] NC_007347, *Ralstonia eutropha* JMP134 chromosome 1, complete sequence gi\|73539706\|ref\|NC_007347.1\|[73539706] NC_004347, *Shewanella oneidensis* MR-1, complete genome gi\|24371600\|ref\|NC_004347.1\|[24371600] NZ_AAAG02000002, *Rhodospirillum rubrum* Rrub02_2, whole genome shotgun sequence gi\|48764549\|ref\|NZ_AAAG02000002.1\|[48764549] AE016776, *Pseudomonas putida* KT2440 section 3 of 21 of the complete genome gi\|26557019\|gb\|AE016776.1\|[26557019] |
| isobutyryl-CoA mutase | U67612, *Streptomyces cinnamonensis* coenzyme B12-dependent isobutyrylCoA mutase (icm) gene, complete cds gi\|3002491\|gb\|U67612.1\|SCU67612[3002491] AJ246005, *Streptomyces cinnamonensis* icmB gene for isobutyryl-CoA mutase, small subunit gi\|6137076\|emb\|AJ246005.1\|SCI246005[6137076] AL939123, *Streptomyces coelicolor* A3(2) complete genome; segment 20/29 gi\|24430032\|emb\|AL939123.1\|SCO939123[24430032] AL9939121, *Streptomyces coelicolor* A3(2) complete genome; segment 18/29 gi\|24429533\|emb\|AL939121.1\|SCO939121[24429533] NC_003155, *Streptomyces avermitilis* MA-4680, complete genome gi\|57833846\|ref\|NC_003155.3\|[57833846] |

Microbial Hosts for Isobutanol Production

Microbial hosts for isobutanol production may be selected from bacteria, cyanobacteria, filamentous fungi and yeasts. The microbial host used for isobutanol production is preferably tolerant to isobutanol so that the yield is not limited by butanol toxicity. Microbes that are metabolically active at high titer levels of isobutanol are not well known in the art. Although butanol-tolerant mutants have been isolated from solventogenic *Clostridia*, little information is available concerning the butanol tolerance of other potentially useful bacterial strains. Most of the studies on the comparison of alcohol tolerance in bacteria suggest that butanol is more toxic than ethanol (de Cavalho et al., *Microsc. Res. Tech.* 64:215-22 (2004) and Kabelitz et al., *FEMS Microbiol. Lett.* 220:223-227 (2003)). Tomas et al. (*J. Bacteriol.* 186:2006-2018 (2004)) report that the yield of 1-butanol during fermentation in *Clostridium acetobutylicum* may be limited by 1-butanol toxicity. The primary effect of 1-butanol on *Clostridium acetobutylicum* is disruption of membrane functions (Hermann et al., *Appl. Environ. Microbiol.* 50:1238-1243 (1985)).

The microbial hosts selected for the production of isobutanol are preferably tolerant to isobutanol and should be able to convert carbohydrates to isobutanol. The criteria for selection of suitable microbial hosts include the following: intrinsic tolerance to isobutanol, high rate of glucose utilization, availability of genetic tools for gene manipulation, and the ability to generate stable chromosomal alterations.

Suitable host strains with a tolerance for isobutanol may be identified by screening based on the intrinsic tolerance of the strain. The intrinsic tolerance of microbes to isobutanol may be measured by determining the concentration of isobutanol that is responsible for 50% inhibition of the growth rate (IC50) when grown in a minimal medium. The IC50 values may be determined using methods known in the art. For example, the microbes of interest may be grown in the presence of various amounts of isobutanol and the growth rate monitored by measuring the optical density at 600 nanometers. The doubling time may be calculated from the logarithmic part of the growth curve and used as a measure of the growth rate. The concentration of isobutanol that produces 50% inhibition of growth may be determined from a graph of the percent inhibition of growth versus the isobutanol concentration. Preferably, the host strain should have an IC50 for isobutanol of greater than about 0.5%.

The microbial host for isobutanol production should also utilize glucose at a high rate. Most microbes are capable of utilizing carbohydrates. However, certain environmental microbes cannot utilize carbohydrates to high efficiency, and therefore would not be suitable hosts.

The ability to genetically modify the host is essential for the production of any recombinant microorganism. The mode of gene transfer technology may be by electroporation, conjugation, transduction or natural transformation. A broad range of host conjugative plasmids and drug resistance markers are available. The cloning vectors are tailored to the host organisms based on the nature of antibiotic resistance markers that can function in that host.

The microbial host also has to be manipulated in order to inactivate competing pathways for carbon flow by deleting various genes. This requires the availability of either transposons to direct inactivation or chromosomal integration vectors. Additionally, the production host should be amenable to chemical mutagenesis so that mutations to improve intrinsic isobutanol tolerance may be obtained.

Based on the criteria described above, suitable microbial hosts for the production of isobutanol include, but are not limited to, members of the genera *Clostridium*, *Zymomonas*, *Escherichia*, *Salmonella*, *Rhodococcus*, *Pseudomonas*,

*Bacillus, Lactobacillus, Enterococcus, Alcaligenes, Klebsiella, Paenibacillus, Arthrobacter, Corynebacterium, Brevibacterium, Pichia, Candida, Hansenula* and *Saccharomyces*. Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis* and *Saccharomyces cerevisiae*.

Construction of Production Host

Recombinant organisms containing the necessary genes that will encode the enzymatic pathway for the conversion of a fermentable carbon substrate to isobutanol may be constructed using techniques well known in the art. In the present invention, genes encoding the enzymes of one of the isobutanol biosynthetic pathways of the invention, for example, acetolactate synthase, acetohydroxy acid isomeroreductase, acetohydroxy acid dehydratase, branched-chain α-keto acid decarboxylase, and branched-chain alcohol dehydrogenase, may be isolated from various sources, as described above.

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer-directed amplification methods such as polymerase chain reaction (U.S. Pat. No. 4,683,202) to obtain amounts of DNA suitable for transformation using appropriate vectors. Tools for codon optimization for expression in a heterologous host are readily available. Some tools for codon optimization are available based on the GC content of the host organism. The GC content of some exemplary microbial hosts is given Table 3.

TABLE 3

GC Content of Microbial Hosts

| Strain | % GC |
| --- | --- |
| B. licheniformis | 46 |
| B. subtilis | 42 |
| C. acetobutylicum | 37 |
| E. coli | 50 |
| P. putida | 61 |
| A. eutrophus | 61 |
| Paenibacillus macerans | 51 |
| Rhodococcus erythropolis | 62 |
| Brevibacillus | 50 |
| Paenibacillus polymyxa | 50 |

Once the relevant pathway genes are identified and isolated they may be transformed into suitable expression hosts by means well known in the art. Vectors or cassettes useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, CYC1, HIS3, GAL1, GAL10, ADH1, PGK, PHO5, GAPDH, ADC1, TRP1, URA3, LEU2, ENO, TPI, CUP1, FBA, GPD, and GPM (useful for expression in *Saccharomyces*); AOX1 (useful for expression in *Pichia*); and lac, ara, tet, trp, $IP_L$, $IP_R$, T7, tac, and trc (useful for expression in *Escherichia coli, Alcaligenes*, and *Pseudomonas*); the amy, apr, npr promoters and various phage promoters useful for expression in *Bacillus subtilis, Bacillus licheniformis*, and *Paenibacillus macerans*; nisA (useful for expression Gram-positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)).

Termination control regions may also be derived from various genes native to the preferred hosts. Optionally, a termination site may be unnecessary, however, it is most preferred if included.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., *Plasmid* 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to effect gene replacement in a range of Gram-positive bacteria (Maguin et al., *J. Bacteriol.* 174(17):5633-5638 (1992)). Additionally, in vitro transposomes are available to create random mutations in a variety of genomes from commercial sources such as EPICENTRE®.

The expression of an isobutanol biosynthetic pathway in various preferred microbial hosts is described in more detail below.

Expression of an Isobutanol Biosynthetic Pathway in *E. coli*

Vectors or cassettes useful for the transformation of *E. coli* are common and commercially available from the companies listed above. For example, the genes of an isobutanol biosynthetic pathway may be isolated from various sources, cloned into a modified pUC19 vector and transformed into *E. coli* NM522, as described in Examples 6 and 7.

Expression of an Isobutanol Biosynthetic Pathway in *Rhodococcus erythropolis*

A series of *E. coli-Rhodococcus* shuttle vectors are available for expression in *R. erythropolis*, including, but not limited to, pRhBR17 and pDA71 (Kostichka et al., *Appl. Microbiol. Biotechnol.* 62:61-68(2003)). Additionally, a series of promoters are available for heterologous gene expression in *R. erythropolis* (see for example Nakashima et al., *Appl. Environ. Microbiol.* 70:5557-5568 (2004), and Tao et al., *Appl. Microbiol. Biotechnol.* 2005, DOI 10.1007/s00253-005-0064). Targeted gene disruption of chromosomal genes in *R. erythropolis* may be created using the method described by Tao et al., supra, and Brans et al. (*Appl. Environ. Microbiol.* 66: 2029-2036 (2000)).

The heterologous genes required for the production of isobutanol, as described above, may be cloned initially in pDA71 or pRhBR71 and transformed into *E. coli*. The vectors may then be transformed into *R. erythropolis* by electroporation, as described by Kostichka et al., supra. The recombinants may be grown in synthetic medium containing glucose and the production of isobutanol can be followed using methods known in the art.

Expression of an Isobutanol Biosynthetic Pathway in *B. subtilis*

Methods for gene expression and creation of mutations in *B. subtilis* are also well known in the art. For example, the genes of an isobutanol biosynthetic pathway may be isolated from various sources, cloned into a modified pUC19 vector and transformed into *Bacillus subtilis* BE1010, as described in Example 8. Additionally, the five genes of an isobutanol biosynthetic pathway can be split into two operons for expression, as described in Example 20. The three genes of the pathway (bubB, ilvD, and kivD) were integrated into the chromosome of *Bacillus subtilis* BE1010 (Payne and Jackson, *J. Bacteriol.* 173:2278-2282 (1991)). The remaining two genes (ilvC and bdhB) were cloned into an expression vector and transformed into the *Bacillus* strain carrying the integrated isobutanol genes Expression of an Isobutanol Biosynthetic Pathway in *B. licheniformis*

Most of the plasmids and shuttle vectors that replicate in *B. subtilis* may be used to transform *B. licheniformis* by either protoplast transformation or electroporation. The genes required for the production of isobutanol may be cloned in plasmids pBE20 or pBE60 derivatives (Nagarajan et al., *Gene* 114:121-126 (1992)). Methods to transform *B. licheniformis* are known in the art (for example see Fleming et al. *Appl. Environ. Microbiol.*, 61(11):3775-3780 (1995)). The plasmids constructed for expression in *B. subtilis* may be transformed into *B. licheniformis* to produce a recombinant microbial host that produces isobutanol.

Expression of an Isobutanol Biosynthetic Pathway in *Paenibacillus macerans*

Plasmids may be constructed as described above for expression in *B. subtilis* and used to transform *Paenibacillus macerans* by protoplast transformation to produce a recombinant microbial host that produces isobutanol.

Expression of the Isobutanol Biosynthetic Pathway in *Alcaligenes (Ralstonia) Eutrophus*

Methods for gene expression and creation of mutations in *Alcaligenes eutrophus* are known in the art (see for example Taghavi et al., *Appl. Environ. Microbiol.*, 60(10):3585-3591 (1994)). The genes for an isobutanol biosynthetic pathway may be cloned in any of the broad host range vectors described above, and electroporated to generate recombinants that produce isobutanol. The poly(hydroxybutyrate) pathway in *Alcaligenes* has been described in detail, a variety of genetic techniques to modify the *Alcaligenes eutrophus* genome is known, and those tools can be applied for engineering an isobutanol biosynthetic pathway.

Expression of an Isobutanol Biosynthetic Pathway in *Pseudomonas putida*

Methods for gene expression in *Pseudomonas putida* are known in the art (see for example Ben-Bassat et al., U.S. Pat. No. 6,586,229, which is incorporated herein by reference). The butanol pathway genes may be inserted into pPCU18 and this ligated DNA may be electroporated into electrocompetent *Pseudomonas putida* DOT-T1 C5aAR1 cells to generate recombinants that produce isobutanol.

Expression of an Isobutanol Biosynthetic Pathway in *Saccharomyces cerevisiae*

Methods for gene expression in *Saccharomyces cerevisiae* are known in the art (see for example *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Expression of genes in yeast typically requires a promoter, followed by the gene of interest, and a transcriptional terminator. A number of yeast promoters can be used in constructing expression cassettes for genes encoding an isobutanol biosynthetic pathway, including, but not limited to constitutive promoters FBA, GPD, ADH1, and GPM, and the inducible promoters GAL1, GAL10, and CUP1. Suitable transcriptional terminators include, but are not limited to FBAt, GPDt, GPMt, ERG10t, GAL1t, CYC1, and ADH1. For example, suitable promoters, transcriptional terminators, and the genes of an isobutanol biosynthetic pathway may be cloned into *E. coli*-yeast shuttle vectors as described in Example 17.

Expression of an Isobutanol Biosynthetic Pathway in *Lactobacillus plantarum*

The *Lactobacillus* genus belongs to the Lactobacillales family and many plasmids and vectors used in the transformation of *Bacillus subtilis* and *Streptococcus* may be used for *lactobacillus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (e.g., van Kranenburg R, Golic N, Bongers R, Leer R J, de Vos W M, Siezen R J, Kleerebezem M. *Appl. Environ. Microbiol.* 2005 March; 71(3): 1223-1230). For example, expression of an isobutanol biosynthetic pathway in *Lactobacillus plantarum* is described in Example 21.

Expression of an Isobutanol Biosynthetic Pathway in *Enterococcus faecium, Enterococcus Gallinarium*, and *Enterococcus faecalis*

The *Enterococcus* genus belongs to the Lactobacillales family and many plasmids and vectors used in the transformation of *Lactobacillus, Bacillus subtilis*, and *Streptococcus* may be used for *Enterococcus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Expression vectors for *E. faecalis* using the nisA gene from *Lactococcus* may also be used (Eichenbaum et al., *Appl. Environ. Microbiol.* 64:2763-2769 (1998). Additionally, vectors for gene replacement in the *E. faecium* chromosome may be used (Nallaapareddy et al., *Appl. Environ. Microbiol.*

72:334-345 (2006)). For example, expression of an isobutanol biosynthetic pathway in *Enterococcus faecalis* is described in Example 22.

Fermentation Media

Fermentation media in the present invention must contain suitable carbon substrates. Suitable substrates may include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for isobutanol production.

Culture Conditions

Typically cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

The amount of isobutanol produced in the fermentation medium can be determined using a number of methods known in the art, for example, high performance liquid chromatography (HPLC) or gas chromatography (GC).

Industrial Batch and Continuous Fermentations

The present process employs a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for isobutanol production.

Methods for Isobutanol Isolation from the Fermentation Medium

The bioproduced isobutanol may be isolated from the fermentation medium using methods known in the art. For example, solids may be removed from the fermentation medium by centrifugation, filtration, decantation, or the like. Then, the isobutanol may be isolated from the fermentation medium, which has been treated to remove solids as described above, using methods such as distillation, liquid-liquid extraction, or membrane-based separation. Because isobutanol forms a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify isobutanol include, but are not limited to, decantation, liquid-liquid extraction, adsorption, and membrane-based techniques. Additionally, isobutanol may be isolated using azeotropic distillation using an entrainer (see for example Doherty and Malone, *Conceptual Design of Distillation Systems*, McGraw Hill, New York, 2001).

The isobutanol-water mixture forms a heterogeneous azeotrope so that distillation may be used in combination with decantation to isolate and purify the isobutanol. In this method, the isobutanol containing fermentation broth is distilled to near the azeotropic composition. Then, the azeotropic mixture is condensed, and the isobutanol is separated from the fermentation medium by decantation. The decanted aqueous phase may be returned to the first distillation column as reflux. The isobutanol-rich decanted organic phase may be further purified by distillation in a second distillation column.

The isobutanol may also be isolated from the fermentation medium using liquid-liquid extraction in combination with distillation. In this method, the isobutanol is extracted from the fermentation broth using liquid-liquid extraction with a suitable solvent. The isobutanol-containing organic phase is then distilled to separate the isobutanol from the solvent.

Distillation in combination with adsorption may also be used to isolate isobutanol from the fermentation medium. In this method, the fermentation broth containing the isobutanol is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the isobutanol from the fermentation medium. In this method, the fermentation broth containing the isobutanol is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., Current *Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified.

Microbial strains were obtained from The American Type Culture Collection (ATCC), Manassas, Va., unless otherwise noted.

The oligonucleotide primers to use in the following Examples are given in Table 4. All the oligonucleotide primers are synthesized by Sigma-Genosys (Woodlands, Tex.).

TABLE 4

Oligonucleotide Cloning, Screening, and Sequencing Primers

| Name | Sequence | Description | SEQ ID NO: |
|------|----------|-------------|------------|
| N80  | CACCATGGACAAACAGTATCCGGTACGCC | budB forward | 11 |
| N81  | CGAAGGGCGATAGCTTTACCAATCC | budB reverse | 12 |
| N100 | CACCATGGCTAACTACTTCAATACACTGA | ilvC forward | 13 |
| N101 | CCAGGAGAAGGCCTTGAGTGTTTCTCC | ilvC reverse | 14 |

TABLE 4-continued

Oligonucleotide Cloning, Screening, and Sequencing Primers

| Name | Sequence | Description | SEQ ID NO: |
|---|---|---|---|
| N102 | CACCATGCCTAAGTACCGTTCCGCCACCA | ilvD forward | 15 |
| N103 | CGCAGCACTGCTCTTAAATATTCGGC | ilvD reverse | 16 |
| N104 | CACCATGAACAACTTTAATCTGCACACCC | yqhD forward | 17 |
| N105 | GCTTAGCGGGCGGCTTCGTATATACGGC | yqhD reverse | 18 |
| N110 | GCATGCCTTAAGAAAGGAGGGGGGTCACATGGACAAACAGTATCC | budB forward | 19 |
| N111 | ATGCATTTAATTAATTACAGAATCTGACTCAGATGCAGC | budB reverse | 20 |
| N112 | GTCGACGCTAGCAAAGGAGGGAATCACCATGGCTAACTACTTCAA | ilvC forward | 21 |
| N113 | TCTAGATTAACCCGCAACAGCAATACGTTTC | ilvC reverse | 22 |
| N114 | TCTAGAAAAGGAGGAATAAAGTATGCCTAAGTACCGTTC | ilvD forward | 23 |
| N115 | GGATCCTTATTAACCCCCCAGTTTCGATTTA | ilvD reverse | 24 |
| N116 | GGATCCAAAGGAGGCTAGACATATGTATACTGTGGGGA | kivD forward | 25 |
| N117 | GAGCTCTTAGCTTTTATTTTGCTCCGCAAAC | kivD reverse | 26 |
| N118 | GAGCTCAAAGGAGGAGCAAGTAATGAACAACTTTAATCT | yqhD forward | 27 |
| N119 | GAATTCACTAGTCCTAGGTTAGCGGGCGGCTTCGTATATACGG | yqhD reverse | 28 |
| BenNF | CAACATTAGCGATTTTCTTTTCTCT | Npr forward | 29 |
| BenASR | CATGAAGCTTACTAGTGGGCTTAAGTTTTGAAAATAATGAAAACT | Npr reverse | 30 |
| N110.2 | GAGCTCACTAGTCAATTGTAAGTAAGTAAAAGGAGGTGGGTCACATGGACAAACAGTATCC | budB forward | 31 |
| N111.2 | GGATCCGATCGACTTAAGCCTCAGCTTACAGAATCTGACTCAGATGCAGC | budB reverse | 32 |
| N112.2 | GAGCTCCTTAAGAAGGAGGTAATCACCATGGCTAACTACTTCAA | ilvC forward | 33 |
| N113.2 | GGATCCGATCGAGCTAGCGCGGCCGCTTAACCCGCAACAGCAATACGTTTC | ilvC reverse | 34 |
| N114.2 | GAGCTCGCTAGCAAGGAGGTATAAAGTATGCCTAAGTACCGTTC | ilvD forward | 35 |
| N115.2 | GGATCCGATCGATTAATTAACCTAAGGTTATTAACCCCCCAGTTTCGATTTA | ilvD reverse | 36 |
| N116.2 | GAGCTCTTAATTAAAAGGAGGTTAGACATATGTATACTGTGGGGA | kivD forward | 37 |
| N117.2 | GGATCCAGATCTCCTAGGACATGTTTAGCTTTTATTTTGCTCCGCAAAC | kivD reverse | 38 |
| N130SeqF1 | TGTTCCAACCTGATCACCG | sequencing primer | 40 |

TABLE 4-continued

Oligonucleotide Cloning, Screening, and Sequencing Primers

| Name | Sequence | Description | SEQ ID NO: |
|---|---|---|---|
| N130SeqF2 | GGAAAACAGCAAGGCGCT | sequencing primer | 41 |
| N130SeqF3 | CAGCTGAACCAGTTTGCC | sequencing primer | 42 |
| N130SeqF4 | AAAATACCAGCGCCTGTCC | sequencing primer | 43 |
| N130SeqR1 | TGAATGGCCACCATGTTG | sequencing primer | 44 |
| N130SeqR2 | GAGGATCTCCGCCGCCTG | sequencing primer | 45 |
| N130SeqR3 | AGGCCGAGCAGGAAGATC | sequencing primer | 46 |
| N130SeqR4 | TGATCAGGTTGGAACAGCC | sequencing primer | 47 |
| N131SeqF1 | AAGAACTGATCCCACAGGC | sequencing primer | 48 |
| N131SeqF2 | ATCCTGTGCGGTATGTTGC | sequencing primer | 49 |
| N131SeqF3 | ATTGCGATGGTGAAAGCG | sequencing primer | 50 |
| N131SeqR1 | ATGGTGTTGGCAATCAGCG | sequencing primer | 51 |
| N131SeqR2 | GTGCTTCGGTGATGGTTT | sequencing primer | 52 |
| N131SeqR3 | TTGAAACCGTGCGAGTAGC | sequencing primer | 53 |
| N132SeqF1 | TATTCACTGCCATCTCGCG | sequencing primer | 54 |
| N132SeqF2 | CCGTAAGCAGCTGTTCCT | sequencing primer | 55 |
| N132SeqF3 | GCTGGAACAATACGACGTTA | sequencing primer | 56 |
| N132SeqF4 | TGCTCTACCCAACCAGCTTC | sequencing primer | 57 |
| N132SeqR1 | ATGGAAAGACCAGAGGTGCC | sequencing primer | 58 |
| N132SeqR2 | TGCCTGTGTGGTACGAAT | sequencing primer | 59 |
| N132SeqR3 | TATTACGCGGCAGTGCACT | sequencing primer | 60 |
| N132SeqR4 | GGTGATTTGTCGCAGTTAGAG | sequencing primer | 61 |
| N133SeqF1 | TCGAAATTGTTGGGTCGC | sequencing primer | 62 |
| N133SeqF2 | GGTCACGCAGTTCATTTCTAAG | sequencing primer | 63 |
| N133SeqF3 | TGTGGCAAGCCGTAGAAA | sequencing primer | 64 |
| N133SeqF4 | AGGATCGCGTGGTGAGTAA | sequencing primer | 65 |

TABLE 4-continued

Oligonucleotide Cloning, Screening, and Sequencing Primers

| Name | Sequence | Description | SEQ ID NO: |
|---|---|---|---|
| N133SeqR1 | GTAGCCGTCGTTATTGATGA | sequencing primer | 66 |
| N133SeqR2 | GCAGCGAACTAATCAGAGATTC | sequencing primer | 67 |
| N133SeqR3 | TGGTCCGATGTATTGGAGG | sequencing primer | 68 |
| N133SeqR4 | TCTGCCATATAGCTCGCGT | sequencing primer | 69 |
| Scr1 | CCTTTCTTTGTGAATCGG | sequencing primer | 72 |
| Scr2 | AGAAACAGGGTGTGATCC | sequencing primer | 73 |
| Scr3 | AGTGATCATCACCTGTTGCC | sequencing primer | 74 |
| Scr4 | AGCACGGCGAGAGTCGACGG | sequencing primer | 75 |
| T-budB (BamHI) | AGATAGATGGATCCGGAGGTGGGTCACATGGACAAACAGT | budB forward | 144 |
| B-kivD (BamHI) | CTCTAGAGGATCCAGACTCCTAGGACATG | kivD reverse | 145 |
| T-groE(XhoI) | AGATAGATCTCGAGAGCTATTGTAACATAATCGGTACGGGGGTG | PgroE forward | 147 |
| B-groEL(SpeI, BamHI) | ATTATGTCAGGATCCACTAGTTTTCCTCCTTTAATTGGGAATTGTTATCCGC | PgroE reverse | 148 |
| T-groEL | AGCTATTGTAACATAATCGGTACGGGGTG | PgroE forward | 149 |
| T-ilvCB.s. (BamHI) | ACATTGATGGATCCCATAACAAGGGAGAGATTGAAATGGTAAAAG | ilvC forward | 150 |
| B-ilvCB.s. (SpeIBamHI) | TAGACAACGGATCCACTAGTTTAATTTTGCGCAACGGAGACCACCGC | ilvC reverse | 151 |
| T-BD64 (DraIII) | TTACCGTGGACTCACCGAGTGGGTAACTAGCCTCGCCGGAAAGAGCG | pBD64 forward | 152 |
| B-BD64 (DraIII) | TCACAGTTAAGACACCTGGTGCCGTTAATGCGCCATGACAGCCATGAT | pBD64 reverse | 153 |
| T-Iaclq (DraIII) | ACAGATAGATCACCAGGTGCAAGCTAATTCCGGTGGAAACGAGGTCATC | laclq forward | 154 |
| B-Iaclq (DraIII) | ACAGTACGATACACGGGGTGTCACTGCCCGCTTTCCAGTCGGGAAACC | laclq reverse | 155 |
| T-groE (DraIII) | TCGGATTACGCACCCCGTGAGCTATTGTAACATAATCGGTACGGGGGTG | PgroE forward | 156 |
| B-B.s.ilvC (DraIII) | CTGCTGATCTCACACCGTGTGTTAATTTTGCGCAACGGAGACCACCGC | ilvC reverse | 157 |
| T-bdhB (DraIII) | TCGATAGCATACACACGGTGGTTAACAAAGGAGGGGTTAAAATGGTTGATTTCG | bdhB forward | 159 |
| B-bdhB (rrnBT1DraIII) | ATCTACGCACTCGGTGATAAAACGAAAGGCCCAGTCTTTCGACTGAGCCTTTCGTTTTATCTTACACAGATTTTTGAATATTTGTAGGAC | bdhB reverse | 160 |
| LDH EcoRV F | GACGTCATGACCACCCGCCGATCCCTTTT | ldhL forward | 161 |

TABLE 4-continued

Oligonucleotide Cloning, Screening, and Sequencing Primers

| Name | Sequence | Description | SEQ ID NO: |
|---|---|---|---|
| LDH AatIIR | GATATCCAACACCAGCGACCGACGTA TTAC | IdhL reverse | 162 |
| Cm F | ATTTAAATCTCGAGTAGAGGATCCCA ACAAACGAAAATTGGATAAAG | Cm forward | 163 |
| Cm R | ACGCGTTATTATAAAAGCCAGTCATT AGG | Cm reverse | 164 |
| P11 F-StuI | CCTAGCGCTATAGTTGTTGACAGAAT GGACATACTATGATATATTGTTGCTA TAGCGA | P11 promoter forward | 165 |
| P11 R-SpeI | CTAGTCGCTATAGCAACAATATATCA TAGTATGTCCATTCTGTCAACAACTA TAGCGCTAGG | P11 promoter reverse | 166 |
| PldhL F-HindIII | AAGCTTGTCGACAAACCAACATTATG ACGTGTCTGGGC | IdhL forward | 167 |
| PldhL R-BamHI | GGATCCTCATCCTCTCGTAGTGAAAA TT | IdhL reverse | 168 |
| F-bdhB-AvrII | TTCCTAGGAAGGAGGTGGTTAAAATG GTTGATTTCG | bdhB forward | 169 |
| R-bdhB-BamHI | TTGGATCCTTACACAGATTTTTTGAA TAT | bdhB reverse | 170 |
| F-ilvC(B.s.)-AfIII | AACTTAAGAAGGAGGTGATTGAAATG GTAAAAGTATATT | ilvC forward | 171 |
| R-ilvC(B.s.)-NotI | AAGCGGCCGCTTAATTTTGCGCAACG GAGACC | ivlC reverse | 172 |
| F-PnisA(HindIII) | TTAAGCTTGACATACTTGAATGACCT AGTC | nisA promoter forward | 173 |
| R-PnisA(SpeIBamHI) | TTGGATCCAAACTAGTATAATTTATT TTGTAGTTCCTTC | nisA promoter reverse | 174 |

Methods for Determining Isobutanol Concentration in Culture Media

The concentration of isobutanol in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Isobutanol had a retention time of 46.6 min under the conditions used. Alternatively, gas chromatography (GC) methods are available. For example, a specific GC method utilized an HP-INNOWax column (30 m×0.53 mm id, 1 µm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of isobutanol was 4.5 min.

The meaning of abbreviations is as follows: "s" means second(s), "min" means minute(s), "h" means hour(s), "psi" means pounds per square inch, "nm" means nanometers, "d" means day(s), "µL" means microliter(s), "mL" means milliliter(s), "L" means liter(s), "mm" means millimeter(s), "nm" means nanometers, "mM" means millimolar, "µM" means micromolar, "M" means molar, "mmol" means millimole(s), "µmol" means micromole(s)", "g" means gram(s), "µg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "IPTG" means isopropyl-β-D-thiogalactopyranoiside, "RBS" means ribosome binding site, "HPLC" means high performance liquid chromatography, and "GC" means gas chromatography. The term "molar selectivity" is the number of moles of product produced per mole of sugar substrate consumed and is reported as a percent.

Example 1

Cloning and Expression of Acetolactate Synthase

The purpose of this Example was to clone the budB gene from *Klebsiella pneumoniae* and express it in *E. coli* BL21-AI. The budB gene was amplified from *Klebsiella pneumo-* niae strain ATCC 25955 genomic DNA using PCR, resulting in a 1.8 kbp product.

Genomic DNA was prepared using the Gentra Puregene kit (Gentra Systems, Inc., Minneapolis, Minn.; catalog number D-5000A). The budB gene was amplified from *Klebsiella pneumoniae* genomic DNA by PCR using primers N80 and N81 (see Table 2), given as SEQ ID NOs:11 and 12, respectively. Other PCR amplification reagents were supplied in manufacturers' kits, for example, Finnzymes Phusion™ High-Fidelity PCR Master Mix (New England Biolabs Inc., Beverly, Mass.; catalog no. F-531) and used according to the manufacturer's protocol. Amplification was carried out in a DNA Thermocycler GeneAmp 9700 (PE Applied Biosystems, Foster city, CA).

For expression studies the Gateway cloning technology (Invitrogen Corp., Carlsbad, Calif.) was used. The entry vector pENTRSDD-TOPO allowed directional cloning and provided a Shine-Dalgarno sequence for the gene of interest. The destination vector pDEST14 used a T7 promoter for expression of the gene with no tag. The forward primer incorporated four bases (CACC) immediately adjacent to the translational start codon to allow directional cloning into pENTRSDD-TOPO (Invitrogen) to generate the plasmid pENTRSDD-TOPObudB. The pENTR construct was transformed into *E. coli* Top10 (Invitrogen) cells and plated according to manufacturer's recommendations. Transformants were grown overnight and plasmid DNA was prepared using the QIAprep Spin Miniprep kit (Qiagen, Valencia, Calif.; catalog no. 27106) according to manufacturer's recommendations. Clones were sequenced to confirm that the genes inserted in the correct orientation and to confirm the sequence. The nucleotide sequence of the open reading frame (ORF) for this gene and the predicted amino acid sequence of the enzyme are given as SEQ ID NO:1 and SEQ ID NO:2, respectively.

To create an expression clone, the budB gene was transferred to the pDEST 14 vector by recombination to generate pDEST14budB. The pDEST14budB vector was transformed into *E. coli* BL21-AI cells (Invitrogen). Transformants were inoculated into Luria Bertani (LB) medium supplemented with 50 µg/mL of ampicillin and grown overnight. An aliquot of the overnight culture was used to inoculate 50 mL of LB supplemented with 50 µg/mL of ampicillin. The culture was incubated at 37° C. with shaking until the $OD_{600}$ reached 0.6-0.8. The culture was split into two 25-mL cultures and arabinose was added to one of the flasks to a final concentration of 0.2% w/v. The negative control flask was not induced with arabinose. The flasks were incubated for 4 h at 37° C. with shaking. Cells were harvested by centrifugation and the cell pellets were resuspended in 50 mM MOPS, pH 7.0 buffer. The cells were disrupted either by sonication or by passage through a French Pressure Cell. The whole cell lysate was centrifuged yielding the supernatant or cell free extract and the pellet or the insoluble fraction. An aliquot of each fraction (whole cell lysate, cell free extract and insoluble fraction) was resuspended in SDS (MES) loading buffer (Invitrogen), heated to 85° C. for 10 min and subjected to SDS-PAGE analysis (NuPAGE 4-12% Bis-Tris Gel, catalog no. NP0322Box, Invitrogen). A protein of the expected molecular weight of about 60 kDa, as deduced from the nucleic acid sequence, was present in the induced culture but not in the uninduced control.

Acetolactate synthase activity in the cell free extracts is measured using the method described by Bauerle et al. (*Biochim. Biophys. Acta* 92(1):142-149 (1964)).

Example 2

Prophetic

Cloning and Expression of Acetohydroxy Acid Reductoisomerase

The purpose of this prophetic Example is to describe how to clone the ilvC gene from *E. coli* K12 and express it in *E. coli* BL21-AI. The ilvC gene is amplified from *E. coli* genomic DNA using PCR.

The ilvC gene is cloned and expressed in the same manner as the budB gene described in Example 1. Genomic DNA from *E. coli* is prepared using the Gentra Puregene kit (Gentra Systems, Inc., Minneapolis, Minn.; catalog number D-5000A). The ilvC gene is amplified by PCR using primers N100 and N101 (see Table 2), given as SEQ ID NOs:13 and 14, respectively, creating a 1.5 kbp product. The forward primer incorporates four bases (CCAC) immediately adjacent to the translational start codon to allow directional cloning into pENTR/SD/D-TOPO (Invitrogen) to generate the plasmid pENTRSDD-TOPOilvC. Clones are sequenced to confirm that the genes are inserted in the correct orientation and to confirm the sequence. The nucleotide sequence of the open reading frame (ORF) for this gene and the predicted amino acid sequence of the enzyme are given as SEQ ID NO:3 and SEQ ID NO:4, respectively.

To create an expression clone, the ilvC gene is transferred to the pDEST 14 (Invitrogen) vector by recombination to generate pDEST14ilvC. The pDEST14ilvC vector is transformed into *E. coli* BL21-AI cells and expression from the T7 promoter is induced by addition of arabinose. A protein of the expected molecular weight of about 54 kDa, as deduced from the nucleic acid sequence, is present in the induced culture, but not in the uninduced control.

Acetohydroxy acid reductoisomerase activity in the cell free extracts is measured using the method described by Arfin and Umbarger (*J. Biol. Chem.* 244(5):1118-1127 (1969)).

Example 3

Prophetic

Cloning and Expression of Acetohydroxy Acid Dehydratase

The purpose of this prophetic Example is to describe how to clone the ilvD gene from *E. coli* K12 and express it in *E. coli* BL21-AI. The ilvD gene is amplified from *E. coli* genomic DNA using PCR.

The ilvD gene is cloned and expressed in the same manner as the budB gene described in Example 1. Genomic DNA from *E. coli* is prepared using the Gentra Puregene kit (Gentra Systems, Inc., Minneapolis, Minn.; catalog number D-5000A). The ilvD gene is amplified by PCR using primers N102 and N103 (see Table 2), given as SEQ ID NOs:15 and 16, respectively, creating a 1.9 kbp product. The forward primer incorporates four bases (CCAC) immediately adjacent to the translational start codon to allow directional cloning into pENTR/SD/D-TOPO (Invitrogen) to generate the plasmid pENTRSDD-TOPOilvD. Clones are submitted for sequencing to confirm that the genes are inserted in the correct orientation and to confirm the sequence. The nucleotide sequence of the open reading frame (ORF) for this gene and the predicted amino acid sequence of the enzyme are given as SEQ ID NO:5 and SEQ ID NO:6, respectively.

To create an expression clone, the ilvD gene is transferred to the pDEST 14 (Invitrogen) vector by recombination to generate pDEST14ilvD. The pDEST14ilvD vector is transformed into *E. coli* BL21-AI cells and expression from the T7 promoter is induced by addition of arabinose. A protein of the expected molecular weight of about 66 kDa, as deduced from the nucleic acid sequence, is present in the induced culture, but not in the uninduced control.

Acetohydroxy acid dehydratase activity in the cell free extracts is measured using the method described by Flint et al. (*J. Biol. Chem.* 268(20):14732-14742 (1993)).

Example 4

Prophetic

Cloning and Expression of Branched-Chain Keto Acid Decarboxylase

The purpose of this prophetic example is to describe how to clone the kivD gene from *Lactococcus lactis* and express it in *E. coli* BL21-AI.

A DNA sequence encoding the branched-chain keto acid decarboxylase (kivD) from *L. lactis* is obtained from GenScript (Piscataway, N.J.). The sequence obtained is codon-optimized for expression in both *E. coli* and *B. subtilis* and is cloned into pUC57, to form pUC57-kivD. The codon-optimized nucleotide sequence of the open reading frame (ORF) for this gene and the predicted amino acid sequence of the enzyme are given as SEQ ID NO:7 and SEQ ID NO:8, respectively.

To create an expression clone NdeI and BamHI restriction sites are utilized to clone the 1.7 kbp kivD fragment from pUC57-kivD into vector pET-3a (Novagen, Madison, Wis.). This creates the expression clone pET-3a-kivD. The pET-3a-kivD vector is transformed into *E. coli* BL21-AI cells and expression from the T7 promoter is induced by addition of arabinose. A protein of the expected molecular weight of about 61 kDa, as deduced from the nucleic acid sequence, is present in the induced culture, but not in the uninduced control.

Branched-chain keto acid decarboxylase activity in the cell free extracts is measured using the method described by Smit et al. (*Appl. Microbiol. Biotechnol.* 64:396-402 (2003)).

Example 5

Prophetic

Cloning and Expression of Branched-Chain Alcohol Dehydrogenase

The purpose of this prophetic Example is to describe how to clone the yqhD gene from *E. coli* K12 and express it in *E. coli* BL21-AI. The yqhD gene is amplified from *E. coli* genomic DNA using PCR.

The yqhD gene is cloned and expressed in the same manner as the budB gene described in Example 1. Genomic DNA from *E. coli* is prepared using the Gentra Puregene kit (Gentra Systems, Inc., Minneapolis, Minn.; catalog number D-5000A). The yqhD gene is amplified by PCR using primers N104 and N105 (see Table 2), given as SEQ ID NOs:17 and 18, respectively, creating a 1.2 kbp product. The forward primer incorporates four bases (CCAC) immediately adjacent to the translational start codon to allow directional cloning into pENTR/SD/D-TOPO (Invitrogen) to generate the plasmid pENTRSDD-TOPOyqhD. Clones are submitted for sequencing to confirm that the genes are inserted in the correct orientation and to confirm the sequence. The nucleotide sequence of the open reading frame (ORF) for this gene and the predicted amino acid sequence of the enzyme are given as SEQ ID NO 9 and SEQ ID NO:10, respectively.

To create an expression clone, the yqhD gene is transferred to the pDEST 14 (Invitrogen) vector by recombination to generate pDEST14yqhD. The pDEST14ilvD vector is transformed into *E. coli* BL21-AI cells and expression from the T7 promoter is induced by addition of arabinose. A protein of the expected molecular weight of about 42 kDa, as deduced from the nucleic acid sequence, is present in the induced culture, but not in the uninduced control.

Branched-chain alcohol dehydrogenase activity in the cell free extracts is measured using the method described by Sulzenbacher et al. (*J. Mol. Biol.* 342(2):489-502 (2004)).

Example 6

Prophetic

Construction of a Transformation Vector for the Genes in an Isobutanol Biosynthetic Pathway The purpose of this prophetic Example is to describe how to construct a transformation vector comprising the genes encoding the five steps in an isobutanol biosynthetic pathway. All genes are placed in a single operon under the control of a single promoter. The individual genes are amplified by PCR with primers that incorporate restriction sites for later cloning and the forward primers contain an optimized *E. coli* ribosome binding site (AAAGGAGG). PCR products are TOPO cloned into the pCR 4Blunt-TOPO vector and transformed into *E. coli* Top10 cells (Invitrogen). Plasmid DNA is prepared from the TOPO clones and the sequence of the genes is verified. Restriction enzymes and T4 DNA ligase (New England Biolabs, Beverly, Mass.) are used according to manufacturer's recommendations. For cloning experiments, restriction fragments are gel-purified using QIAquick Gel Extraction kit (Qiagen). After confirmation of the sequence, the genes are subcloned into a modified pUC19 vector as a cloning platform. The pUC19 vector is modified by HindIII/SapI digestion, creating pUC19dHS. The digest removes the lac promoter adjacent to the MCS (multiple cloning site), preventing transcription of the operons in the vector.

The budB gene is amplified from *K. pneumoniae* ATCC 25955 genomic DNA by PCR using primer pair N110 and N111 (see Table 2), given as SEQ ID NOs:19 and 20, respectively, creating a 1.8 kbp product. The forward primer incorporates SphI and AflII restriction sites and a ribosome binding site (RBS). The reverse primer incorporates PacI and NsiI restriction sites. The PCR product is cloned into pCR4 Blunt-TOPO creating pCR4 Blunt-TOPO-budB. Plasmid DNA is prepared from the TOPO clones and the sequence of the gene is verified.

The ilvC gene is amplified from *E. coli* K12 genomic DNA by PCR using primer pair N112 and N113 (see Table 2) given as SEQ ID NOs:21 and 22, respectively, creating a 1.5 kbp product. The forward primer incorporates SalI and NheI restriction sites and a RBS. The reverse primer incorporates a XbaI restriction site. The PCR product is cloned into pCR4 Blunt-TOPO creating pCR4 Blunt-TOPO-ilvC. Plasmid DNA is prepared from the TOPO clones and the sequence of the gene is verified.

The ilvD gene is amplified from *E. coli* K12 genomic DNA by PCR using primer pair N114 and N115 (see Table 2) given as SEQ ID NOs:23 and 24, respectively, creating a 1.9 kbp product. The forward primer incorporates a XbaI restriction site and a RBS. The reverse primer incorporates a BamHI restriction site. The PCR product is cloned into pCR4 Blunt-TOPO creating pCR4 Blunt-TOPO-ilvD. Plasmid DNA is prepared from the TOPO clones and the sequence of the gene is verified.

The kivD gene is amplified from pUC57-kivD (described in Example 4) by PCR using primer pair N116 and N117 (see Table 2), given as SEQ ID NOs:25 and 26, respectively, creating a 1.7 bp product. The forward primer incorporates a BamHI restriction site and a RBS. The reverse primer incorporates a SacI restriction site. The PCR product is cloned into pCR4 Blunt-TOPO creating pCR4 Blunt-TOPO-kivD. Plasmid DNA is prepared from the TOPO clones and the sequence of the gene is verified.

The yqhD gene is amplified from *E. coli* K12 genomic DNA by PCR using primer pair N118 and N119 (see Table 2) given as SEQ ID NOs:27 and 28, respectively, creating a 1.2 kbp product. The forward primer incorporates a SacI restriction site. The reverse primer incorporates SpeI and EcoRI restriction sites. The PCR product is cloned into pCR4 Blunt-TOPO creating pCR4 Blunt-TOPO-yqhD. Plasmid DNA is prepared from the TOPO clones and the sequence of the gene is verified.

To construct the isobutanol pathway operon, the yqhD gene is excised from pCR4 Blunt-TOPO-yqhD with SacI and EcoRI, releasing a 1.2 kbp fragment. This is ligated with pUC19dHS, which has previously been digested with SacI and EcoRI. The resulting clone, pUC19dHS-yqhD, is confirmed by restriction digest. Next, the ilvC gene is excised from pCR4 Blunt-TOPO-ilvC with SalI and XbaI, releasing a 1.5 kbp fragment. This is ligated with pUC19dHS-yqhD, which has previously been digested with SalI and XbaI. The resulting clone, pUC19dHS-ilvC-yqhD, is confirmed by restriction digest. The budB gene is then excised from pCR4 Blunt-TOPO-budB with SphI and NsiI, releasing a 1.8 kbp fragment. pUC19dHS-ilvC-yqhD is digested with SphI and PstI and ligated with the SphI/NsiI budB fragment (NsiI and PstI generate compatible ends), forming pUC19dHS-budB-ilvC-yqhD. A 1.9 kbp fragment containing the ilvD gene is excised from pCR4 Blunt-TOPO-ilvD with XbaI and BamHI and ligated with pUC19dHS-budB-ilvC-yqhD, which is digested with these same enzymes, forming pUC19dHS-budB-ilvC-ilvD-yqhD. Finally, kivD is excised from pCR4 Blunt-TOPO-kivD with BamHI and SacI, releasing a 1.7 kbp fragment. This fragment is ligated with pUC19dHS-budB-ilvC-ilvD-yqhD, which has previously been digested with BamHI and SacI, forming pUC19dHS-budB-ilvC-ilvD-kivD-yqhD.

The pUC19dHS-budB-ilvC-ilvD-kivD-yqhD vector is digested with AflIII and SpeI to release a 8.2 kbp operon fragment that is cloned into pBenAS, an *E. coli-B. subtilis* shuttle vector. Plasmid pBenAS is created by modification of the pBE93 vector, which is described by Nagarajan, (WO 93/24631, Example 4). To make pBenAS the *Bacillus amyloliquefaciens* neutral protease promoter (NPR), signal sequence, and the phoA gene are removed with a NcoI/HindIII digest of pBE93. The NPR promoter is PCR amplified from pBE93 by primers BenNF and BenASR, given as SEQ ID NOS:29 and 30, respectively. Primer BenASR incorporates AflIII, SpeI. and HindIII sites downstream of the promoter. The PCR product is digested with NcoI and HindIII and the fragment is cloned into the corresponding sites in the vector creating pBenAS. The operon fragment is subcloned into the AflIII and SpeI sites in pBenAS creating pBen-budB-ilvC-ilvD-kivD-yqh D.

Example 7

Prophetic

Expression of the Isobutanol Biosynthetic Pathway in *E. coli*

The purpose of this prophetic Example is to describe how to express an isobutanol biosynthetic pathway in *E. coli*.

The plasmid pBen-budB-ilvC-ilvD-kivD-yqhD, constructed as described in Example 6, is transformed into *E. coli* NM522 (ATCC No. 47000) to give *E. coli* strain NM522/pBen-budB-ilvC-ilvD-kivD-yqhD and expression of the genes in the operon is monitored by SDS-PAGE analysis, enzyme assay and Western blot analysis. For Western blots, antibodies are raised to synthetic peptides by Sigma-Genosys (The Woodlands, Tex.).

*E. coli* strain NM522/pBen-budB-ilvC-ilvD-kivD-yqhD is inoculated into a 250 mL shake flask containing 50 mL of medium and shaken at 250 rpm and 35° C. The medium is composed of: glucose (5 g/L), MOPS (0.05 M), ammonium sulfate (0.01 M), potassium phosphate, monobasic (0.005 M), S10 metal mix (1% (v/v)) yeast extract (0.1% (w/v)), casamino acids (0.1% (w/v)), thiamine (0.1 mg/L), proline (0.05 mg/L), and biotin (0.002 mg/L), and is titrated to pH 7.0 with KOH. S10 metal mix contains: $MgCl_2$ (200 mM), $CaCl_2$ (70 mM), $MnCl_2$ (5 mM), $FeCl_3$ (0.1 mM), $ZnCl_2$ (0.1 mM), thiamine hydrochloride (0.2 mM), $CuSO_4$ (172 µM), $CoCl_2$ (253 µM), and $Na_2MoO_4$ (242 µM). After 18 h, isobutanol is detected by HPLC or GC analysis, using methods that are well known in the art, for example, as described in the General Methods section above.

Example 8

Prophetic

Expression of the Isobutanol Biosynthetic Pathway in *Bacillus subtilis*

The purpose of this prophetic Example is to describe how to express an isobutanol biosynthetic pathway in *Bacillus subtilis*. The same approach as described in Example 7 is used.

The plasmid pBen-budB-ilvC-ilvD-kivD-yqhD, constructed as described in Example 6, is used. This plasmid is transformed into *Bacillus subtilis* BE1010 (*J. Bacteriol.* 173: 2278-2282 (1991)) to give *B. subtilis* strain BE1010/pBen-budB-ilvC-ilvD-kivD-yqhD and expression of the genes in each operon is monitored as described in Example 7.

*B. subtilis* strain BE1010/pBen-budB-ilvC-ilvD-kivD-yqhD is inoculated into a 250 mL shake flask containing 50 mL of medium and shaken at 250 rpm and 35° C. for 18 h. The medium is composed of: dextrose (5 g/L), MOPS (0.05 M), glutamic acid (0.02 M), ammonium sulfate (0.01 M), potassium phosphate, monobasic buffer (0.005 M), S10 metal mix (as described in Example 11, 1% (v/v)), yeast extract (0.1% (w/v)), casamino acids (0.1% (w/v)), tryptophan (50 mg/L), methionine (50 mg/L), and lysine (50 mg/L), and is titrated to pH 7.0 with KOH. After 18 h, isobutanol is detected by HPLC or GC analysis using methods that are well known in the art, for example, as described in the General Methods section above.

Example 9

Cloning and Expression of Acetolactate Synthase

To create another acetolactate synthase expression clone, the budB gene was cloned into the vector pTrc99A. The budB gene was first amplified from pENTRSDD-TOPObudB (described in Example 1) using primers (N110.2 and N111.2, given as SEQ ID NOs:31 and 32, respectively) that introduced SacI, SpeI and MfeI sites at the 5' end and BbvCI, AflII, and BamHI sites at the 3' end. The resulting 1.75 kbp PCR product was cloned into pCR4-Blunt TOPO (Invitrogen) and the DNA sequence was confirmed (using N130Seq sequencing primers F1-F4 and R1-R4, given as SEQ ID NOs:40-47, respectively). The budB gene was then excised from this vector using SacI and BamHI and cloned into pTrc99A (Amann et al. *Gene* 69(2):301-315 (1988)), generating pTrc99A::budB. The pTrc99A::budB vector was transformed into *E. coli* TOP10 cells and the transformants were inoculated into LB medium supplemented with 50 μg/mL of ampicillin and grown overnight at 37° C. An aliquot of the overnight culture was used to inoculate 50 mL of LB medium supplemented with 50 μg/mL of ampicillin. The culture was incubated at 37° C. with shaking until the OD$_{600}$ reached 0.6 to 0.8. Expression of budB from the Trc promoter was then induced by the addition of 0.4 mM IPTG. Negative control flasks were also prepared that were not induced with IPTG. The flasks were incubated for 4 h at 37° C. with shaking. Cell-free extracts were prepared as described in Example 1.

Acetolactate synthase activity in the cell free extracts was measured as described in Example 1. Three hours after induction with IPTG, an acetolactate synthase activity of 8 units/mg was detected. The control strain carrying only the pTrc99A plasmid exhibited 0.03 units/mg of acetolactate synthase activity.

Example 10

Cloning and Expression of Acetohydroxy Acid Reductoisomerase

The purpose of this Example was to clone the ilvC gene from *E. coli* K12 and express it in *E. coli* TOP10. The ilvC gene was amplified from *E. coli* K12 strain FM5 (ATCC 53911) genomic DNA using PCR.

The ilvC gene was cloned and expressed in a similar manner as described for the cloning and expression of ilvC in Example 2 above. PCR was used to amplify ilvC from the *E. coli* FM5 genome using primers N112.2 and N113.2 (SEQ ID NOs:33 and 34, respectively). The primers created SacI and AflII sites and an optimal RBS at the 5' end and NotI, NheI and BamHI sites at the 3' end of ilvC. The 1.5 kbp PCR product was cloned into pCR4Blunt TOPO according to the manufacturer's protocol (Invitrogen) generating pCR4Blunt TOPO::ilvC. The sequence of the PCR product was confirmed using sequencing primers (N131SeqF1-F3, and N131SeqR1-R3, given as SEQ ID NOs:48-53, respectively). To create an expression clone, the ilvC gene was excised from pCR4Blunt TOPO::ilvC using SacI and BamHI and cloned into pTrc99A. The pTrc99A::ilvC vector was transformed into *E. coli* TOP10 cells and expression from the Trc promoter was induced by addition of IPTG, as described in Example 9. Cell-free extracts were prepared as described in Example 1.

Acetohydroxy acid reductoisomerase activity in the cell free extracts was measured as described in Example 2. Three hours after induction with IPTG, an acetohydroxy acid reductoisomerase activity of 0.026 units/mg was detected. The control strain carrying only the pTrc99A plasmid exhibited less than 0.001 units/mg of acetohydroxy acid reductoisomerase activity.

Example 11

Cloning and Expression of Acetohydroxy Acid Dehydratase

The purpose of this Example was to clone the ilvD gene from *E. coli* K12 and express it in *E. coli* Top10. The ilvD gene was amplified from *E. coli* K12 strain FM5 (ATCC 53911) genomic DNA using PCR.

The ilvD gene was cloned and expressed in a similar manner as the ilvC gene described in Example 10. PCR was used to amplify ilvD from the *E. coli* FM5 genome using primers N114.2 and N115.2 (SEQ ID NOs:35 and 36, respectively). The primers created SacI and NheI sites and an optimal RBS at the 5' end and Bsu36I, PacI and BamHI sites at the 3' end of ilvD. The 1.9 kbp PCR product was cloned into pCR4Blunt TOPO according to the manufacturer's protocol (Invitrogen) generating pCR4Blunt TOPO::ilvD. The sequence of the PCR product was confirmed (sequencing primers N132SeqF1-F4 and N132SeqR1-R4, given as SEQ ID NOs: 54-61, respectively). To create an expression clone, the ilvD gene was excised from plasmid pCR4Blunt TOPO::ilvD using SacI and BamHI, and cloned into pTrc99A. The pTrc99A::ilvD vector was transformed into *E. coli* TOP10 cells and expression from the Trc promoter was induced by addition of IPTG, as described in Example 9. Cell-free extracts were prepared as described in Example 1.

Acetohydroxy acid dehydratase activity in the cell free extracts was measured as described in Example 3. Three hours after induction with IPTG, an acetohydroxy acid dehydratase activity of 46 units/mg was measured. The control strain carrying only the pTrc99A plasmid exhibited no detectable acetohydroxy acid dehydratase activity.

Example 12

Cloning and Expression of Branched-Chain Keto Acid Decarboxylase

The purpose of this Example was to clone the kivD gene from *Lactococcus lactis* and express it in *E. coli* TOP10.

The kivD gene was cloned and expressed in a similar manner as that described for ilvC in Example 10 above. PCR was used to amplify kivD from the plasmid pUC57-kivD (see Example 4, above) using primers N116.2 and N117.2 (SEQ ID NOs:37 and 38, respectively). The primers created SacI and PacI sites and an optimal RBS at the 5' end and PciI, AvrII, BglII and BamHI sites at the 3' end of kivD. The 1.7 kbp PCR product was cloned into pCR4Blunt TOPO according to the manufacturer's protocol (Invitrogen) generating pCR4Blunt TOPO::kivD. The sequence of the PCR product was confirmed using primers N133SeqF1-F4 and N133SeqR1-R4 (given as SEQ ID NOs:62-69, respectively). To create an expression clone, the kivD gene was excised from plasmid pCR4Blunt TOPO::kivD using SacI and BamHI, and cloned into pTrc99A. The pTrc99A::kivD vector was transformed into *E. coli* TOP10 cells and expression from the Trc promoter was induced by addition of IPTG, as described in Example 9. Cell-free extracts were prepared as described in Example 1.

Branched-chain keto acid decarboxylase activity in the cell free extracts was measured as described in Example 4, except that Purpald® reagent (Aldrich, Catalog No. 162892) was used to detect and quantify the aldehyde reaction products. Three hours after induction with IPTG, a branched-chain keto acid decarboxylase activity of greater than 3.7 units/mg was detected. The control strain carrying only the pTrc99A plasmid exhibited no detectable branched-chain keto acid decarboxylase activity.

Example 13

Expression of Branched-Chain Alcohol Dehydrogenase

E. coli contains a native gene (yqhD) that was identified as a 1,3-propanediol dehydrogenase (U.S. Pat. No. 6,514,733). The YqhD protein has 40% identity to AdhB (encoded by adhB) from Clostridium, a putative NADH-dependent butanol dehydrogenase. The yqhD gene was placed under the constitutive expression of a variant of the glucose isomerase promoter 1.6GI (SEQ ID NO. 70) in E. coli strain MG1655 1.6yqhD::Cm (WO 2004/033646) using λ Red technology (Datsenko and Wanner, Proc. Natl. Acad. Sci. U.S.A. 97:6640 (2000)). MG1655 1.6yqhD::Cm contains a FRT-CmR-FRT cassette so that the antibiotic marker can be removed. Similarly, the native promoter was replaced by the 1.5GI promoter (WO 2003/089621) (SEQ ID NO. 71), creating strain MG1655 1.5GI-yqhD::Cm, thus, replacing the 1.6GI promoter of MG1655 1.6yqhD::Cm with the 1.5GI promoter.

Strain MG1655 1.5GI-yqhD::Cm was grown in LB medium to mid-log phase and cell free extracts were prepared as described in Example 1. This strain was found to have NADPH-dependent isobutyraldehyde reductase activity when the cell extracts were assayed by following the decrease in absorbance at 340 nm at pH 7.5 and 35° C.

To generate a second expression strain containing 1.5GI yqhD::Cm, a P1 lysate was prepared from MG1655 1.5GI yqhD::Cm and the cassette was transferred to BL21 (DE3) (Invitrogen) by transduction, creating BL21 (DE3) 1.5GI-yqhD::Cm.

Example 14

Construction of a Transformation Vector for the First Four

Genes in an Isobutanol Biosynthetic Pathway

The purpose of this Example was to construct a transformation vector comprising the first four genes (i.e., budB, ilvC, ilvD and kivD) in an isobutanol biosynthetic pathway. To construct the transformation vector, first, the ilvC gene was obtained from pTrc99A::ilvC (described in Example 10) by digestion with AflIII and BamHI and cloned into pTrc99A:: budB (described in Example 9), which was digested with AflIII and BamHI to produce plasmid pTrc99A::budB-ilvC. Next, the ilvD and kivD genes were obtained from pTrc99A:: ilvD (described in Example 11) and pTrc99A::kivD (described in Example 12), respectively, by digestion with NheI and PacI (ilvD) and PacI and BamHI (kivD). These genes were introduced into pTrc99A::budB-ilvC, which was first digested with NheI and BamHI, by three-way ligation. The presence of all four genes in the final plasmid, pTrc99A:: budB-ilvC-ilvD-kivD, was confirmed by PCR screening and restriction digestion.

Example 15

Expression of an Isobutanol Biosynthetic Pathway in E. coli Grown on Glucose

To create E. coli isobutanol production strains, pTrc99A:: budB-ilvC-ilvD-kivD (described in Example 14) was transormed into E. coli MG1655 1.5GI yqhD::Cm and E. coli BL21 (DE3) 1.5GI yqhD::Cm (described in Example 13). Transformants were initially grown in LB medium containing 50 μg/mL kanamycin and 100 μg/mL carbenicillin. The cells from these cultures were used to inoculate shake flasks (approximately 175 mL total volume) containing 50 or 170 mL of TM3a/glucose medium (with appropriate antibiotics) to represent high and low oxygen conditions, respectively. TM3a/glucose medium contained (per liter): glucose (10 g), $KH_2PO_4$ (13.6 g), citric acid monohydrate (2.0 g), $(NH_4)_2SO_4$ (3.0 g), $MgSO_4.7H_2O$ (2.0 g), $CaCl_2.2H_2O$ (0.2 g), ferric ammonium citrate (0.33 g), thiamine.HCl (1.0 mg), yeast extract (0.50 g), and 10 mL of trace elements solution. The pH was adjusted to 6.8 with $NH_4OH$. The trace elements solution contained: citric acid.$H_2O$ (4.0 g/L), $MnSO_4.H_2O$ (3.0 g/L), NaCl (1.0 g/L), $FeSO_4.7H_2O$ (0.10 g/L), $CoCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4.2H_2O$ (0.010 g/L).

The flasks were inoculated at a starting $OD_{600}$ of ≤0.01 units and incubated at 34° C. with shaking at 300 rpm. The flasks containing 50 mL of medium were closed with 0.2 μm filter caps; the flasks containing 150 mL of medium were closed with sealed caps. IPTG was added to a final concentration of 0.04 mM when the cells reached an $OD_{600}$ of ≥0.4 units. Approximately 18 h after induction, an aliquot of the broth was analyzed by HPLC (Shodex Sugar SH1011 column (Showa Denko America, Inc. NY) with refractive index (RI) detection) and GC (Varian CP-WAX 58(FFAP) CB, 0.25 mm×0.2 μm×25 m (Varian, Inc., Palo Alto, Calif.) with flame ionization detection (FID)) for isobutanol content, as described in the General Methods section. No isobutanol was detected in control strains carrying only the pTrc99A vector (results not shown). Molar selectivities and titers of isobutanol produced by strains carrying pTrc99A::budB-ilvC-ilvD-kivD are shown in Table 5. Significantly higher titers of isobutanol were obtained in the cultures grown under low oxygen conditions.

TABLE 5

Production of Isobutanol by E. coli Strains Grown on Glucose

| Strain | $O_2$ Conditions | Isobutanol mM* | Molar Selectivity (%) |
|---|---|---|---|
| MG1655 1.5GI yqhD/ pTrc99A::budB-ilvC-ilvD-kivD | High | 0.4 | 4.2 |
| MG1655 1.5GI yqhD/ pTrc99A::budB-ilvC-ilvD-kivD | Low | 9.9 | 39 |
| BL21 (DE3) 1.5GI yqhD/ pTrc99A::budB-ilvC-ilvD-kivD | High | 0.3 | 3.9 |
| BL21 (DE3) 1.5GI yqhD/ pTrc99A::budB-ilvC-ilvD-kivD | Low | 1.2 | 12 |

*Determined by HPLC.

Example 16

Expression of an Isobutanol Biosynthetic Pathway in E. coli Grown on Sucrose

Since the strains described in Example 15 were not capable of growth on sucrose, an additional plasmid was constructed to allow utilization of sucrose for isobutanol production. A sucrose utilization gene cluster cscBKA, given as SEQ ID NO:39, was isolated from genomic DNA of a sucrose-utilizing E. coli strain derived from ATCC strain 13281. The sucrose utilization genes (cscA, cscK, and cscB) encode a sucrose hydrolase (CscA), given as SEQ ID NO:139, D-fructokinase (CscK), given as SEQ ID NO:140, and sucrose permease (CscB), given as SEQ ID NO:141. The sucrose-specific repressor gene cscR was not included so that the three genes cscBKA were expressed constitutively from their native promoters in E. coli.

Genomic DNA from the sucrose-utilizing E. coli strain was digested to completion with BamHI and EcoRI. Fragments having an average size of about 4 kbp were isolated from an agarose gel and were ligated to plasmid pLitmus28 (New England Biolabs), digested with BamHI and EcoRI and transformed into ultracompetent E. coli TOP10F' cells (Invitrogen). The transformants were streaked onto MacConkey agar plates containing 1% sucrose and ampicillin (100 µg/mL) and screened for the appearance of purple colonies. Plasmid DNA was isolated from the purple transformants, and sequenced with M13 Forward and Reverse primers (Invitrogen), and Scr1-4 (given as SEQ ID NOs:72-75, respectively). The plasmid containing cscB, cscK, and cscA (cscBKA) genes was designated pScr1.

To create a sucrose utilization plasmid that was compatible with the isobutanol pathway plasmid (Example 14), the operon from pScr1 was subcloned into pBHR1 (MoBiTec, Goettingen, Germany). The cscBKA genes were isolated by digestion of pScr1 with XhoI (followed by incubation with Klenow enzyme to generate blunt ends) and then by digestion with AgeI. The resulting 4.2 kbp fragment was ligated into pBHR1 that had been digested with NaeI and AgeI, resulting in the 9.3 kbp plasmid pBHR1::cscBKA.

The sucrose plasmid pBHR1::cscBKA was transformed into E. coli BL21 (DE3) 1.5 yqhD/pTrc99A::budB-ilvC-ilvD-kivD and E. coli MG1655 1.5yqhD/pTrc99A::budB-ilvC-ilvD-kivD (described in Example 15) by electroporation. Transformants were first selected on LB medium containing 100 µg/mL ampicillin and 50 µg/mL kanamycin and then screened on MacConkey sucrose (1%) plates to confirm functional expression of the sucrose operon. For production of isobutanol, strains were grown in TM3a minimal defined medium (described in Example 15) containing 1% sucrose instead of glucose, and the culture medium was analyzed for the amount of isobutanol produced, as described in Example 15, except that samples were taken 14 h after induction. Again, no isobutanol was detected in control strains carrying only the pTrc99A vector (results not shown). Molar selectivities and titers of isobutanol produced by MG1655 1.5yqhD carrying pTrc99A::budB-ilvC-ilvD-kivD are shown in Table 6. Similar results were obtained with the analogous BL21 (DE3) strain.

TABLE 6

Production of Isobutanol by E. coli strain MG1655 1.5yqhD/pTrc99A::budB-ilvC-ilvD-kivD/pBHR1::cscBKA Grown on Sucrose

| O₂ Conditions | IPTG, mM | Isobutanol, mM* | Molar Selectivity, % |
| --- | --- | --- | --- |
| High | 0.04 | 0.17 | 2 |
| High | 0.4 | 1.59 | 21 |
| Low | 0.04 | 4.03 | 26 |
| Low | 0.4 | 3.95 | 29 |

*Determined by HPLC.

Example 17

Expression of Isobutanol Pathway Genes in Saccharomyces Cerevisiae

To express isobutanol pathway genes in Saccharomyces cerevisiae, a number of E. coli-yeast shuttle vectors were constructed. A PCR approach (Yu, et al. Fungal Genet. Biol. 41:973-981(2004)) was used to fuse genes with yeast promoters and terminators. Specifically, the GPD promoter (SEQ ID NO:76) and CYC1 terminator (SEQ ID NO:77) were fused to the alsS gene from Bacillus subtilis (SEQ ID NO:78), the FBA promoter (SEQ ID NO:79) and CYC1 terminator were fused to the ILV5 gene from S. cerevisiae (SEQ ID NO:80), the ADH1 promoter (SEQ ID NO:81) and ADH1 terminator (SEQ ID NO:82) were fused to the ILV3 gene from S. cerevisiae (SEQ ID NO:83), and the GPM promoter (SEQ ID NO:84) and ADH1 terminator were fused to the kivD gene from Lactococcus lactis (SEQ ID NO:7). The primers, given in Table 7, were designed to include restriction sites for cloning promoter/gene/terminator products into E. coli-yeast shuttle vectors from the pRS400 series (Christianson et al. Gene 110:119-122 (1992)) and for exchanging promoters between constructs. Primers for the 5' ends of ILV5 and ILV3 (N138 and N155, respectively, given as SEQ ID NOs: 95 and 107, respectively) generated new start codons to eliminate mitochondrial targeting of these enzymes.

All fused PCR products were first cloned into pCR4-Blunt by TOPO cloning reaction (Invitrogen) and the sequences were confirmed (using M13 forward and reverse primers (Invitrogen) and the sequencing primers provided in Table 7. Two additional promoters (CUP1 and GAL1) were cloned by TOPO reaction into pCR4-Blunt and confirmed by sequencing; primer sequences are indicated in Table 7. The plasmids that were constructed are described in Table 8. The plasmids were transformed into either Saccharomyces cerevisiae BY4743 (ATCC 201390) or YJR148w (ATCC 4036939) to assess enzyme specific activities using the enzyme assays described in Examples 1-4 and Examples 9-12. For the determination of enzyme activities, cultures were grown to an $OD_{600}$ of 1.0 in synthetic complete medium (Methods in Yeast Genetics, 2005, Cold Spring Harbor Laboratory Press, Cold Spring Harbor, N.Y., pp. 201-202) lacking any metabolite(s) necessary for selection of the expression plasmid(s), harvested by centrifugation (2600×g for 8 min at 4° C.), washed with buffer, centrifuged again, and frozen at −80° C. The cells were thawed, resuspended in 20 mM Tris-HCl, pH 8.0 to a final volume of 2 mL, and then disrupted using a bead beater with 1.2 g of glass beads (0.5 mm size). Each sample was processed on high speed for 3 minutes total (with incubation on ice after each minute of beating). Extracts were cleared of cell debris by centrifugation (20,000×g for 10 min at 4° C.).

TABLE 7

Primer Sequences for Cloning and Sequencing of S. cerevisiae Expression Vectors

| Name | Sequence | Description | SEQ ID NO: |
|---|---|---|---|
| N98SeqF1 | CGTGTTAGTCACATCAGGAC | B. subtilis alsS sequencing primer | 85 |
| N98SeqF2 | GGCCATAGCAAAAATCCAAACAGC | B. subtilis alsS sequencing primer | 86 |
| N98SeqF3 | CCACGATCAATCATATCGAACACG | B. subtilis alsS sequencing primer | 87 |
| N98SeqF4 | GGTTTCTGTCTCTGGTGACG | B. subtilis alsS sequencing primer | 88 |
| N99SeqR1 | GTCTGGTGATTCTACGCGCAAG | B. subtilis alsS sequencing primer | 89 |
| N99SeqR2 | CATCGACTGCATTACGCAACTC | B. subtilis alsS sequencing primer | 90 |
| N99SeqR3 | CGATCGTCAGAACAACATCTGC | B. subtilis alsS sequencing primer | 91 |
| N99SeqR4 | CCTTCAGTGTTCGCTGTCAG | B. subtilis alsS sequencing primer | 92 |
| N136 | CCGCGGATAGATCTGAAATGAATAACAATACTGACA | FBA promoter forward primer with SaclL/BglII sites | 93 |
| N137 | TACCACCGAAGTTGATTTGCTTCAACATCCTCAGCTCTAGATTTGAATATGTATTACTTGGTTAT | FBA promoter reverse primer with BbvCI site and ILV5-annealing region | 94 |
| N138 | ATGTTGAAGCAAATCAACTTCGGTGGTA | ILV5 forward primer (creates alternate start codon) | 95 |
| N139 | TTATTGGTTTTCTGGTCTCAC | A ILV5 reverse primer | 96 |
| N140 | AAGTTGAGACCAGAAAACCAATAATTAATTAATCATGTAATTAGTTATGTCACGCTT | CYC terminator forward primer with PacI site and ILV5-annealing region | 97 |
| N141 | GCGGCCGCCCGCAAATTAAAGCCTTCGAGC | CYC terminator reverse primer with NotI site | 98 |
| N142 | GGATCCGCATGCTTGCATTTAGTCGTGC | GPM promoter forward primer with BamHI site | 99 |
| N143 | CAGGTAATCCCCCACAGTATACATCCTCAGCTATTGTAATATGTGTGTTTGTTTGG | GPM promoter reverse primer with BbvCI site and kivD-annealing region | 100 |
| N144 | ATGTATACTGTGGGGGATTACC | kivD forward primer | 101 |
| N145 | TTAGCTTTTATTTTGCTCCGCA | kivD reverse primer | 102 |
| N146 | TTTGCGGAGCAAAATAAAAGCTAATTAATTAAGAGTAAGCGAATTTCTTATGATTTA | ADH terminator forward primer with PacI site and kivD-annealing region | 103 |
| N147 | ACTAGTACCACAGGTGTTGTCCTCTGAG | ADH terminator reverse primer with SpeI site | 104 |
| N151 | CTAGAGAGCTTTCGTTTTCATG | alsS reverse primer | 105 |
| N152 | CTCATGAAAACGAAAGCTCTCTAGTTAATTAATCATGTAATTAGTTATGTCACGCTT | CYC terminator forward primer with PacI site and alsS-annealing region | 106 |
| N155 | ATGGCAAAGAAGCTCAACAAGTACT | ILV3 forward primer (alternate start codon) | 107 |
| N156 | TCAAGCATCTAAAACACAACCG | ILV3 reverse primer | 108 |

TABLE 7-continued

Primer Sequences for Cloning and Sequencing of
*S. cerevisiae* Expression Vectors

| Name | Sequence | Description | SEQ ID NO: |
|---|---|---|---|
| N157 | AACGGTTGTGTTTTAGATGCTTGA TTAATTAAGAGTAAGCGAATTTCT TATGATTTA | ADH terminator forward primer with PacI site and ILV3-annealing region | 109 |
| N158 | GGATCCTTTTCTGGCAACCAAACC CATA | ADH promoter forward primer with BamHI site | 110 |
| N159 | CGAGTACTTGTTGAGCTTCTTTGC CATCCTCAGCGAGATAGTTGATTG TATGCTTG | ADH promoter reverse primer with BbvCI site and ILV3-annealing region | 111 |
| N160SeqF1 | GAAAACGTGGCATCCTCTC | FBA::ILV5::CYC sequencing primer | 112 |
| N160SeqF2 | GCTGACTGGCCAAGAGAAA | FBA::ILV5::CYC sequencing primer | 113 |
| N160SeqF3 | TGTACTTCTCCCACGGTTTC | FBA::ILV5::CYC sequencing primer | 114 |
| N160SeqF4 | AGCTACCCAATCTCTATACCCA | FBA::ILV5::CYC sequencing primer | 115 |
| N160SeqF5 | CCTGAAGTCTAGGTCCCTATTT | FBA::ILV5::CYC sequencing primer | 116 |
| N160SeqR1 | GCGTGAATGTAAGCGTGAC | FBA::ILV5::CYC sequencing primer | 117 |
| N160SeqR2 | CGTCGTATTGAGCCAAGAAC | FBA::ILV5::CYC sequencing primer | 118 |
| N160SeqR3 | GCATCGGACAACAAGTTCAT | FBA::ILV5::CYC sequencing primer | 119 |
| N160SeqR4 | TCGTTCTTGAAGTAGTCCAACA | FBA::ILV5::CYC sequencing primer | 120 |
| N160SeqR5 | TGAGCCCGAAAGAGAGGAT | FBA::ILV5::CYC sequencing primer | 121 |
| N161SeqF1 | ACGGTATACGGCCTTCCTT | ADH::ILV3::ADH sequencing primer | 122 |
| N161SeqF2 | GGGTTTGAAAGCTATGCAGT | ADH::ILV3::ADH sequencing primer | 123 |
| N161SeqF3 | GGTGGTATGTATACTGCCAACA | ADH::ILV3::ADH sequencing primer | 124 |
| N161SeqF4 | GGTGGTACCCAATCTGTGATTA | ADH::ILV3::ADH sequencing primer | 125 |
| N161SeqF5 | CGGTTTGGGTAAAGATGTTG | ADH::ILV3::ADH sequencing primer | 126 |
| N161SeqF6 | AAACGAAAATTCTTATTCTTGA | ADH::ILVD::ADH sequencing primer | 127 |
| N161SeqR1 | TCGTTTTAAAACCTAAGAGTCA | ADH::ILV3::ADH sequencing primer | 128 |
| N161SeqR2 | CCAAACCGTAACCCATCAG | ADH::ILV3::ADH sequencing primer | 129 |
| N161SeqR3 | CACAGATTGGGTACCACCA | ADH::ILV3::ADH sequencing primer | 130 |
| N161SeqR4 | ACCACAAGAACCAGGACCTG | ADH::ILV3::ADH sequencing primer | 131 |
| N161SeqR5 | CATAGCTTTCAAACCCGCT | ADH::ILV3::ADH sequencing primer | 132 |

TABLE 7-continued

Primer Sequences for Cloning and Sequencing of *S. cerevisiae* Expression Vectors

| Name | Sequence | Description | SEQ ID NO: |
|---|---|---|---|
| N161SeqR6 | CGTATACCGTTGCTCATTAGAG | ADH::ILV3::ADH sequencing primer | 133 |
| N162 | ATGTTGACAAAAGCAACAAAAGA | alsS forward primer | 134 |
| N189 | ATCCGCGGATAGATCTAGTTCGAGTTTATCATTATCAA | GPD forward primer with SacII/BglII sites | 135 |
| N190.1 | TTCTTTTGTTGCTTTTGTCAACATCCTCAGCGTTTATGTGTGTTTATTCGAAA | GPD promoter reverse primer with BbvCI site and alsS-annealing region | 136 |
| N176 | ATCCGCGGATAGATCTATTAGAAGCCGCCGAGCGGGCG | GAL1 promoter forward primer with SacII/BglII sites | 137 |
| N177 | ATCCTCAGCTTTTCTCCTTGACGTTAAAGTA | GAL1 promoter reverse with BbvCI site | 138 |
| N191 | ATCCGCGGATAGATCTCCCATTACCGACATTTGGGCGC | CUP1 promoter forward primer with SacII/BglII sites | 175 |
| N192 | ATCCTCAGCGATGATTGATTGATTGATTGTA | CUP1 promoter reverse with BbvCI site | 176 |

TABLE 8

*E. coli*-Yeast Shuttle Vectors Carrying Isobutanol Pathway Genes

| Plasmid Name | Construction |
|---|---|
| pRS426 [ATCC No. 77107], URA3 selection | — |
| pRS426::GPD::alsS::CYC | GPD::alsS::CYC PCR product digested with SacII/NotI cloned into pRS426 digested with same |
| pRS426::FBA::ILV5::CYC | FBA::ILV5::CYC PCR product digested with SacII/NotI cloned into pRS426 digested with same |
| pRS425 [ATCC No. 77106], LEU2 selection | — |
| pRS425::ADH::ILV3::ADH | ADH::ILV3::ADH PCR product digested with BamHI/SpeI cloned into pRS425 digested with same |
| pRS425::GPM::kivD::ADH | GPM::kivD::ADH PCR product digested with BamHI/SpeI cloned into pRS425 digested with same |
| pRS426::CUP1::alsS | 7.7 kbp SacII/BbvCI fragment from pRS426::GPD::alsS::CYC ligated with SacII/BbvCI CUP1 fragment |
| pRS426::GAL1::ILV5 | 7 kbp SacII/BbvCI fragment from pRS426::FBA::ILV5::CYC ligated with SacII/BbvCI GAL1 fragment |
| pRS425::FBA::ILV3 | 8.9 kbp BamHI/BbvCI fragment from pRS425::ADH::ILV3::ADH ligated with 0.65 kbp BglII/BbvCI FBA fragment from pRS426::FBA::ILV5::CYC |
| pRS425::CUP1-alsS + FBA-ILV3 | 2.4 kbp SacII/NotI fragment from pRS426::CUP1::alsS cloned into pRS425::FBA::ILV3 cut with SacII/NotI |
| pRS426::FBA-ILV5 + GPM-kivD | 2.7 kbp BamHI/SpeI fragment from pRS425::GPM::kivD::ADH cloned into pRS426::FBA::ILV5::CYC cut with BamHI/SpeI |
| pRS426::GAL1-FBA + GPM-kivD | 8.5 kbp SacII/NotI fragment from pRS426::FBA-ILV5 + GPM-kivD ligated with 1.8 kbp SacII/NotI fragment from pRS426::GAL1::ILV5 |
| pRS423 [ATCC No. 77104], HIS3 selection | — |
| pRS423::CUP1-alsS + FBA-ILV3 | 5.2 kbp SacI/SalI fragment from pRS425::CUP1-alsS + FBA-ILV3 ligated into pRS423 cut with SacI/SalI |
| pHR81 [ATCC No. 87541], URA3 and leu2-d selection | — |

TABLE 8-continued

E. coli-Yeast Shuttle Vectors Carrying Isobutanol Pathway Genes

| Plasmid Name | Construction |
|---|---|
| pHR81::FBA-ILV5 + GPM-kivD | 4.7 kbp SacI/BamHI fragment from pRS426::FBA-ILV5 + GPM-kivD ligated into pHR81 cut with SacI/BamHI |

Example 18

Production of Isobutanol by Recombinant *Saccharomyces Cerevisiae*

Plasmids pRS423::CUP1-alsS+FBA-ILV3 and pHR81::FBA-ILV5+GPM-kivD (described in Example 17) were transformed into *Saccharomyces cerevisiae* YJR148w to produce strain YJR148w/pRS423::CUP1-alsS+FBA-ILV3/pHR81::FBA-ILV5+GPM-kivD. A control strain was prepared by transforming vectors pRS423 and pHR81 (described in Example 17) into *Saccharomyces cerevisiae* YJR148w (strain YJR148w/pRS423/pHR81). Strains were maintained on standard *S. cerevisiae* synthetic complete medium (*Methods in Yeast Genetics*, 2005, Cold Spring Harbor Laboratory Press, Cold Spring Harbor, N.Y., pp. 201-202) containing either 2% glucose or sucrose but lacking uracil and histidine to ensure maintenance of plasmids.

For isobutanol production, cells were transferred to synthetic complete medium lacking uracil, histidine and leucine. Removal of leucine from the medium was intended to trigger an increase in copy number of the pHR81-based plasmid due to poor transcription of the leu2-d allele (Erhart and Hollenberg, *J. Bacteriol.* 156:625-635 (1983)). Aerobic cultures were grown in 175 mL capacity flasks containing 50 mL of medium in an Innova4000 incubator (New Brunswick Scientific, Edison, N.J.) at 30° C. and 200 rpm. Low oxygen cultures were prepared by adding 45 mL of medium to 60 mL serum vials that were sealed with crimped caps after inoculation and kept at 30° C. Sterile syringes were used for sampling and addition of inducer, as needed. Approximately 24 h after inoculation, the inducer CuSO$_4$ was added to a final concentration of 0.03 mM. Control cultures for each strain without CuSO$_4$ addition were also prepared. Culture supernatants were analyzed 18 or 19 h and 35 h after CuSO$_4$ addition by both GC and HPLC for isobutanol content, as described above in Example 15. The results for *S. cerevisiae* YJR148w/pRS423::CUP1-alsS+FBA-ILV3/pHR81::FBA-ILV5+GPM-kivD grown on glucose are presented in Table 9. For the results given in Table 9, the samples from the aerobic cultures were taken at 35 h and the samples from the low oxygen cultures were taken at 19 h and measured by HPLC.

The results for *S. cerevisiae* YJR148w/pRS423::CUP1-alsS+FBA-ILV3/pHR81::FBA-ILV5+GPM-kivD grown on sucrose are presented in Table 10. The results in this table were obtained with samples taken at 18 h and measured by HPLC.

TABLE 9

Production of Isobutanol by *S. cerevisiae* YJR148w/pRS423::CUP1-alsS + FBA-ILV3/pHR81::FBA-ILV5 + GPM-kivD Grown on Glucose

| Strain | O$_2$ level | Isobutanol, mM | Molar Selectivity % |
|---|---|---|---|
| YJR148w/pRS423/pHR81 (control) | Aerobic | 0.12 | 0.04 |
| YJR148w/pRS423/pHR81 (control) | Aerobic | 0.11 | 0.04 |

TABLE 9-continued

Production of Isobutanol by *S. cerevisiae* YJR148w/pRS423::CUP1-alsS + FBA-ILV3/pHR81::FBA-ILV5 + GPM-kivD Grown on Glucose

| Strain | O$_2$ level | Isobutanol, mM | Molar Selectivity % |
|---|---|---|---|
| YJR148w/pRS423::CUP1-alsS + FBA-ILV3/pHR81::FBA-ILV5 + GPM-kivD a | Aerobic | 0.97 | 0.34 |
| YJR148w/pRS423::CUP1-alsS + FBA-ILV3/pHR81::FBA-ILV5 + GPM-kivD b | Aerobic | 0.93 | 0.33 |
| YJR148w/pRS423::CUP1-alsS + FBA-ILV3/pHR81::FBA-ILV5 + GPM-kivD c | Aerobic | 0.85 | 0.30 |
| YJR148w/pRS423/pHR81 (control) | Low | 0.11 | 0.1 |
| YJR148w/pRS423/pHR81 (control) | Low | 0.08 | 0.1 |
| YJR148w/pRS423::CUP1-alsS + FBA-ILV3/pHR81::FBA-ILV5 + GPM-kivD a | Low | 0.28 | 0.5 |
| YJR148w/pRS423::CUP1-alsS + FBA-ILV3/pHR81::FBA-ILV5 + GPM-kivD b | Low | 0.20 | 0.3 |
| YJR148w/pRS423::CUP1-alsS + FBA-ILV3/pHR81::FBA-ILV5 + GPM-kivD c | Low | 0.33 | 0.6 |

TABLE 10

Production of Isobutanol by *S. cerevisiae* YJR148w/pRS423::CUP1-alsS + FBA-ILV3/pHR81::FBA-ILV5 + GPM-kivD Grown on Sucrose

| Strain | O$_2$ Level | Isobutanol mM | Molar Selectivity, % |
|---|---|---|---|
| YJR148w/pRS423/pHR81 (control) | Aerobic | 0.32 | 0.6 |
| YJR148w/pRS423/pHR81 (control) | Aerobic | 0.17 | 0.3 |
| YJR148w/pRS423::CUP1-alsS + FBA-ILV3/pHR81::FBA-ILV5 + GPM-kivD a | Aerobic | 0.68 | 1.7 |
| YJR148w/pRS423::CUP1-alsS + FBA-ILV3/pHR81::FBA-ILV5 + GPM-kivD b | Aerobic | 0.54 | 1.2 |
| YJR148w/pRS423::CUP1-alsS + FBA-ILV3/pHR81::FBA-ILV5 + GPM-kivD c | Aerobic | 0.92 | 2.0 |
| YJR148w/pRS423/pHR81 (control) | Low | 0.18 | 0.3 |
| YJR148w/pRS423/pHR81 (control) | Low | 0.15 | 0.3 |
| YJR148w/pRS423::CUP1-alsS + FBA-ILV3/pHR81::FBA-ILV5 + GPM-kivD a | Low | 0.27 | 1.2 |
| YJR148w/pRS423::CUP1-alsS + FBA-ILV3/pHR81::FBA-ILV5 + GPM-kivD b | Low | 0.30 | 1.1 |
| YJR148w/pRS423::CUP1-alsS + FBA-ILV3/pHR81::FBA-ILV5 + GPM-kivD c | Low | 0.21 | 0.8 |

Strain suffixes "a", "b", and "c" indicate separate isolates.

The results indicate that, when grown on glucose or sucrose under both aerobic and low oxygen conditions, strain YJR148w/pRS423::CUP1-alsS+FBA-ILV3/pHR81::FBA-ILV5+GPM-kivD produced consistently higher levels of isobutanol than the control strain.

Example 19

Production of Isobutanol by Recombinant *Saccharomyces Cerevisiae*

Plasmids pRS425::CUP1-alsS+FBA-ILV3 and pRS426::GAL1-ILV5+GPM-kivD (described in Example 17) were transformed into *Saccharomyces cerevisiae* YJR148w to produce strain YJR148w/pRS425::CUP1-alsS+FBA-ILV3/pRS426::GAL1-ILV5+GPM-kivD. A control strain was prepared by transforming vectors pRS425 and pRS426 (described in Example 17) into *Saccharomyces cerevisiae* YJR148w (strain YJR148w/pRS425/pRS426). Strains were maintained on synthetic complete medium, as described in Example 18.

For isobutanol production, cells were transferred to synthetic complete medium containing 2% galactose and 1% raffinose, and lacking uracil and leucine. Aerobic and low oxygen cultures were prepared as described in Example 18. Approximately 12 h after inoculation, the inducer $CuSO_4$ was added up to a final concentration of 0.5 mM. Control cultures for each strain without $CuSO_4$ addition were also prepared. Culture supernatants were sampled 23 h after $CuSO_4$ addition for determination of isobutanol by HPLC, as described in Example 18. The results are presented in Table 11. Due to the widely different final optical densities observed and associated with quantifying the residual carbon source, the concentration of isobutanol per $OD_{600}$ unit (instead of molar selectivities) is provided in the table to allow comparison of strains containing the isobutanol biosynthetic pathway genes with the controls.

TABLE 11

Production of Isobutanol by *S. cerevisiae* YJR148w/pRS425::CUP1-alsS + FBA-ILV3/pRS426::GAL1-ILV5 + GPM-kivD Grown on Galactose and Raffinose

| Strain | $O_2$ level | $CuSO_4$, mM | Iso-butanol mM | mM Iso-butanol per OD unit |
|---|---|---|---|---|
| YJR148w/pRS425/pRS426 (control) | Aerobic | 0.1 | 0.12 | 0.01 |
| YJR148w/pRS425/pRS426 (control) | Aerobic | 0.5 | 0.13 | 0.01 |
| YJR148w/pRS425::CUP1-alsS + FBA-ILV3/pRS426::GAL1-ILV5 + GPM-kivD a | Aerobic | 0 | 0.20 | 0.03 |
| YJR148w/pRS425::CUP1-alsS + FBA-ILV3/pRS426::GAL1-ILV5 + GPM-kivD b | Aerobic | 0.03 | 0.82 | 0.09 |
| YJR148w/pRS425::CUP1-alsS + FBA-ILV3/pRS426::GAL1-ILV5 + GPM-kivD c | Aerobic | 0.1 | 0.81 | 0.09 |
| YJR148w/pRS425::CUP1-alsS + FBA-ILV3/pRS426::GAL1-ILV5 + GPM-kivD d | Aerobic | 0.5 | 0.16 | 0.04 |
| YJR148w/pRS425::CUP1-alsS + FBA-ILV3/pRS426::GAL1-ILV5 + GPM-kivD e | Aerobic | 0.5 | 0.18 | 0.01 |
| YJR148w/pRS425/pRS426 (control) | Low | 0.1 | 0.042 | 0.007 |
| YJR148w/pRS425/pRS426 (control) | Low | 0.5 | 0.023 | 0.006 |
| YJR148w/pRS425::CUP1-alsS + FBA-ILV3/pRS426::GAL1-ILV5 + GPM-kivD a | Low | 0 | 0.1 | 0.04 |
| YJR148w/pRS425::CUP1-alsS + FBA-ILV3/pRS426::GAL1-ILV5 + GPM-kivD b | Low | 0.03 | 0.024 | 0.02 |
| YJR148w/pRS425::CUP1-alsS + FBA-ILV3/pRS426::GAL1-ILV5 + GPM-kivD c | Low | 0.1 | 0.030 | 0.04 |
| YJR148w/pRS425::CUP1-alsS + FBA-ILV3/pRS426::GAL1-ILV5 + GPM-kivD d | Low | 0.5 | 0.008 | 0.02 |
| YJR148w/pRS425::CUP1-alsS + FBA-ILV3/pRS426::GAL1-ILV5 + GPM-kivD e | Low | 0.5 | 0.008 | 0.004 |

Strain suffixes "a", "b", "c", "d" and "e" indicate separate isolates.

The results indicate that in general, higher levels of isobutanol per optical density unit were produced by the YJR148w/pRS425::CUP1-alsS+FBA-ILV3/pRS426::GAL1-ILV5+GPM-kivD strain compared to the control strain under both aerobic and low oxygen conditions.

Example 20

Expression of an Isobutanol Biosynthetic Pathway in *Bacillus subtilis*

The purpose of this Example was to express an isobutanol biosynthetic pathway in *Bacillus subtilis*. The five genes of the isobutanol pathway (pathway steps (a) through (e) in FIG. 1) were split into two operons for expression. The three genes budB, ilvD, and kivD, encoding acetolactate synthase, acetohydroxy acid dehydratase, and branched-chain keto acid decarboxylase, respectively, were integrated into the chromosome of *B. subtilis* BE1010 (Payne and Jackson, *J. Bacteriol.* 173:2278-2282 (1991)). The two genes ilvC and bdhB, encoding acetohydroxy acid isomeroreductase and butanol dehydrogenase, respectively, were cloned into an expression vector and transformed into the *Bacillus* strain carrying the integrated isobutanol genes.

Integration of the Three Genes, budB, ilvD and kivD into the Chromosome of *B. subtilis* BE1010.

*Bacillus* integration vectors pFP988DssPspac and pFP988DssPgroE were used for the chromosomal integration of the three genes, budB (SEQ ID NO:1), ilvD (SEQ ID NO:5), and kivD (SEQ ID NO:7). Both plasmids contain an *E. coli* replicon from pBR322, an ampicillin antibiotic marker for selection in *E. coli* and two sections of homology to the sacB gene in the *Bacillus* chromosome that direct integration of the vector and intervening sequence by homologous recombination. Between the sacB homology regions is a spac promoter (PgroE) on pFP988DssPspac or a groEL promoter (PgroE) on pFP988DssPgroE, and a selectable marker for *Bacillus*, erythromycin. The promoter region also contains the lacO sequence for regulation of expression by a lacI repressor protein. The sequences of pFP988DssPspac (6,341 bp) and pFP988DssPgroE (6,221 bp) are given as SEQ ID NO:142 and SEQ ID NO:143 respectively.

The cassette with three genes budB-ilvD-kivD was constructed by deleting the ilvC gene from plasmid pTrc99a budB-ilvC-ilvD-kivD. The construction of the plasmid pTrc99A::budB-ilvC-ilvD-kivD is described in Example 14. Plasmid pTrc99A::budB-ilvC-ilvD-kivD was digested with AflII and NheI, treated with the Klenow fragment of DNA polymerase to make blunt ends, and the resulting 9.4 kbp fragment containing pTrc99a vector, budB, ilvD, and kivD was gel-purified. The 9.4 kbp vector fragment was self-ligated to create pTrc99A::budB-ilvD-kivD, and transformed into DH5α competent cells (Invitrogen). A clone of pTrc99a budB-ilvD-kivD was confirmed for the ilvC gene deletion by restriction mapping. The resulting plasmid pTrc99A::budB-ilvD-kivD was digested with SacI and treated with the Klenow fragment of DNA polymerase to make blunt ends. The plasmid was then digested with BamHI and the resulting 5,297 bp budB-ilvD-kivD fragment was gel-purified. The 5,297 bp budB-ilvD-kivD fragment was ligated into the SmaI and BamHI sites of the integration vector pFP988DssPspac. The ligation mixture was transformed into DH5α competent cells. Transformants were screened by PCR amplification of the 5.3 kbp budB-ilvD-kivD fragment with primers T-budB (BamHI) (SEQ ID NO:144) and B-kivD(BamHI) (SEQ ID NO:145). The correct clone was named pFP988DssPspac-budB-ilvD-kivD.

Plasmid pFP988DssPspac-budB-ilvD-kivD was prepared from the *E. coli* transformant, and transformed into *B. subtilis* BE1010 competent cells, which had been prepared as described by Doyle et al. (*J. Bacteriol.* 144:957 (1980)). Competent cells were harvested by centrifugation and the cell pellets were resuspended in a small volume of the supernatant. To one volume of competent cells, two volumes of SPII-EGTA medium (*Methods for General and Molecular Bacteriology*, P. Gerhardt et al., Ed., American Society for Microbiology, Washington, D.C. (1994)) was added. Aliquots (0.3 mL) of cells were dispensed into test tubes and then 2 to 3 µg of plasmid pFP988DssPspac-budB-ilvD-kivD was added to the tubes. The tubes were incubated for 30 min at 37° C. with shaking, after which 0.1 mL of 10% yeast extract was added to each tube and they were further incubated for 60 min. Transformants were grown for selection on LB plates containing erythromycin (1.0 µg/mL) using the double agar overlay method (*Methods for General and Molecular Bacteriology*, supra). Transformants were screened by PCR amplification with primers N130SeqF1 (SEQ ID NO:40) and N130SeqR1 (SEQ ID NO:44) for budB, and N133SeqF1 (SEQ ID NO:62) and N133SeqR1 (SEQ ID NO:66) for kivD. Positive integrants showed the expected 1.7 kbp budB and 1.7 kbp kivD PCR products. Two positive integrants were identified and named *B. subtilis* BE1010 ΔsacB::Pspac-budB-ilvD-kivD #2-3-2 and *B. subtilis* BE1010 ΔsacB::Pspac-budB-ilvD-kivD #6-12-7.

Assay of the enzyme activities in integrants *B. subtilis* BE1010 ΔsacB::Pspac-budB-ilvD-kivD #2-3-2 and *B. subtilis* BE1010 ΔsacB::Pspac-budB-ilvD-kivD #6-12-7 indicated that the activities of BudB, IlvD and KivD were low under the control of the spac promoter (Pspac). To improve expression of functional enzymes, the Pspac promoter was replaced by a PgroE promoter from plasmid pHT01 (MoBitec, Goettingen, Germany).

A 6,039 bp pFP988Dss vector fragment, given as SEQ ID NO:146, was excised from an unrelated plasmid by restriction digestion with XhoI and BamHI, and was gel-purified. The PgroE promoter was PCR-amplified from plasmid pHT01 with primers T-groE(XhoI) (SEQ ID NO:147) and B-groEL(SpeI,BamH1) (SEQ ID NO:148). The PCR product was digested with XhoI and BamHI, ligated with the 6,039 bp pFP988Dss vector fragment, and transformed into DH5α competent cells. Transformants were screened by PCR amplification with primers T-groE(XhoI) and B-groEL(SpeI, BamH1). Positive clones showed the expected 174 bp PgroE PCR product and were named pFP988DssPgroE. The plasmid pFP988DssPgroE was also confirmed by DNA sequence.

Plasmid pFP988DssPspac-budB-ilvD-kivD was digested with SpeI and PmeI and the resulting 5,313 bp budB-ilvD-kivD fragment was gel-purified. The budB-ilvD-kivD fragment was ligated into SpeI and PmeI sites of pFP988DssPgroE and transformed into DH5α competent cells. Positive clones were screened for a 1,690 bp PCR product by PCR amplification with primers T-groEL (SEQ ID NO:149) and N111 (SEQ ID NO:20). The positive clone was named pFP988DssPgroE-budB-ilvD-kivD.

Plasmid pFP988DssPgroE-budB-ilvD-kivD was prepared from the *E. coli* transformant, and transformed into *Bacillus subtilis* BE1010 competent cells as described above. Transformants were screened by PCR amplification with primers N130SeqF1 (SEQ ID NO:40) and N130SeqR1 (SEQ ID NO:44) for budB, and N133SeqF1 (SEQ ID NO:62) and N133SeqR1 (SEQ ID NO:66) for kivD. Positive integrants showed the expected 1.7 kbp budB and 1.7 kbp kivD PCR products. Two positive integrants were isolated and named *B. subtilis* BE1010 ΔsacB::PgroE-budB-ilvD-kivD #1-7 and *B. subtilis* BE1010 ΔsacB::PgroE-budB-ilvD-kivD #8-16.

Plasmid Expression of ilvC and bdhB Genes.

Two remaining isobutanol genes, ilvC and bdhB, were expressed from a plasmid. Plasmid pHT01 (MoBitec), a *Bacillus-E. coli* shuttle vector, was used to fuse an ilvC gene from *B. subtilis* to a PgroE promoter so that the ilvC gene was expressed from the PgroE promoter containing a lacO sequence. The ilvC gene, given as SEQ ID NO:186, was PCR-amplified from *B. subtilis* BR151 (ATCC 33677) genomic DNA with primers T-ilvCB.s.(BamHI) (SEQ ID NO:150) and B-ilvCB.s.(SpeI BamHI) (SEQ ID NO:151). The 1,067 bp ilvC PCR product was digested with BamHI and ligated into the BamHI site of pHT01. The ligation mixture was transformed into DH5α competent cells. Positive clones were screened for a 1,188 bp PCR product by PCR amplification with primers T-groEL and B-ilvB.s.(SpeI BamHI). The positive clone was named pHT01-ilvC(B.s). Plasmid pHT01-ilvC(B.s) was used as a template for PCR amplification of the PgroE-ilvC fused fragment.

Plasmid pBD64 (Minton et al., *Nucleic Acids Res.* 18:1651 (1990)) is a fairly stable vector for expression of foreign genes in *B. subtilis* and contains a repB gene and chloramphenicol and kanamycin resistance genes for selection in *B. subtilis*. This plasmid was used for expression of ilvC and bdhB under the control of a PgroE promoter. To clone PgroE-ilvC, bdhB and a lacI repressor gene into plasmid pBD64, a one-step assembly method was used (Tsuge et al., *Nucleic Acids Res.* 31:e133 (2003)). A 3,588 bp pBD64 fragment containing a repB gene, which included the replication function, and the kanamycin antibiotic marker was PCR-amplified from pBD64 with primers T-BD64(DraIII) (SEQ ID NO:152), which introduced a DraIII sequence (CAC<u>CGA</u>GTG), and B-BD64(DraIII) (SEQ ID NO:153), which introduced a DraIII sequence (CAC<u>CTG</u>GTG). A 1,327 bp lacI repressor gene was PCR-amplified from pMUTIN4 (Vagner et al., *Microbiol.* 144:3097-3104 (1998)) with T-lacIq(DraIII) (SEQ ID NO:154), which introduced a DraIII sequence (CAC<u>CAG</u>GTG) and B-lacIq(DraIII) (SEQ ID NO:155), which introduced a DraIII sequence (CAC<u>GGG</u>GTG). A 1,224 bp PgroE-ilvC fused cassette was PCR-amplified from pHT01-ilvC(B.s) with T-groE(DraIII) (SEQ ID NO:156), which introduced a DraIII sequence (CAC<u>CCC</u>GTG), and B-B.s.ilvC(DraIII) (SEQ ID NO:157), which introduced a DraIII sequence (CAC<u>CGT</u>GTG). A 1.2 kbp bdhB gene (SEQ ID NO:158) was PCR-amplified from *Clostridium acetobutylicum* (ATCC 824) genomic DNA with primers T-bdhB(DraIII) (SEQ ID NO:159), which introduced a DraIII sequence (CAC<u>ACG</u>GTG), and B-bdhB (rrnBT1DraIII) (SEQ ID NO:160), which introduced a DraIII sequence (CAC<u>TCG</u>GTG). The three underlined letters in the variable region of the DraIII recognition sequences were designed for specific base-pairing to assemble the four fragments with an order of pBD64-lacI-PgroEilvC-bdhB. Each PCR product with DraIII sites at both ends was digested separately with DraIII, and the resulting DraIII fragments, 3,588 bp pBD64, lacI, PgroEilvC, and bdhB were gel-purified using a QIAGEN gel extraction kit (QIAGEN). A mixture containing an equimolar concentration of each fragment with a total DNA concentration of 30 to 50 µg/100 µL was prepared for ligation. The ligation solution was then incubated at 16° C. overnight. The ligation generated high molecular weight tandem repeat DNA. The ligated long, linear DNA mixture was directly transformed into competent *B. subtilis* BE1010, prepared as described above. *B. subtilis* preferentially takes up long repeated linear DNA forms, rather than circular DNA to establish a plasmid. After transformation the culture was spread onto an LB plate containing 10 μg/mL of kanamycin for selection. Positive recombinant plasmids were screened by DraIII digestion, giving four fragments with an expected size of 3,588 bp (pBD64), 1,327 bp (lacI), 1,224 bp (PgorE-ilvC), and 1,194 bp (bdhB). The positive plasmid was named pBDPgroE-ilvC(B.s.)-bdhB.

Demonstration of Isobutanol Production from Glucose or Sucrose by B. subtilis BE1010 ΔsacB::PgroE-budB-ilvD-kivD/pBDPgroE-ilvC(B.s.)-bdhB.

To construct the recombinant B. subtilis expressing the five genes of the isobutanol biosynthetic pathway, competent cells of the two integrants B. subtilis BE1010 ΔsacB-PgroE-budB-ilvD-kivD #1-7 and B. subtilis BE1010 ΔsacB::PgroE-budB-ilvD-kivD #8-16 were prepared as described above, and transformed with plasmid pBDPgroE-ilvC(B.s.)-bdhB, yielding B. subtilis BE1010 ΔsacB::PgroE-budB-ilvD-kivD #1-7/pBDPgroE-ilvC(B.s.)-bdhB and B. subtilis BE1010 ΔsacB::PgroE-budB-ilvD-kivD #8-16/pBDPgroE-ilvC(B.s.)-bdhB.

The two recombinant strains were inoculated in either 25 mL or 100 mL of glucose medium containing kanamycin (10 μg/mL) in 125 mL flasks to simulate high and low oxygen conditions, respectively, and aerobically grown at 37° C. with shaking at 200 rpm. The medium consisted of 10 mM $(NH_4)_2SO_4$, 5 mM potassium phosphate buffer (pH 7.0), 100 mM MOPS/KOH buffer (pH 7.0), 20 mM glutamic acid/KOH (pH 7.0), 2% S10 metal mix, 1% glucose, 0.01% yeast extract, 0.01% casamino acids, and 50 μg/mL each of L-tryptophan, L-methionine, and L-lysine. The S10 metal mix consisted of 200 mM $MgCl_2$, 70 mM $CaCl_2$, 5 mM $MnCl_2$, 0.1 mM $FeCl_3$, 0.1 mM $ZnCl_2$, 0.2 mM thiamine hydrochloride, 0.172 mM $CuSO_4$, 0.253 mM $CoCl_2$, and 0.242 mM $Na_2MoO_4$. The cells were induced with 1.0 mM isopropyl-β-D-thiogalactopyranoiside (IPTG) at early-log phase ($OD_{600}$ of approximately 0.2). At 24 h after inoculation, an aliquot of the broth was analyzed by HPLC (Shodex Sugar SH1011 column) with refractive index (RI) detection for isobutanol content, as described in the General Methods section. The HPLC results are shown in Table 12.

TABLE 12

Production of Isobutanol from Glucose by B. subtilis BE1010 ΔsacB::PgroE-budB-ilvD-kivD/pBDPgroE-ilvC(B.s.)-bdhB Strains

| Strain | $O_2$ Level | isobutanol, mM | molar selectivity, % |
|---|---|---|---|
| B. subtilis a (induced) | high | 1.00 | 1.8 |
| B. subtilis b (induced) | high | 0.87 | 1.6 |
| B. subtilis a (induced) | low | 0.06 | 0.1 |
| B. subtilis b (induced) | low | 0.14 | 0.3 |

B. subtilis a is B. subtilis BE1010 ΔsacB::PgroE-budB-ilvD-kivD #1-7/ pBDPgroE-ilvC (B.s.)-bdhB
B. subtilis b is B. subtilis BE1010 ΔsacB::PgroE-budB-ilvD-kivD #8-16/pBDPgroE-ilvC (B.s.)-bdhB The isolate of B. subtilis BE1010 ΔsacB::PgroE-budB-ilvD-kivD #1-7/pBDPgroE-ilvC(B.s.)-bdhB was also examined for isobutanol production from sucrose, essentially as described above. The recombinant strain was inoculated in 25 mL or 75 mL of sucrose medium containing kanamycin (10 μg/mL) in 125 mL flasks to simulate high and medium oxygen levels, and grown at 37° C. with shaking at 200 rpm. The sucrose medium was identical to the glucose medium except that glucose (10 g/L) was replaced with 10 g/L of sucrose. The cells were uninduced, or induced with 1.0 mM isopropyl-β-D-thiogalactopyranoiside (IPTG) at early-log phase ($OD_{600}$ of approximately 0.2). At 24 h after inoculation, an aliquot of the broth was analyzed by HPLC (Shodex Sugar SH1011 column) with refractive index (RI) detection for isobutanol content, as described in the General Methods section. The HPLC results are given in Table 13.

TABLE 13

Production of Isobutanol from Sucrose by B. subtilis Strain BE1010 ΔsacB::PgroE-budB-ilvD-kivD/pBDPgroE-ilvC(B.s.)-bdhB

| Strain | $O_2$ Level | isobutanol, mM | molar selectivity, % |
|---|---|---|---|
| B. subtilis a (uninduced) | high | Not detected | Not detected |
| B. subtilis a (induced) | high | 0.44 | 4.9 |
| B. subtilis a (induced) | medium | 0.83 | 8.6 |

B. subtilis a is B. subtilis BE1010 ΔsacB::PgroE-budB-ilvD-kivD #1-7/pBDPgroE-ilvC (B.s.)-bdhB Example 21

Prophetic

Expression of an Isobutanol Biosynthetic Pathway in Lactobacillus plantarum

The purpose of this prophetic Example is to describe how to express an isobutanol biosynthetic pathway in Lactobacillus plantarum. The five genes of the isobutanol pathway, encoding five enzyme activities, are divided into two operons for expression. The budB, ilvD and kivD genes, encoding the enzymes acetolactate synthase, acetohydroxy acid dehydratase, and branched-chain α-keto acid decarboxylase, respectively, are integrated into the chromosome of Lactobacillus plantarum by homologous recombination using the method described by Hols et al. (Appl. Environ. Microbiol. 60:1401-1413 (1994)). The remaining two genes (ilvC and bdhB, encoding the enzymes acetohydroxy acid reductoisomerase and butanol dehydrogenase, respectively) are cloned into an expression plasmid and transformed into the Lactobacillus strain carrying the integrated isobutanol genes. Lactobacillus plantarum is grown in MRS medium (Difco Laboratories, Detroit, Mich.) at 37° C., and chromosomal DNA is isolated as described by Moreira et al. (BMC Microbiol. 5:15 (2005)).

Integration.

The budB-ilvD-kivD cassette under the control of the synthetic P11 promoter (Rud et al., Microbiology 152:1011-1019 (2006)) is integrated into the chromosome of Lactobacillus plantarum ATCC BAA-793 (NCIMB 8826) at the IdhL1 locus by homologous recombination. To build the IdhL integration targeting vector, a DNA fragment from Lactobacillus plantarum (Genbank NC_004567) with homology to IdhL is PCR amplified with primers LDH EcoRV F (SEQ ID NO:161) and LDH AatIIR (SEQ ID NO:162). The 1986 bp PCR fragment is cloned into pCR4Blunt-TOPO and sequenced. The pCR4Blunt-TOPO-IdhL1 clone is digested with EcoRV and AatII releasing a 1982 bp IdhL1 fragment that is gel-purified. The integration vector pFP988, given as SEQ ID NO:177, is digested with HindIII and treated with Klenow DNA polymerase to blunt the ends. The linearized plasmid is then digested with AatII and the 2931 bp vector fragment is gel purified. The EcoRV/AatII IdhL1 fragment is ligated with the pFP988 vector fragment and transformed into E. coli Top10 cells. Transformants are selected on LB agar plates containing ampicillin (100 µg/mL) and are screened by colony PCR to confirm construction of pFP988-IdhL.

To add a selectable marker to the integrating DNA, the Cm gene with its promoter is PCR amplified from pC194 (GenBank NC_002013, SEQ ID NO:267) with primers Cm F (SEQ ID NO:163) and Cm R (SEQ ID NO:164), amplifying a 836 bp PCR product. This PCR product is cloned into pCR4Blunt-TOPO and transformed into E. coli Top10 cells, creating pCR4Blunt-TOPO-Cm. After sequencing to confirm that no errors are introduced by PCR, the Cm cassette is digested from pCR4Blunt-TOPO-Cm as an 828 bp MluI/SwaI fragment and is gel purified. The IdhL-homology containing integration vector pFP988-IdhL is digested with MluI and SwaI and the 4740 bp vector fragment is gel purified. The Cm cassette fragment is ligated with the pFP988-IdhL vector creating pFP988-DldhL::Cm.

Finally the budB-ilvD-kivD cassette from pFP988DssPspac-budB-ilvD-kivD, described in Example 20, is modified to replace the amylase promoter with the synthetic P11 promoter. Then, the whole operon is moved into pFP988-DldhL::Cm. The P11 promoter is built by oligonucleotide annealing with primer P11 F-StuI (SEQ ID NO:165) and P11 R-SpeI (SEQ ID NO:166). The annealed oligonucleotide is gel-purified on a 6% Ultra PAGE gel (Embi Tec, San Diego, Calif.). The plasmid pFP988DssPspac-budB-ilvD-kivD, containing the amylase promoter, is digested with StuI and SpeI and the resulting 10.9 kbp vector fragment is gel-purified. The isolated P11 fragment is ligated with the digested pFP988DssPspac-budB-ilvD-kivD to create pFP988-P11-budB-ilvD-kivD. Plasmid pFP988-P11-budB-ilvD-kivD is then digested with StuI and BamHI and the resulting 5.4 kbp P11-budB-ilvD-kivD fragment is gel-purified. pFP988-DldhL::Cm is digested with HpaI and BamHI and the 5.5 kbp vector fragment isolated. The budB-ilvD-kivD operon is ligated with the integration vector pFP988-DldhL::Cm to create pFP988-DldhL-P11-budB-ilvD-kivD::Cm.

Integration of pFP988-DldhL-P11-budB-ilvD-kivD::Cm into L. plantarum BAA-793 to Form L. plantarum ΔIdhL1::budB-ilvD-kivD::Cm Comprising Exogenous budB, ilvD, and kivD Genes.

Electrocompetent cells of L. plantarum are prepared as described by Aukrust, T. W., et al. (In: Electroporation Protocols for Microorganisms; Nickoloff, J. A., Ed.; Methods in Molecular Biology, Vol. 47; Humana Press, Inc., Totowa, N.J., 1995, pp 201-208). After electroporation, cells are outgrown in MRSSM medium (MRS medium supplemented with 0.5 M sucrose and 0.1 M MgCl$_2$) as described by Aukrust et al. supra for 2 h at 37° C. without shaking. Electroporated cells are plated for selection on MRS plates containing chloramphenicol (10 µg/mL) and incubated at 37° C. Transformants are initially screened by colony PCR amplification to confirm integration, and initial positive clones are then more rigorously screened by PCR amplification with a battery of primers.

Plasmid Expression of ilvC and bdhB Genes.

The remaining two isobutanol genes are expressed from plasmid pTRKH3 (O'Sullivan D J and Klaenhammer T R, Gene 137:227-231 (1993)) under the control of the L. plantarum IdhL promoter (Ferain et al., J. Bacteriol. 176:596-601 (1994)). The IdhL promoter is PCR amplified from the genome of L. plantarum ATCC BAA-793 using primers PldhL F-HindIII (SEQ ID NO:167) and PldhL R-BamHI (SEQ ID NO:168). The 411 bp PCR product is cloned into pCR4Blunt-TOPO and sequenced. The resulting plasmid, pCR4Blunt-TOPO-PldhL is digested with HindIII and BamHI releasing the PldhL fragment.

Plasmid pTRKH3 is digested with HindIII and SphI and the gel-purified vector fragment is ligated with the PldhL fragment and the gel-purified 2.4 kbp BamHI/SphI fragment containing ilvC(B.s.)-bdhB from the Bacillus expression plasmid pBDPgroE-ilvC(B.s.)-bdhB (Example 20) in a three-way ligation. The ligation mixture is transformed into E. coli Top 10 cells and transformants are grown on Brain Heart Infusion (BHI, Difco Laboratories, Detroit, Mich.) plates containing erythromycin (150 mg/L). Transformants are screened by PCR to confirm construction. The resulting expression plasmid, pTRKH3-ilvC(B.s.)-bdhB is transformed into L. plantarum ΔIdhL1::budB-ilvD-kivD::Cm by electroporation, as described above.

L. plantarum ΔIdhL1::budB-ilvD-kivD::Cm containing pTRKH3-ilvC(B.s.)-bdhB is inoculated into a 250 mL shake flask containing 50 mL of MRS medium plus erythromycin (10 µg/mL) and grown at 37° C. for 18 to 24 h without shaking, after which isobutanol is detected by HPLC or GC analysis, as described in the General Methods section.

Example 22

Prophetic

Expression of an Isobutanol Biosynthetic Pathway in *Enterococcus faecalis*

The purpose of this prophetic Example is to describe how to express an isobutanol biosynthetic pathway in *Enterococcus faecalis*. The complete genome sequence of *Enterococcus faecalis* strain V583, which is used as the host strain for the expression of the isobutanol biosynthetic pathway in this Example, has been published (Paulsen et al., Science 299: 2071-2074 (2003)). An E. coli/Gram-positive shuttle vector, Plasmid pTRKH3 (O'Sullivan D J and Klaenhammer T R, Gene 137:227-231 (1993)), is used for expression of the five genes (budB, ilvC, ilvD, kivD, bdhB) of the isobutanol pathway in one operon. pTRKH3 contains an E. coli plasmid p15A replication origin, the pAMβ1 replicon, and two antibiotic resistance selection markers for tetracycline and erythromycin. Tetracycline resistance is only expressed in E. coli, and erythromycin resistance is expressed in both E. coli and Gram-positive bacteria. Plasmid pAMβ1 derivatives can replicate in E. faecalis (Poyart et al., FEMS Microbiol. Lett. 156:193-198 (1997)). The inducible nisA promoter (PnisA), which has been used for efficient control of gene expression by nisin in a variety of Gram-positive bacteria including *Enterococcus faecalis* (Eichenbaum et al., Appl. Environ. Microbiol. 64:2763-2769 (1998)), is used to control expression of the five desired genes encoding the enzymes of the isobutanol biosynthetic pathway.

The plasmid pTrc99A::budB-ilvC-ilvD-kivD (described in Example 14), which contains the isobutanol pathway operon, is modified to replace the E. coli ilvC gene (SEQ ID NO:3) with the B. subtilis ilvC gene (SEQ ID NO: 184). Additionally, the bdhB gene (SEQ ID NO:158) from *Clostridium acetobutylicum* is added to the end of the operon. First, the bdhB gene from pBDPgroE-ilvC(B.s.)-bdhB (described in Example 20) is amplified using primers F-bdhB-AvrII (SEQ ID NO:169) and R-bdhB-BamHI (SEQ ID NO:170), and then TOPO cloned and sequenced. The 1194 bp bdhB fragment is isolated by digestion with AvrII and BamHI, followed by gel purification. This bdhB fragment is ligated with pTrc99A::budB-ilvC-ilvD-kivD that has previously been digested with AvrII and BamHI and the resulting fragment is gel purified. The ligation mixture is transformed into E. coli Top10 cells by electroporation and transformants are selected following overnight growth at 37° C. on LB agar plates containing ampicillin (100 μg/mL). The transformants are then screened by colony PCR to confirm the correct clone containing pTrc99A::budB-ilvC-ilvD-kivD-bdhB.

Next, ilvC(B.s.) is amplified from pBDPgroE-ilvC(B.s.)-bdhB (described in Example 20) using primers F-ilvC(B.s.)-AflIII (SEQ ID NO:171) and R-ilvC(B.s.)-NotI (SEQ ID NO:172). The PCR product is TOPO cloned and sequenced. The 1051 bp ilvC(B.s.) fragment is isolated by digestion with AflIII and NotI followed by gel purification. This fragment is ligated with pTrc99A::budB-ilvC-ilvD-kivD-bdhB that has been cut with AflIII and NotI to release the E. coli ilvC (the 10.7 kbp vector band is gel purified prior to ligation with ilvC(B.s.)). The ligation mixture is transformed into E. coli Top10 cells by electroporation and transformants are selected following overnight growth at 37° C. on LB agar plates containing ampicillin (100 μg/mL). The transformants are then screened by colony PCR to confirm the correct clone containing pTrc99A::budB-ilvC(B.s.)-ilvD-kivD-bdhB.

To provide a promoter for the E. coli/Gram-positive shuttle vector pTRKH3, the nisA promoter (Chandrapati et al., *Mol. Microbiol.* 46(2):467-477 (2002)) is PCR-amplified from *Lactococcus lactis* genomic DNA with primers F-PnisA(HindIII) (SEQ ID NO:173) and R-PnisA(SpeI BamHI) (SEQ ID NO:174) and then TOPO cloned. After sequencing, the 213 bp nisA promoter fragment is isolated by digestion with HindIII and BamHI followed by gel purification. Plasmid pTRKH3 is digested with HindIII and BamHI and the vector fragment is gel-purified. The linearized pTRKH3 is ligated with the PnisA fragment and transformed into E. coli Top10 cells by electroporation. Transformants are selected following overnight growth at 37° C. on LB agar plates containing erythromycin (25 μg/mL). The transformants are then screened by colony PCR to confirm the correct clone of pTRKH3-PnisA.

Plasmid pTRKH3-PnisA is digested with SpeI and BamHI, and the vector is gel-purified. Plasmid pTrc99A::budB-ilvC(B.s.)-ilvD-kivD-bdhB, described above, is digested with SpeI and BamHI, and the 7.5 kbp fragment is gel-purified. The 7.5 kbp budB-ilvC(B.s.)-ilvD-kivD-bdhB fragment is ligated into the pTRKH3-PnisA vector at the SpeI and BamHI sites. The ligation mixture is transformed into E. coli Top10 cells by electroporation and transformants are selected following overnight growth on LB agar plates containing erythromycin (25 μg/mL) at 37° C. The transformants are then screened by colony PCR. The resulting plasmid is named pTRKH3-PnisA-budB-ilvC(B.s.)-ilvD-kivD-bdhB. This plasmid is prepared from the E. coli transformants and transformed into electrocompetent E. faecalis V583 cells by electroporation using methods known in the art (Aukrust, T. W., et al. In: *Electroporation Protocols for Microorganisms*; Nickoloff, J. A., Ed.; *Methods in Molecular Biology*, Vol. 47; Humana Press, Inc., Totowa, N.J., 1995, pp 217-226), resulting in E. faecalis V583/pTRKH3-PnisA-budB-ilvC(B.s)-ilvD-kivD-bdhB.

The second plasmid containing nisA regulatory genes, nisR and nisK, the add9 spectinomycin resistance gene, and the pSH71 origin of replication is transformed into E. faecalis V583/pTRKH3-PnisA-budB-ilvC(B.s.)-ilvD-kivD-bdhB by electroporation. The plasmid containing pSH71 origin of replication is compatible with pAMβ1 derivatives in E. faecalis (Eichenbaum et al., supra). Double drug resistant transformants are selected on LB agar plates containing erythromycin (25 μg/mL) and spectinomycin (100 μg/mL), grown at 37° C.

The resulting E. faecalis strain V5838 harboring two plasmids, i.e., an expression plasmid (pTRKH3-PnisA-budB-ilvC(B.s.)-ilvD-kivD-bdhB) and a regulatory plasmid (pSH71-nisRK), is inoculated into a 250 mL shake flask containing 50 mL of Todd-Hewitt broth supplemented with yeast extract (0.2%) (Fischetti et al., *J. Exp. Med.* 161:1384-1401 (1985)), nisin (20 μg/mL) (Eichenbaum et al., supra), erythromycin (25 μg/mL), and spectinomycin (100 μg/mL). The flask is incubated without shaking at 37° C. for 18-24 h, after which time, isobutanol production is measured by HPLC or GC analysis, as described in the General Methods section.

What is claimed is:

1. A method comprising:
   a) providing a recombinant yeast host cell that expresses an engineered biosynthetic isobutanol pathway, wherein the engineered biosynthetic isobutanol pathway comprises an acetolactate synthase (ALS) enzyme, a ketol-acid reductoisomerase (KARI) enzyme, a dihydroxy-acid dehydratase (DHAD) enzyme, a branched chain keto acid decarboxylase enzyme (DC), and an alcohol dehydrogenase (ADH) enzyme, each of which is encoded by a heterologous gene that lacks a mitochondrial targeting sequence, and wherein the yeast host cell is provided in a growth phase;
   b) growing the yeast host cells in fermentation medium, whereby isobutanol is bioproduced; and
   c) recovering the bioproduced isobutanol;
   wherein the yeast host cells are capable of producing 7- to 8-fold more isobutanol when grown on glucose under aerobic conditions compared to a recombinant yeast host cell lacking said engineered biosynthetic isobutanol pathway.

2. The method of claim 1, further comprising blending the bioproduced isobutanol with a fossil fuel to make a fuel or fuel additive.

3. The method of claim 1, wherein the bioproduced isobutanol is a chemical feedstock.

4. The method of claim 1, wherein the ALS enzyme has an increased affinity for pyruvate over ketobuytrate.

5. The method of claim 1, wherein the ALS enzyme is from *Lactococcus lactis*.

6. The method of claim 1, wherein the ALS enzyme is from *Klebsiella pneumonia*.

7. The method of claim 1, wherein the ALS enzyme is from *Bacillus subtilis*.

8. The method of claim 1, wherein the ALS enzyme is capable of producing an activity of 8 units/mg as measured in a cell free extract when expressed on a pTrc99A plasmid in *E. coli* TOP10 cells grown at 37° C. for three hours following induction with 0.4 mM isopropyl β-D-1-thiogalactopyran (IPTG).

9. The method of claim 1, wherein the DC enzyme is capable of producing an activity of 3.7 units/mg as measured in a cell free extract when expressed on a pTrc99A plasmid in *E. coli* TOP10 cells grown at 37° C. for three hours following induction with 0.4 mM isopropyl β-D-1-thiogalactopyran (IPTG).

10. The method of claim 1, wherein the ALS enzyme has an amino acid sequence selected from SEQ ID NOs: 2, 178, or 180.

11. The method of claim 1, wherein the KARL enzyme has an amino acid sequence selected from SEQ ID NOs: 4, 181, 183, or 185.

12. The method of claim 1, wherein the DHAD enzyme has an amino acid sequence selected from SEQ ID NOs: 6, 186, 188, or 190.

13. The method of claim 1, wherein the branched chain keto acid decarboxylase enzyme has an amino acid sequence selected from SEQ ID NOs: 8, 193, 195, or 197.

14. The method of claim 1, wherein the ADH enzyme has an amino acid sequence selected from SEQ ID NOs: 10, 199, 201, 203, or 204.

15. The method of claim 1, further comprising removing solids from the fermentation medium.

16. The method of claim 1, wherein the recovering is by distillation, liquid-liquid extraction, adsorption, decantation, pervaporation, or combinations thereof.

17. The method of claim 15, wherein the removing is by centrifugation, filtration, or decantation.

18. The method of claim 15, wherein the removing occurs before the recovering.

* * * * *